US012735750B2

(12) United States Patent
Diehn et al.

(10) Patent No.: US 12,735,750 B2
(45) **Date of Patent: *Sep. 15, 2026**

(54) IDENTIFICATION AND USE OF CIRCULATING NUCLEIC ACID TUMOR MARKERS

(71) Applicant: The Board of Trustees of the Leland Stanford Junior University, Stanford, CA (US)

(72) Inventors: Maximilian Diehn, San Carlos, CA (US); Arash Ash Alizadeh, San Mateo, CA (US); Aaron M. Newman, Palo Alto, CA (US); Scott V. Bratman, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/270,341

(22) Filed: Jul. 15, 2025

(65) Prior Publication Data

US 2025/0346960 A1 Nov. 13, 2025

Related U.S. Application Data

(63) Continuation of application No. 18/803,351, filed on Aug. 13, 2024, now Pat. No. 12,421,559, which is a (Continued)

(51) Int. Cl.

*C12Q 1/6886* (2018.01)
*C12Q 1/6806* (2018.01)
*C12Q 1/6827* (2018.01)

(52) U.S. Cl.

CPC ......... *C12Q 1/6886* (2013.01); *C12Q 1/6806* (2013.01); *C12Q 1/6827* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 6,150,112 | A | 11/2000 | Weissman et al. |
| 11,085,084 | B2 | 8/2021 | Diehn et al. |

(Continued)

FOREIGN PATENT DOCUMENTS

| | | |
|---|---|---|
| CN | 102482711 | 5/2012 |
| CN | 102586420 | 7/2012 |

(Continued)

OTHER PUBLICATIONS

Bratman et al. Radiation Oncology. 84(3): Supplement 7, Abstract S713 (Year: 2012).*

(Continued)

*Primary Examiner* — Carla J Myers

(74) *Attorney, Agent, or Firm* — Andrew R. Guzman; Pamela J. Sherwood; Bozicevic, Field & Francis LLP

(57) ABSTRACT

Methods for creating a selector of mutated genomic regions and for using the selector set to analyze genetic alterations in a cell-free nucleic acid sample are provided. The methods can be used to measure tumor-derived nucleic acids in a blood sample from a subject and thus to monitor the progression of disease in the subject. The methods can also be used for cancer screening, cancer diagnosis, cancer prognosis, and cancer therapy designation.

18 Claims, 50 Drawing Sheets

Specification includes a Sequence Listing.

Related U.S. Application Data continuation of application No. 17/406,948, filed on Aug. 19, 2021, which is a continuation of application No. 14/774,518, filed as application No. PCT/US2014/025020 on Mar. 12, 2014, now abandoned.

(60) Provisional application No. 61/798,925, filed on Mar. 15, 2013.

(56) References Cited

U.S. PATENT DOCUMENTS

| | | | |
|---|---|---|---|
| 2003/0211504 | A1 | 11/2003 | Fechtel et al. |
| 2006/0040282 | A1 | 2/2006 | Monforte et al. |
| 2007/0172839 | A1 | 7/2007 | Smith et al. |
| 2008/0161420 | A1 | 7/2008 | Shuber et al. |
| 2010/0029498 | A1 | 2/2010 | Gnirke et al. |
| 2010/0041048 | A1 | 2/2010 | Diehl et al. |
| 2012/0122701 | A1 | 5/2012 | Ryan et al. |
| 2012/0183967 | A1 | 7/2012 | Dressman et al. |
| 2012/0214678 | A1 | 8/2012 | Rava et al. |
| 2012/0237928 | A1 | 9/2012 | Rava et al. |
| 2012/0264121 | A1 | 10/2012 | Rava et al. |
| 2013/0024127 | A1 | 1/2013 | Stuelpnagel et al. |
| 2013/0034546 | A1 | 2/2013 | Rava et al. |
| 2013/0231253 | A1 | 9/2013 | Amorese |
| 2014/0066317 | A1 | 3/2014 | Talasaz |
| 2014/0100121 | A1 | 4/2014 | Cuhk |
| 2014/0235506 | A1 | 8/2014 | Hindson et al. |
| 2021/0363597 | A1 | 11/2021 | Diehn et al. |

FOREIGN PATENT DOCUMENTS

| | | |
|---|---|---|
| WO | WO2006047787 | 5/2006 |
| WO | WO2010141955 | 12/2010 |
| WO | WO2011103236 | 8/2011 |
| WO | WO2012071621 | 6/2012 |
| WO | WO2013142389 | 9/2013 |
| WO | WO 2013181170 | 12/2013 |
| WO | WO2013190441 | 12/2013 |
| WO | WO2014151117 | 9/2014 |
| WO | WO 2015100427 | 7/2015 |
| WO | WO2016040901 | 3/2016 |

OTHER PUBLICATIONS

Dees et al. (2012) "MuSiC: identifying mutational significance in cancer genomes." *Genome research,* 22(8), pp. 1589-1598.

Kan et al. (2010) "Diverse somatic mutation patterns and pathway alterations in human cancers." *Nature,* 466(7308), pp. 869-875.

Tam (2013) "Oncodrive-CIS: a method to reveal likely driver genes based on the impact of their copy number changes on expression." *PLoS One,* 8(2), e55489, pp. 1-9.

Vandin et al. (2012) "De novo discovery of mutated driver pathways in cancer." *Genome research,* 22(2), pp. 375-385.

Butler et al. PLoS ONE Aug. 28, 2015. 10(8): e0136407 (Year: 2015).

Hohaus et al. Annals of Oncology. 20: 1408-1483 (Year: 2009).

Mamanova et al. Nature Methods. 7(2): 111-118 and Supplementary figures and text, 44 pages (Year: 2010).

Baudet, C. et al; "Cassis: detection of genomic rearrangement breakpoints"; Bioinformatics, vol. 26, No. 15 (2010); p. 1897-1898. (Year: 2010).

Blumenstiel, B. et al; (201 0), Targeted Exon Sequencing by In-Solution Hybrid Selection. Current Protocols in Human Genetics, 66: 18.4.1-18.4.24 (Year: 201 0).

Bosch et al.(2008) "Keeping Up With the Next Generation Massively Parallel Sequencing in Clinical Diagnostics" Journal of Molecular Diagnostics vol. 10, pp. 484-492.

Campbell, P. J. et al.; "Identification of somatically acquired rearrangements in cancer using genome-wide massively parallel paired-end sequencing"; Nature Genetics, vol. 40, No. 6; Jun. 2006; p. 722-729. (Year: 2006).

Craig et al. (2008) "Identification of genetic variants using bar-coded multiplexed sequencing", Nature Methods vol. 5, pp. 887-893.

Diehl et al., "Circulating mutant DNA to assess tumor dynamics", Nature Medicine, Sep. 1, 2008, pp. 985-990, vol. 14, No. 9, Nature Medicine, New York, NY.

Duncavage et al., "Targeted next generation sequencing of clinically significant gene mutations and translocations in leukemia", Modern Pathology, Mar. 16, 2012, pp. 795-804, vol. 25, No. 6, Springer Nature Limited, New York City, NY.

Forshew et al. Noninvasive identification and monitoring of cancer mutations by targeted deep sequencing of plasma DNA. Science Transl Med, May 30, 2012, vol. 4, No. 136, pp. 136ra68, p. 1-12, plus Supplementary Materials doi: 10.1126/scitranslmed.3003726.

Fu et al., "Molecular indexing enables quantitative targeted RNA sequencing and reveals poor efficiencies in standard library preparations", Proc Nat Acad Sci, Feb. 4, 2014, pp. 1891-1896, vol. 111 No 5, PNAS, Washington, DC.

Gnirke et al. (2009) Solution hybrid selection with ultra-long oligonucleotides for massively parallel targeted sequencing. Nature Biotechnology, 27(2):182-189.

Jiang, Y. et al.; "PRISM: Pair-read informed split-read mapping for base-pair level detection w of insertion, deletion and structural variants"; Bioinformatics, vol. 28, No. 20 (2012) p. 2576-2583. (Year: 2012).

Johansson et al., "Targeted resequencing of candidate genes using selector probes," Nucleic Acids Research, Nov. 8, 2010, pp. 1-13, vol. 39, No. 2, Oxford University Press, Oxford, United Kingdom.

Leary et al., "Development of Personalized Tumor Biomarkers Using Massively Parallel Sequencing", Science Translational Medicine, Feb. 24, 2010, pp. 1-7, 2(20), American Association for the Advancement of Science, Washington, D.C.

Luo et al., "Diagnostic value of circulating free DNA for the detection of EGFR mutation status in NSCLC: a systematic review and meta-analysis," Scientific Reports, Sep. 9, 2014, pp. 1-7, 4(1), Macmillan Publishers Limited, Basingstoke, United Kingdom.

Mardis, E.; "A decade's perspective on DNA sequencing technology"; Nature; vol. 470; Feb. 10, 2011; p. 198-203 (Year: 2011).

Martinez et al., "Computational optimisation of targeted DNA sequencing for cancer detection", Scientific Reports, Dec. 3, 2013, pp. 1-8, vol. 3, article No. 3309, Nature Publishing Group, London, United Kingdom.

McBride et al. (201 0) Use of Cancer-Specific Genomic Rearrangements to Quantify Disease Burden in Plasma from Patients with Solid Tumors. Genes, Chromosomes, & Cancer, 49:1062-1069.

Mcpherson, A. et. al.; "nFuse: Discovery of complex genomic rearrangements in cancer using high-throughput sequencing"; (2012) Genome Research, 22:2250-2261. (Year: 2012).

Narayan et al., "Ultrasensitive Measurement of Hotspot Mutations in Tumor DNA in Blood Using Error-Suppressed Multiplexed Deep Sequencing", Cancer Research, May 10, 2012, pp. 3492-3498, vol. 72, No. 14, American Association for Cancer Research, Philadelphia, PA.

Newman et al., "An ultrasensitive method for quantitating circulating tumor DNA with broad patient coverage," Nature Medicine, Apr. 6, 2014, pp. 548-556 and Online supplementary material, Nature Medicine, Apr. 6, 2014, pp. 1-22, Macmillan Publishers Limited, Basingstoke, United Kingdom.

Pao et al. (2011) New driver mutations in non-small-cell lung cancer. The Lancet, 12:175-180.

Qu, W. "Efficient frequency-based de novo short-read clustering for error trimming in next generation sequencing"; Genome Res. 2009 19: 1309-1315. (Year: 2009).

Rausch, T. et al; "DELLY: structural variant discovery by integrated paired-end and split-read analysis"; Bioinformatics, vol. 28, Issue 18, Sep. 15, 2012, pp. i333-i339 (Year: 2012).

EP20191562.6 "Decision and Minutes from Oral Proceedings" Reason for the decision, 2025-06-06, pp. 1-38.

Sboner, A. et al.; "FusionSeq: a modular a modular framework for finding gene fusions by analyzing paired-end RNA-sequencing data"; Genome Biology2010, 11:R104, p. 1-9 (Year: 2010).

(56) References Cited

OTHER PUBLICATIONS

Suzuki, S. et. al; "CiipCrop: a tool for detecting structural variations with u single-base resolution using soft clipping information", BMC Bioinformatics 2011, 12(Suppl 14):S7 (Year: 2011).
Teer et al., "Systematic comparison of three genomic enrichment methods for massively parallel DNA sequencing", Genome Research, Sep. 1, 2010, pp. 1420-1431, vol. 20, No. 10, Cold Spring Harbor Press, Cold Spring Harbor, NY.
Van Dijk et al.(2014) "Ten years of next-generation sequencing technology", Trends in Genetics vol. 30, pp. 418-426.
Venter, J. C. et. al; "The Sequence of the Human Genome"; Science, vol. 291; Feb. 16, 2001; p. 1305-1351. (Year: 2001).
Wagle et al., "High-Throughput Detection of Actionable Genomic Alterations in Clinical Tumor Samples by Targeted, Massively Parallel Sequencing", Cancer Discovery, Jan. 2012, pp. 82-93, 2(1), American Association for Cancer Research, Philadelphia, PA.
Comparison, with changes tracked, between the revoked main request of EP Patent No. 3,421,613 and the granted claims of the opposed patent.
Decision of Jul. 5, 2023 Revoking European Patent 342613.
Samowitz et al. (1999) "BAT-26 and BAT-40 Instability in Colorectal Adenomas and Carcinomas and Germline Polymorphisms", American Journal of Pathology, 154(6): 1637-1641.
Schmitt et al. (2012) "Detection of Ultra-Rare Mutations by Next-Generation Sequencing", PNAS, vol. 109(36), p. 14508-14513.
Supplementary Table 4 referred to in D2 at p. 184, left column, fifth line from the bottom.
Bratman et al. (2013) Abstract 223: "Noninvasive and Ultrasensitive Quantitation of Circulating Tumor DNA by Hybrid Capture and Deep Sequencing", International Journal of Radiation Oncolo.av, 87(25):S92.
Gautschi et al., "Origin and prognostic value of circulating KRAS mutations in lung cancer patients", Cancer letters (2007), 254(2): 265-273.
He et al (2011) "IgH gene rearrangements as plasma biomarkers in Non-Hodgkin's Lymphoma patients" Oncotarget, 2(3): 178-185.
He et. al. "Supplemental Table 4", pp. 1-2.
Heitzer et al (2013) "Tumor-associated copy number changes in 06 the circulation of patients with prostate cancer identified through whole genome sequencing"; Genome Medicine, 1-16.
HERMAN et at (2009) "Filter-based hybridization capture of sub genomes enables resequencing and copy-number detection"; Nat Methods, 6(7): 507-510.
Kinde et al., "Detection and quantification of rare mutations with massively parallel sequencing", PNAS USA (2011), 108:9530-9535.
Kuang et al., "Noninvasive detection of EGFR T790M in gefitinib or erlotinib resistant nonsmall cell lung cancer", Clin Cancer Res (2009), 15:2630-2636.
Mamanova et al. (2010) "Target-enrichment strategies for next generation sequencing", Nature Methods, 7(2):111-118.
Mertes et al., (2011) "Targeted enrichment of genomic DNA regions for next-generation sequencing." A Briefings in Functional Genomics, vol. 10, No. 6, pp. 374-386.
Murtaza et al (2013) "Non-invasive analysis of acquired resistance to cancer therapy by sequencing of plasma DNA"; Nature, vol | 497, pp. 108-112.
Rachlin et al., "Computational tradeoffs in multiplex PCR assay design for SNP genotyping", BMC Genomics (2005), 6:102.
Rosell et al., "Screening for Epidermal Growth Factor Receptor Mutations in Lung Cancer", N Engl J Med (2009), 361(10):958-967.
Schwarzenbach et al. (2011) "Cell-free nucleic acids as biomarkers in cancer patients", Nature Reviews Cancer, 11 :426-37.
Taniguchi et al., "Quantitative detection of EGFR mutations in circulating tumor DNA derived from lung adenocarcinomas", Clin Cancer Res (2011), 17(24):7808-15.

* cited by examiner

Figure 2A
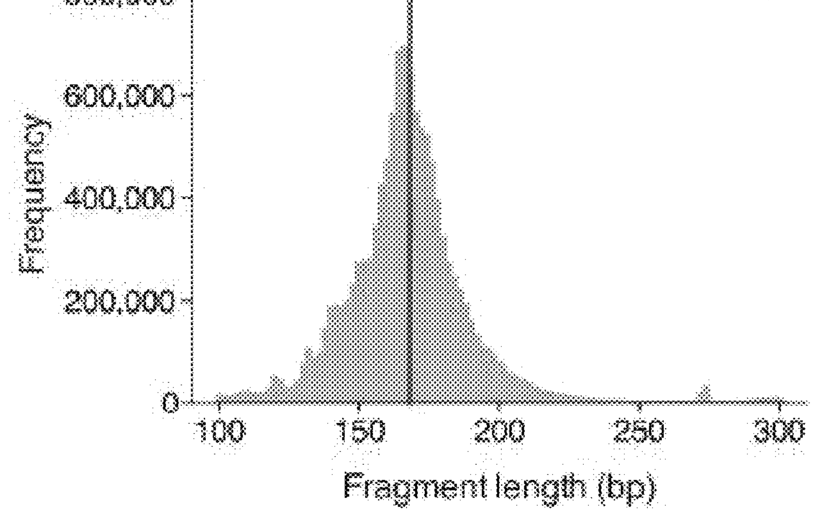
Figure 2B
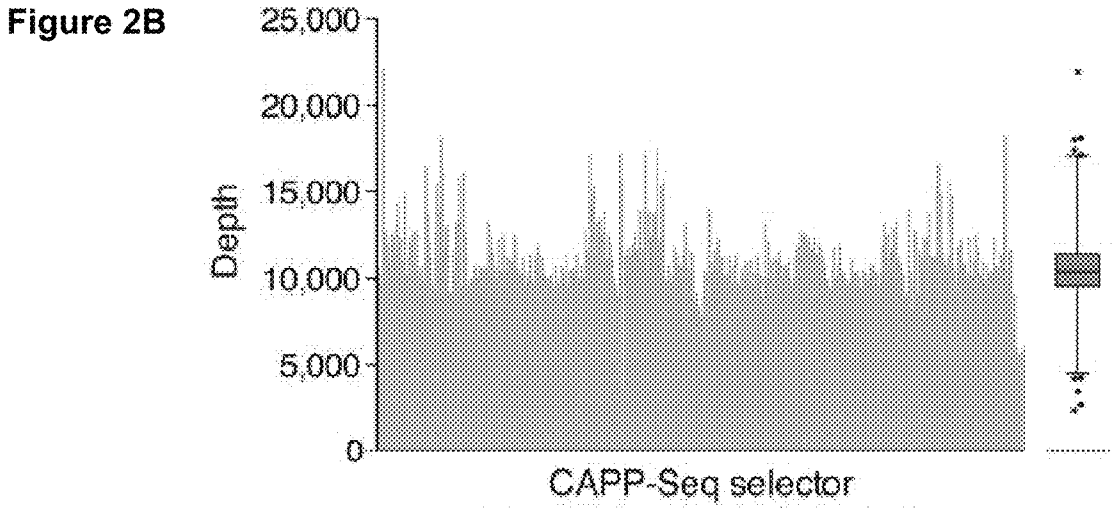
Figure 2C
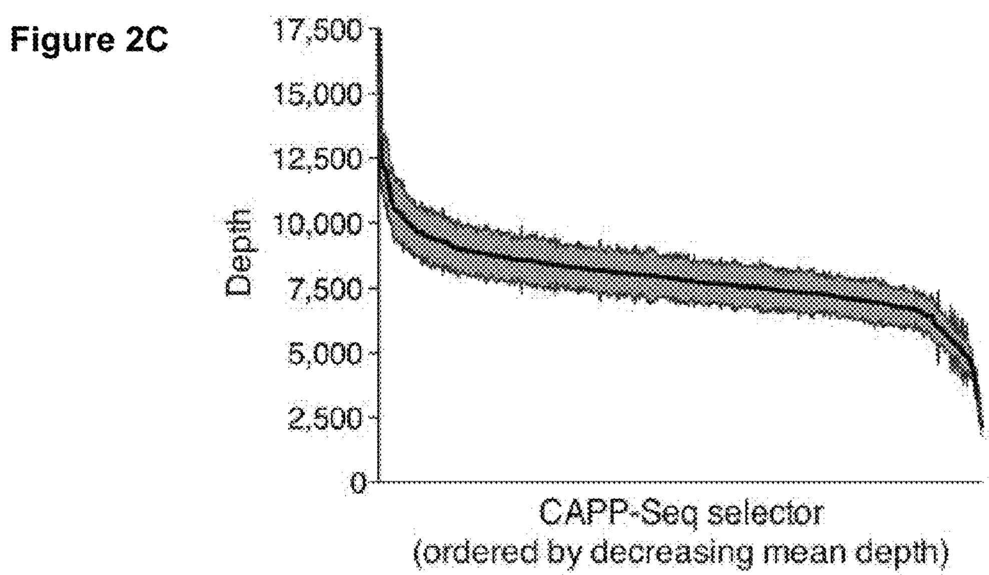

NSCLC

Healthy 0.8
0.6
0.4
0.2
0

Biological background rate (%)

~0.01%

Plasma DNA samples
(n = 35 NSCLC samples, 5 healthy)

Patient-specific reporters
Stage I
Stages II to IV
P12*
P17
P16*
P1*
P13
P14
P2*
P3
P15*
P4
P5
P6**
P9**
NSCLC
Healthy
Plasma DNA samples (n = 18)
P12
P17
P16
P1
P13
P14
P2
P3
P15
P4
P5
P6
P9
C1
C2
C3
C4
C5
FN
FP
TP
TN
TP
TN
FP
FN
* includes indel(s)
** includes fusion(s)

Tumor volume (cm³)
1,000
100
10
1
Stage I
$R^2 = 0.89$
$P = 0.0002$
1
10
100
1000
ctDNA (pg mL⁻¹)

P5 (Stage IV)

Tumor

Plasma

Mutant allele frequency (%)

50

40

30

20

10

0

5

4

3

2

1

0

Mutant allele frequency (%)

Dominant clone: all SNVs ($n$ = 3)

Dominant clone: EGFR L858R

Sublone: EGFR T790M

Cost comparison for equal detection limit in plasma

| Feature | CAPP-Seq | Whole exome | Whole genome |
|---|---|---|---|
| Bases covered | 0.125 Mb | 50 Mb | 3,000 Mb |
| No. mutations | 4 | 218 | 15,659 |
| Depth | 10,000x | 1,100x | 120x |
| Gbs sequenced | 2.1 | 92 | 360 |
| **Relative cost** | **1x** | **44x** | **171x** |

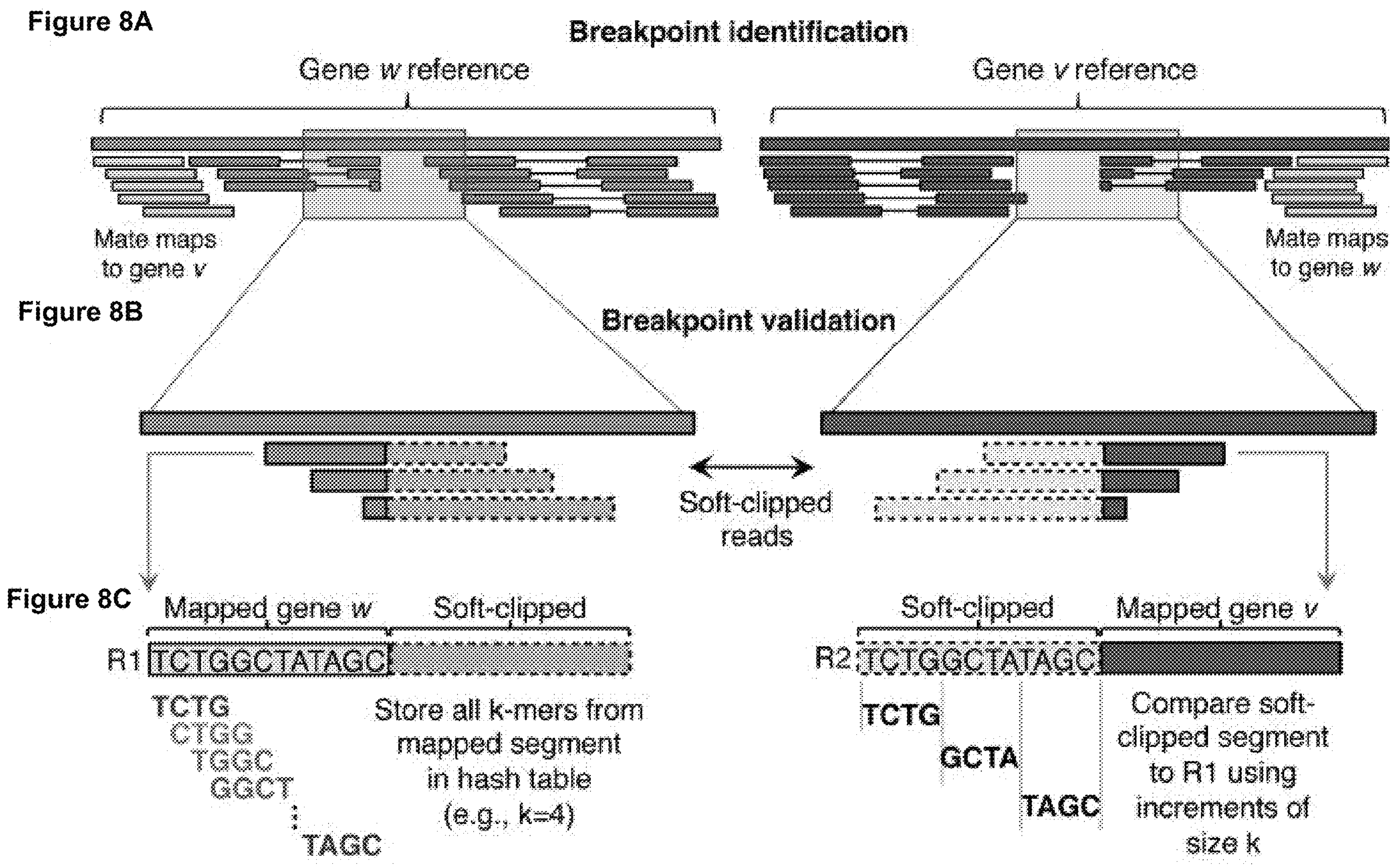
Figure 8A
Breakpoint identification
Gene w reference
Gene v reference
Mate maps to gene v
Mate maps to gene w
Figure 8B
Breakpoint validation
Soft-clipped reads
Figure 8C
Mapped gene w
Soft-clipped
R1 TCTGGCTATAGC
TCTG
CTGG
TGGC
GGCT
TAGC
Store all k-mers from mapped segment in hash table (e.g., k=4)
Soft-clipped
Mapped gene v
R2 TCTGGCTATAGC
TCTG
GCTA
TAGC
Compare soft-clipped segment to R1 using increments of size k Possible orientations
Case 1a
R1
R2
Case 2a
R1
R2
Case 1b
R1
R2
Reverse Comp.
≈ Case 1a
Case 2b
R1
R2
≈ Case 2a Breakpoint adjustment
Case 1
x
j
bp1
R1
R2
i
y
bp2
Breakpoint 2 = bp2 + (x − y)
Case 2
bp1
x
j
R1
R2
bp2
y
i
Breakpoint 2 = bp2 + (y − x)

Figure 9A (contd.)

GAACA
GAACAAGAGTGAA
GAACAAGAGTGAAACCCCATCTCAAAAA
GAACAAGAGTGAAACCCCATCTCAAAAAC
GAACAAGAGTGAAACCCCATCTCAAAAACAA
GAACAAGAGTGAAACCCCATCTCAAAAACAAA
GAACAAGAGTGAAACCCCATCTCAAAAACAAACAAACA
GAACAAGAGTGAAACCCCATCTCAAAAACAAACAAACAAAACAAAAC
GAACAAGAGTGAAACCCCATCTCAAAAACAAACAAACAAAACAAAACAAAAAAAACTAAG

```
TCTGG
TCTGGGTGACAC
TCTGGGTGACACAAAG
TCTGGGTGACACAAAGGACC
TCTGGGTGACACAAAGGACCATGGATTTCT
TCTGGGTGACACAAAGGACCATGGATTTCTGCAA
TCTGGGTGACACAAAGGACCATGGATTTCTGCAACCCTTGGTG
TCTGGGTGACACAAAGGACCATGGATTTCTGCAACCCTTGGTGCCTTTCT
TCTGGGTGACACAAAGGACCATGGATTTCTGCAACCCTTGGTGCCTTTCTTGGGAACCCAT
```

Figure 9B
*(Contnued)*

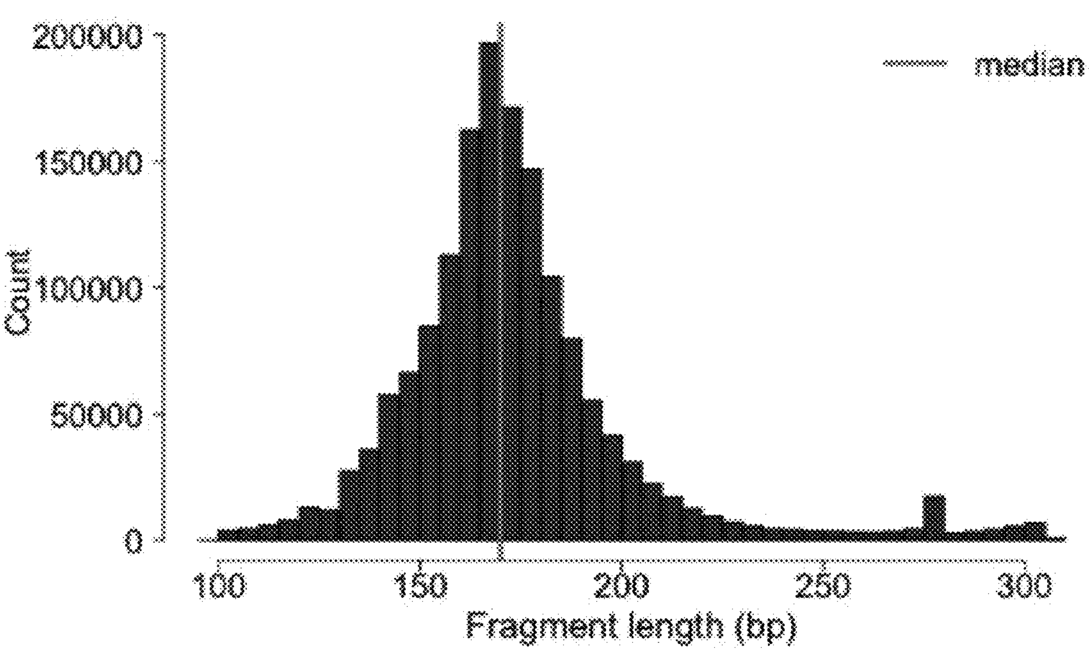
Figure 12A
*(Continued)*
Figure 12B
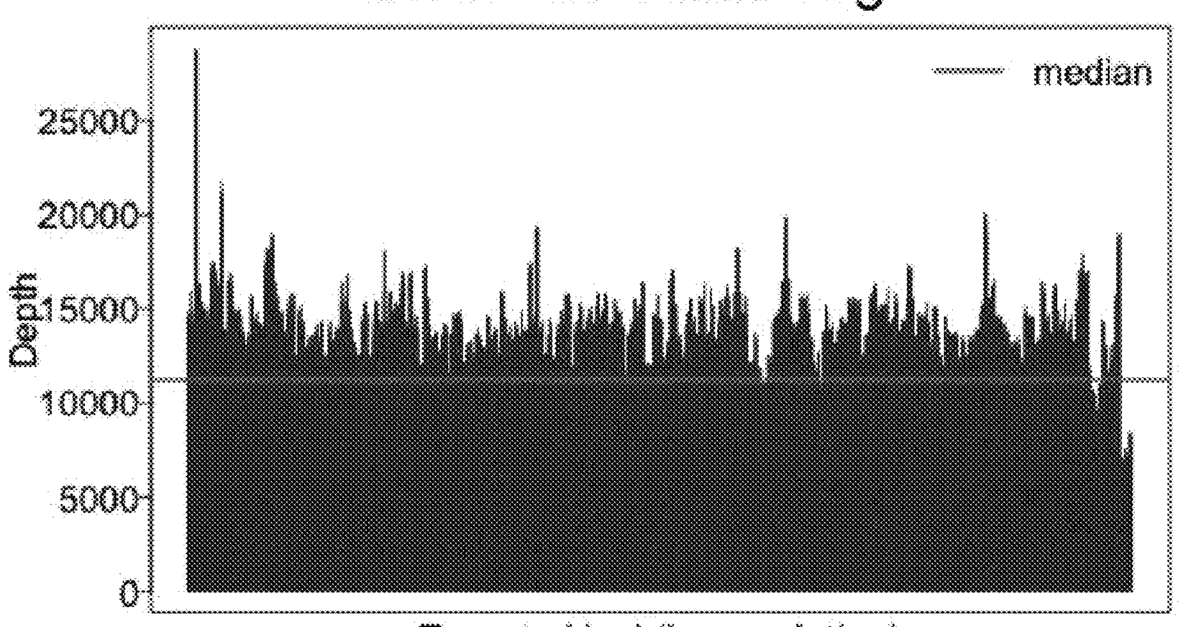

Figure 17A

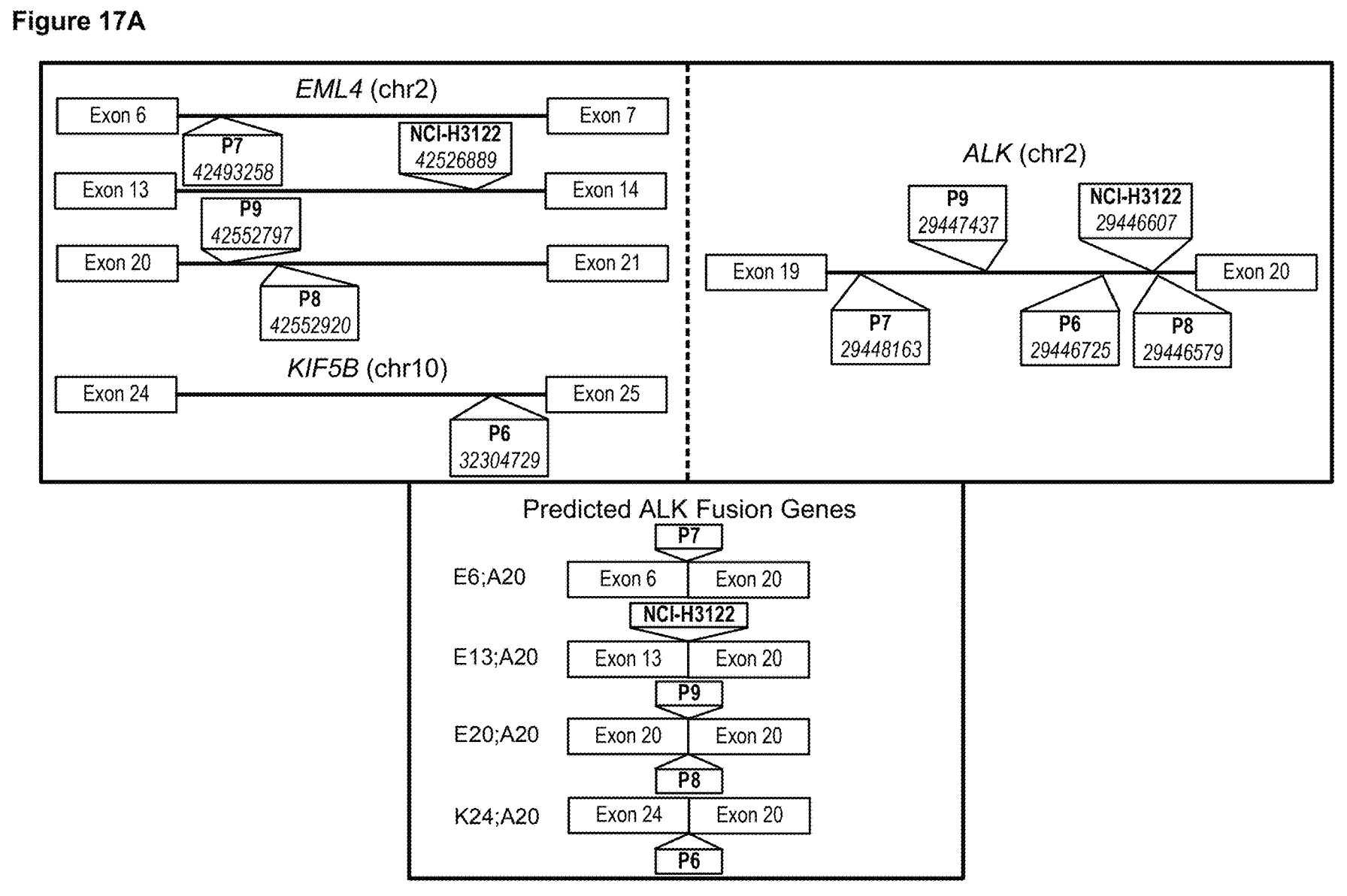

*EML4* (chr2)
Exon 6
P7 42493258
NCI-H3122 42526889
Exon 7
Exon 13
Exon 14
P9 42552797
Exon 20
Exon 21
P8 42552920
*KIF5B* (chr10)
Exon 24
Exon 25
P6 32304729

*ALK* (chr2)
P9 29447437
NCI-H3122 29446607
Exon 19
Exon 20
P7 29448163
P6 29446725
P8 29446579

Predicted ALK Fusion Genes
P7
E6;A20 Exon 6 Exon 20
NCI-H3122
E13;A20 Exon 13 Exon 20
P9
E20;A20 Exon 20 Exon 20
P8
K24;A20 Exon 24 Exon 20
P6

Figure 19A
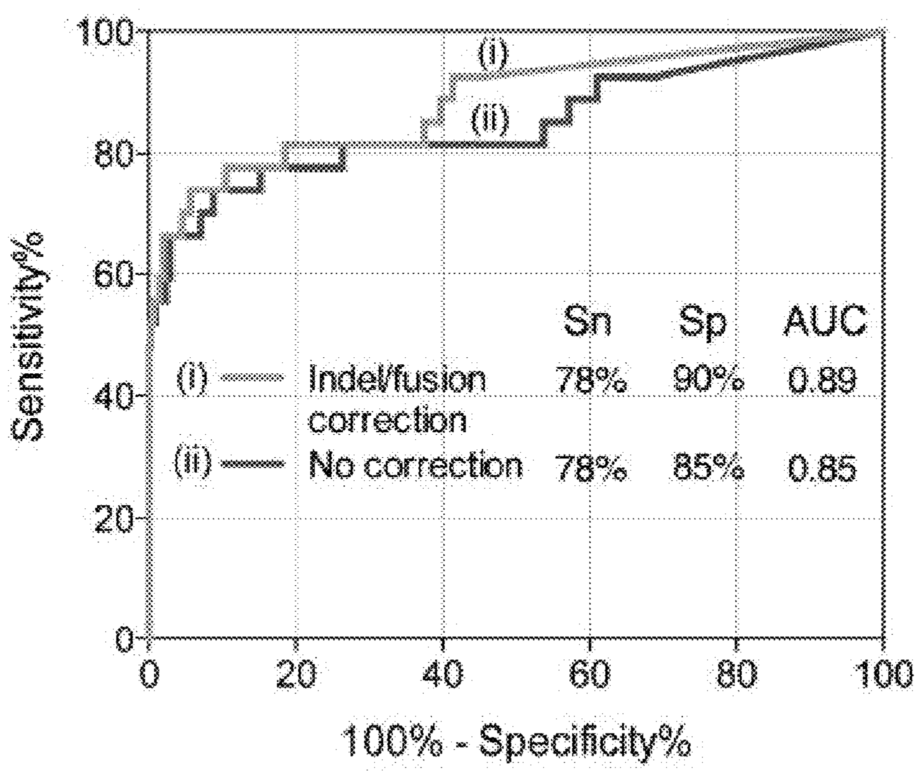
Figure 19B
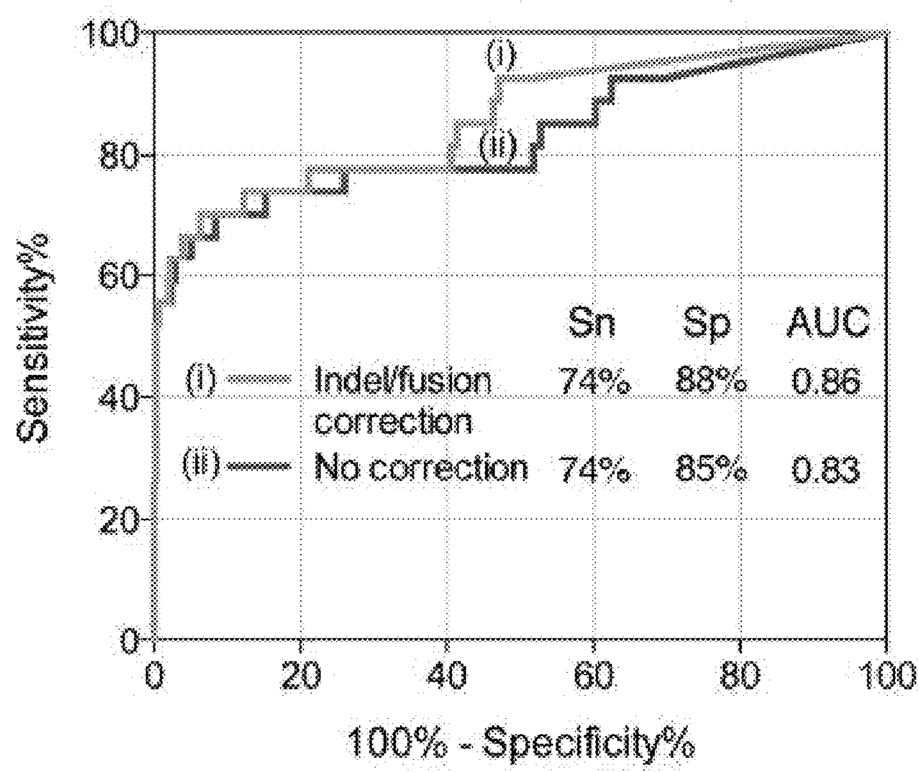

(0) Pre-filter
(1) Germline filter
(2) Background filter
(3) Outlier detection

No. tags (nondeduped)
No. tags (deduped)
Background allele
Known SNV
Cutpoint (Rho<0.85)
Square root of quantiles of chi-square
Robust Mahalanobis distance
Iterative correlation
Post-Op plasma DNA (P1)

No. tags (nondeduped)
No. tags (deduped)
400
300
200
100
0
20
40
60
80
100
Square root of quantiles of chi-square
Robust Mahalanobis distance
Iterative correlation
Post-Op plasma DNA (P1)

IDENTIFICATION AND USE OF CIRCULATING NUCLEIC ACID TUMOR MARKERS

CROSS-REFERENCE TO RELATED APPLICATIONS

This application is a Continuation and claims the benefit of application Ser. No. 18/803,351, filed Aug. 13, 2024, which claims the benefit of application Ser. No. 17/406,948, filed Aug. 19, 2021, which claims the benefit of application Ser. No. 14/774,518, filed Sep. 10, 2015, now abandoned, which claims the benefit of PCT Application No. PCT/US2014/025020, filed Mar. 12, 2014, which claims the benefit of U.S. Provisional Application No. 61/798,925, filed Mar. 15, 2013, which applications are incorporated herein by reference in their entirety.

STATEMENT OF GOVERNMENTAL SUPPORT

This invention was made with Government support under contract W81XWH-12-1-0285 awarded by the Department of Defense. The Government has certain rights in the invention.

REFERENCE TO ELECTRONIC SEQUENCE LISTING

The contents of the electronic sequence listing (STAN-866CON3_Seq List.xml; Size: 50,834 bytes; and Date of Creation: Jul. 9, 2025) is herein incorporated by reference in its entirety.

BACKGROUND OF THE INVENTION

Tumors continually shed DNA into the circulation, where it is readily accessible (Stroun et al. (1987) *Eur J Cancer Clin Oncol* 23:707-712). Analysis of such cancer-derived cell-free DNA (cfDNA) has the potential to revolutionize detection and monitoring of cancer. Noninvasive access to malignant DNA is particularly attractive for solid tumors, which cannot be repeatedly sampled without invasive procedures. In non-small cell lung cancer (NSCLC), PCR-based assays have been used previously to detect recurrent point mutations in genes such as KRAS or EGFR in plasma DNA (Taniguchi et al. (2011) Clin. Cancer Res. 17:7808-7815; Gautschi et al. (2007) Cancer Lett. 254:265-273; Kuang et al. (2009) Clin. Cancer Res. 15:2630-2636; Rosell et al. (2009) N. Engl. J. Med. 361:958-967), but the majority of patients lack mutations in these genes.

Other studies have proposed identifying patient-specific chromosomal rearrangements in tumors via whole genome sequencing (WGS), followed by breakpoint qPCR from cfDNA (Leary et al. (2010) Sci. Transl. Med. 2:20ra14; McBride et al. (2010) Genes Chrom. Cancer 49:1062-1069). While sensitive, such methods require optimization of molecular assays for each patient, limiting their widespread clinical application. More recently, several groups have reported amplicon-based deep sequencing methods to detect cfDNA mutations in up to 6 recurrently mutated genes (Forshew et al. (2012) Sci. Transl. Med. 4:136ra168; Narayan et al. (2012) Cancer Res. 72:3492-3498; Kinde et al. (2011) Proc. Natl Acad. Sci. USA 108:9530-9535). While powerful, these approaches are limited by the number of mutations that can be interrogated (Rachlin et al. (2005) BMC Genomics 6:102) and the inability to detect genomic fusions.

PCT International Patent Publication No. 2011/103236 describes methods for identifying personalized tumor markers in a cancer patient using "mate-paired" libraries. The methods are limited to monitoring somatic chromosomal rearrangements, however, and must be personalized for each patient, thus limiting their applicability and increasing their cost.

U.S. Patent Application Publication No. 2010/0041048 A1 describes the quantitation of tumor-specific cell-free DNA in colorectal cancer patients using the "BEAMing" technique (Beads, Emulsion, Amplification, and Magnetics). While this technique provides high sensitivity and specificity, this method is for single mutations and thus any given assay can only be applied to a subset of patients and/or requires patient-specific optimization. U.S. Patent Application Publication No. 2012/0183967 A1 describes additional methods to identify and quantify genetic variations, including the analysis of minor variants in a DNA population, using the "BEAMing" technique.

U.S. Patent Application Publication No. 2012/0214678 A1 describes methods and compositions for detecting fetal nucleic acids and determining the fraction of cell-free fetal nucleic acid circulating in a maternal sample. While sensitive, these methods analyze polymorphisms occurring between maternal and fetal nucleic acids rather than polymorphisms that result from somatic mutations in tumor cells. In addition, methods that detect fetal nucleic acids in maternal circulation require much less sensitivity than methods that detect tumor nucleic acids in cancer patient circulation, because fetal nucleic acids are much more abundant than tumor nucleic acids.

U.S. Patent Application Publication Nos. 2012/0237928 A1 and 2013/0034546 describe methods for determining copy number variations of a sequence of interest in a test sample comprising a mixture of nucleic acids. While potentially applicable to the analysis of cancer, these methods are directed to measuring major structural changes in nucleic acids, such as translocations, deletions, and amplifications, rather than single nucleotide variations.

U.S. Patent Application Publication No. 2012/0264121 A1 describes methods for estimating a genomic fraction, for example, a fetal fraction, from polymorphisms such as small base variations or insertions-deletions. These methods do not, however, make use of optimized libraries of polymorphisms, such as, for example, libraries containing recurrently-mutated genomic regions.

U.S. Patent Application Publication No. 2013/0024127 A1 describes computer-implemented methods for calculating a percent contribution of cell-free nucleic acids from a major source and a minor source in a mixed sample. The methods do not, however, provide any advantages in identifying or making use of optimized libraries of polymorphisms in the analysis.

PCT International Publication No. WO 2010/141955 A2 describes methods of detecting cancer by analyzing panels of genes from a patient-obtained sample and determining the mutational status of the genes in the panel. The methods rely on a relatively small number of known cancer genes, however, and they do not provide any ranking of the genes according to effectiveness in detection of relevant mutations. In addition, the methods were unable to detect the presence of mutations in the majority of serum samples from actual cancer patients.

There is thus a need for new and improved methods to detect and monitor tumor-related nucleic acids in cancer patients.

SUMMARY OF THE INVENTION

Compositions and methods, including methods of bioinformatic analysis, are provided for the highly sensitive analysis of circulating tumor DNA (ctDNA), e.g. DNA sequences present in the blood of an individual that are derived from tumor cells. The methods of the invention may be referred to as CAncer Personalized Profiling by Deep Sequencing (CAPP-Seq). Tumors of particular interest are solid tumors, including without limitation carcinomas, sarcomas, gliomas, lymphomas, melanomas, etc., although hematologic cancers, such as leukemias, are not excluded.

The methods of the invention combine optimized library preparation methods with a multi-phase bioinformatics approach to design a "selector" population of DNA oligonucleotides, which correspond to recurrently mutated regions in the cancer of interest. The selector population of DNA oligonucleotides, which may be referred to as a selector set, comprises probes for a plurality of genomic regions, and is designed such that at least one mutation within the plurality of genomic regions is present in a majority of all subjects with the specific cancer; and in preferred embodiments multiple mutations are present in a majority of all subjects with the specific cancer.

In some embodiments of the invention, methods are provided for the identification of a selector set appropriate for a specific tumor type. Also provided are oligonucleotide compositions of selector sets, which may be provided adhered to a solid substrate, tagged for affinity selection, etc.; and kits containing such selector sets. Included, without limitation, is a selector set suitable for analysis of non-small cell lung carcinoma (NSCLC). Such kits may include executable instructions for bioinformatics analysis of the CAPP-Seq data.

In other embodiments, methods are provided for the use of a selector set in the diagnosis and monitoring of cancer in an individual patient. In such embodiments the selector set is used to enrich, e.g. by hybrid selection, for ctDNA that corresponds to the regions of the genome that are most likely to contain tumor-specific somatic mutations. The "selected" ctDNA is then amplified and sequenced to determine which of the selected genomic regions are mutated in the individual tumor. An initial comparison is optionally made with the individual's germline DNA sequence and/or a tumor biopsy sample from the individual. These somatic mutations provide a means of distinguishing ctDNA from germline DNA, and thus provide useful information about the presence and quantity of tumor cells in the individual.

In some embodiments, the ctDNA content in an individual's blood, or blood derivative, sample is determined at one or more time points, optionally in conjunction with a therapeutic regimen. The presence of the ctDNA correlates with tumor burden, and is useful in monitoring response to therapy, monitoring residual disease, monitoring for the presence of metastases, monitoring total tumor burden, and the like. Although not required, for some methods CAPP-Seq may be performed in conjunction with tumor imaging methods, e.g. PET/CT scans and the like.

In other embodiments, CAPP-seq is used for cancer screening and biopsy-free tumor genotyping, where a patient ctDNA sample is analyzed without reference to a biopsy sample. In some such embodiments, where CAPP-Seq identifies a mutation in a clinically actionable target from a ctDNA sample, the methods include providing a therapy appropriate for the target. Such mutations include, without limitation, rearrangements and other mutations involving oncogenes, receptor tyrosine kinases, etc. Actionable targets may include, for example, ALK, ROS1, RET, EGFR, KRAS, and the like.

The CAPP-Seq methods may include steps of data analysis, which may be provided as a program of instructions executable by computer and performed by means of software components loaded into the computer. Such methods include the design for identification selector set for a cancer of interest. Other bioinformatics methods are provided for determining and quantitating when circulating tumor DNA is detectable above background, e.g. using an approach that integrates information content and classes of mutation into a detection index.

Disclosed herein is a method for determining the presence of tumor nucleic acids (tNA) in a cell-free nucleic acids (cfNA) sample from an individual by detection of somatic mutations. The method may comprise (a) obtaining a cfNA sample; (b) selecting the cfNA for sequences corresponding to a plurality of regions of mutations in a cancer of interest; (c) sequencing the selected cfNA; (d) determining the presence of somatic mutations, wherein the presence of the somatic mutations may be indicative of tumor cells present in the individual; and (e) providing the individual with an assessment of the presence of tumor cells.

The cell-free nucleic acid may be cell-free DNA (cfDNA). The cell-free nucleic acid may be cell-free RNA (cfRNA). The cell-free nucleic acids may be a mixture of cell-free DNA (cfDNA) and cell-free RNA (cfRNA). The tumor nucleic acid may be a nucleic acid originating from a tumor cell. The tumor nucleic acid may be tumor-derived DNA (tDNA). The tumor nucleic acid may be a circulating tumor DNA (ctDNA). The tumor nucleic acid may be tumor-derived RNA (tRNA). The tumor nucleic acid may be a circulating tumor RNA (ctRNA). The tumor nucleic acids may be a mixture of tumor-derived DNA and tumor-derived RNA. The tumor nucleic acids may be a mixture of ctDNA and ctRNA.

Selecting the cfNA may comprise (i) hybridizing the cell-free nucleic acid sample to a plurality of selector set probes comprising a specific binding member; (ii) binding hybridized nucleic acids to a complementary specific binding member; and (iii) washing away unbound DNA.

The cfNA sample may be compared to a known tumor DNA sequence from the individual.

The cfNA sample may be de novo analyzed for the presence of somatic mutations.

The somatic mutations may include single nucleotide variants, insertions, deletions, copy number variations, and rearrangements.

The plurality of regions of mutations may comprise at least 5, 10, 15, 20, 25, 30, 35, 40, 45, 50, 55, 60, 65, 70, 75, 80, 85, 90, 95, 100, 125, 150, 175 or 200 different genomic regions. The plurality of regions of mutations may comprise at least 500 different genomic regions. The plurality of genomic regions of mutations may comprise a total of from 100 to 500 kb of sequence.

At least one somatic mutation may be present in at least 60%, 65%, 70%, 72%, 75%, 77%, 80%, 82%, 85%, 87%, 90%, 92%, 95%, 97%, or 99% of individuals in a patient population for the cancer of interest.

The cancer of interest may be a leukemia. The cancer of interest may be a solid tumor. The cancer may be a carcinoma. The carcinoma may be an adenocarcinoma or a squamous cell carcinoma. The carcinoma may be non-small cell lung cancer.

The individual may be not previously diagnosed with cancer. The individual may be undergoing treatment for cancer.

Two or more samples may be obtained from the individual over a period of time and compared for residual disease or tumor burden.

The method may further comprise treating the individual in accordance with the analysis of the presence of tumor cells. The method may further comprise treating the individual based on the detection of the somatic mutations.

Determining the presence of somatic mutations may comprise: (i) integrating cfDNA fractions across all somatic SNVs; (ii) performing a position-specific background adjustment; and (iii) evaluating statistical significance by Monte Carlo sampling of background alleles across the selector, wherein steps (i)-(iii) are embodied as a program of instructions executable by computer and performed by means of software components loaded into the computer.

The method may further comprise analysis of insertions and/or deletions by comparing its fractional abundance in a given cfDNA sample against its fractional abundance in a cohort. The method may further comprise combining the fractional abundance into a single Z-score.

The method may further comprise integrating different mutation types to estimate the significance of tumor burden quantitation.

Determining the presence of somatic mutations may be identification of genomic fusion events and breakpoints by the method comprising: (i) identification of discordant reads; (ii) detection of breakpoints at base pair-resolution, and (iii) in silico validation of candidate fusions, wherein steps (i)-(iii) are embodied as a program of instructions executable by computer and performed by means of software components loaded into the computer.

Determining the presence of somatic mutation may comprise the steps of (i) taking allele frequencies from a single cfDNA sample and selecting high quality data; (ii) testing whether a given input cfDNA allele may be significantly different from the corresponding paired germline allele; (iii) assembling a database of cfDNA background allele frequencies by binomial distribution; (iv) testing whether a given input allele differs significantly from cfDNA background at the same position, and selecting those with an average background frequency of a predetermined threshold; and (v) distinguishing tumor-derived SNVs from remaining background noise by outlier analysis, wherein steps (i)-(v) may be embodied as a program of instructions executable by computer and performed by means of software components loaded into the computer.

The selector set probes may comprise sequences corresponding to a mutated genomic regions identified by the method comprising identifying a plurality of genomic regions from a group of genomic regions that may be mutated in a specific cancer.

Identifying the plurality of genomic regions may comprise for each genomic region in the plurality of genomic regions, ranking the genomic region to maximize the number of all subjects with the specific cancer having at least one mutation within the genomic region.

Identifying the plurality of genomic regions may comprise: (i) selecting genes known to be drivers in the cancer of interest to generate a pool of known drivers; (ii) selecting exons from known drivers with the highest recurrence index (RI) that identify at least one new patient compared to step (a); and repeating until no further exons meet these criteria; (iii) identifying remaining exons of known drivers with an RI≥30 and with SNVs covering ≥3 patients in the relevant database that result in the largest reduction in patients with only 1 SNV; and repeating until no further exons meet these criteria; (iv) repeating step (b) using RI≥20; (v) adding in all exons from additional genes previously predicted to harbor driver mutations; and (vi) adding for known recurrent rearrangement the introns most frequently implicated in the fusion event and the flanking exons, wherein steps (i)-(vi) are embodied as a program of instructions executable by computer and performed by means of software components loaded into the computer.

The plurality of regions of mutations in a cancer of interest may be selected from the regions set forth in Table 2.

The plurality of regions of mutations may comprise at least 5, 10, 15, 20, 25, 30, 35, 40, 45, 50, 55, 60, 65, 70, 75, 80, 85, 90, 95, or 100 regions set forth in Table 2.

Further disclosed herein are compositions comprising selector set probes. The composition may comprise a set of selector set probes of at least about 25 nucleotides in length, comprising a specific binding member, and comprising sequences from at least 100 regions set forth in Table 2.

The set of selector probes may comprise oligonucleotides comprising sequences from at least 300 regions from Table 2. The set of selector probes may comprise oligonucleotides comprising sequences from at least 500 regions from Table 2.

Further disclosed herein are populations of cell-free DNA (cfDNA). The population of cfDNA may be an enriched population. The enriched population of cfDNA may be produced by hybrid selection. Hybrid selection may comprise of use of one or more selector set probes. The selector set probes may be attached to a solid or semi-solid support. The support may comprise an array. The support may comprise a bead. The bead may be a coated bead. The bead may be a streptavidin bead. The solid support may comprise a flat surface. The solid support may comprise a slide. The solid support may comprise a glass slide.

Further disclosed herein are methods for detecting, diagnosing, prognosing, or therapy selection for a subject suffering from a disease or condition. The method may comprise: (a) obtaining sequence information of a cell-free DNA (cfDNA) sample derived from the subject; and (b) using sequence information derived from (a) to detect cell-free non-germline DNA (cfNG-DNA) in the sample, wherein the method may be capable of detecting a percentage of cfNG-DNA that may be less than 2% of total cfDNA.

The method may be capable of detecting a percentage of ctDNA that may be less than 1.5% of the total cfDNA. The method may be capable of detecting a percentage of ctDNA that may be less than 1% of the total cfDNA. The method may be capable of detecting a percentage of ctDNA that may be less than 0.5% of the total cfDNA. The method may be capable of detecting a percentage of ctDNA that may be less than 0.1% of the total cfDNA. The method may be capable of detecting a percentage of ctDNA that may be less than 0.01% of the total cfDNA. The method may be capable of detecting a percentage of ctDNA that may be less than 0.001% of the total cfDNA. The method may be capable of detecting a percentage of ctDNA that may be less than 0.0001% of the total cfDNA.

The sample may be a plasma or serum sample (sweat, breath, tears, saliva, urine, stool, amniotic fluid). The sample may be a cerebral spinal fluid sample. In some instances, the sample is not a pap smear fluid sample. In some instances, the sample is not a cyst fluid sample. In some instances, the sample is not a pancreatic fluid sample.

The sequence information may comprise information related to at least 10, 20, 30, 40, 100, 200, or 300 genomic regions. The genomic regions may comprise genes, exonic regions, intronic regions, untranslated regions, non-coding regions or a combination thereof. The genomic regions may comprise two or more of exonic regions, intronic regions, and untranslated regions. The genomic regions may comprise at least one exonic region and at least one intronic region. At least 5% of the genomic regions may comprise intronic regions. At least about 20% of the genomic regions may comprise exonic regions.

The genomic regions may comprise less than 1.5 megabases (Mb) of the genome. The genomic regions may comprise less than 1 Mb of the genome. The genomic regions may comprise less than 500 kilobases (kb) of the genome. The genomic regions may comprise less than 50, 75, 100 or 350 kb of the genome. The genomic regions may comprise between 100 kb to 300 kb of the genome.

The sequence information may comprise information pertaining to 1, 2, 3, 4, 5, 6, 7, 8, 9, 10, 15, 20 or more genomic regions from a selector set comprising a plurality of genomic regions. The sequence information may comprise information pertaining to 25, 30, 40, 50, 60, 70, 80, 90, 100 or more genomic regions from a selector set comprising a plurality of genomic regions. The sequence information may comprise information pertaining to a plurality of genomic regions.

The plurality of genomic regions may be based on a selector set comprising genomic regions comprising one or more mutations present in one or more subjects from a population of cancer subjects. At least about 5%, 10%, 15%, 20%, 25%, 30%, 35%, 40%, 45%, 50%, 55%, 60%, 65%, 70%, 75%, 80%, 85%, 90%, or 95% of the plurality of genomic regions may be based on a selector set comprising genomic regions comprising one or more mutations present in one or more subjects from a population of cancer subjects.

The total size of the genomic regions of the selector set may comprise less than 1.5 megabases (Mb), 1 Mb, 500 kilobases (kb), 350 kb, 300 kb, 250 kb, 200 kb, or 150 kb of the genome. The total size of the genomic regions of the selector set may be between 100 kb to 300 kb of the genome.

The selector set may comprise 1, 2, 3, 4, 5, 6, 7, 8, 9, 10, 15, 20, 25, 30, 40, 50, 60, 70, 80, 90, 100 or more genomic regions selected from Table 2. The selector set may comprise 1, 2, 3, 4, 5, 6, 7, 8, 9, 10, 15, 20, 25, 30, 40, 50, 60, 70, 80, 90, 100 or more genomic regions selected from Table 6. The selector set may comprise 1, 2, 3, 4, 5, 6, 7, 8, 9, 10, 15, 20, 25, 30, 40, 50, 60, 70, 80, 90, 100 or more genomic regions selected from Table 7. The selector set may comprise 1, 2, 3, 4, 5, 6, 7, 8, 9, 10, 15, 20, 25, 30, 40, 50, 60, 70, 80, 90, 100 or more genomic regions selected from Table 8. The selector set may comprise 1, 2, 3, 4, 5, 6, 7, 8, 9, 10, 15, 20, 25, 30, 40, 50, 60, 70, 80, 90, 100 or more genomic regions selected from Table 9. The selector set may comprise 1, 2, 3, 4, 5, 6, 7, 8, 9, 10, 15, 20, 25, 30, 40, 50, 60, 70, 80, 90, 100 or more genomic regions selected from Table 10. The selector set may comprise 1, 2, 3, 4, 5, 6, 7, 8, 9, 10, 15, 20, 25, 30, 40, 50, 60, 70, 80, 90, 100 or more genomic regions selected from Table 11. The selector set may comprise 1, 2, 3, 4, 5, 6, 7, 8, 9, 10, 15, 20, 25, 30, 40, 50, 60, 70, 80, 90, 100 or more genomic regions selected from Table 12. The selector set may comprise 1, 2, 3, 4, 5, 6, 7, 8, 9, 10, 15, 20, 25, 30, 40, 50, 60, 70, 80, 90, 100 or more genomic regions selected from Table 13. The selector set may comprise 1, 2, 3, 4, 5, 6, 7, 8, 9, 10, 15, 20, 25, 30, 40, 50, 60, 70, 80, 90, 100 or more genomic regions selected from Table 14. The selector set may comprise 1, 2, 3, 4, 5, 6, 7, 8, 9, 10, 15, 20, 25, 30, 40, 50, 60, 70, 80, 90, 100 or more genomic regions selected from Table 15. The selector set may comprise 1, 2, 3, 4, 5, 6, 7, 8, 9, 10, 15, 20, 25, 30, 40, 50, 60, 70, 80, 90, 100 or more genomic regions selected from Table 16. The selector set may comprise 1, 2, 3, 4, 5, 6, 7, 8, 9, 10, 15, 20, 25, 30, 40, 50, 60, 70, 80, 90, 100 or more genomic regions selected from Table 17. The selector set may comprise 1, 2, 3, 4, 5, 6, 7, 8, 9, 10, 15, 20, 25, 30, 40, 50, 60, 70, 80, 90, 100 or more genomic regions selected from Table 18. In some instances, the subject is not suffering from a pancreatic cancer.

Obtaining sequence information of the cell-free DNA sample may comprise performing massively parallel sequencing. Massively parallel sequencing may be performed on a subset of a genome of cfDNA from the cfDNA sample. The subset of the genome may comprise less than 1.5 megabases (Mb), 1 Mb, 500 kilobases (kb), 350 kb, 300 kb, 250 kb, 200 kb, or 150 kb of the genome. The subset of the genome may comprise between 100 kb to 300 kb of the genome.

Obtaining sequence information of the cell-free DNA sample may comprise using single molecule barcoding. Using single molecule barcoding may comprise attaching barcodes comprising different sequences to nucleic acids from the cfDNA sample.

The sequence information may comprise sequence information pertaining to the adaptors. The sequence information may comprise sequence information pertaining to the molecular barcodes. The sequence information may comprise sequence information pertaining to the sample indexes.

The method may comprise obtaining sequencing information of cell-free DNA samples from two or more samples from the subject. The method may comprise obtaining sequencing information of cell-free DNA samples from two or more different subjects. The two or more samples may be the same type of sample. The two or more samples may be two different types of sample. The two or more samples may be obtained from the subject at the same time point. The two or more samples may be obtained from the subject at two or more time points. The samples from two or more different subjects may be indexed and pooled together prior to sequencing.

Using the sequence information may comprise detecting one or more mutations. The one or more mutations may comprise one or more SNVs, indels, fusions, breakpoints, structural variants, variable number of tandem repeats, hypervariable regions, minisatellites, dinucleotide repeats, trinucleotide repeats, tetranucleotide repeats, simple sequence repeats, copy number variants or a combination thereof in selected regions of the subject's genome. Using the sequence information may comprise detecting one or more of SNVs, indels, copy number variants, and rearrangements in selected regions of the subject's genome. Using the sequence information may comprise detecting two or more of SNVs, indels, copy number variants, and rearrangements in selected regions of the subject's genome. Using the sequence information may comprise detecting at least one SNV, indel, copy number variant, and rearrangement in selected regions of the subject's genome.

In some instances, detecting the one or more mutations does not involve performing digital PCR (dPCR).

Detecting the one or more mutations may comprise applying an algorithm to the sequence information to determine a quantity of one or more genomic regions from a selector set. The selector set may comprise a plurality of genomic regions comprising one or more mutations present in one or more cancer subjects from a population of cancer subjects.

The selector set may comprise a plurality of genomic regions comprising one or more mutations present in at least about 60% of cancer subjects from population of cancer subjects.

The cfNG-DNA may be derived from a tumor in the subject. The method may further comprise detecting a cancer in the subject based on the detection of the cfNG-DNA. The method may further comprise diagnosing a cancer in the subject based on the detection of the cfNG-DNA. Diagnosing the cancer may have a sensitivity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. Diagnosing the cancer may have a specificity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. The method may further comprise prognosing a cancer in the subject based on the detection of the cfNG-DNA. Prognosing the cancer may have a sensitivity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. Prognosing the cancer may have a specificity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. The method may further comprise determining a therapeutic regimen for the subject based on the detection of the cfNG-DNA. The method may further comprise administering an anti-cancer therapy to the subject based on the detection of the cfNG-DNA.

The cfNG-DNA may be derived from a fetus in the subject. The method may further comprise diagnosing a disease or condition in the fetus based on the detection of the cfNG-DNA. Diagnosing the disease or condition in the fetus may have a sensitivity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. Diagnosing the disease or condition in the fetus may have a specificity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%.

The cfNG-DNA may be derived from a transplanted organ, cell or tissue in the subject. The method may further comprise diagnosing an organ transplant rejection in the subject based on the detection of the cfNG-DNA. Diagnosing the organ transplant rejection may have a sensitivity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. Diagnosing the organ transplant rejection may have a specificity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. The method may further comprise prognosing a risk of organ transplant rejection in the subject based on the detection of the cfNG-DNA. Prognosing the risk of organ transplant rejection may have a sensitivity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. Prognosing the risk of organ transplant rejection may have a specificity of at least about 50%, 52%, 55%, 57%, 60%, 62%, 65%, 67%, 70%, 72%, 75%, 77%, 80%, 82%, 85%, 87%, 89%, 90%, 91%, 92%, 93%, 94%, 95%, 96%, 97%, or 99%. The method may further comprise determining an immunosuppresive therapy for the subject based on the detection of the cfNG-DNA. The method may further comprise administering an immunosuppresive therapy to the subject based on the detection of the cfNG-DNA.

Further disclosed herein are methods of diagnosing a cancer. The method may comprise (a) obtaining sequence information of cell-free genomic DNA derived from a sample from a subject, wherein the sequence information may be derived from regions that are mutated in at least 80% of a population of subjects afflicted with a cancer; and (b) diagnosing a cancer selected from a group consisting of lung cancer, breast cancer, colorectal cancer and prostate cancer in the subject based on the sequence information, wherein the method has a sensitivity of at least 80%.

The regions that are mutated may comprise a total size of less than 1.5 Mb of the genome. The regions that are mutated may comprise a total size of less than 1 Mb of the genome. The regions that are mutated may comprise a total size of less than 500 kb of the genome. The regions that are mutated may comprise a total size of less than 350 kb of the genome. The regions that are mutated may comprise a total size of less than 300 kb of the genome. The regions that are mutated may comprise a total size of less than 250 kb of the genome. The regions that are mutated may comprise a total size of less than 200 kb of the genome. The regions that are mutated may comprise a total size of less than 150 kb of the genome. The regions that are mutated may comprise a total size of less than 100 kb of the genome. The regions that are mutated may comprise a total size of less than 50 kb of the genome. The regions that are mutated may comprise a total size of less than 40 kb of the genome. The regions that are mutated may comprise a total size of less than 30 kb of the genome. The regions that are mutated may comprise a total size of less than 20 kb of the genome. The regions that are mutated may comprise a total size of less than 10 kb of the genome.

The regions that are mutated may comprise a total size between 100 kb-300 kb of the genome. The regions that are mutated may comprise a total size between 5 kb-200 kb of the genome. The regions that are mutated may comprise a total size between 5 kb-150 kb of the genome. The regions that are mutated may comprise a total size between 5 kb-100 kb of the genome. The regions that are mutated may comprise a total size between 5 kb-75 kb of the genome. The regions that are mutated may comprise a total size between 1 kb-50 kb of the genome.

The sequence information may be derived from 2 or more regions. The sequence information may be derived from 3 or more regions. The sequence information may be derived from 4 or more regions. The sequence information may be derived from 5 or more regions. The sequence information may be derived from 6 or more regions. The sequence information may be derived from 7 or more regions. The sequence information may be derived from 8 or more regions. The sequence information may be derived from 9 or more regions. The sequence information may be derived from 10 or more regions. The sequence information may be derived from 20 or more regions. The sequence information may be derived from 30 or more regions. The sequence information may be derived from 40 or more regions. The sequence information may be derived from 50 or more regions. The sequence information may be derived from 60 or more regions. The sequence information may be derived from 70 or more regions. The sequence information may be derived from 80 or more regions. The sequence information may be derived from 90 or more regions. The sequence information may be derived from 100 or more regions.

The population of subjects afflicted with the cancer may be subjects from one or more databases. The one or more databases may comprise The Cancer Genome Atlas (TCGA).

The sequence information may comprise information pertaining to at least one mutation that may be present in at least about 60% of the population of subjects afflicted with the cancer. The sequence information may comprise information pertaining to at least one mutation that may be present in at least about 70% of the population of subjects afflicted with the cancer. The sequence information may comprise information pertaining to at least one mutation that may be present in at least about 80% of the population of subjects afflicted with the cancer. The sequence information may comprise information pertaining to at least one mutation that may be present in at least about 90% of the population of subjects afflicted with the cancer. The sequence information may comprise information pertaining to at least one mutation that may be present in at least about 95% of the population of subjects afflicted with the cancer. The sequence information may comprise information pertaining to at least one mutation that may be present in at least about 99% of the population of subjects afflicted with the cancer.

The sequence information may be derived from regions that may be mutated in at least 65% of the population of subjects afflicted with the cancer. The sequence information may be derived from regions that may be mutated in at least 70% of the population of subjects afflicted with the cancer. The sequence information may be derived from regions that may be mutated in at least 75% of the population of subjects afflicted with the cancer. The sequence information may be derived from regions that may be mutated in at least 80% of the population of subjects afflicted with the cancer. The sequence information may be derived from regions that may be mutated in at least 85% of the population of subjects afflicted with the cancer. The sequence information may be derived from regions that may be mutated in at least 90% of the population of subjects afflicted with the cancer. The sequence information may be derived from regions that may be mutated in at least 95% of the population of subjects afflicted with the cancer. The sequence information may be derived from regions that may be mutated in at least 99% of the population of subjects afflicted with the cancer.

Obtaining the sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof.

Alternatively, or additionally, obtaining the sequence information may comprise sequencing protein coding regions. The protein coding regions may comprise one or more exons, introns, untranslated regions, or a combination thereof.

In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1.

The method may further comprise detecting mutations in the regions based on the sequencing information. Diagnosing the cancer may be based on the detection of the mutations. The detection of at least 3 mutations may be indicative of the cancer. The detection of one or more mutations in three or more regions may be indicative of the cancer.

The breast cancer may be a BRCA1 cancer.

The method may have a sensitivity of at least 85%, 87%, 90%, 91%, 92%, 93%, 94%, 95%, 96%, 97%, 98%, or 99%.

The method may have a specificity of at least 50%, 52%, 55%, 57%, 60%, 62%, 65%, 67%, 70%, 72%, 75%, 77%, 80%, 82%, 85%, 87%, 90%, 91%, 92%, 93%, 94%, 95%, 96%, 97%, 98%, or 99%.

The method may further comprise providing a computer-generated report comprising the diagnosis of the cancer.

Further disclosed herein are methods of determining a prognosis of a condition or disease in a subject in need thereof. The method may comprise (a) obtaining sequence information of cell-free genomic DNA derived from a sample from a subject, wherein the sequence information may be derived from regions that are mutated in at least 80% of a population of subjects afflicted with a condition; and (b) determining a prognosis of a condition or disease in the subject based on the sequence information.

The regions that are mutated may comprise a total size of less than 1.5 Mb of the genome. The regions that are mutated may comprise a total size of less than 1 Mb of the genome. The regions that are mutated may comprise a total size of less than 500 kb of the genome. The regions that are mutated may comprise a total size of less than 350 kb of the genome. The regions that are mutated may comprise a total size of less than 300 kb of the genome. The regions that are mutated may comprise a total size of less than 250 kb of the genome. The regions that are mutated may comprise a total size of less than 200 kb of the genome. The regions that are mutated may comprise a total size of less than 150 kb of the genome. The regions that are mutated may comprise a total size of less than 100 kb of the genome. The regions that are mutated may comprise a total size of less than 50 kb of the genome. The regions that are mutated may comprise a total size of less than 40 kb of the genome. The regions that are mutated may comprise a total size of less than 30 kb of the genome. The regions that are mutated may comprise a total size of less than 20 kb of the genome. The regions that are mutated may comprise a total size of less than 10 kb of the genome.

The regions that are mutated may comprise a total size between 100 kb-300 kb of the genome. The regions that are mutated may comprise a total size between 5 kb-200 kb of the genome. The regions that are mutated may comprise a total size between 5 kb-150 kb of the genome. The regions that are mutated may comprise a total size between 5 kb-100 kb of the genome. The regions that are mutated may comprise a total size between 5 kb-75 kb of the genome. The regions that are mutated may comprise a total size between 1 kb-50 kb of the genome.

The sequence information may be derived from 2 or more regions. The sequence information may be derived from 3 or more regions. The sequence information may be derived from 4 or more regions. The sequence information may be derived from 5 or more regions. The sequence information may be derived from 6 or more regions. The sequence information may be derived from 7 or more regions. The sequence information may be derived from 8 or more regions. The sequence information may be derived from 9 or more regions. The sequence information may be derived from 10 or more regions. The sequence information may be derived from 20 or more regions. The sequence information may be derived from 30 or more regions. The sequence information may be derived from 40 or more regions. The sequence information may be derived from 50 or more regions. The sequence information may be derived from 60 or more regions. The sequence information may be derived from 70 or more regions. The sequence information may be derived from 80 or more regions. The sequence information may be derived from 90 or more regions. The sequence information may be derived from 100 or more regions.

The population of subjects afflicted with the cancer may be subjects from one or more databases. The one or more databases may comprise The Cancer Genome Atlas (TCGA).

The sequence information may be derived from regions that may be mutated in at least 65% of the population of subjects afflicted with the cancer. The sequence information may be derived from regions that may be mutated in at least 70% of the population of subjects afflicted with the cancer. The sequence information may be derived from regions that may be mutated in at least 75% of the population of subjects afflicted with the cancer. The sequence information may be derived from regions that may be mutated in at least 80% of the population of subjects afflicted with the cancer. The sequence information may be derived from regions that may be mutated in at least 85% of the population of subjects afflicted with the cancer. The sequence information may be derived from regions that may be mutated in at least 90% of the population of subjects afflicted with the cancer. The sequence information may be derived from regions that may be mutated in at least 95% of the population of subjects afflicted with the cancer. The sequence information may be derived from regions that may be mutated in at least 99% of the population of subjects afflicted with the cancer.

Obtaining the sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof.

Alternatively, or additionally, obtaining the sequence information may comprise sequencing protein coding regions. The protein coding regions may comprise one or more exons, introns, untranslated regions, or a combination thereof.

In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1.

The method may further comprise detecting mutations in the regions based on the sequencing information. Prognosing the condition or disease may be based on the detection of the mutations. The detection of at least 3 mutations may be indicative of an outcome of the condition or disease. The detection of one or more mutations in three or more regions may be indicative of an outcome of the condition or disease.

The condition may be a cancer. The cancer may be a solid tumor. The solid tumor may be non-small cell lung cancer (NSCLC). The cancer may be a breast cancer. The breast cancer may be a BRCA1 cancer. The cancer may be a lung cancer, colorectal cancer, prostate cancer, ovarian cancer, esophageal cancer, breast cancer, lymphoma, or leukemia.

The method may have a sensitivity of at least 50%, 52%, 55%, 57%, 60%, 62%, 65%, 67%, 70%, 72%, 75%, 77%, 80%, 82%, 85%, 87%, 90%, 91%, 92%, 93%, 94%, 95%, 96%, 97%, 98%, or 99%.

The method may have a specificity of at least 50%, 52%, 55%, 57%, 60%, 62%, 65%, 67%, 70%, 72%, 75%, 77%, 80%, 82%, 85%, 87%, 90%, 91%, 92%, 93%, 94%, 95%, 96%, 97%, 98%, or 99%.

The method may further comprise providing a computer-generated report comprising the prognosis of the condition.

Further disclosed herein are methods of diagnosing, prognosing, or determining a therapeutic regimen for a subject afflicted with or susceptible of having a cancer. The method may comprise (a) obtaining sequence information for selected regions of genomic DNA from a cell-free DNA sample from the subject; (b) using the sequence information to determine the presence or absence of one or more mutations in the selected regions, wherein at least 70% of a population of subjects afflicted with the cancer have mutation(s) in the regions; and (c) providing a report with a diagnosis, prognosis or treatment regimen to the subject, based on the presence or absence of the one or more mutations.

The selected regions may comprise a total size of less than 1.5 Mb of the genome. The selected regions may comprise a total size of less than 1 Mb of the genome. The selected regions may comprise a total size of less than 500 kb of the genome. The selected regions may comprise a total size of less than 350 kb of the genome. The selected regions may comprise a total size of less than 300 kb of the genome. The selected regions may comprise a total size of less than 250 kb of the genome. The selected regions may comprise a total size of less than 200 kb of the genome. The selected regions may comprise a total size of less than 150 kb of the genome. The selected regions may comprise a total size of less than 100 kb of the genome. The selected regions may comprise a total size of less than 50 kb of the genome. The selected regions may comprise a total size of less than 40 kb of the genome. The selected regions may comprise a total size of less than 30 kb of the genome. The selected regions may comprise a total size of less than 20 kb of the genome. The selected regions may comprise a total size of less than 10 kb of the genome.

The selected regions may comprise a total size between 100 kb-300 kb of the genome. The selected regions may comprise a total size between 5 kb-200 kb of the genome. The selected regions may comprise a total size between 5 kb-150 kb of the genome. The selected regions may comprise a total size between 5 kb-100 kb of the genome. The selected regions may comprise a total size between 5 kb-75 kb of the genome. The selected regions may comprise a total size between 1 kb-50 kb of the genome.

The sequence information may be derived from 2 or more regions. The sequence information may be derived from 3 or more regions. The sequence information may be derived from 4 or more regions. The sequence information may be derived from 5 or more regions. The sequence information may be derived from 6 or more regions. The sequence information may be derived from 7 or more regions. The sequence information may be derived from 8 or more regions. The sequence information may be derived from 9 or more regions. The sequence information may be derived from 10 or more regions. The sequence information may be derived from 20 or more regions. The sequence information may be derived from 30 or more regions. The sequence information may be derived from 40 or more regions. The sequence information may be derived from 50 or more regions. The sequence information may be derived from 60 or more regions. The sequence information may be derived from 70 or more regions. The sequence information may be derived from 80 or more regions. The sequence information may be derived from 90 or more regions. The sequence information may be derived from 100 or more regions.

The population of subjects afflicted with the cancer may be subjects from one or more databases. The one or more databases may comprise The Cancer Genome Atlas (TCGA).

The sequence information may be derived from regions that may be mutated in at least 65% of the population of subjects afflicted with the cancer. The sequence information may be derived from regions that may be mutated in at least 70% of the population of subjects afflicted with the cancer. The sequence information may be derived from regions that may be mutated in at least 75% of the population of subjects afflicted with the cancer. The sequence information may be derived from regions that may be mutated in at least 80% of the population of subjects afflicted with the cancer. The sequence information may be derived from regions that may be mutated in at least 85% of the population of subjects afflicted with the cancer. The sequence information may be derived from regions that may be mutated in at least 90% of the population of subjects afflicted with the cancer. The sequence information may be derived from regions that may be mutated in at least 95% of the population of subjects afflicted with the cancer. The sequence information may be derived from regions that may be mutated in at least 99% of the population of subjects afflicted with the cancer.

Obtaining the sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof.

Alternatively, or additionally, obtaining the sequence information may comprise sequencing protein coding regions. The protein coding regions may comprise one or more exons, introns, untranslated regions, or a combination thereof.

In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1.

Detection of at least 3 mutations may be indicative of an outcome of the cancer. Detection of at least 4 mutations may be indicative of an outcome of the cancer. Detection of at least 5 mutations may be indicative of an outcome of the cancer. Detection of at least 6 mutations may be indicative of an outcome of the cancer.

Detection of one or more mutations in three or more regions may be indicative of an outcome of the cancer. Detection of one or more mutations in four or more regions may be indicative of an outcome of the cancer. Detection of one or more mutations in five or more regions may be indicative of an outcome of the cancer. Detection of one or more mutations in six or more regions may be indicative of an outcome of the cancer.

The cancer may be non-small cell lung cancer (NSCLC). The cancer may be a breast cancer. The breast cancer may be a BRCA1 cancer. The cancer may be a lung cancer, colorectal cancer, prostate cancer, ovarian cancer, esophageal cancer, breast cancer, lymphoma, or leukemia.

The method of diagnosing or prognosing the cancer may have a sensitivity of at least 50%, 52%, 55%, 57%, 60%, 62%, 65%, 67%, 70%, 72%, 75%, 77%, 80%, 82%, 85%, 87%, 90%, 91%, 92%, 93%, 94%, 95%, 96%, 97%, 98%, or 99%. The method of diagnosing or prognosing the cancer may have a specificity of at least 50%, 52%, 55%, 57%, 60%, 62%, 65%, 67%, 70%, 72%, 75%, 77%, 80%, 82%, 85%, 87%, 90%, 91%, 92%, 93%, 94%, 95%, 96%, 97%, 98%, or 99%.

The may further comprise administering a therapeutic drug to the subject. The may further comprise modifying a therapeutic regimen. Modifying the therapeutic regimen may comprise terminating the therapeutic regimen. Modifying the therapeutic regimen may comprise increasing a dosage or frequency of the therapeutic regimen. Modifying the therapeutic regimen may comprise decreasing a dosage or frequency of the therapeutic regimen. Modifying the therapeutic regimen may comprise starting the therapeutic regimen.

Further disclosed herein are methods of determining a therapeutic region for the treatment of a condition in a subject in need thereof. The method may comprise (a) obtaining sequence information of cell-free genomic DNA derived from a sample from a subject, wherein the sequence information may be derived from regions that are mutated in at least 80% of a population of subjects afflicted with a condition; and (b) determining a therapeutic regimen for a condition in the subject based on the sequence information.

The regions that are mutated may comprise a total size of less than 1.5 Mb of the genome. The regions that are mutated may comprise a total size of less than 1 Mb of the genome. The regions that are mutated may comprise a total size of less than 500 kb of the genome. The regions that are mutated may comprise a total size of less than 350 kb of the genome. The regions that are mutated may comprise a total size of less than 300 kb of the genome. The regions that are mutated may comprise a total size of less than 250 kb of the genome. The regions that are mutated may comprise a total size of less than 200 kb of the genome. The regions that are mutated may comprise a total size of less than 150 kb of the genome. The regions that are mutated may comprise a total size of less than 100 kb of the genome. The regions that are mutated may comprise a total size of less than 50 kb of the genome. The regions that are mutated may comprise a total size of less than 40 kb of the genome. The regions that are mutated may comprise a total size of less than 30 kb of the genome. The regions that are mutated may comprise a total size of less than 20 kb of the genome. The regions that are mutated may comprise a total size of less than 10 kb of the genome.

The regions that are mutated may comprise a total size between 100 kb-300 kb of the genome. The regions that are mutated may comprise a total size between 5 kb-200 kb of the genome. The regions that are mutated may comprise a total size between 5 kb-150 kb of the genome. The regions that are mutated may comprise a total size between 5 kb-100 kb of the genome. The regions that are mutated may comprise a total size between 5 kb-75 kb of the genome. The regions that are mutated may comprise a total size between 1 kb-50 kb of the genome.

The sequence information may be derived from 2 or more regions. The sequence information may be derived from 3 or more regions. The sequence information may be derived from 4 or more regions. The sequence information may be derived from 5 or more regions. The sequence information may be derived from 6 or more regions. The sequence information may be derived from 7 or more regions. The sequence information may be derived from 8 or more regions. The sequence information may be derived from 9 or more regions. The sequence information may be derived from 10 or more regions. The sequence information may be derived from 20 or more regions. The sequence information may be derived from 30 or more regions. The sequence information may be derived from 40 or more regions. The sequence information may be derived from 50 or more regions. The sequence information may be derived from 60 or more regions. The sequence information may be derived from 70 or more regions. The sequence information may be derived from 80 or more regions. The sequence information may be derived from 90 or more regions. The sequence information may be derived from 100 or more regions.

The population of subjects afflicted with the cancer may be subjects from one or more databases. The one or more databases may comprise The Cancer Genome Atlas (TCGA).

The sequence information may comprise information pertaining to at least one mutation that may be present in at least about 60% of the population of subjects afflicted with the cancer. The sequence information may comprise information pertaining to at least one mutation that may be present in at least about 70% of the population of subjects afflicted with the cancer. The sequence information may comprise information pertaining to at least one mutation that may be present in at least about 80% of the population of subjects afflicted with the cancer. The sequence information may comprise information pertaining to at least one mutation that may be present in at least about 90% of the population of subjects afflicted with the cancer. The sequence information may comprise information pertaining to at least one mutation that may be present in at least about 95% of the population of subjects afflicted with the cancer. The sequence information may comprise information pertaining to at least one mutation that may be present in at least about 99% of the population of subjects afflicted with the cancer.

The sequence information may be derived from regions that may be mutated in at least 65% of the population of subjects afflicted with the cancer. The sequence information may be derived from regions that may be mutated in at least 70% of the population of subjects afflicted with the cancer. The sequence information may be derived from regions that may be mutated in at least 75% of the population of subjects afflicted with the cancer. The sequence information may be derived from regions that may be mutated in at least 80% of the population of subjects afflicted with the cancer. The sequence information may be derived from regions that may be mutated in at least 85% of the population of subjects afflicted with the cancer. The sequence information may be derived from regions that may be mutated in at least 90% of the population of subjects afflicted with the cancer. The sequence information may be derived from regions that may be mutated in at least 95% of the population of subjects afflicted with the cancer. The sequence information may be derived from regions that may be mutated in at least 99% of the population of subjects afflicted with the cancer.

Obtaining the sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof.

Alternatively, or additionally, obtaining the sequence information may comprise sequencing protein coding regions. The protein coding regions may comprise one or more exons, introns, untranslated regions, or a combination thereof.

In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1.

The method may further comprise detecting mutations in the regions based on the sequencing information. Determining the therapeutic regimen may be based on the detection of the mutations.

The condition may be a cancer. The cancer may be a solid tumor. The solid tumor may be non-small cell lung cancer (NSCLC). The cancer may be a breast cancer. The breast cancer may be a BRCA1 cancer. The cancer may be a lung cancer, colorectal cancer, prostate cancer, ovarian cancer, esophageal cancer, breast cancer, lymphoma, or leukemia.

Further disclosed herein are methods of assessing tumor burden in a subject in need thereof. The method may comprise (a) obtaining sequence information on cell-free nucleic acids derived from a sample from the subject; (b) using a computer readable medium to determine quantities of circulating tumor DNA (ctDNA) in the sample; (c) assessing tumor burden based on the quantities of ctDNA; and (d) reporting the tumor burden to the subject or a representative of the subject.

Determining quantities of ctDNA may comprise determining absolute quantities of ctDNA. Determining quantities of ctDNA may comprise determining relative quantities of ctDNA. Determining quantities of ctDNA may be performed by counting sequence reads pertaining to the ctDNA. Determining quantities of ctDNA may be performed by quantitative PCR. Determining quantities of ctDNA may be performed by digital PCR. Determining quantities of ctDNA may comprise counting sequencing reads of the ctDNA.

Determining quantities of ctDNA may be performed by molecular barcoding of the ctDNA. Molecular barcoding of the ctDNA may comprise attaching adaptors to one or more ends of the ctDNA. The adaptor may comprise a plurality of oligonucleotides. The adaptor may comprise one or more deoxyribonucleotides. The adaptor may comprise ribonucleotides. The adaptor may be single-stranded. The adaptor may be double-stranded. The adaptor may comprise double-stranded and single-stranded portions. For example, the adaptor may be a Y-shaped adaptor. The adaptor may be a linear adaptor. The adaptor may be a circular adaptor. The adaptor may comprise a molecular barcode, sample index, primer sequence, linker sequence or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

The adaptor may comprise a molecular barcode. The molecular barcode may comprise a random sequence. The molecular barcode may comprise a predetermined sequence. Two or more adaptors may comprise two or more different molecular barcodes. The molecular barcodes may be optimized to minimize dimerization. The molecular barcodes may be optimized to enable identification even with amplification or sequencing errors. For examples, amplification of a first molecular barcode may introduce a single base error. The first molecular barcode may comprise greater than a single base difference from the other molecular barcodes. Thus, the first molecular barcode with the single base error may still be identified as the first molecular barcode. The molecular barcode may comprise at least 2, 3, 4, 5, 6, 7, 8, 9, 10 or more nucleotides. The molecular barcode may comprise at least 3 nucleotides. The molecular barcode may comprise at least 4 nucleotides. The molecular barcode may comprise less than 20, 19, 18, 17, 16, or 15 nucleotides. The molecular barcode may comprise less than 10 nucleotides. The molecular barcode may comprise less than 8 nucleotides. The molecular barcode may comprise less than 6 nucleotides. The molecular barcode may comprise 2 to 15 nucleotides. The molecular barcode may comprise 2 to 12 nucleotides. The molecular barcode may comprise 3 to 10 nucleotides. The molecular barcode may comprise 3 to 8 nucleotides. The molecular barcode may comprise 4 to 8 nucleotides. The molecular barcode may comprise 4 to 6 nucleotides.

The adaptor may comprise a sample index. The sample index may comprise a random sequence. The sample index may comprise a predetermined sequence. Two or more sets of adaptors may comprise two or more different sample indexes. Adaptors within a set of adaptors may comprise identical sample indexes. The sample indexes may be optimized to minimize dimerization. The sample indexes may be optimized to enable identification even with amplification or sequencing errors. For examples, amplification of a first sample index may introduce a single base error. The first sample index may comprise greater than a single base difference from the other sample indexes. Thus, the first sample index with the single base error may still be identified as the first molecular barcode. The sample index may comprise at least 2, 3, 4, 5, 6, 7, 8, 9, 10 or more nucleotides. The sample index may comprise at least 3 nucleotides. The sample index may comprise at least 4 nucleotides. The sample index may comprise less than 20, 19, 18, 17, 16, or 15 nucleotides. The sample index may comprise less than 10 nucleotides. The sample index may comprise less than 8 nucleotides. The sample index may comprise less than 6 nucleotides. The sample index may comprise 2 to 15 nucleotides. The sample index may comprise 2 to 12 nucleotides. The sample index may comprise 3 to 10 nucleotides. The sample index may comprise 3 to 8 nucleotides. The sample index may comprise 4 to 8 nucleotides. The sample index may comprise 4 to 6 nucleotides.

The adaptor may comprise a primer sequence. The primer sequence may be a PCR primer sequence. The primer sequence may be a sequencing primer.

Adaptors may be attached to one end of a nucleic acid from a sample. The nucleic acids may be DNA. The DNA may be cell-free DNA (cfDNA). The DNA may be circulating tumor DNA (ctDNA). The nucleic acids may be RNA. Adaptors may be attached to both ends of the nucleic acid. Adaptors may be attached to one or more ends of a single-stranded nucleic acid. Adaptors may be attached to one or more ends of a double-stranded nucleic acid.

Adaptors may be attached to the nucleic acid by ligation. Ligation may be blunt end ligation. Ligation may be sticky end ligation. Adaptors may be attached to the nucleic acid by primer extension. Adaptors may be attached to the nucleic acid by reverse transcription. Adaptors may be attached to the nucleic acids by hybridization. Adaptors may comprise a sequence that is at least partially complementary to the nucleic acid. Alternatively, in some instances, adaptors do not comprise a sequence that is complementary to the nucleic acid.

The sequence information may comprise information related to one or more genomic regions. The sequence information may comprise information related to at least 2, 3, 4, 5, 6, 7, 8, 9, 10, 20, 30, 40, 100, 200, 300 genomic regions. The genomic regions may comprise genes, exonic regions, intronic regions, untranslated regions, non-coding regions or a combination thereof.

The genomic regions may comprise two or more of exonic regions, intronic regions, and untranslated regions. The genomic regions may comprise at least one exonic region and at least one intronic region. At least 1%, 2%, 3%, 4%, 5%, 6%, 7%, 8%, 9%, 10%, 15%, 20%, or 25% of the genomic regions may comprise intronic regions. At least 1%, 2%, 3%, 4%, 5%, 6%, 7%, 8%, 9%, 10%, 15%, 20%, or 25% of the genomic regions may comprise untranslated regions. At least about 10%, 15%, 20%, 25%, 30%, 35%, 40%, 45%, 50%, 55%, 60%, 65%, 70%, 75%, 80%, 85%, 90%, or 95% of the genomic regions may comprise exonic regions. At least less than about 97%, 95%, 93%, 90%, 87%, 85%, 83%, 80%, 75%, 70%, 65%, 60%, 55%, 50% of the genomic regions may comprise exonic regions.

The genomic regions may comprise less than 1.5 megabases (Mb) of the genome. The genomic regions may comprise less than 1 Mb of the genome.

The genomic regions may comprise less than 500 kilobases (kb) of the genome.

The genomic regions may comprise less than 350 kb of the genome. The genomic regions may comprise less than 300 kb of the genome. The genomic regions may comprise less than 250 kb of the genome. The genomic regions may comprise less than 200 kb of the genome. The genomic regions may comprise less than 150 kb of the genome. The genomic regions may comprise less than 100 kb of the genome. The genomic regions may comprise less than 50 kb of the genome. The genomic regions may comprise less than 40 kb, 30 kb, 20 kb, or 10 kb of the genome.

The genomic regions may comprise between 100 kb to 300 kb of the genome. The genomic regions may comprise between 100 kb to 200 kb of the genome. The genomic regions may comprise between 10 kb to 300 kb of the genome. The genomic regions may comprise between 10 kb to 300 kb of the genome. The genomic regions may comprise between 10 kb to 200 kb of the genome. The genomic regions may comprise between 10 kb to 150 kb of the genome. The genomic regions may comprise between 10 kb to 100 kb of the genome. The genomic regions may comprise between 10 kb to 75 kb of the genome. The genomic regions may comprise between 5 kb to 70 kb of the genome. The genomic regions may comprise between 1 kb to 50 kb of the genome.

The sequence information may comprise information pertaining to 1, 2, 3, 4, 5, 6, 7, 8, 9, 10, 15, 20 or more genomic regions from a selector set comprising a plurality of genomic regions. The sequence information may comprise information pertaining to 25, 30, 40, 50, 60, 70, 80, 90, 100 or more genomic regions from a selector set comprising a plurality of genomic regions.

The sequence information may comprise information pertaining to a plurality of genomic regions.

The plurality of genomic regions may be based on a selector set comprising genomic regions comprising one or more mutations present in one or more subjects from a population of cancer subjects. At least about 5%, 10%, 15%, 20%, 25%, 30%, 35%, 40%, 45%, 50%, 55%, 60%, 65%, 70%, 75%, 80%, 85%, 90%, or 95% of the plurality of genomic regions may be based on a selector set comprising genomic regions comprising one or more mutations present in one or more subjects from a population of cancer subjects.

The total size of the genomic regions of the selector set may comprise less than 1.5 megabases (Mb), 1 Mb, 500 kilobases (kb), 350 kb, 300 kb, 250 kb, 200 kb, or 150 kb of the genome. The total size of the genomic regions of the selector set may be between 100 kb to 300 kb of the genome.

The selector set may comprise 1, 2, 3, 4, 5, 6, 7, 8, 9, 10, 15, 20, 25, 30, 40, 50, 60, 70, 80, 90, 100 or more genomic regions selected from Table 2.

Obtaining sequence information may comprise performing massively parallel sequencing. Massively parallel sequencing may be performed on a subset of a genome of the cell-free nucleic acids from the sample.

The subset of the genome may comprise less than 1.5 megabases (Mb), 1 Mb, 500 kilobases (kb), 350 kb, 300 kb, 250 kb, 200 kb, 150 kb, 100 kb, 75 kb, 50 kb, 40 kb, 30 kb, 20 kb, 10 kb, or 5 kb of the genome. The subset of the genome may comprise between 100 kb to 300 kb of the genome. The subset of the genome may comprise between 100 kb to 200 kb of the genome. The subset of the genome may comprise between 10 kb to 300 kb of the genome. The subset of the genome may comprise between 10 kb to 200 kb of the genome. The subset of the genome may comprise between 10 kb to 100 kb of the genome. The subset of the genome may comprise between 5 kb to 100 kb of the genome. The subset of the genome may comprise between 5 kb to 70 kb of the genome. The subset of the genome may comprise between 1 kb to 50 kb of the genome.

The method may comprise obtaining sequencing information of cell-free DNA samples from two or more samples from the subject. The method may comprise obtaining sequencing information of cell-free DNA samples from two or more samples from two or more subjects. The two or more samples may be the same type of sample. The two or more samples may be two different types of sample. The two or more samples may be obtained at the same time point. The two or more samples may be obtained at two or more time points.

Determining the quantities of ctDNA may comprise detecting one or more mutations. Determining the quantities of ctDNA may comprise detecting two or more different types of mutations. The types of mutations include, but are not limited to, SNVs, indels, fusions, breakpoints, structural variants, variable number of tandem repeats, hypervariable regions, minisatellites, dinucleotide repeats, trinucleotide repeats, tetranucleotide repeats, simple sequence repeats, or a combination thereof in selected regions of the subject's genome. Determining the quantities of ctDNA may comprise detecting one or more of SNVs, indels, copy number variants, and rearrangements in selected regions of the subject's genome. Determining the quantities of ctDNA may comprise detecting two or more of SNVs, indels, copy number variants, and rearrangements in selected regions of the subject's genome. Determining the quantities of ctDNA may comprise detecting at least one SNV, indel, copy number variant, and rearrangement in selected regions of the subject's genome.

In some instances, determining the quantities of ctDNA does comprise performing digital PCR (dPCR). Determining the quantities of ctDNA may comprise applying an algorithm to the sequence information to determine a quantity of one or more genomic regions from a selector set.

The selector set may comprise a plurality of genomic regions comprising one or more mutations present in one or more cancer subjects from a population of cancer subjects. The selector set may comprise a plurality of genomic regions comprise two or more different types of mutations present in one or more cancer subjects from a population of cancer subjects. The selector set may comprise a plurality of genomic regions comprising one or more mutations present in at least about 60% of cancer subjects from population of cancer subjects.

The representative of the subject may be a healthcare provider. The healthcare provider may be a nurse, physician, medical technician, or hospital personnel. The representative of the subject may be a family member of the subject. The representative of the subject may be a legal guardian of the subject.

Further disclosed herein are methods of determining a disease state of a cancer in a subject. The method may comprise (a) obtaining a quantity of circulating tumor DNA (ctDNA) in a sample from the subject; (b) obtaining a volume of a tumor in the subject; and (c) determining a disease state of a cancer in the subject based on a ratio of the quantity of ctDNA to the volume of the tumor. A high ctDNA to volume ratio may be indicative of radiographically occult disease. A low ctDNA to volume ratio may be indicative of non-malignant state.

The method may further comprise modifying a diagnosis or prognosis of the cancer based on the ratio of the quantity of the ctDNA to the volume of the tumor. The method may comprise diagnosing a stage of the cancer based on the ratio of the quantity of the ctDNA to the volume of the tumor. Modifying the diagnosis may comprise changing the stage of the cancer based on the ratio of the quantity of the ctDNA to the volume of the tumor. For example, a subject may be diagnosed with a stage III cancer. However, a low ratio of the quantity of the ctDNA to the volume of the tumor may result in adjusting the diagnosis of the cancer to a stage I or II cancer. Modifying a prognosis of the cancer may comprise changing the predicted outcome or status of the cancer. For example, a doctor may predict that a cancer in the subject is in remission based on the tumor volume. However, a high ratio of the quantity of the ctDNA to the volume of the tumor may result in a prediction that the cancer is recurrent.

Obtaining the volume of the tumor may comprise obtaining an image of the tumor. Obtaining the volume of the tumor may comprise obtaining a CT scan of the tumor.

Obtaining the quantity of ctDNA may comprise PCR. Obtaining the quantity of ctDNA may comprise digital PCR. Obtaining the quantity of ctDNA may comprise quantitative PCR.

Obtaining the quantity of ctDNA may comprise obtaining sequencing information on the ctDNA. The sequencing information may comprise information relating to one or more genomic regions based on a selector set.

Obtaining the quantity of ctDNA may comprise hybridization of the ctDNA to an array. The array may comprise a plurality of probes for selective hybridization of one or more genomic regions based on a selector set. The selector set may comprise one or more genomic regions from Table 2.

The selector set may comprise one or more genomic regions comprising one or more mutations, wherein the one or more mutations may be present in a population of subjects suffering from a cancer. The selector set may comprise a plurality of genomic regions comprising a plurality of mutations, wherein the plurality of mutations may be present in at least 60% of a population of subjects suffering from a cancer.

Further disclosed herein are methods of detecting stage I cancer in a subject in need thereof. The method may comprise (a) performing sequencing on cell-free DNA derived from a sample, wherein the cell-free DNA to be sequenced may be based on a selector set comprising a plurality of genomic regions; (b) using a computer readable medium to determine a quantity of the cell-free DNA; and (c) detecting a stage I cancer in the sample based on the quantity of the cell-free DNA.

Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR.

Determining quantities of cell-free DNA (cfDNA) may be performed by molecular barcoding of the cfDNA. Molecular barcoding of the cfDNA may comprise attaching adaptors to one or more ends of the cfDNA. The adaptor may comprise a plurality of oligonucleotides. The adaptor may comprise one or more deoxyribonucleotides. The adaptor may comprise ribonucleotides. The adaptor may be single-stranded. The adaptor may be double-stranded. The adaptor may comprise double-stranded and single-stranded portions. For example, the adaptor may be a Y-shaped adaptor. The adaptor may be a linear adaptor. The adaptor may be a circular adaptor. The adaptor may comprise a molecular barcode, sample index, primer sequence, linker sequence or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

The adaptor may comprise a molecular barcode. The molecular barcode may comprise a random sequence. The molecular barcode may comprise a predetermined sequence. Two or more adaptors may comprise two or more different molecular barcodes. The molecular barcodes may be optimized to minimize dimerization. The molecular barcodes may be optimized to enable identification even with amplification or sequencing errors. For examples, amplification of a first molecular barcode may introduce a single base error. The first molecular barcode may comprise greater than a single base difference from the other molecular barcodes. Thus, the first molecular barcode with the single base error may still be identified as the first molecular barcode. The molecular barcode may comprise at least 2, 3, 4, 5, 6, 7, 8, 9, 10 or more nucleotides. The molecular barcode may comprise at least 3 nucleotides. The molecular barcode may comprise at least 4 nucleotides. The molecular barcode may comprise less than 20, 19, 18, 17, 16, or 15 nucleotides. The molecular barcode may comprise less than 10 nucleotides. The molecular barcode may comprise less than 8 nucleotides. The molecular barcode may comprise less than 6 nucleotides. The molecular barcode may comprise 2 to 15 nucleotides. The molecular barcode may comprise 2 to 12 nucleotides. The molecular barcode may comprise 3 to 10 nucleotides. The molecular barcode may comprise 3 to 8 nucleotides. The molecular barcode may comprise 4 to 8 nucleotides. The molecular barcode may comprise 4 to 6 nucleotides.

The adaptor may comprise a sample index. The sample index may comprise a random sequence. The sample index may comprise a predetermined sequence. Two or more sets of adaptors may comprise two or more different sample indexes. Adaptors within a set of adaptors may comprise identical sample indexes. The sample indexes may be optimized to minimize dimerization. The sample indexes may be optimized to enable identification even with amplification or sequencing errors. For examples, amplification of a first sample index may introduce a single base error. The first sample index may comprise greater than a single base difference from the other sample indexes. Thus, the first sample index with the single base error may still be identified as the first molecular barcode. The sample index may comprise at least 2, 3, 4, 5, 6, 7, 8, 9, 10 or more nucleotides. The sample index may comprise at least 3 nucleotides. The sample index may comprise at least 4 nucleotides. The sample index may comprise less than 20, 19, 18, 17, 16, or 15 nucleotides. The sample index may comprise less than 10 nucleotides. The sample index may comprise less than 8 nucleotides. The sample index may comprise less than 6 nucleotides. The sample index may comprise 2 to 15 nucleotides. The sample index may comprise 2 to 12 nucleotides. The sample index may comprise 3 to 10 nucleotides. The sample index may comprise 3 to 8 nucleotides. The sample index may comprise 4 to 8 nucleotides. The sample index may comprise 4 to 6 nucleotides.

The adaptor may comprise a primer sequence. The primer sequence may be a PCR primer sequence. The primer sequence may be a sequencing primer.

Adaptors may be attached to one end of the cfDNA. Adaptors may be attached to both ends of the cfDNA. Adaptors may be attached to one or more ends of a single-stranded cfDNA. Adaptors may be attached to one or more ends of a double-stranded cfDNA.

Adaptors may be attached to the cfDNA by ligation. Ligation may be blunt end ligation. Ligation may be sticky end ligation. Adaptors may be attached to the cfDNA by primer extension. Adaptors may be attached to the cfDNA by reverse transcription. Adaptors may be attached to the cfDNA by hybridization. Adaptors may comprise a sequence that is at least partially complementary to the cfDNA. Alternatively, in some instances, adaptors do not comprise a sequence that is complementary to the cfDNA.

Sequencing may comprise massively parallel sequencing. Sequencing may comprise shotgun sequencing.

The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2.

At least 20%, 30%, 35%, 40%, 45%, 50%, 55%, 60%, 65%, 70%, 75%, 80%, 85%, 90%, or 95% or more of the genomic regions in the selector set may be based on genomic regions from Table 2.

The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer.

The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may comprise less than 100 kb, 90 kb, 80 kb, 70 kb, 60 kb, 50 kb, 40 kb, 30 kb, 20 kb, 10 kb, 5 kb, or 1 kb of a genome.

The total size of the plurality of genomic regions of the selector set may be between 100 kb to 300 kb of a genome. The total size of the plurality of genomic regions of the selector set may be between 100 kb to 200 kb of a genome. The total size of the plurality of genomic regions of the selector set may be between 10 kb to 300 kb of a genome. The total size of the plurality of genomic regions of the selector set may be between 10 kb to 200 kb of a genome. The total size of the plurality of genomic regions of the selector set may be between 10 kb to 100 kb of a genome. The total size of the plurality of genomic regions of the selector set may be between 5 kb to 100 kb of a genome. The total size of the plurality of genomic regions of the selector set may be between 5 kb to 75 kb of a genome. The total size of the plurality of genomic regions of the selector set may be between 5 kb to 50 kb of a genome.

The method of detecting the stage I cancer may have a sensitivity of at least 60%, 65%, 70%, 75%, 77%, 80%, 82%, 85%, 87%, 90%, 92%, 95%, 97%, or 99% or more. The method of detecting the stage I cancer may have a sensitivity of at least 60%. The method of detecting the stage I cancer may have a sensitivity of at least 70%. The method of detecting the stage I cancer may have a sensitivity of at least 80%. The method of detecting the stage I cancer may have a sensitivity of at least 90%. The method of detecting the stage I cancer may have a sensitivity of at least 95%.

The method of detecting the stage I cancer may have a specificity of at least 60%, 65%, 70%, 75%, 77%, 80%, 82%, 85%, 87%, 90%, 92%, 95%, 97%, or 99% or more. The method of detecting the stage I cancer may have a specificity of at least 60%. The method of detecting the stage I cancer may have a specificity of at least 70%. The method of detecting the stage I cancer may have a specificity of at least 80%. The method of detecting the stage I cancer may have a specificity of at least 90%. The method of detecting the stage I cancer may have a specificity of at least 95%.

The method may detect at least 50%, 52%, 55%, 57%, 60%, 62%, 65%, 70%, 72%, 75%, 77%, 80%, 82%, 85%, 87%, 90%, 92%, 95%, 97% or more of stage I cancer. The method may detect at least 50% or more of stage I cancer. The method may detect at least 60% or more of stage I cancer. The method may detect at least 70% or more of stage I cancer. The method may detect at least 75% or more of stage I cancer.

Further disclosed herein are methods of detecting stage II cancer. The method may comprise (a) performing sequencing on cell-free DNA derived from a sample, wherein the cell-free DNA to be sequenced may be based on a selector set comprising a plurality of genomic regions; (b) using a computer readable medium to determine a quantity of the cell-free DNA; and (c) detecting a stage II cancer in the sample based on the quantity of the cell-free DNA.

Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR.

Determining quantities of cell-free DNA (cfDNA) may be performed by molecular barcoding of the cfDNA. Molecular barcoding of the cfDNA may comprise attaching adaptors to one or more ends of the cfDNA. The adaptor may comprise a plurality of oligonucleotides. The adaptor may comprise one or more deoxyribonucleotides. The adaptor may comprise ribonucleotides. The adaptor may be single-stranded. The adaptor may be double-stranded. The adaptor may comprise double-stranded and single-stranded portions. For example, the adaptor may be a Y-shaped adaptor. The adaptor may be a linear adaptor. The adaptor may be a circular adaptor. The adaptor may comprise a molecular barcode, sample index, primer sequence, linker sequence or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

The adaptor may comprise a molecular barcode. The molecular barcode may comprise a random sequence. The molecular barcode may comprise a predetermined sequence. Two or more adaptors may comprise two or more different molecular barcodes. The molecular barcodes may be optimized to minimize dimerization. The molecular barcodes may be optimized to enable identification even with amplification or sequencing errors. For examples, amplification of a first molecular barcode may introduce a single base error. The first molecular barcode may comprise greater than a single base difference from the other molecular barcodes. Thus, the first molecular barcode with the single base error may still be identified as the first molecular barcode. The molecular barcode may comprise at least 2, 3, 4, 5, 6, 7, 8, 9, 10 or more nucleotides. The molecular barcode may comprise at least 3 nucleotides. The molecular barcode may comprise at least 4 nucleotides. The molecular barcode may comprise less than 20, 19, 18, 17, 16, or 15 nucleotides. The molecular barcode may comprise less than 10 nucleotides. The molecular barcode may comprise less than 8 nucleotides. The molecular barcode may comprise less than 6 nucleotides. The molecular barcode may comprise 2 to 15 nucleotides. The molecular barcode may comprise 2 to 12 nucleotides. The molecular barcode may comprise 3 to 10 nucleotides. The molecular barcode may comprise 3 to 8 nucleotides. The molecular barcode may comprise 4 to 8 nucleotides. The molecular barcode may comprise 4 to 6 nucleotides.

The adaptor may comprise a sample index. The sample index may comprise a random sequence. The sample index may comprise a predetermined sequence. Two or more sets of adaptors may comprise two or more different sample indexes. Adaptors within a set of adaptors may comprise identical sample indexes. The sample indexes may be optimized to minimize dimerization. The sample indexes may be optimized to enable identification even with amplification or sequencing errors. For examples, amplification of a first sample index may introduce a single base error. The first sample index may comprise greater than a single base difference from the other sample indexes. Thus, the first sample index with the single base error may still be identified as the first molecular barcode. The sample index may comprise at least 2, 3, 4, 5, 6, 7, 8, 9, 10 or more nucleotides. The sample index may comprise at least 3 nucleotides. The sample index may comprise at least 4 nucleotides. The sample index may comprise less than 20, 19, 18, 17, 16, or 15 nucleotides. The sample index may comprise less than 10 nucleotides. The sample index may comprise less than 8 nucleotides. The sample index may comprise less than 6 nucleotides. The sample index may comprise 2 to 15 nucleotides. The sample index may comprise 2 to 12 nucleotides. The sample index may comprise 3 to 10 nucleotides. The sample index may comprise 3 to 8 nucleotides. The sample index may comprise 4 to 8 nucleotides. The sample index may comprise 4 to 6 nucleotides.

The adaptor may comprise a primer sequence. The primer sequence may be a PCR primer sequence. The primer sequence may be a sequencing primer.

Adaptors may be attached to one end of the cfDNA. Adaptors may be attached to both ends of the cfDNA. Adaptors may be attached to one or more ends of a single-stranded cfDNA. Adaptors may be attached to one or more ends of a double-stranded cfDNA.

Adaptors may be attached to the cfDNA by ligation. Ligation may be blunt end ligation. Ligation may be sticky end ligation. Adaptors may be attached to the cfDNA by primer extension. Adaptors may be attached to the cfDNA by reverse transcription. Adaptors may be attached to the cfDNA by hybridization. Adaptors may comprise a sequence that is at least partially complementary to the cfDNA. Alternatively, in some instances, adaptors do not comprise a sequence that is complementary to the cfDNA.

Sequencing may comprise massively parallel sequencing. Sequencing may comprise shotgun sequencing.

The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2.

At least 20%, 30%, 35%, 40%, 45%, 50%, 55%, 60%, 65%, 70%, 75%, 80%, 85%, 90%, or 95% or more of the genomic regions in the selector set may be based on genomic regions from Table 2.

The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer.

The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may comprise less than 100 kb, 90 kb, 80 kb, 70 kb, 60 kb, 50 kb, 40 kb, 30 kb, 20 kb, 10 kb, 5 kb, or 1 kb of a genome.

The total size of the plurality of genomic regions of the selector set may be between 100 kb to 300 kb of a genome. The total size of the plurality of genomic regions of the selector set may be between 100 kb to 200 kb of a genome. The total size of the plurality of genomic regions of the selector set may be between 10 kb to 300 kb of a genome. The total size of the plurality of genomic regions of the selector set may be between 10 kb to 200 kb of a genome. The total size of the plurality of genomic regions of the selector set may be between 10 kb to 100 kb of a genome. The total size of the plurality of genomic regions of the selector set may be between 5 kb to 100 kb of a genome. The total size of the plurality of genomic regions of the selector set may be between 5 kb to 75 kb of a genome. The total size of the plurality of genomic regions of the selector set may be between 5 kb to 50 kb of a genome.

The method of detecting the stage II cancer may have a sensitivity of at least 60%, 65%, 70%, 75%, 77%, 80%, 82%, 85%, 87%, 90%, 92%, 95%, 97%, or 99% or more. The method of detecting the stage II cancer may have a sensitivity of at least 60%. The method of detecting the stage II cancer may have a sensitivity of at least 70%. The method of detecting the stage II cancer may have a sensitivity of at least 80%. The method of detecting the stage II cancer may have a sensitivity of at least 90%. The method of detecting the stage II cancer may have a sensitivity of at least 95%.

The method of detecting the stage II cancer may have a specificity of at least 60%, 65%, 70%, 75%, 77%, 80%, 82%, 85%, 87%, 90%, 92%, 95%, 97%, or 99% or more. The method of detecting the stage II cancer may have a specificity of at least 60%. The method of detecting the stage II cancer may have a specificity of at least 70%. The method of detecting the stage II cancer may have a specificity of at least 80%. The method of detecting the stage II cancer may have a specificity of at least 90%. The method of detecting the stage II cancer may have a specificity of at least 95%.

The method may detect at least 50%, 52%, 55%, 57%, 60%, 62%, 65%, 70%, 72%, 75%, 77%, 80%, 82%, 85%, 87%, 90%, 92%, 95%, 97% or more of stage II cancer. The method may detect at least 50% or more of stage II cancer. The method may detect at least 60% or more of stage II cancer. The method may detect at least 70% or more of stage II cancer. The method may detect at least 75% or more of stage II cancer. The method may detect at least 80% or more of stage II cancer. The method may detect at least 85% or more of stage II cancer. The method may detect at least 90% or more stage II cancer.

Further disclosed herein are methods of detecting stage III cancer in a subject in need thereof. The method may comprise (a) performing sequencing on cell-free DNA derived from a sample, wherein the cell-free DNA to be sequenced may be based on a selector set comprising a plurality of genomic regions; (b) using a computer readable medium to determine a quantity of the cell-free DNA; and (c) detecting a stage III cancer in the sample based on the quantity of the cell-free DNA.

Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR.

Determining quantities of cell-free DNA (cfDNA) may be performed by molecular barcoding of the cfDNA. Molecular barcoding of the cfDNA may comprise attaching adaptors to one or more ends of the cfDNA. The adaptor may comprise a plurality of oligonucleotides. The adaptor may comprise one or more deoxyribonucleotides. The adaptor may comprise ribonucleotides. The adaptor may be single-stranded. The adaptor may be double-stranded. The adaptor may comprise double-stranded and single-stranded portions. For example, the adaptor may be a Y-shaped adaptor. The adaptor may be a linear adaptor. The adaptor may be a circular adaptor. The adaptor may comprise a molecular barcode, sample index, primer sequence, linker sequence or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

The adaptor may comprise a molecular barcode. The molecular barcode may comprise a random sequence. The molecular barcode may comprise a predetermined sequence. Two or more adaptors may comprise two or more different molecular barcodes. The molecular barcodes may be optimized to minimize dimerization. The molecular barcodes may be optimized to enable identification even with amplification or sequencing errors. For examples, amplification of a first molecular barcode may introduce a single base error. The first molecular barcode may comprise greater than a single base difference from the other molecular barcodes. Thus, the first molecular barcode with the single base error may still be identified as the first molecular barcode. The molecular barcode may comprise at least 2, 3, 4, 5, 6, 7, 8, 9, 10 or more nucleotides. The molecular barcode may comprise at least 3 nucleotides. The molecular barcode may comprise at least 4 nucleotides. The molecular barcode may comprise less than 20, 19, 18, 17, 16, or 15 nucleotides. The molecular barcode may comprise less than 10 nucleotides. The molecular barcode may comprise less than 8 nucleotides. The molecular barcode may comprise less than 6 nucleotides. The molecular barcode may comprise 2 to 15 nucleotides. The molecular barcode may comprise 2 to 12 nucleotides. The molecular barcode may comprise 3 to 10 nucleotides. The molecular barcode may comprise 3 to 8 nucleotides. The molecular barcode may comprise 4 to 8 nucleotides. The molecular barcode may comprise 4 to 6 nucleotides.

The adaptor may comprise a sample index. The sample index may comprise a random sequence. The sample index may comprise a predetermined sequence. Two or more sets of adaptors may comprise two or more different sample indexes. Adaptors within a set of adaptors may comprise identical sample indexes. The sample indexes may be optimized to minimize dimerization. The sample indexes may be optimized to enable identification even with amplification or sequencing errors. For examples, amplification of a first sample index may introduce a single base error. The first sample index may comprise greater than a single base difference from the other sample indexes. Thus, the first sample index with the single base error may still be identified as the first molecular barcode. The sample index may comprise at least 2, 3, 4, 5, 6, 7, 8, 9, 10 or more nucleotides. The sample index may comprise at least 3 nucleotides. The sample index may comprise at least 4 nucleotides. The sample index may comprise less than 20, 19, 18, 17, 16, or 15 nucleotides. The sample index may comprise less than 10 nucleotides. The sample index may comprise less than 8 nucleotides. The sample index may comprise less than 6 nucleotides. The sample index may comprise 2 to 15 nucleotides. The sample index may comprise 2 to 12 nucleotides. The sample index may comprise 3 to 10 nucleotides. The sample index may comprise 3 to 8 nucleotides. The sample index may comprise 4 to 8 nucleotides. The sample index may comprise 4 to 6 nucleotides.

The adaptor may comprise a primer sequence. The primer sequence may be a PCR primer sequence. The primer sequence may be a sequencing primer.

Adaptors may be attached to one end of the cfDNA. Adaptors may be attached to both ends of the cfDNA. Adaptors may be attached to one or more ends of a single-stranded cfDNA. Adaptors may be attached to one or more ends of a double-stranded cfDNA.

Adaptors may be attached to the cfDNA by ligation. Ligation may be blunt end ligation. Ligation may be sticky end ligation. Adaptors may be attached to the cfDNA by primer extension. Adaptors may be attached to the cfDNA by reverse transcription. Adaptors may be attached to the cfDNA by hybridization. Adaptors may comprise a sequence that is at least partially complementary to the cfDNA. Alternatively, in some instances, adaptors do not comprise a sequence that is complementary to the cfDNA.

Sequencing may comprise massively parallel sequencing. Sequencing may comprise shotgun sequencing.

The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2.

At least 20%, 30%, 35%, 40%, 45%, 50%, 55%, 60%, 65%, 70%, 75%, 80%, 85%, 90%, or 95% or more of the genomic regions in the selector set may be based on genomic regions from Table 2.

The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer.

The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may comprise less than 100 kb, 90 kb, 80 kb, 70 kb, 60 kb, 50 kb, 40 kb, 30 kb, 20 kb, 10 kb, 5 kb, or 1 kb of a genome.

The total size of the plurality of genomic regions of the selector set may be between 100 kb to 300 kb of a genome. The total size of the plurality of genomic regions of the selector set may be between 100 kb to 200 kb of a genome. The total size of the plurality of genomic regions of the selector set may be between 10 kb to 300 kb of a genome. The total size of the plurality of genomic regions of the selector set may be between 10 kb to 200 kb of a genome. The total size of the plurality of genomic regions of the selector set may be between 10 kb to 100 kb of a genome. The total size of the plurality of genomic regions of the selector set may be between 5 kb to 100 kb of a genome. The total size of the plurality of genomic regions of the selector set may be between 5 kb to 75 kb of a genome. The total size of the plurality of genomic regions of the selector set may be between 5 kb to 50 kb of a genome.

The method of detecting the stage III cancer may have a sensitivity of at least 60%, 65%, 70%, 75%, 77%, 80%, 82%, 85%, 87%, 90%, 92%, 95%, 97%, or 99% or more. The method of detecting the stage III cancer may have a sensitivity of at least 60%. The method of detecting the stage III cancer may have a sensitivity of at least 70%. The method of detecting the stage III cancer may have a sensitivity of at least 80%. The method of detecting the stage III cancer may have a sensitivity of at least 90%. The method of detecting the stage III cancer may have a sensitivity of at least 95%.

The method of detecting the stage III cancer may have a specificity of at least 60%, 65%, 70%, 75%, 77%, 80%, 82%, 85%, 87%, 90%, 92%, 95%, 97%, or 99% or more. The method of detecting the stage III cancer may have a specificity of at least 60%. The method of detecting the stage III cancer may have a specificity of at least 70%. The method of detecting the stage III cancer may have a specificity of at least 80%. The method of detecting the stage III cancer may have a specificity of at least 90%. The method of detecting the stage III cancer may have a specificity of at least 95%.

The method may detect at least 50%, 52%, 55%, 57%, 60%, 62%, 65%, 70%, 72%, 75%, 77%, 80%, 82%, 85%, 87%, 90%, 92%, 95%, 97% or more of stage III cancer. The method may detect at least 50% or more of stage III cancer. The method may detect at least 60% or more of stage III cancer. The method may detect at least 70% or more of stage III cancer. The method may detect at least 75% or more of stage III cancer. The method may detect at least 80% or more of stage III cancer. The method may detect at least 85% or more of stage III cancer. The method may detect at least 90% or more of stage III cancer.

Further disclosed herein is a method of detecting stage IV cancer in a subject in need thereof. The method may comprise (a) performing sequencing on cell-free DNA derived from a sample, wherein the cell-free DNA to be sequenced may be based on a selector set comprising a plurality of genomic regions; (b) using a computer readable medium to determine a quantity of the cell-free DNA; and (c) detecting a stage IV cancer in the sample based on the quantity of the cell-free DNA.

Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR.

Determining quantities of cell-free DNA (cfDNA) may be performed by molecular barcoding of the cfDNA. Molecular barcoding of the cfDNA may comprise attaching adaptors to one or more ends of the cfDNA. The adaptor may comprise a plurality of oligonucleotides. The adaptor may comprise one or more deoxyribonucleotides. The adaptor may comprise ribonucleotides. The adaptor may be single-stranded. The adaptor may be double-stranded. The adaptor may comprise double-stranded and single-stranded portions. For example, the adaptor may be a Y-shaped adaptor. The adaptor may be a linear adaptor. The adaptor may be a circular adaptor. The adaptor may comprise a molecular barcode, sample index, primer sequence, linker sequence or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

The adaptor may comprise a molecular barcode. The molecular barcode may comprise a random sequence. The molecular barcode may comprise a predetermined sequence. Two or more adaptors may comprise two or more different molecular barcodes. The molecular barcodes may be optimized to minimize dimerization. The molecular barcodes may be optimized to enable identification even with amplification or sequencing errors. For examples, amplification of a first molecular barcode may introduce a single base error. The first molecular barcode may comprise greater than a single base difference from the other molecular barcodes. Thus, the first molecular barcode with the single base error may still be identified as the first molecular barcode. The molecular barcode may comprise at least 2, 3, 4, 5, 6, 7, 8, 9, 10 or more nucleotides. The molecular barcode may comprise at least 3 nucleotides. The molecular barcode may comprise at least 4 nucleotides. The molecular barcode may comprise less than 20, 19, 18, 17, 16, or 15 nucleotides. The molecular barcode may comprise less than 10 nucleotides. The molecular barcode may comprise less than 8 nucleotides. The molecular barcode may comprise less than 6 nucleotides. The molecular barcode may comprise 2 to 15 nucleotides. The molecular barcode may comprise 2 to 12 nucleotides. The molecular barcode may comprise 3 to 10 nucleotides. The molecular barcode may comprise 3 to 8 nucleotides. The molecular barcode may comprise 4 to 8 nucleotides. The molecular barcode may comprise 4 to 6 nucleotides.

The adaptor may comprise a sample index. The sample index may comprise a random sequence. The sample index may comprise a predetermined sequence. Two or more sets of adaptors may comprise two or more different sample indexes. Adaptors within a set of adaptors may comprise identical sample indexes. The sample indexes may be optimized to minimize dimerization. The sample indexes may be optimized to enable identification even with amplification or sequencing errors. For examples, amplification of a first sample index may introduce a single base error. The first sample index may comprise greater than a single base difference from the other sample indexes. Thus, the first sample index with the single base error may still be identified as the first molecular barcode. The sample index may comprise at least 2, 3, 4, 5, 6, 7, 8, 9, 10 or more nucleotides. The sample index may comprise at least 3 nucleotides. The sample index may comprise at least 4 nucleotides. The sample index may comprise less than 20, 19, 18, 17, 16, or 15 nucleotides. The sample index may comprise less than 10 nucleotides. The sample index may comprise less than 8 nucleotides. The sample index may comprise less than 6 nucleotides. The sample index may comprise 2 to 15 nucleotides. The sample index may comprise 2 to 12 nucleotides. The sample index may comprise 3 to 10 nucleotides. The sample index may comprise 3 to 8 nucleotides. The sample index may comprise 4 to 8 nucleotides. The sample index may comprise 4 to 6 nucleotides.

The adaptor may comprise a primer sequence. The primer sequence may be a PCR primer sequence. The primer sequence may be a sequencing primer.

Adaptors may be attached to one end of the cfDNA. Adaptors may be attached to both ends of the cfDNA. Adaptors may be attached to one or more ends of a single-stranded cfDNA. Adaptors may be attached to one or more ends of a double-stranded cfDNA.

Adaptors may be attached to the cfDNA by ligation. Ligation may be blunt end ligation. Ligation may be sticky end ligation. Adaptors may be attached to the cfDNA by primer extension. Adaptors may be attached to the cfDNA by reverse transcription. Adaptors may be attached to the cfDNA by hybridization. Adaptors may comprise a sequence that is at least partially complementary to the cfDNA. Alternatively, in some instances, adaptors do not comprise a sequence that is complementary to the cfDNA.

Sequencing may comprise massively parallel sequencing. Sequencing may comprise shotgun sequencing.

The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2.

At least 20%, 30%, 35%, 40%, 45%, 50%, 55%, 60%, 65%, 70%, 75%, 80%, 85%, 90%, or 95% or more of the genomic regions in the selector set may be based on genomic regions from Table 2.

The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer.

The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may comprise less than 100 kb, 90 kb, 80 kb, 70 kb, 60 kb, 50 kb, 40 kb, 30 kb, 20 kb, 10 kb, 5 kb, or 1 kb of a genome.

The total size of the plurality of genomic regions of the selector set may be between 100 kb to 300 kb of a genome. The total size of the plurality of genomic regions of the selector set may be between 100 kb to 200 kb of a genome. The total size of the plurality of genomic regions of the selector set may be between 10 kb to 300 kb of a genome. The total size of the plurality of genomic regions of the selector set may be between 10 kb to 200 kb of a genome. The total size of the plurality of genomic regions of the selector set may be between 10 kb to 100 kb of a genome. The total size of the plurality of genomic regions of the selector set may be between 5 kb to 100 kb of a genome. The total size of the plurality of genomic regions of the selector set may be between 5 kb to 75 kb of a genome. The total size of the plurality of genomic regions of the selector set may be between 5 kb to 50 kb of a genome.

The method of detecting the stage IV cancer may have a sensitivity of at least 60%, 65%, 70%, 75%, 77%, 80%, 82%, 85%, 87%, 90%, 92%, 95%, 97%, or 99% or more. The method of detecting the stage IV cancer may have a sensitivity of at least 60%. The method of detecting the stage IV cancer may have a sensitivity of at least 70%. The method of detecting the stage IV cancer may have a sensitivity of at least 80%. The method of detecting the stage IV cancer may have a sensitivity of at least 90%. The method of detecting the stage IV cancer may have a sensitivity of at least 95%.

The method of detecting the stage IV cancer may have a specificity of at least 60%, 65%, 70%, 75%, 77%, 80%, 82%, 85%, 87%, 90%, 92%, 95%, 97%, or 99% or more. The method of detecting the stage IV cancer may have a specificity of at least 60%. The method of detecting the stage IV cancer may have a specificity of at least 70%. The method of detecting the stage IV cancer may have a specificity of at least 80%. The method of detecting the stage IV cancer may have a specificity of at least 90%. The method of detecting the stage IV cancer may have a specificity of at least 95%.

The method may detect at least 50%, 52%, 55%, 57%, 60%, 62%, 65%, 70%, 72%, 75%, 77%, 80%, 82%, 85%, 87%, 90%, 92%, 95%, 97% or more of stage IV cancer. The method may detect at least 50% or more of stage IV cancer. The method may detect at least 60% or more of stage IV cancer. The method may detect at least 70% or more of stage IV cancer. The method may detect at least 75% or more of stage IV cancer. The method may detect at least 80% or more of stage IV cancer. The method may detect at least 85% or more of stage IV cancer. The method may detect at least 90% or more of stage IV cancer.

Further disclosed herein are methods of producing a selector set. The method may comprise (a) identifying genomic regions comprising mutations in one or more subjects from a population of subjects suffering from the cancer; (b) ranking the genomic regions based on a Recurrence Index (RI), wherein the RI of the genomic region is determined by dividing a number of subjects or tumors with mutations in the genomic region by a size of the genomic region; and (c) producing a selector set comprising one or more genomic regions based on the RI.

At least a subset of the genomic regions that are ranked may be exon regions. At least 20%, 2%, 30%, 35%, 40%, 45%, 50%, 55%, 60%, 65%, 70%, 75%, 80%, 85%, 90%, 95%, or 97% of the genomic regions that are ranked may comprise exon regions. At least 30% of the genomic regions that are ranked may comprise exon regions. At least 40% of the genomic regions that are ranked may comprise exon regions. At least 50% of the genomic regions that are ranked may comprise exon regions. At least 60% of the genomic regions that are ranked may comprise exon regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions that are ranked may comprise exon regions. Less than 97% of the genomic regions that are ranked may comprise exon regions. Less than 92% of the genomic regions that are ranked may comprise exon regions. Less than 84% of the genomic regions that are ranked may comprise exon regions. Less than 75% of the genomic regions that are ranked may comprise exon regions. Less than 65% of the genomic regions that are ranked may comprise exon regions.

At least a subset of the genomic regions of the selector set may comprise exon regions. At least 20%, 2%, 30%, 35%, 40%, 45%, 50%, 55%, 60%, 65%, 70%, 75%, 80%, 85%, 90%, 95%, or 97% of the genomic regions of the selector set may comprise exon regions. At least 30% of the genomic regions of the selector set may comprise exon regions. At least 40% of the genomic regions of the selector set may comprise exon regions. At least 50% of the genomic regions of the selector set may comprise exon regions. At least 60% of the genomic regions of the selector set may comprise exon regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions of the selector set may comprise exon regions. Less than 97% of the genomic regions of the selector set may comprise exon regions. Less than 92% of the genomic regions of the selector set may comprise exon regions. Less than 84% of the genomic regions of the selector set may comprise exon regions. Less than 75% of the genomic regions of the selector set may comprise exon regions. Less than 65% of the genomic regions of the selector set may comprise exon regions.

At least a subset of the genomic regions that are ranked may be intron regions. At least 20%, 2%, 30%, 35%, 40%, 45%, 50%, 55%, 60%, 65%, 70%, 75%, 80%, 85%, 90%, 95%, or 97% of the genomic regions that are ranked may comprise intron regions. At least 30% of the genomic regions that are ranked may comprise intron regions. At least 40% of the genomic regions that are ranked may comprise intron regions. At least 50% of the genomic regions that are ranked may comprise intron regions. At least 60% of the genomic regions that are ranked may comprise intron regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions that are ranked may comprise intron regions. Less than 97% of the genomic regions that are ranked may comprise intron regions. Less than 92% of the genomic regions that are ranked may comprise intron regions. Less than 84% of the genomic regions that are ranked may comprise intron regions. Less than 75% of the genomic regions that are ranked may comprise intron regions. Less than 65% of the genomic regions that are ranked may comprise intron regions.

At least a subset of the genomic regions of the selector set may comprise intron regions. At least 20%, 2%, 30%, 35%, 40%, 45%, 50%, 55%, 60%, 65%, 70%, 75%, 80%, 85%, 90%, 95%, or 97% of the genomic regions of the selector set may comprise intron regions. At least 30% of the genomic regions of the selector set may comprise intron regions. At least 40% of the genomic regions of the selector set may comprise intron regions. At least 50% of the genomic regions of the selector set may comprise intron regions. At least 60% of the genomic regions of the selector set may comprise intron regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions of the selector set may comprise intron regions. Less than 97% of the genomic regions of the selector set may comprise intron regions. Less than 92% of the genomic regions of the selector set may comprise intron regions. Less than 84% of the genomic regions of the selector set may comprise intron regions. Less than 75% of the genomic regions of the selector set may comprise intron regions. Less than 65% of the genomic regions of the selector set may comprise intron regions.

At least a subset of the genomic regions that are ranked may be untranslated regions. At least 20%, 2%, 30%, 35%, 40%, 45%, 50%, 55%, 60%, 65%, 70%, 75%, 80%, 85%, 90%, 95%, or 97% of the genomic regions that are ranked may comprise untranslated regions. At least 30% of the genomic regions that are ranked may comprise untranslated regions. At least 40% of the genomic regions that are ranked may comprise untranslated regions. At least 50% of the genomic regions that are ranked may comprise untranslated regions. At least 60% of the genomic regions that are ranked may comprise untranslated regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions that are ranked may comprise untranslated regions. Less than 97% of the genomic regions that are ranked may comprise untranslated regions. Less than 92% of the genomic regions that are ranked may comprise untranslated regions. Less than 84% of the genomic regions that are ranked may comprise untranslated regions. Less than 75% of the genomic regions that are ranked may comprise untranslated regions. Less than 65% of the genomic regions that are ranked may comprise untranslated regions.

At least a subset of the genomic regions of the selector set may comprise untranslated regions. At least 20%, 2%, 30%, 35%, 40%, 45%, 50%, 55%, 60%, 65%, 70%, 75%, 80%, 85%, 90%, 95%, or 97% of the genomic regions of the selector set may comprise untranslated regions. At least 30% of the genomic regions of the selector set may comprise untranslated regions. At least 40% of the genomic regions of the selector set may comprise untranslated regions. At least 50% of the genomic regions of the selector set may comprise untranslated regions. At least 60% of the genomic regions of the selector set may comprise untranslated regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions of the selector set may comprise untranslated regions. Less than 97% of the genomic regions of the selector set may comprise untranslated regions. Less than 92% of the genomic regions of the selector set may comprise untranslated regions. Less than 84% of the genomic regions of the selector set may comprise untranslated regions. Less than 75% of the genomic regions of the selector set may comprise untranslated regions. Less than 65% of the genomic regions of the selector set may comprise untranslated regions.

At least a subset of the genomic regions that are ranked may be non-coding regions. At least 20%, 2%, 30%, 35%, 40%, 45%, 50%, 55%, 60%, 65%, 70%, 75%, 80%, 85%, 90%, 95%, or 97% of the genomic regions that are ranked may comprise non-coding regions. At least 30% of the genomic regions that are ranked may comprise non-coding regions. At least 40% of the genomic regions that are ranked may comprise non-coding regions. At least 50% of the genomic regions that are ranked may comprise non-coding regions. At least 60% of the genomic regions that are ranked may comprise non-coding regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions that are ranked may comprise non-coding regions. Less than 97% of the genomic regions that are ranked may comprise non-coding regions. Less than 92% of the genomic regions that are ranked may comprise non-coding regions. Less than 84% of the genomic regions that are ranked may comprise non-coding regions. Less than 75% of the genomic regions that are ranked may comprise non-coding regions. Less than 65% of the genomic regions that are ranked may comprise non-coding regions.

At least a subset of the genomic regions of the selector set may comprise non-coding regions. At least 20%, 2%, 30%, 35%, 40%, 45%, 50%, 55%, 60%, 65%, 70%, 75%, 80%, 85%, 90%, 95%, or 97% of the genomic regions of the selector set may comprise non-coding regions. At least 30% of the genomic regions of the selector set may comprise non-coding regions. At least 40% of the genomic regions of the selector set may comprise non-coding regions. At least 50% of the genomic regions of the selector set may comprise non-coding regions. At least 60% of the genomic regions of the selector set may comprise non-coding regions. Less than 97%, 95%, 92%, 90%, 87%, 85%, 82%, 80%, 77%, 75%, 72%, 70%, 67%, 65%, 62%, 60%, 57%, 55%, 52%, 50%, 45%, or 40% of the genomic regions of the selector set may comprise non-coding regions. Less than 97% of the genomic regions of the selector set may comprise non-coding regions. Less than 92% of the genomic regions of the selector set may comprise non-coding regions. Less than 84% of the genomic regions of the selector set may comprise non-coding regions. Less than 75% of the genomic regions of the selector set may comprise non-coding regions. Less than 65% of the genomic regions of the selector set may comprise non-coding regions.

Producing the selector set based on the RI may comprise selecting genomic regions that have a recurrence index in the top $60^{th}$, $65^{th}$, $70^{th}$, $72^{nd}$, $75^{th}$, $77^{th}$, $80^{th}$, $82^{nd}$, $85^{th}$, $87^{th}$, $90^{th}$, $92^{nd}$, $95^{th}$, or $97^{th}$ or greater percentile. Producing the selector set based on the RI may comprise selecting genomic regions that have a recurrence index in the top $80^{th}$ or greater percentile. Producing the selector set based on the RI may comprise selecting genomic regions that have a recurrence index in the top $70^{th}$ or greater percentile. Producing the selector set based on the RI may comprise selecting genomic regions that have a recurrence index in the top $90^{th}$ or greater percentile.

Producing the selector set further may comprise selecting genomic regions that result in the largest reduction in a number of subjects with one mutation in the genomic region.

Producing the selector set may comprise applying an algorithm to a subset of the ranked genomic regions. The algorithm may be applied 2, 3, 4, 5, 6, 7, 8, 9, 10 or more times. The algorithm may be applied two or more times. The algorithm may be applied three or more times.

Producing the selector set may comprise selecting genomic regions that maximize a median number of mutations per subject of the selector set. Producing the selector set may comprise selecting genomic regions that maximize the number of subjects in the selector set.

Producing the selector set may comprise selecting genomic regions that minimize the total size of the genomic regions.

The selector set may comprise information pertaining to a plurality of genomic regions comprising one or more mutations present in at least one subject suffering from a cancer. The selector set may comprise information pertaining to a plurality of genomic regions comprising 1, 2, 3, 4, 5, 6, 8, 9, 10, 11, 12, 13, 14, 15, 16, 17, 18, 19, 20 or more mutations present in at least one subject suffering from a cancer. The selector set may comprise information pertaining to a plurality of genomic regions comprising 25, 30, 35, 40, 45, 50, 55, 60, 65, 70, 75, 80, 85, 90, 95, 100, 110, 120, 130, 140, 150, 160, 170, 180, 190, 200 or more mutations present in at least one subject suffering from a cancer.

The selector set may comprise information pertaining to a plurality of genomic regions comprising one or more mutations present in at least one subject suffering from a cancer. The one or more mutations within the plurality of genomic regions may be present in at least 1, 2, 3, 4, 5, 6, 8, 9, 10, 11, 12, 13, 14, 15, 16, 17, 18, 19, 20 or more subjects suffering from a cancer. The one or more mutations within the genomic regions may be present in at least 25, 30, 35, 40, 45, 50, 55, 60, 65, 70, 75, 80, 85, 90, 95, 100, 110, 120, 130, 140, 150, 160, 170, 180, 190, 200 or more subjects suffering from a cancer.

The selector set may comprise information pertaining to a plurality of genomic regions comprising one or more mutations present in at least one subject suffering from a cancer. The one or more mutations within the plurality of genomic regions may be present in at least 1%, 2%, 3%, 4%, 5%, 6%, 8%, 9%, 10%, 11%, 12%, 13%, 14%, 15%, 16%, 17%, 18%, 19%, 20% or more subjects from a population of subjects suffering from a cancer. The one or more mutations within the plurality of genomic regions may be present in at least 25%, 30%, 35%, 40%, 45%, 50%, 55%, 60%, 65%, 70%, 75%, 80%, 85%, 90%, 95% or more subjects from a population of subjects suffering from a cancer.

The selector set may comprise sequence information pertaining to a plurality of genomic regions comprising one or more mutations present in at least one subject suffering from a cancer. The selector set may comprise sequence information pertaining to a plurality of genomic regions comprising 1, 2, 3, 4, 5, 6, 8, 9, 10, 11, 12, 13, 14, 15, 16, 17, 18, 19, 20 or more mutations present in at least one subject suffering from a cancer. The selector set may comprise sequence information pertaining to a plurality of genomic regions comprising 25, 30, 35, 40, 45, 50, 55, 60, 65, 70, 75, 80, 85, 90, 95, 100, 110, 120, 130, 140, 150, 160, 170, 180, 190, 200 or more mutations present in at least one subject suffering from a cancer.

The selector set may comprise sequence information pertaining to a plurality of genomic regions comprising one or more mutations present in at least one subject suffering from a cancer. The one or more mutations within the plurality of genomic regions may be present in at least 1, 2, 3, 4, 5, 6, 8, 9, 10, 11, 12, 13, 14, 15, 16, 17, 18, 19, 20 or more subjects suffering from a cancer. The one or more mutations within the genomic regions may be present in at least 25, 30, 35, 40, 45, 50, 55, 60, 65, 70, 75, 80, 85, 90, 95, 100, 110, 120, 130, 140, 150, 160, 170, 180, 190, 200 or more subjects suffering from a cancer.

The selector set may comprise sequence information pertaining to a plurality of genomic regions comprising one or more mutations present in at least one subject suffering from a cancer. The one or more mutations within the plurality of genomic regions may be present in at least 1%, 2%, 3%, 4%, 5%, 6%, 8%, 9%, 10%, 11%, 12%, 13%, 14%, 15%, 16%, 17%, 18%, 19%, 20% or more subjects from a population of subjects suffering from a cancer. The one or more mutations within the plurality of genomic regions may be present in at least 25%, 30%, 35%, 40%, 45%, 50%, 55%, 60%, 65%, 70%, 75%, 80%, 85%, 90%, 95% or more subjects from a population of subjects suffering from a cancer.

The selector set may comprise genomic coordinates pertaining to a plurality of genomic regions comprising one or more mutations present in at least one subject suffering from a cancer. The selector set may comprise genomic coordinates pertaining to a plurality of genomic regions comprising 1, 2, 3, 4, 5, 6, 8, 9, 10, 11, 12, 13, 14, 15, 16, 17, 18, 19, 20 or more mutations present in at least one subject suffering from a cancer. The selector set may comprise genomic coordinates pertaining to a plurality of genomic regions comprising 25, 30, 35, 40, 45, 50, 55, 60, 65, 70, 75, 80, 85, 90, 95, 100, 110, 120, 130, 140, 150, 160, 170, 180, 190, 200 or more mutations present in at least one subject suffering from a cancer.

The selector set may comprise genomic coordinates pertaining to a plurality of genomic regions comprising one or more mutations present in at least one subject suffering from a cancer. The one or more mutations within the plurality of genomic regions may be present in at least 1, 2, 3, 4, 5, 6, 8, 9, 10, 11, 12, 13, 14, 15, 16, 17, 18, 19, 20 or more subjects suffering from a cancer. The one or more mutations within the plurality of genomic regions may be present in at least 25, 30, 35, 40, 45, 50, 55, 60, 65, 70, 75, 80, 85, 90, 95, 100, 110, 120, 130, 140, 150, 160, 170, 180, 190, 200 or more subjects suffering from a cancer.

The selector set may comprise genomic coordinates pertaining to a plurality of genomic regions comprising one or more mutations present in at least one subject suffering from a cancer. The one or more mutations within the plurality of genomic regions may be present in at least 1%, 2%, 3%, 4%, 5%, 6%, 8%, 9%, 10%, 11%, 12%, 13%, 14%, 15%, 16%, 17%, 18%, 19%, 20% or more subjects from a population of subjects suffering from a cancer. The one or more mutations within the plurality of genomic regions may be present in at least 25%, 30%, 35%, 40%, 45%, 50%, 55%, 60%, 65%, 70%, 75%, 80%, 85%, 90%, 95% or more subjects from a population of subjects suffering from a cancer.

The selector set may comprise genomic regions comprising one or more types of mutations. The selector set may comprise genomic regions comprising two or more types of mutations. The selector set may comprise genomic regions comprising three or more types of mutations. The selector set may comprise genomic regions comprising four or more types of mutations. The types of mutations may include, but are not limited to, single nucleotide variants (SNVs), insertions/deletions (indels), rearrangements, and copy number variants (CNVs).

The selector set may comprise genomic regions comprising two or more different types of mutations selected from a group consisting of single nucleotide variants (SNVs), insertions/deletions (indels), rearrangements, and copy number variants (CNVs). The selector set may comprise genomic regions comprising three or more different types of mutations selected from a group consisting of single nucleotide variants (SNVs), insertions/deletions (indels), rearrangements, and copy number variants (CNVs). The selector set may comprise genomic regions comprising four or more different types of mutations selected from a group consisting of single nucleotide variants (SNVs), insertions/deletions (indels), rearrangements, and copy number variants (CNVs).

The selector set may comprise a genomic region comprising at least one SNV and a genomic region comprising at least one other type of mutation. The selector set may comprise a genomic region comprising at least one SNV and a genomic region comprising at least one indel. The selector set may comprise a genomic region comprising at least one SNV and a genomic region comprising at least one rearrangement. The selector set may comprise a genomic region comprising at least one SNV and a genomic region comprising at least one CNV.

The selector set may comprise a genomic region comprising at least one indel and a genomic region comprising at least one other type of mutation. The selector set may comprise a genomic region comprising at least one indel and a genomic region comprising at least one SNV. The selector set may comprise a genomic region comprising at least one indel and a genomic region comprising at least one rearrangement. The selector set may comprise a genomic region comprising at least one indel and a genomic region comprising at least one CNV.

The selector set may comprise a genomic region comprising at least one rearrangement. The selector set may comprise a genomic region comprising at least one rearrangement and a genomic region comprising at least one other type of mutation. The selector set may comprise a genomic region comprising at least one rearrangement and a genomic region comprising at least one SNV. The selector set may comprise a genomic region comprising at least one rearrangement and a genomic region comprising at least one indel. The selector set may comprise a genomic region comprising at least one rearrangement and a genomic region comprising at least one CNV.

The selector set may comprise a genomic region comprising at least one CNV and a genomic region comprising at least one other type of mutation. The selector set may comprise a genomic region comprising at least one CNV and a genomic region comprising at least one SNV. The selector set may comprise a genomic region comprising at least one CNV and a genomic region comprising at least one indel. The selector set may comprise a genomic region comprising at least one CNV and a genomic region comprising at least one rearrangement.

At least about 1%, 2%, 3%, 4%, 5%, 6%, 7%, 8%, 9%, 10%, 11%, 12%, 13%, 14%, 15%, 16%, 17%, 18%, 19%, or 20% of the genomic regions of the selector set may comprise a SNV. At least about 25%, 30%, 35%, 40%, 45%, 50%, 55%, or 60% of the genomic regions of the selector set may comprise a SNV. At least about 10% of the genomic regions of the selector set may comprise a SNV. At least about 15% of the genomic regions of the selector set may comprise a SNV. At least about 20% of the genomic regions of the selector set may comprise a SNV. At least about 30% of the genomic regions of the selector set may comprise a SNV. At least about 40% of the genomic regions of the selector set may comprise a SNV. At least about 50% of the genomic regions of the selector set may comprise a SNV. At least about 60% of the genomic regions of the selector set may comprise a SNV.

Less than 99%, 98%, 97%, 95%, 92%, 90%, 87%, 85%, 82%, 80%, 77%, 75%, 72%, 70%, 67%, 65%, 62%, 60%, 57%, 55%, 52%, 50% of the genomic regions of the selector set may comprise a SNV. Less than 97% of the genomic regions of the selector set may comprise a SNV. Less than 95% of the genomic regions of the selector set may comprise a SNV. Less than 90% of the genomic regions of the selector set may comprise a SNV. Less than 85% of the genomic regions of the selector set may comprise a SNV. Less than 77% of the genomic regions of the selector set may comprise a SNV.

The genomic regions of the selector set may comprise between about 10% to about 95% SNVs. The genomic regions of the selector set may comprise between about 10% to about 90% SNVs. The genomic regions of the selector set may comprise between about 15% to about 95% SNVs. The genomic regions of the selector set may comprise between about 20% to about 95% SNVs. The genomic regions of the selector set may comprise between about 30% to about 95% SNVs. The genomic regions of the selector set may comprise between about 30% to about 90% SNVs. The genomic regions of the selector set may comprise between about 30% to about 85% SNVs. The genomic regions of the selector set may comprise between about 30% to about 80% SNVs.

At least about 1%, 2%, 3%, 4%, 5%, 6%, 7%, 8%, 9%, 10%, 11%, 12%, 13%, 14%, 15%, 16%, 17%, 18%, 19%, or 20% of the genomic regions of the selector set may comprise an indel. At least about 25%, 30%, 35%, 40%, 45%, 50%, 55%, or 60% of the genomic regions of the selector set may comprise an indel. At least about 1% of the genomic regions of the selector set may comprise an indel. At least about 3% of the genomic regions of the selector set may comprise an indel. At least about 5% of the genomic regions of the selector set may comprise an indel. At least about 8% of the genomic regions of the selector set may comprise an indel. At least about 10% of the genomic regions of the selector set may comprise an indel. At least about 15% of the genomic regions of the selector set may comprise an indel. At least about 30% of the genomic regions of the selector set may comprise an indel.

Less than 99%, 98%, 97%, 95%, 92%, 90%, 87%, 85%, 82%, 80%, 77%, 75%, 72%, 70%, 67%, 65%, 62%, 60%, 57%, 55%, 52%, 50% of the genomic regions of the selector set may comprise an indel. Less than 97% of the genomic regions of the selector set may comprise an indel. Less than 95% of the genomic regions of the selector set may comprise an indel. Less than 90% of the genomic regions of the selector set may comprise an indel. Less than 85% of the genomic regions of the selector set may comprise an indel. Less than 77% of the genomic regions of the selector set may comprise an indel.

The genomic regions of the selector set may comprise between about 10% to about 95% indels. The genomic regions of the selector set may comprise between about 10% to about 90% indels. The genomic regions of the selector set may comprise between about 10% to about 85% indels. The genomic regions of the selector set may comprise between about 10% to about 80% indels. The genomic regions of the selector set may comprise between about 10% to about 75% indels. The genomic regions of the selector set may comprise between about 10% to about 70% indels. The genomic regions of the selector set may comprise between about 10% to about 60% indels. The genomic regions of the selector set may comprise between about 10% to about 50% indels.

At least about 1%, 2%, 3%, 4%, 5%, 6%, 7%, 8%, 9%, 10%, 11%, 12%, 13%, 14%, 15%, 16%, 17%, 18%, 19%, or 20% of the genomic regions of the selector set may comprise a rearrangement. At least about 1% of the genomic regions of the selector set may comprise a rearrangement. At least about 2% of the genomic regions of the selector set may comprise a rearrangement. At least about 3% of the genomic regions of the selector set may comprise a rearrangement. At least about 4% of the genomic regions of the selector set may comprise a rearrangement. At least about 5% of the genomic regions of the selector set may comprise a rearrangement.

At least about 1%, 2%, 3%, 4%, 5%, 6%, 7%, 8%, 9%, 10%, 11%, 12%, 13%, 14%, 15%, 16%, 17%, 18%, 19%, or 20% of the genomic regions of the selector set may comprise a CNV. At least about 25%, 30%, 35%, 40%, 45%, 50%, 55%, or 60% of the genomic regions of the selector set may comprise a CNV. At least about 1% of the genomic regions of the selector set may comprise a CNV. At least about 3% of the genomic regions of the selector set may comprise a CNV. At least about 5% of the genomic regions of the selector set may comprise a CNV. At least about 8% of the genomic regions of the selector set may comprise a CNV. At least about 10% of the genomic regions of the selector set may comprise a CNV. At least about 15% of the genomic regions of the selector set may comprise a CNV. At least about 30% of the genomic regions of the selector set may comprise a CNV.

Less than 99%, 98%, 97%, 95%, 92%, 90%, 87%, 85%, 82%, 80%, 77%, 75%, 72%, 70%, 67%, 65%, 62%, 60%, 57%, 55%, 52%, 50% of the genomic regions of the selector set may comprise a CNV. Less than 97% of the genomic regions of the selector set may comprise a CNV. Less than 95% of the genomic regions of the selector set may comprise a CNV. Less than 90% of the genomic regions of the selector set may comprise a CNV. Less than 85% of the genomic regions of the selector set may comprise a CNV. Less than 77% of the genomic regions of the selector set may comprise a CNV.

The genomic regions of the selector set may comprise between about 5% to about 80% CNVs. The genomic regions of the selector set may comprise between about 5% to about 70% CNVs. The genomic regions of the selector set may comprise between about 5% to about 60% CNVs. The genomic regions of the selector set may comprise between about 5% to about 50% CNVs. The genomic regions of the selector set may comprise between about 5% to about 40% CNVs. The genomic regions of the selector set may comprise between about 5% to about 35% CNVs. The genomic regions of the selector set may comprise between about 5% to about 30% CNVs. The genomic regions of the selector set may comprise between about 5% to about 25% CNVs.

The selector set may be used to classify a sample from a subject. The selector set may be used to classify 2, 3, 4, 5, 6, 7, 8, 9, 10, 11, 12, 13, 14, or 15 or more samples from a subject.

The selector set may be used to classify two or more samples from a subject. The selector set may be used to classify one or more samples from one or more subjects. The selector set may be used to classify two or more samples from two or more subjects. The selector set may be used to classify a plurality of samples from 2, 3, 4, 5, 6, 7, 8, 9, 10, 11, 12, 13, 14, 15, 16, 17, 18, 19, or 20 or more subjects.

The samples may be the same type of sample. The samples may be two or more different types of samples. The sample may be a plasma sample. The sample may be a tumor sample. The sample may be a germline sample. The sample may comprise tumor-derived molecules. The sample may comprise non-tumor-derived molecules.

The selector set may classify the sample as tumor-containing. The selector set may classify the sample as tumor-free.

The selector set may be a personalized selector set. The selector set may be used to diagnose a cancer in a subject in need thereof. The selector set may be used to prognosticate a status or outcome of a cancer in a subject in need thereof. The selector set may be used to determine a therapeutic regimen for treating a cancer in a subject in need thereof.

Alternatively, the selector set may be a universal selector set. The selector set may be used to diagnose a cancer in a plurality of subjects in need thereof. The selector set may be used to prognosticate a status or outcome of a cancer in a plurality of subjects in need thereof. The selector set may be used to determine a therapeutic regimen for treating a cancer in a plurality of subjects in need thereof.

The plurality of subjects may comprise 5, 10, 15, 20, 25, 30, 35, 40, 50, 60, 70, 80, 90, or 100 or more subjects. The plurality of subjects may comprise 5 or more subjects. The plurality of subjects may comprise 10 or more subjects. The plurality of subjects may comprise 25 or more subjects. The plurality of subjects may comprise 50 or more subjects. The plurality of subjects may comprise 75 or more subjects. The plurality of subjects may comprise 100 or more subjects.

The selector set may be used to classify one or more subjects based on one or more samples from the one or more subjects. The selector set may be used to classify a subject as a responder to a therapy. The selector set may be used to classify a subject as a non-responder to a therapy.

The selector set may be used to design a plurality of oligonucleotides. The plurality of oligonucleotides may selectively hybridize to one or more genomic regions identified by the selector set. At least two oligonucleotides may selectively hybridize to one genomic region. At least three oligonucleotides may selectively hybridize to one genomic region. At least four oligonucleotides may selectively hybridize to one genomic region.

An oligonucleotide of the plurality of oligonucleotides may be at least about 10, 15, 20, 25, 30, 35, 40, 45, 50, 55, 60, 65, 70, 75, 80, 85, 90, 95, or 100 nucleotides in length. An oligonucleotide may be at least about 20 nucleotides in length. An oligonucleotide may be at least about 30 nucleotides in length. An oligonucleotide may be at least about 40 nucleotides in length. An oligonucleotide may be at least about 45 nucleotides in length. An oligonucleotide may be at least about 50 nucleotides in length.

An oligonucleotide of the plurality of oligonucleotides may be less than or equal to 300, 275, 250, 225, 200, 190, 180, 170, 160, 150, 140, 130, 125, 120, 115, 110, 105, 100, 95, 90, 85, 80, 75, or 70 nucleotides in length. An oligonucleotide of the plurality of oligonucleotides may be less than or equal to 200 nucleotides in length. An oligonucleotide of the plurality of oligonucleotides may be less than or equal to 150 nucleotides in length. An oligonucleotide of the plurality of oligonucleotides may be less than or equal to 110 nucleotides in length. An oligonucleotide of the plurality of oligonucleotides may be less than or equal to 100 nucleotides in length. An oligonucleotide of the plurality of oligonucleotides may be less than or equal to 80 nucleotides in length.

An oligonucleotide of the plurality of oligonucleotides may be between about 20 to 200 nucleotides in length. An oligonucleotide of the plurality of oligonucleotides may be between about 20 to 170 nucleotides in length. An oligonucleotide of the plurality of oligonucleotides may be between about 20 to 150 nucleotides in length. An oligonucleotide of the plurality of oligonucleotides may be between about 20 to 130 nucleotides in length. An oligonucleotide of the plurality of oligonucleotides may be between about 20 to 120 nucleotides in length. An oligonucleotide of the plurality of oligonucleotides may be between about 30 to 150 nucleotides in length. An oligonucleotide of the plurality of oligonucleotides may be between about 30 to 120 nucleotides in length. An oligonucleotide of the plurality of oligonucleotides may be between about 40 to 150 nucleotides in length. An oligonucleotide of the plurality of oligonucleotides may be between about 40 to 120 nucleotides in length. An oligonucleotide of the plurality of oligonucleotides may be between about 50 to 150 nucleotides in length. An oligonucleotide of the plurality of oligonucleotides may be between about 50 to 120 nucleotides in length.

An oligonucleotide of the plurality of oligonucleotides may be attached to a solid support. The solid support may be a bead. The bead may be a coated bead. The bead may be a streptavidin coated bead. The solid support may be an array. The solid support may be a glass slide.

Further disclosed herein are methods of producing a personalized selector set. The method may comprise (a)

obtaining a genotype of a tumor in a subject; (b) identifying genomic regions comprising one or more mutations based on the genotype of the tumor; and (c) producing a selector set comprising at least one genomic region.

Obtaining the genotype of the tumor in the subject may comprise conducting a sequencing reaction on a sample from the subject. Sequencing may comprise whole genome sequencing. Sequencing may comprise whole exome sequencing.

Sequencing may comprise use of one or more adaptors. The adaptors may be attached to one or more nucleic acids from the sample. The adaptor may comprise a plurality of oligonucleotides. The adaptor may comprise one or more deoxyribonucleotides. The adaptor may comprise ribonucleotides. The adaptor may be single-stranded. The adaptor may be double-stranded. The adaptor may comprise double-stranded and single-stranded portions. For example, the adaptor may be a Y-shaped adaptor. The adaptor may be a linear adaptor. The adaptor may be a circular adaptor. The adaptor may comprise a molecular barcode, sample index, primer sequence, linker sequence or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

The adaptor may comprise a molecular barcode. The molecular barcode may comprise a random sequence. The molecular barcode may comprise a predetermined sequence. Two or more adaptors may comprise two or more different molecular barcodes. The molecular barcodes may be optimized to minimize dimerization. The molecular barcodes may be optimized to enable identification even with amplification or sequencing errors. For examples, amplification of a first molecular barcode may introduce a single base error. The first molecular barcode may comprise greater than a single base difference from the other molecular barcodes. Thus, the first molecular barcode with the single base error may still be identified as the first molecular barcode. The molecular barcode may comprise at least 2, 3, 4, 5, 6, 7, 8, 9, 10 or more nucleotides. The molecular barcode may comprise at least 3 nucleotides. The molecular barcode may comprise at least 4 nucleotides. The molecular barcode may comprise less than 20, 19, 18, 17, 16, or 15 nucleotides. The molecular barcode may comprise less than 10 nucleotides. The molecular barcode may comprise less than 8 nucleotides. The molecular barcode may comprise less than 6 nucleotides. The molecular barcode may comprise 2 to 15 nucleotides. The molecular barcode may comprise 2 to 12 nucleotides. The molecular barcode may comprise 3 to 10 nucleotides. The molecular barcode may comprise 3 to 8 nucleotides. The molecular barcode may comprise 4 to 8 nucleotides. The molecular barcode may comprise 4 to 6 nucleotides.

The adaptor may comprise a sample index. The sample index may comprise a random sequence. The sample index may comprise a predetermined sequence. Two or more sets of adaptors may comprise two or more different sample indexes. Adaptors within a set of adaptors may comprise identical sample indexes. The sample indexes may be optimized to minimize dimerization. The sample indexes may be optimized to enable identification even with amplification or sequencing errors. For examples, amplification of a first sample index may introduce a single base error. The first sample index may comprise greater than a single base difference from the other sample indexes. Thus, the first sample index with the single base error may still be identified as the first molecular barcode. The sample index may comprise at least 2, 3, 4, 5, 6, 7, 8, 9, 10 or more nucleotides. The sample index may comprise at least 3 nucleotides. The sample index may comprise at least 4 nucleotides. The sample index may comprise less than 20, 19, 18, 17, 16, or 15 nucleotides. The sample index may comprise less than 10 nucleotides. The sample index may comprise less than 8 nucleotides. The sample index may comprise less than 6 nucleotides. The sample index may comprise 2 to 15 nucleotides. The sample index may comprise 2 to 12 nucleotides. The sample index may comprise 3 to 10 nucleotides. The sample index may comprise 3 to 8 nucleotides. The sample index may comprise 4 to 8 nucleotides. The sample index may comprise 4 to 6 nucleotides.

The adaptor may comprise a primer sequence. The primer sequence may be a PCR primer sequence. The primer sequence may be a sequencing primer.

Adaptors may be attached to one end of a nucleic acid from a sample. The nucleic acids may be DNA. The DNA may be cell-free DNA (cfDNA). The DNA may be circulating tumor DNA (ctDNA). The nucleic acids may be RNA. Adaptors may be attached to both ends of the nucleic acid. Adaptors may be attached to one or more ends of a single-stranded nucleic acid. Adaptors may be attached to one or more ends of a double-stranded nucleic acid.

Adaptors may be attached to the nucleic acid by ligation. Ligation may be blunt end ligation. Ligation may be sticky end ligation. Adaptors may be attached to the nucleic acid by primer extension. Adaptors may be attached to the nucleic acid by reverse transcription. Adaptors may be attached to the nucleic acids by hybridization. Adaptors may comprise a sequence that is at least partially complementary to the nucleic acid. Alternatively, in some instances, adaptors do not comprise a sequence that is complementary to the nucleic acid.

Identifying genomic regions comprising one or more mutations based on the genotype of the tumor may comprise determining a consensus sequence for the genomic region comprising the one or more mutations. Determining the consensus sequence may be based on the adaptors. Determining the consensus sequence may be based on the molecular barcode portion of the adaptor. Determining the consensus sequence may comprise analyzing sequence reads pertaining to a molecular barcode. Determining the consensus sequence may comprise determining a percentage of sequence reads with identical sequences based on the molecular barcode. Identifying genomic regions comprising one or more mutations may comprise producing a list of genomic regions based on a percentage of the consensus sequence. Producing the list of genomic regions may comprise selecting genomic regions with at least 80%, 82%, 85%, 87%, 90%, 91%, 92%, 93%, 94%, 95%, 96%, 97%, 98%, 99%, or 100% consensus based on the molecular barcode. For example, sequence information may be arranged into molecular barcode families (e.g., sequences with identical molecular barcodes are grouped together). Analysis of a molecular barcode family may reveal two different sequences. 1000 sequence reads may be associated with a first sequence and 10 sequence reads may be associated with a second sequence. The dominant sequence (e.g., the first sequence) may have a consensus of 99% (e.g., (1000 divided by 1010) times 100%). The list of genomic regions may comprise the dominant sequence of the genomic region. The list of genomic regions may comprise genomic regions with 90% consensus based on the molecular barcode. The list of genomic regions may comprise genomic regions with 95% consensus based on the molecular barcode. The list of genomic regions may comprise genomic regions with 98% consensus based on the molecular barcode. The list of genomic regions may comprise genomic regions with 100% sequence consensus based on the molecular barcode. Identifying genomic regions comprising one or more mutations based on the genotype of the tumor may comprise producing a list of genomic regions ranked by a percentage of their sequence consensus.

Identifying genomic regions comprising one or more mutations based on the genotype of the tumor may comprise calculating a fractional abundance of the genomic region. Identifying genomic regions comprising one or more mutations based on the genotype of the tumor may comprise calculating a fractional abundance of the genomic region from the list of genomic regions ranked by the percentage of their sequence consensus. The fractional abundance may be calculated by dividing a number of sequence reads that pertain to a genomic region with the one or more mutations by a total number of sequence reads for the genomic regions. For example, a genomic region may comprise exon 2 of gene X. A total number of sequence reads pertaining to the genomic region may be 1000, with 100 of the sequence reads containing an insertion in exon 2 of gene X. The fractional abundance of the genomic region containing the insertion in exon 2 of gene X would be 0.1 (e.g., 100 sequence reads divided by 1000). Identifying genomic regions comprising one or more mutations based on the genotype of the tumor may comprise producing a list of genomic regions ranked by their fractional abundance.

Producing the selector set may comprise selecting one or more genomic regions from the list of genomic regions ranked by their fractional abundance. Producing the selector set may comprise selecting one or more genomic regions with a fractional abundance of less than 50%, 47%, 45%, 42%, 40%, 37%, 35%, 34%, 33%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%. Producing the selector set may comprise selecting one or more genomic regions with a fractional abundance of less than 37%. Producing the selector set may comprise selecting one or more genomic regions with a fractional abundance of less than 33%. Producing the selector set may comprise selecting one or more genomic regions with a fractional abundance of less than 30%. Producing the selector set may comprise selecting one or more genomic regions with a fractional abundance of less than 27%. Producing the selector set may comprise selecting one or more genomic regions with a fractional abundance of less than 25%. Producing the selector set may comprise selecting one or more genomic regions with a fractional abundance of between about 0.00001% to about 35%. Producing the selector set may comprise selecting one or more genomic regions with a fractional abundance of between about 0.00001% to about 30%. Producing the selector set may comprise selecting one or more genomic regions with a fractional abundance of between about 0.00001% to about 27%.

The selector set may comprise at least 1, 2, 3, 4, 5, 6, 7, 8, 9, 10 or more genomic regions. The selector set may comprise one genomic region. The selector set may comprise at least 2 genomic regions. The selector set may comprise at least 3 genomic regions.

The genomic regions of the selector set may comprise one or more previously unidentified mutations. The genomic regions of the selector set may comprise 2 or more previously unidentified mutations. The genomic regions of the selector set may comprise 3 or more previously unidentified mutations. The genomic regions of the selector set may comprise 4 or more previously unidentified mutations.

The genomic regions may comprise one or more mutations selected from a group consisting of SNVs, indels, rearrangements, and CNVs. The genomic regions may comprise two or more mutations selected from a group consisting of SNVs, indels, rearrangements, and CNVs. The genomic regions may comprise three or more mutations selected from a group consisting of SNVs, indels, rearrangements, and CNVs. The genomic regions may comprise four or more mutations selected from a group consisting of SNVs, indels, rearrangements, and CNVs.

The genomic regions may comprise one or more types of mutations selected from a group consisting of SNVs, indels, rearrangements, and CNVs. The genomic regions may comprise two or more types of mutations selected from a group consisting of SNVs, indels, rearrangements, and CNVs. The genomic regions may comprise three or more types of mutations selected from a group consisting of SNVs, indels, rearrangements, and CNVs. The genomic regions may comprise four or more types of mutations selected from a group consisting of SNVs, indels, rearrangements, and CNVs.

Further disclosed herein are computer readable media for use in the methods disclosed herein. The computer readable medium may comprise sequence information for two or more genomic regions wherein (a) the genomic regions may comprise one or more mutations in greater than 80% of tumors from a population of subjects afflicted with a cancer; (b) the genomic regions represent less than 1.5 Mb of the genome; and (c) one or more of the following (i) the condition may be not hairy cell leukemia, ovarian cancer, Waldenstrom's macroglobulinemia; (ii) a genomic region may comprise at least one mutation in at least one subject afflicted with the cancer; (iii) the cancer includes two or more different types of cancer; (iv) the two or more genomic regions may be derived from two or more different genes; (v) the genomic regions may comprise two or more mutations; or (vi) the two or more genomic regions may comprise at least 10 kb.

In some instances, the condition is not hairy cell leukemia.

The genomic regions may comprise one or more mutations in greater than 60% of tumors from an additional population of subjects afflicted with another type of cancer.

The genomic regions may be derived from 2, 3, 4, 5, 6, 7, 8, 9, 10, 11, 12, 13, 14, 15, 16, 17, 18, 19, 20 or more different genes. The genomic regions may be derived from 25, 30, 35, 40, 45, 50, 60, 70, 80, 90, 100 or more different genes.

The genomic regions may comprise at least 1, 2, 3, 4, 5, 6, 7, 8, 9, 10, 15, 20, 25, 30, 35, 40, 45, or 50 kb. The genomic regions may comprise at least 5 kb. The genomic regions may comprise at least 10 kb. The genomic regions may comprise at least 50 kb.

The sequence information may comprise genomic coordinates pertaining to the 2, 3, 4, 5, 6, 7, 8, 9, 10, 11, 12, 13, 14, 15, 16, 17, 18, 19, 20 or more genomic regions. The sequence information may comprise genomic coordinates pertaining to the 25, 30, 35, 40, 45, 50, 55, 60, 65, 70, 75, 80, 85, 90, 95, 100 or more genomic regions. The sequence information may comprise genomic coordinates pertaining to the 125, 150, 175, 200, 225, 250, 275, 300, 325, 350, 375, 400, 425, 450, 475, 500 or more genomic regions.

The sequence information may comprise a nucleic acid sequence pertaining to the 2, 3, 4, 5, 6, 7, 8, 9, 10, 11, 12, 13, 14, 15, 16, 17, 18, 19, 20 or more genomic regions. The sequence information may comprise a nucleic acid sequence pertaining to the 25, 30, 35, 40, 45, 50, 55, 60, 65, 70, 75, 80, 85, 90, 95, 100 or more genomic regions. The sequence information may comprise a nucleic acid sequence pertaining to the 125, 150, 175, 200, 225, 250, 275, 300, 325, 350, 375, 400, 425, 450, 475, 500 or more genomic regions.

The sequence information may comprise a length of the 2, 3, 4, 5, 6, 7, 8, 9, 10, 11, 12, 13, 14, 15, 16, 17, 18, 19, 20 or more genomic regions. The sequence information may comprise a length of the 25, 30, 35, 40, 45, 50, 55, 60, 65, 70, 75, 80, 85, 90, 95, 100 or more genomic regions. The sequence information may comprise a length of the 125, 150, 175, 200, 225, 250, 275, 300, 325, 350, 375, 400, 425, 450, 475, 500 or more genomic regions.

Further disclosed herein are compositions for use in the methods and systems disclosed herein. The composition may comprise a set of oligonucleotides that selectively hybridize to a plurality of genomic regions, wherein (a) greater than 80% of tumors from a population of cancer subjects include one or more mutations in the genomic regions; (b) the plurality of genomic regions represent less than 1.5 Mb of the genome; and (c) the set of oligonucleotides may comprise 5 or more different oligonucleotides that selectively hybridize to the plurality of genomic regions.

An oligonucleotide of the set of oligonucleotides may comprise a tag. The tag may be biotin. The tag may be a label. The label may be a fluorescent label or dye. The tag may be an adaptor.

The genomic regions may comprise at least 2, 3, 4, 5, 6, 7, 8, 9, 10, 11, 12, 13, 14, 15, 16, 17, 18, 19, 20 or more regions from those identified in Table 2. The genomic regions may comprise at least 25, 30, 35, 40, 45, 50, 55, 60, 65, 70, 75, 80, 85, 90, 95, 100, 150, 200, 250, 300, 350, 400, 450, 500, or 525 regions from those identified in Table 2. The genomic regions may comprise at least 2 regions from those identified in Table 2. The genomic regions may comprise at least 20 regions from those identified in Table 2. The genomic regions may comprise at least 60 regions from those identified in Table 2. The genomic regions may comprise at least 100 regions from those identified in Table 2. The genomic regions may comprise at least 300 regions from those identified in Table 2. The genomic regions may comprise at least 400 regions from those identified in Table 2. The genomic regions may comprise at least 500 regions from those identified in Table 2.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 2. At least about 5% of the genomic regions may be regions identified in Table 2. At least about 10% of the genomic regions may be regions identified in Table 2. At least about 20% of the genomic regions may be regions identified in Table 2. At least about 30% of the genomic regions may be regions identified in Table 2. At least about 40% of the genomic regions may be regions identified in Table 2.

The genomic regions may comprise at least 2, 3, 4, 5, 6, 7, 8, 9, 10, 11, 12, 13, 14, 15, 16, 17, 18, 19, 20 or more regions from those identified in Table 6. The genomic regions may comprise at least 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, or 830 regions from those identified in Table 6. The genomic regions may comprise at least 2 regions from those identified in Table 6. The genomic regions may comprise at least 20 regions from those identified in Table 6. The genomic regions may comprise at least 60 regions from those identified in Table 6. The genomic regions may comprise at least 100 regions from those identified in Table 6. The genomic regions may comprise at least 300 regions from those identified in Table 6. The genomic regions may comprise at least 600 regions from those identified in Table 6. The genomic regions may comprise at least 800 regions from those identified in Table 6.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 6. At least about 5% of the genomic regions may be regions identified in Table 6. At least about 10% of the genomic regions may be regions identified in Table 6. At least about 20% of the genomic regions may be regions identified in Table 6. At least about 30% of the genomic regions may be regions identified in Table 6. At least about 40% of the genomic regions may be regions identified in Table 6.

The genomic regions may comprise at least 2, 3, 4, 5, 6, 7, 8, 9, 10, 11, 12, 13, 14, 15, 16, 17, 18, 19, 20 or more regions from those identified in Table 7. The genomic regions may comprise at least 25, 30, 35, 40, 45, 50, 55, 60, 65, 70, 75, 80, 85, 90, 95, 100, 125, 150, 175, 200, 225, 250, 275, 300, 325, 350, 375, 400, 425, or 450 regions from those identified in Table 7. The genomic regions may comprise at least 2 regions from those identified in Table 7. The genomic regions may comprise at least 20 regions from those identified in Table 7. The genomic regions may comprise at least 60 regions from those identified in Table 7. The genomic regions may comprise at least 100 regions from those identified in Table 7. The genomic regions may comprise at least 200 regions from those identified in Table 7. The genomic regions may comprise at least 300 regions from those identified in Table 7. The genomic regions may comprise at least 400 regions from those identified in Table 7.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 7. At least about 5% of the genomic regions may be regions identified in Table 7. At least about 10% of the genomic regions may be regions identified in Table 7. At least about 20% of the genomic regions may be regions identified in Table 7. At least about 30% of the genomic regions may be regions identified in Table 7. At least about 40% of the genomic regions may be regions identified in Table 7.

The genomic regions may comprise at least 2, 3, 4, 5, 6, 7, 8, 9, 10, 11, 12, 13, 14, 15, 16, 17, 18, 19, 20 or more regions from those identified in Table 8. The genomic regions may comprise at least 25, 30, 35, 40, 45, 50, 55, 60, 65, 70, 75, 80, 85, 90, 95, 100 regions from those identified in Table 8. The genomic regions may comprise at least 250, 300, 350, 400, 450, 500, 550, 600, 650, 700, 750, 800, 850, 900, 950, 1000, or 1050 regions from those identified in Table 8. The genomic regions may comprise at least 2 regions from those identified in Table 8. The genomic regions may comprise at least 20 regions from those identified in Table 8. The genomic regions may comprise at least 60 regions from those identified in Table 8. The genomic regions may comprise at least 100 regions from those identified in Table 8. The genomic regions may comprise at least 300 regions from those identified in Table 8. The genomic regions may comprise at least 600 regions from those identified in Table 8. The genomic regions may comprise at least 800 regions from those identified in Table 8. The genomic regions may comprise at least 1000 regions from those identified in Table 8.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 8. At least about 5% of the genomic regions may be regions identified in Table 8. At least about 10% of the genomic regions may be regions identified in Table 8. At least about 20% of the genomic regions may be regions identified in Table 8. At least about 30% of the genomic regions may be regions identified in Table 8. At least about 40% of the genomic regions may be regions identified in Table 8.

The genomic regions may comprise at least 2, 3, 4, 5, 6, 7, 8, 9, 10, 11, 12, 13, 14, 15, 16, 17, 18, 19, 20 or more regions from those identified in Table 9. The genomic regions may comprise at least 25, 30, 35, 40, 45, 50, 55, 60, 65, 70, 75, 80, 85, 90, 95, 100 regions from those identified in Table 9. The genomic regions may comprise at least 250, 300, 350, 400, 450, 500, 550, 600, 650, 700, 750, 800, 850, 900, 950, 1000, 1100, 1200, 1300, 1400, or 1500 regions from those identified in Table 9. The genomic regions may comprise at least 2 regions from those identified in Table 9. The genomic regions may comprise at least 20 regions from those identified in Table 9. The genomic regions may comprise at least 60 regions from those identified in Table 9. The genomic regions may comprise at least 100 regions from those identified in Table 9. The genomic regions may comprise at least 300 regions from those identified in Table 9. The genomic regions may comprise at least 500 regions from those identified in Table 9. The genomic regions may comprise at least 1000 regions from those identified in Table 9. The genomic regions may comprise at least 1300 regions from those identified in Table 9.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 9. At least about 5% of the genomic regions may be regions identified in Table 9. At least about 10% of the genomic regions may be regions identified in Table 9. At least about 20% of the genomic regions may be regions identified in Table 9. At least about 30% of the genomic regions may be regions identified in Table 9. At least about 40% of the genomic regions may be regions identified in Table 9.

The genomic regions may comprise at least 2, 3, 4, 5, 6, 7, 8, 9, 10, 11, 12, 13, 14, 15, 16, 17, 18, 19, 20 or more regions from those identified in Table 10. The genomic regions may comprise at least 25, 30, 35, 40, 45, 50, 55, 60, 65, 70, 75, 80, 85, 90, 95, 100 regions from those identified in Table 10. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, or 330 regions from those identified in Table 10. The genomic regions may comprise at least 2 regions from those identified in Table 10. The genomic regions may comprise at least 20 regions from those identified in Table 10. The genomic regions may comprise at least 60 regions from those identified in Table 10.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 10. At least about 5% of the genomic regions may be regions identified in Table 10. At least about 10% of the genomic regions may be regions identified in Table 10. At least about 20% of the genomic regions may be regions identified in Table 10. At least about 30% of the genomic regions may be regions identified in Table 10. At least about 40% of the genomic regions may be regions identified in Table 10.

The genomic regions may comprise at least 2, 3, 4, 5, 6, 7, 8, 9, 10, 11, 12, 13, 14, 15, 16, 17, 18, 19, 20 or more regions from those identified in Table 11. The genomic regions may comprise at least 25, 30, 35, 40, 45, 50, 55, 60, 65, 70, 75, 80, 85, 90, 95, 100 regions from those identified in Table 11. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, or 460 regions from those identified in Table 11. The genomic regions may comprise at least 2 regions from those identified in Table 11. The genomic regions may comprise at least 20 regions from those identified in Table 11. The genomic regions may comprise at least 60 regions from those identified in Table 11. The genomic regions may comprise at least 100 regions from those identified in Table 11. The genomic regions may comprise at least 200 regions from those identified in Table 11. The genomic regions may comprise at least 300 regions from those identified in Table 11. The genomic regions may comprise at least 400 regions from those identified in Table 11.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 11. At least about 5% of the genomic regions may be regions identified in Table 11. At least about 10% of the genomic regions may be regions identified in Table 11. At least about 20% of the genomic regions may be regions identified in Table 11. At least about 30% of the genomic regions may be regions identified in Table 11. At least about 40% of the genomic regions may be regions identified in Table 11.

The genomic regions may comprise at least 2, 3, 4, 5, 6, 7, 8, 9, 10, 11, 12, 13, 14, 15, 16, 17, 18, 19, 20 or more regions from those identified in Table 12. The genomic regions may comprise at least 25, 30, 35, 40, 45, 50, 55, 60, 65, 70, 75, 80, 85, 90, 95, 100 regions from those identified in Table 12. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480 or 500 regions from those identified in Table 12. The genomic regions may comprise at least 2 regions from those identified in Table 12. The genomic regions may comprise at least 20 regions from those identified in Table 12. The genomic regions may comprise at least 60 regions from those identified in Table 12. The genomic regions may comprise at least 100 regions from those identified in Table 12. The genomic regions may comprise at least 200 regions from those identified in Table 12. The genomic regions may comprise at least 300 regions from those identified in Table 12. The genomic regions may comprise at least 400 regions from those identified in Table 12. The genomic regions may comprise at least 500 regions from those identified in Table 12.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 12. At least about 5% of the genomic regions may be regions identified in Table 12. At least about 10% of the genomic regions may be regions identified in Table 12. At least about 20% of the genomic regions may be regions identified in Table 12. At least about 30% of the genomic regions may be regions identified in Table 12. At least about 40% of the genomic regions may be regions identified in Table 12.

The genomic regions may comprise at least 2, 3, 4, 5, 6, 7, 8, 9, 10, 11, 12, 13, 14, 15, 16, 17, 18, 19, 20 or more regions from those identified in Table 13. The genomic regions may comprise at least 25, 30, 35, 40, 45, 50, 55, 60, 65, 70, 75, 80, 85, 90, 95, 100 regions from those identified in Table 13. The genomic regions may comprise at least 250, 300, 350, 400, 450, 500, 550, 600, 650, 700, 750, 800, 850, 900, 950, 1000, 1050, 1100, 1150, 1200, 1250, 1300, 1350, 1400, or 1450 regions from those identified in Table 13. The genomic regions may comprise at least 2 regions from those identified in Table 13. The genomic regions may comprise at least 20 regions from those identified in Table 13. The genomic regions may comprise at least 60 regions from those identified in Table 13. The genomic regions may comprise at least 100 regions from those identified in Table 13. The genomic regions may comprise at least 300 regions from those identified in Table 13. The genomic regions may comprise at least 500 regions from those identified in Table 13. The genomic regions may comprise at least 1000 regions from those identified in Table 13. The genomic regions may comprise at least 1300 regions from those identified in Table 13.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 13. At least about 5% of the genomic regions may be regions identified in Table 13. At least about 10% of the genomic regions may be regions identified in Table 13. At least about 20% of the genomic regions may be regions identified in Table 13. At least about 30% of the genomic regions may be regions identified in Table 13. At least about 40% of the genomic regions may be regions identified in Table 13.

The genomic regions may comprise at least 2, 3, 4, 5, 6, 7, 8, 9, 10, 11, 12, 13, 14, 15, 16, 17, 18, 19, 20 or more regions from those identified in Table 14. The genomic regions may comprise at least 25, 30, 35, 40, 45, 50, 55, 60, 65, 70, 75, 80, 85, 90, 95, 100 regions from those identified in Table 14. The genomic regions may comprise at least 250, 300, 350, 400, 450, 500, 550, 600, 650, 700, 750, 800, 850, 900, 950, 1000, 1050, 1100, 1150, 1200, 1210, 1220, 1230, or 1240 regions from those identified in Table 14. The genomic regions may comprise at least 2 regions from those identified in Table 14. The genomic regions may comprise at least 20 regions from those identified in Table 14. The genomic regions may comprise at least 60 regions from those identified in Table 14. The genomic regions may comprise at least 100 regions from those identified in Table 14. The genomic regions may comprise at least 300 regions from those identified in Table 14. The genomic regions may comprise at least 500 regions from those identified in Table 14. The genomic regions may comprise at least 1000 regions from those identified in Table 14. The genomic regions may comprise at least 1100 regions from those identified in Table 14. The genomic regions may comprise at least 1200 regions from those identified in Table 14.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 14. At least about 5% of the genomic regions may be regions identified in Table 14. At least about 10% of the genomic regions may be regions identified in Table 14. At least about 20% of the genomic regions may be regions identified in Table 14. At least about 30% of the genomic regions may be regions identified in Table 14. At least about 40% of the genomic regions may be regions identified in Table 14.

The genomic regions may comprise at least 2, 3, 4, 5, 6, 7, 8, 9, 10, 11, 12, 13, 14, 15, 16, 17, 18, 19, 20 or more regions from those identified in Table 15. The genomic regions may comprise at least 25, 30, 35, 40, 45, 50, 55, 60, 65, 70, 75, 80, 85, 90, 95, 100, 110, 120, 130, 140, 150, 160, or 170 regions from those identified in Table 15. The genomic regions may comprise at least 2 regions from those identified in Table 15. The genomic regions may comprise at least 20 regions from those identified in Table 15. The genomic regions may comprise at least 60 regions from those identified in Table 15. The genomic regions may comprise at least 100 regions from those identified in Table 15. The genomic regions may comprise at least 120 regions from those identified in Table 15. The genomic regions may comprise at least 150 regions from those identified in Table 15.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 15. At least about 5% of the genomic regions may be regions identified in Table 15. At least about 10% of the genomic regions may be regions identified in Table 15. At least about 20% of the genomic regions may be regions identified in Table 15. At least about 30% of the genomic regions may be regions identified in Table 15. At least about 40% of the genomic regions may be regions identified in Table 15.

The genomic regions may comprise at least 2, 3, 4, 5, 6, 7, 8, 9, 10, 11, 12, 13, 14, 15, 16, 17, 18, 19, 20 or more regions from those identified in Table 16. The genomic regions may comprise at least 25, 30, 35, 40, 45, 50, 55, 60, 65, 70, 75, 80, 85, 90, 95, 100 regions from those identified in Table 16. The genomic regions may comprise at least 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or 2050 regions from those identified in Table 16. The genomic regions may comprise at least 2 regions from those identified in Table 16. The genomic regions may comprise at least 20 regions from those identified in Table 16. The genomic regions may comprise at least 60 regions from those identified in Table 16. The genomic regions may comprise at least 100 regions from those identified in Table 16. The genomic regions may comprise at least 300 regions from those identified in Table 16. The genomic regions may comprise at least 500 regions from those identified in Table 16. The genomic regions may comprise at least 1000 regions from those identified in Table 16. The genomic regions may comprise at least 1200 regions from those identified in Table 16. The genomic regions may comprise at least 1500 regions from those identified in Table 16. The genomic regions may comprise at least 1700 regions from those identified in Table 16. The genomic regions may comprise at least 2000 regions from those identified in Table 16.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 16. At least about 5% of the genomic regions may be regions identified in Table 16. At least about 10% of the genomic regions may be regions identified in Table 16. At least about 20% of the genomic regions may be regions identified in Table 16. At least about 30% of the genomic regions may be regions identified in Table 16. At least about 40% of the genomic regions may be regions identified in Table 16.

The genomic regions may comprise at least 2, 3, 4, 5, 6, 7, 8, 9, 10, 11, 12, 13, 14, 15, 16, 17, 18, 19, 20 or more regions from those identified in Table 17. The genomic regions may comprise at least 25, 30, 35, 40, 45, 50, 55, 60, 65, 70, 75, 80, 85, 90, 95, 100 regions from those identified in Table 17. The genomic regions may comprise at least 250, 300, 350, 400, 450, 500, 550, 600, 650, 700, 750, 800, 850, 900, 950, 1000, 1010, 1020, 1030, 1040, 1050, 1060, 1070, or 1080 regions from those identified in Table 17. The genomic regions may comprise at least 2 regions from those identified in Table 17. The genomic regions may comprise at least 20 regions from those identified in Table 17. The genomic regions may comprise at least 60 regions from those identified in Table 17. The genomic regions may comprise at least 100 regions from those identified in Table 17. The genomic regions may comprise at least 300 regions from those identified in Table 17. The genomic regions may comprise at least 500 regions from those identified in Table 17. The genomic regions may comprise at least 1000 regions from those identified in Table 17. The genomic regions may comprise at least 1050 regions from those identified in Table 17.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 17. At least about 5% of the genomic regions may be regions identified in Table 17. At least about 10% of the genomic regions may be regions identified in Table 17. At least about 20% of the genomic regions may be regions identified in Table 17. At least about 30% of the genomic regions may be regions identified in Table 17. At least about 40% of the genomic regions may be regions identified in Table 17.

The genomic regions may comprise at least 2, 3, 4, 5, 6, 7, 8, 9, 10, 11, 12, 13, 14, 15, 16, 17, 18, 19, 20 or more regions from those identified in Table 18. The genomic regions may comprise at least 25, 30, 35, 40, 45, 50, 55, 60, 65, 70, 75, 80, 85, 90, 95, 100 regions from those identified in Table 18. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480, 500, 520, 540, or 555 regions from those identified in Table 18. The genomic regions may comprise at least 2 regions from those identified in Table 18. The genomic regions may comprise at least 20 regions from those identified in Table 18. The genomic regions may comprise at least 60 regions from those identified in Table 18. The genomic regions may comprise at least 100 regions from those identified in Table 18. The genomic regions may comprise at least 200 regions from those identified in Table 18. The genomic regions may comprise at least 300 regions from those identified in Table 18. The genomic regions may comprise at least 400 regions from those identified in Table 18. The genomic regions may comprise at least 500 regions from those identified in Table 18.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 18. At least about 5% of the genomic regions may be regions identified in Table 18. At least about 10% of the genomic regions may be regions identified in Table 18. At least about 20% of the genomic regions may be regions identified in Table 18. At least about 30% of the genomic regions may be regions identified in Table 18. At least about 40% of the genomic regions may be regions identified in Table 18.

The set of oligonucleotides may hybridize to less than 1.5, 1.45, 1.4, 1.35, 1.3, 1.25, 1.2, 1.15, 1.1, 1.05, or 1.0 Megabases (Mb) of the genome. The set of oligonucleotides may hybridize to less than 1000, 900, 800, 700, 600, 550, 500, 450, 400, 350, 300, 250, 200, 150, or 100 kb of the genome. The set of oligonucleotides may hybridize to less than 1.5 Megabases (Mb) of the genome. The set of oligonucleotides may hybridize to less than 1.25 Megabases (Mb) of the genome. The set of oligonucleotides may hybridize to less than 1 Megabases (Mb) of the genome. The set of oligonucleotides may hybridize to less than 1000 kb of the genome. The set of oligonucleotides may hybridize to less than 500 kb of the genome. The set of oligonucleotides may hybridize to less than 300 kb of the genome. The set of oligonucleotides may hybridize to less than 100 kb of the genome. The set of oligonucleotides may be capable of hybridizing to greater than 50 kb of the genome.

The set of oligonucleotides may be capable of hybridizing to 5, 10, 15, 20, 25, 30, 35, 40, 45, 50, 60, 70, 80, 90, 100, 150, 200, 250, 300, 350, 400, 450, or 500 or more different genomic regions. The set of oligonucleotides may be capable of hybridizing to 5 or more different genomic regions. The set of oligonucleotides may be capable of hybridizing to 20 or more different genomic regions. The set of oligonucleotides may be capable of hybridizing to 50 or more different genomic regions. The set of oligonucleotides may be capable of hybridizing to 100 or more different genomic regions.

The plurality of genomic regions may comprise 2, 3, 4, 5, 6, 7, 8, 9, 10, 15, 20, 25, 30, 35, 40, 45, 50, 60, 70, 80, 90, 100 or more different protein-coding regions. The protein-coding regions may comprise an exon, intron, untranslated region, or a combination thereof.

The plurality of genomic regions may comprise 2, 3, 4, 5, 6, 7, 8, 9, 10, 15, 20, 25, 30, 35, 40, 45, 50, 60, 70, 80, 90, 100 or more different non-coding regions. The non-coding regions may comprise a non-coding RNA, ribosomal RNA (rRNA), transfer RNA (tRNA), or a combination thereof.

The oligonucleotides may be attached to a solid support. The solid support may be a bead. The bead may be a coated bead. The bead may be a streptavidin bead. The solid support may be an array. The solid support may be a glass slide.

Disclosed herein are populations of circulating tumor DNA (ctDNA) for use in any of the methods or systems disclosed herein. A population of circulating tumor DNA (ctDNA) may comprise ctDNA enriched by hybrid selection using any of the compositions comprising the set of oligonucleotides disclosed herein. A population of ctDNA may comprise ctDNA enriched by selective hybridization of the ctDNA using the set of oligonucleotides based on the selector sets disclosed herein. A population of ctDNA may comprise ctDNA enriched by selective hybridization using a set of oligonucleotides based on any of Tables 2 and 6-18.

Further disclosed herein are arrays for use in any of the methods and systems disclosed herein. The array may comprise a plurality of oligonucleotides to selectively capture genomic regions, wherein the genomic regions may comprise a plurality of mutations present in greater 60% of a population of subjects suffering from a cancer.

The plurality of mutations may be present in greater 60% of an additional population of subjects suffering from an additional type of cancer. The plurality of mutations may be present in greater 60% of an additional population of subjects suffering from two or more additional types of cancer. The plurality of mutations may be present in greater 60% of an additional population of subjects suffering from three or more additional types of cancer. The plurality of mutations may be present in greater 60% of an additional population of subjects suffering from four or more additional types of cancer.

An oligonucleotide of the set of oligonucleotides may comprise a tag. The tag may be biotin. The tag may comprise a label. The label may be a fluorescent label or dye. The tag may be an adaptor. The adaptor may comprise a molecular barcode. The adaptor may comprise a sample index.

The genomic regions may comprise at least 2, 3, 4, 5, 6, 7, 8, 9, 10, 11, 12, 13, 14, 15, 16, 17, 18, 19, 20 or more regions from those identified in Table 2. The genomic regions may comprise at least 25, 30, 35, 40, 45, 50, 55, 60, 65, 70, 75, 80, 85, 90, 95, 100, 150, 200, 250, 300, 350, 400, 450, 500, or 525 regions from those identified in Table 2. The genomic regions may comprise at least 2 regions from those identified in Table 2. The genomic regions may comprise at least 20 regions from those identified in Table 2. The genomic regions may comprise at least 60 regions from those identified in Table 2. The genomic regions may comprise at least 100 regions from those identified in Table 2. The genomic regions may comprise at least 300 regions from those identified in Table 2. The genomic regions may comprise at least 400 regions from those identified in Table 2. The genomic regions may comprise at least 500 regions from those identified in Table 2.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 2. At least about 5% of the genomic regions may be regions identified in Table 2. At least about 10% of the genomic regions may be regions identified in Table 2. At least about 20% of the genomic regions may be regions identified in Table 2. At least about 30% of the genomic regions may be regions identified in Table 2. At least about 40% of the genomic regions may be regions identified in Table 2.

The genomic regions may comprise at least 2, 3, 4, 5, 6, 7, 8, 9, 10, 11, 12, 13, 14, 15, 16, 17, 18, 19, 20 or more regions from those identified in Table 6. The genomic regions may comprise at least 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, or 830 regions from those identified in Table 6. The genomic regions may comprise at least 2 regions from those identified in Table 6. The genomic regions may comprise at least 20 regions from those identified in Table 6. The genomic regions may comprise at least 60 regions from those identified in Table 6. The genomic regions may comprise at least 100 regions from those identified in Table 6. The genomic regions may comprise at least 300 regions from those identified in Table 6. The genomic regions may comprise at least 600 regions from those identified in Table 6. The genomic regions may comprise at least 800 regions from those identified in Table 6.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 6. At least about 5% of the genomic regions may be regions identified in Table 6. At least about 10% of the genomic regions may be regions identified in Table 6. At least about 20% of the genomic regions may be regions identified in Table 6. At least about 30% of the genomic regions may be regions identified in Table 6. At least about 40% of the genomic regions may be regions identified in Table 6.

The genomic regions may comprise at least 2, 3, 4, 5, 6, 7, 8, 9, 10, 11, 12, 13, 14, 15, 16, 17, 18, 19, 20 or more regions from those identified in Table 7. The genomic regions may comprise at least 25, 30, 35, 40, 45, 50, 55, 60, 65, 70, 75, 80, 85, 90, 95, 100, 125, 150, 175, 200, 225, 250, 275, 300, 325, 350, 375, 400, 425, or 450 regions from those identified in Table 7. The genomic regions may comprise at least 2 regions from those identified in Table 7. The genomic regions may comprise at least 20 regions from those identified in Table 7. The genomic regions may comprise at least 60 regions from those identified in Table 7. The genomic regions may comprise at least 100 regions from those identified in Table 7. The genomic regions may comprise at least 200 regions from those identified in Table 7. The genomic regions may comprise at least 300 regions from those identified in Table 7. The genomic regions may comprise at least 400 regions from those identified in Table 7.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 7. At least about 5% of the genomic regions may be regions identified in Table 7. At least about 10% of the genomic regions may be regions identified in Table 7. At least about 20% of the genomic regions may be regions identified in Table 7. At least about 30% of the genomic regions may be regions identified in Table 7. At least about 40% of the genomic regions may be regions identified in Table 7.

The genomic regions may comprise at least 2, 3, 4, 5, 6, 7, 8, 9, 10, 11, 12, 13, 14, 15, 16, 17, 18, 19, 20 or more regions from those identified in Table 8. The genomic regions may comprise at least 25, 30, 35, 40, 45, 50, 55, 60, 65, 70, 75, 80, 85, 90, 95, 100 regions from those identified in Table 8. The genomic regions may comprise at least 250, 300, 350, 400, 450, 500, 550, 600, 650, 700, 750, 800, 850, 900, 950, 1000, or 1050 regions from those identified in Table 8. The genomic regions may comprise at least 2 regions from those identified in Table 8. The genomic regions may comprise at least 20 regions from those identified in Table 8. The genomic regions may comprise at least 60 regions from those identified in Table 8. The genomic regions may comprise at least 100 regions from those identified in Table 8. The genomic regions may comprise at least 300 regions from those identified in Table 8. The genomic regions may comprise at least 600 regions from those identified in Table 8. The genomic regions may comprise at least 800 regions from those identified in Table 8. The genomic regions may comprise at least 1000 regions from those identified in Table 8.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 8. At least about 5% of the genomic regions may be regions identified in Table 8. At least about 10% of the genomic regions may be regions identified in Table 8. At least about 20% of the genomic regions may be regions identified in Table 8. At least about 30% of the genomic regions may be regions identified in Table 8. At least about 40% of the genomic regions may be regions identified in Table 8.

The genomic regions may comprise at least 2, 3, 4, 5, 6, 7, 8, 9, 10, 11, 12, 13, 14, 15, 16, 17, 18, 19, 20 or more regions from those identified in Table 9. The genomic regions may comprise at least 25, 30, 35, 40, 45, 50, 55, 60, 65, 70, 75, 80, 85, 90, 95, 100 regions from those identified in Table 9. The genomic regions may comprise at least 250, 300, 350, 400, 450, 500, 550, 600, 650, 700, 750, 800, 850, 900, 950, 1000, 1100, 1200, 1300, 1400, or 1500 regions from those identified in Table 9. The genomic regions may comprise at least 2 regions from those identified in Table 9. The genomic regions may comprise at least 20 regions from those identified in Table 9. The genomic regions may comprise at least 60 regions from those identified in Table 9. The genomic regions may comprise at least 100 regions from those identified in Table 9. The genomic regions may comprise at least 300 regions from those identified in Table 9. The genomic regions may comprise at least 500 regions from those identified in Table 9. The genomic regions may comprise at least 1000 regions from those identified in Table 9. The genomic regions may comprise at least 1300 regions from those identified in Table 9.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 9. At least about 5% of the genomic regions may be regions identified in Table 9. At least about 10% of the genomic regions may be regions identified in Table 9. At least about 20% of the genomic regions may be regions identified in Table 9. At least about 30% of the genomic regions may be regions identified in Table 9. At least about 40% of the genomic regions may be regions identified in Table 9.

The genomic regions may comprise at least 2, 3, 4, 5, 6, 7, 8, 9, 10, 11, 12, 13, 14, 15, 16, 17, 18, 19, 20 or more regions from those identified in Table 10. The genomic regions may comprise at least 25, 30, 35, 40, 45, 50, 55, 60, 65, 70, 75, 80, 85, 90, 95, 100 regions from those identified in Table 10. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, or 330 regions from those identified in Table 10. The genomic regions may comprise at least 2 regions from those identified in Table 10. The genomic regions may comprise at least 20 regions from those identified in Table 10. The genomic regions may comprise at least 60 regions from those identified in Table 10.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 10. At least about 5% of the genomic regions may be regions identified in Table 10. At least about 10% of the genomic regions may be regions identified in Table 10. At least about 20% of the genomic regions may be regions identified in Table 10. At least about 30% of the genomic regions may be regions identified in Table 10. At least about 40% of the genomic regions may be regions identified in Table 10.

The genomic regions may comprise at least 2, 3, 4, 5, 6, 7, 8, 9, 10, 11, 12, 13, 14, 15, 16, 17, 18, 19, 20 or more regions from those identified in Table 11. The genomic regions may comprise at least 25, 30, 35, 40, 45, 50, 55, 60, 65, 70, 75, 80, 85, 90, 95, 100 regions from those identified in Table 11. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, or 460 regions from those identified in Table 11. The genomic regions may comprise at least 2 regions from those identified in Table 11. The genomic regions may comprise at least 20 regions from those identified in Table 11. The genomic regions may comprise at least 60 regions from those identified in Table 11. The genomic regions may comprise at least 100 regions from those identified in Table 11. The genomic regions may comprise at least 200 regions from those identified in Table 11. The genomic regions may comprise at least 300 regions from those identified in Table 11. The genomic regions may comprise at least 400 regions from those identified in Table 11.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 11. At least about 5% of the genomic regions may be regions identified in Table 11. At least about 10% of the genomic regions may be regions identified in Table 11. At least about 20% of the genomic regions may be regions identified in Table 11. At least about 30% of the genomic regions may be regions identified in Table 11. At least about 40% of the genomic regions may be regions identified in Table 11.

The genomic regions may comprise at least 2, 3, 4, 5, 6, 7, 8, 9, 10, 11, 12, 13, 14, 15, 16, 17, 18, 19, 20 or more regions from those identified in Table 12. The genomic regions may comprise at least 25, 30, 35, 40, 45, 50, 55, 60, 65, 70, 75, 80, 85, 90, 95, 100 regions from those identified in Table 12. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480 or 500 regions from those identified in Table 12. The genomic regions may comprise at least 2 regions from those identified in Table 12. The genomic regions may comprise at least 20 regions from those identified in Table 12. The genomic regions may comprise at least 60 regions from those identified in Table 12. The genomic regions may comprise at least 100 regions from those identified in Table 12. The genomic regions may comprise at least 200 regions from those identified in Table 12. The genomic regions may comprise at least 300 regions from those identified in Table 12. The genomic regions may comprise at least 400 regions from those identified in Table 12. The genomic regions may comprise at least 500 regions from those identified in Table 12.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 12. At least about 5% of the genomic regions may be regions identified in Table 12. At least about 10% of the genomic regions may be regions identified in Table 12. At least about 20% of the genomic regions may be regions identified in Table 12. At least about 30% of the genomic regions may be regions identified in Table 12. At least about 40% of the genomic regions may be regions identified in Table 12.

The genomic regions may comprise at least 2, 3, 4, 5, 6, 7, 8, 9, 10, 11, 12, 13, 14, 15, 16, 17, 18, 19, 20 or more regions from those identified in Table 13. The genomic regions may comprise at least 25, 30, 35, 40, 45, 50, 55, 60, 65, 70, 75, 80, 85, 90, 95, 100 regions from those identified in Table 13. The genomic regions may comprise at least 250, 300, 350, 400, 450, 500, 550, 600, 650, 700, 750, 800, 850, 900, 950, 1000, 1050, 1100, 1150, 1200, 1250, 1300, 1350, 1400, or 1450 regions from those identified in Table 13. The genomic regions may comprise at least 2 regions from those identified in Table 13. The genomic regions may comprise at least 20 regions from those identified in Table 13. The genomic regions may comprise at least 60 regions from those identified in Table 13. The genomic regions may comprise at least 100 regions from those identified in Table 13. The genomic regions may comprise at least 300 regions from those identified in Table 13. The genomic regions may comprise at least 500 regions from those identified in Table 13. The genomic regions may comprise at least 1000 regions from those identified in Table 13. The genomic regions may comprise at least 1300 regions from those identified in Table 13.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 13. At least about 5% of the genomic regions may be regions identified in Table 13. At least about 10% of the genomic regions may be regions identified in Table 13. At least about 20% of the genomic regions may be regions identified in Table 13. At least about 30% of the genomic regions may be regions identified in Table 13. At least about 40% of the genomic regions may be regions identified in Table 13.

The genomic regions may comprise at least 2, 3, 4, 5, 6, 7, 8, 9, 10, 11, 12, 13, 14, 15, 16, 17, 18, 19, 20 or more regions from those identified in Table 14. The genomic regions may comprise at least 25, 30, 35, 40, 45, 50, 55, 60, 65, 70, 75, 80, 85, 90, 95, 100 regions from those identified in Table 14. The genomic regions may comprise at least 250, 300, 350, 400, 450, 500, 550, 600, 650, 700, 750, 800, 850, 900, 950, 1000, 1050, 1100, 1150, 1200, 1210, 1220, 1230, or 1240 regions from those identified in Table 14. The genomic regions may comprise at least 2 regions from those identified in Table 14. The genomic regions may comprise at least 20 regions from those identified in Table 14. The genomic regions may comprise at least 60 regions from those identified in Table 14. The genomic regions may comprise at least 100 regions from those identified in Table 14. The genomic regions may comprise at least 300 regions from those identified in Table 14. The genomic regions may comprise at least 500 regions from those identified in Table 14. The genomic regions may comprise at least 1000 regions from those identified in Table 14. The genomic regions may comprise at least 1100 regions from those identified in Table 14. The genomic regions may comprise at least 1200 regions from those identified in Table 14.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 14. At least about 5% of the genomic regions may be regions identified in Table 14. At least about 10% of the genomic regions may be regions identified in Table 14. At least about 20% of the genomic regions may be regions identified in Table 14. At least about 30% of the genomic regions may be regions identified in Table 14. At least about 40% of the genomic regions may be regions identified in Table 14.

The genomic regions may comprise at least 2, 3, 4, 5, 6, 7, 8, 9, 10, 11, 12, 13, 14, 15, 16, 17, 18, 19, 20 or more regions from those identified in Table 15. The genomic regions may comprise at least 25, 30, 35, 40, 45, 50, 55, 60, 65, 70, 75, 80, 85, 90, 95, 100, 110, 120, 130, 140, 150, 160, or 170 regions from those identified in Table 15. The genomic regions may comprise at least 2 regions from those identified in Table 15. The genomic regions may comprise at least 20 regions from those identified in Table 15. The genomic regions may comprise at least 60 regions from those identified in Table 15. The genomic regions may comprise at least 100 regions from those identified in Table 15. The genomic regions may comprise at least 120 regions from those identified in Table 15. The genomic regions may comprise at least 150 regions from those identified in Table 15.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 15. At least about 5% of the genomic regions may be regions identified in Table 15. At least about 10% of the genomic regions may be regions identified in Table 15. At least about 20% of the genomic regions may be regions identified in Table 15. At least about 30% of the genomic regions may be regions identified in Table 15. At least about 40% of the genomic regions may be regions identified in Table 15.

The genomic regions may comprise at least 2, 3, 4, 5, 6, 7, 8, 9, 10, 11, 12, 13, 14, 15, 16, 17, 18, 19, 20 or more regions from those identified in Table 16. The genomic regions may comprise at least 25, 30, 35, 40, 45, 50, 55, 60, 65, 70, 75, 80, 85, 90, 95, 100 regions from those identified in Table 16. The genomic regions may comprise at least 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or 2050 regions from those identified in Table 16. The genomic regions may comprise at least 2 regions from those identified in Table 16. The genomic regions may comprise at least 20 regions from those identified in Table 16. The genomic regions may comprise at least 60 regions from those identified in Table 16. The genomic regions may comprise at least 100 regions from those identified in Table 16. The genomic regions may comprise at least 300 regions from those identified in Table 16. The genomic regions may comprise at least 500 regions from those identified in Table 16. The genomic regions may comprise at least 1000 regions from those identified in Table 16. The genomic regions may comprise at least 1200 regions from those identified in Table 16. The genomic regions may comprise at least 1500 regions from those identified in Table 16. The genomic regions may comprise at least 1700 regions from those identified in Table 16. The genomic regions may comprise at least 2000 regions from those identified in Table 16.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 16. At least about 5% of the genomic regions may be regions identified in Table 16. At least about 10% of the genomic regions may be regions identified in Table 16. At least about 20% of the genomic regions may be regions identified in Table 16. At least about 30% of the genomic regions may be regions identified in Table 16. At least about 40% of the genomic regions may be regions identified in Table 16.

The genomic regions may comprise at least 2, 3, 4, 5, 6, 7, 8, 9, 10, 11, 12, 13, 14, 15, 16, 17, 18, 19, 20 or more regions from those identified in Table 17. The genomic regions may comprise at least 25, 30, 35, 40, 45, 50, 55, 60, 65, 70, 75, 80, 85, 90, 95, 100 regions from those identified in Table 17. The genomic regions may comprise at least 250, 300, 350, 400, 450, 500, 550, 600, 650, 700, 750, 800, 850, 900, 950, 1000, 1010, 1020, 1030, 1040, 1050, 1060, 1070, or 1080 regions from those identified in Table 17. The genomic regions may comprise at least 2 regions from those identified in Table 17. The genomic regions may comprise at least 20 regions from those identified in Table 17. The genomic regions may comprise at least 60 regions from those identified in Table 17. The genomic regions may comprise at least 100 regions from those identified in Table 17. The genomic regions may comprise at least 300 regions from those identified in Table 17. The genomic regions may comprise at least 500 regions from those identified in Table 17. The genomic regions may comprise at least 1000 regions from those identified in Table 17. The genomic regions may comprise at least 1050 regions from those identified in Table 17.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 17. At least about 5% of the genomic regions may be regions identified in Table 17. At least about 10% of the genomic regions may be regions identified in Table 17. At least about 20% of the genomic regions may be regions identified in Table 17. At least about 30% of the genomic regions may be regions identified in Table 17. At least about 40% of the genomic regions may be regions identified in Table 17.

The genomic regions may comprise at least 2, 3, 4, 5, 6, 7, 8, 9, 10, 11, 12, 13, 14, 15, 16, 17, 18, 19, 20 or more regions from those identified in Table 18. The genomic regions may comprise at least 25, 30, 35, 40, 45, 50, 55, 60, 65, 70, 75, 80, 85, 90, 95, 100 regions from those identified in Table 18. The genomic regions may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480, 500, 520, 540, or 555 regions from those identified in Table 18. The genomic regions may comprise at least 2 regions from those identified in Table 18. The genomic regions may comprise at least 20 regions from those identified in Table 18. The genomic regions may comprise at least 60 regions from those identified in Table 18. The genomic regions may comprise at least 100 regions from those identified in Table 18. The genomic regions may comprise at least 200 regions from those identified in Table 18. The genomic regions may comprise at least 300 regions from those identified in Table 18. The genomic regions may comprise at least 400 regions from those identified in Table 18. The genomic regions may comprise at least 500 regions from those identified in Table 18.

At least about 5%, 10%, 15%, 20%, 25%, 30%, 35%, 40%, 45%, 50%, 55%, 60%, 65%, 70%, 75%, 80%, 85%, 90%, or 95% of the genomic regions may be regions identified in Table 18. At least about 5% of the genomic regions may be regions identified in Table 18. At least about 10% of the genomic regions may be regions identified in Table 18. At least about 20% of the genomic regions may be regions identified in Table 18. At least about 30% of the genomic regions may be regions identified in Table 18. At least about 40% of the genomic regions may be regions identified in Table 18.

The oligonucleotides may selectively capture 5, 10, 15, 20, 25, or 30 or more different genomic regions.

The oligonucleotides may hybridize to less than 1.5, 1.47, 1.45, 1.42, 1.40, 1.37, 1.35, 1.32, 1.30, 1.27, 1.25, 1.22, 1.20, 1.17, 1.15, 1.12, 1.10, 1.07, 1.05, 1.02, or 1.0 Megabases (Mb) of the genome. The oligonucleotides may hybridize to less than 1000, 900, 800, 700, 600, 500, 400, 300, 200, 100, 90, 80, 70, 60, 50, 40, 30, 20, or 10 kb of the genome.

The oligonucleotides may be capable of hybridizing to greater than 1, 2, 3, 4, 5, 6, 7, 8, 9, 10, 15, 20, 25, 30, 35, 40, 45, or 50 kb of the genome. The oligonucleotides may be capable of hybridizing to greater than 5 kb of the genome. The oligonucleotides may be capable of hybridizing to greater than 10 kb of the genome. The oligonucleotides may be capable of hybridizing to greater than 30 kb of the genome. The oligonucleotides may be capable of hybridizing to greater than 50 kb of the genome.

The plurality of genomic regions may comprise 2 or more different protein-coding regions. The plurality of genomic regions may comprise at least 3 different protein-coding regions. The protein-coding regions may comprise an exon, intron, untranslated region, or a combination thereof.

The plurality of genomic regions may comprise at least one non-coding region. The non-coding region may comprise a non-coding RNA, ribosomal RNA (rRNA), transfer RNA (tRNA), or a combination thereof.

Further disclosed herein are methods of determining a quantity of circulating tumor DNA (ctDNA). The method may comprise (a) ligating one or more adaptors to cell-free DNA (cfDNA) derived from a sample from a subject to produce one or more adaptor-ligated cfDNA; (b) performing sequencing on the one or more adaptor-ligated cfDNA, wherein the adaptor-ligated cfDNA to be sequenced are based on a selector set comprising a plurality of genomic regions; and (c) using a computer readable medium to determine a quantity of cfDNA originating from a tumor based on the sequencing information obtained from the adaptor-ligated cfDNA.

In some instances, sequencing does not comprise whole genome sequencing. In some instances, sequencing does not comprise whole exome sequencing. Sequencing may comprise massively parallel sequencing.

The genomic regions of the selector set may comprise at least 2, 3, 4, 5, 6, 7, 8, 9, 10, 11, 12, 13, 14, 15, 16, 17, 18, 19, 20 or more regions from those identified in Table 2. The genomic regions of the selector set may comprise at least 25, 30, 35, 40, 45, 50, 55, 60, 65, 70, 75, 80, 85, 90, 95, 100, 150, 200, 250, 300, 350, 400, 450, 500, or 525 regions from those identified in Table 2. The genomic regions of the selector set may comprise at least 2 regions from those identified in Table 2. The genomic regions of the selector set may comprise at least 20 regions from those identified in Table 2. The genomic regions of the selector set may comprise at least 60 regions from those identified in Table 2. The genomic regions of the selector set may comprise at least 100 regions from those identified in Table 2. The genomic regions of the selector set may comprise at least 300 regions from those identified in Table 2. The genomic regions of the selector set may comprise at least 400 regions from those identified in Table 2. The genomic regions of the selector set may comprise at least 500 regions from those identified in Table 2.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 2. At least about 5% of the genomic regions of the selector set may be regions identified in Table 2. At least about 10% of the genomic regions of the selector set may be regions identified in Table 2. At least about 20% of the genomic regions of the selector set may be regions identified in Table 2. At least about 30% of the genomic regions of the selector set may be regions identified in Table 2. At least about 40% of the genomic regions of the selector set may be regions identified in Table 2.

The genomic regions of the selector set may comprise at least 2, 3, 4, 5, 6, 7, 8, 9, 10, 11, 12, 13, 14, 15, 16, 17, 18, 19, 20 or more regions from those identified in Table 6. The genomic regions of the selector set may comprise at least 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, or 830 regions from those identified in Table 6. The genomic regions of the selector set may comprise at least 2 regions from those identified in Table 6. The genomic regions of the selector set may comprise at least 20 regions from those identified in Table 6. The genomic regions of the selector set may comprise at least 60 regions from those identified in Table 6. The genomic regions of the selector set may comprise at least 100 regions from those identified in Table 6. The genomic regions of the selector set may comprise at least 300 regions from those identified in Table 6. The genomic regions of the selector set may comprise at least 600 regions from those identified in Table 6. The genomic regions of the selector set may comprise at least 800 regions from those identified in Table 6.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 6. At least about 5% of the genomic regions of the selector set may be regions identified in Table 6. At least about 10% of the genomic regions of the selector set may be regions identified in Table 6. At least about 20% of the genomic regions of the selector set may be regions identified in Table 6. At least about 30% of the genomic regions of the selector set may be regions identified in Table 6. At least about 40% of the genomic regions of the selector set may be regions identified in Table 6.

The genomic regions of the selector set may comprise at least 2, 3, 4, 5, 6, 7, 8, 9, 10, 11, 12, 13, 14, 15, 16, 17, 18, 19, 20 or more regions from those identified in Table 7. The genomic regions of the selector set may comprise at least 25, 30, 35, 40, 45, 50, 55, 60, 65, 70, 75, 80, 85, 90, 95, 100, 125, 150, 175, 200, 225, 250, 275, 300, 325, 350, 375, 400, 425, or 450 regions from those identified in Table 7. The genomic regions of the selector set may comprise at least 2 regions from those identified in Table 7. The genomic regions of the selector set may comprise at least 20 regions from those identified in Table 7. The genomic regions of the selector set may comprise at least 60 regions from those identified in Table 7. The genomic regions of the selector set may comprise at least 100 regions from those identified in Table 7. The genomic regions of the selector set may comprise at least 200 regions from those identified in Table 7. The genomic regions of the selector set may comprise at least 300 regions from those identified in Table 7. The genomic regions of the selector set may comprise at least 400 regions from those identified in Table 7.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 7. At least about 5% of the genomic regions of the selector set may be regions identified in Table 7. At least about 10% of the genomic regions of the selector set may be regions identified in Table 7. At least about 20% of the genomic regions of the selector set may be regions identified in Table 7. At least about 30% of the genomic regions of the selector set may be regions identified in Table 7. At least about 40% of the genomic regions of the selector set may be regions identified in Table 7.

The genomic regions of the selector set may comprise at least 2, 3, 4, 5, 6, 7, 8, 9, 10, 11, 12, 13, 14, 15, 16, 17, 18, 19, 20 or more regions from those identified in Table 8. The genomic regions of the selector set may comprise at least 25, 30, 35, 40, 45, 50, 55, 60, 65, 70, 75, 80, 85, 90, 95, 100 regions from those identified in Table 8. The genomic regions of the selector set may comprise at least 250, 300, 350, 400, 450, 500, 550, 600, 650, 700, 750, 800, 850, 900, 950, 1000, or 1050 regions from those identified in Table 8. The genomic regions of the selector set may comprise at least 2 regions from those identified in Table 8. The genomic regions of the selector set may comprise at least 20 regions from those identified in Table 8. The genomic regions of the selector set may comprise at least 60 regions from those identified in Table 8. The genomic regions of the selector set may comprise at least 100 regions from those identified in Table 8. The genomic regions of the selector set may comprise at least 300 regions from those identified in Table 8. The genomic regions of the selector set may comprise at least 600 regions from those identified in Table 8. The genomic regions of the selector set may comprise at least 800 regions from those identified in Table 8. The genomic regions of the selector set may comprise at least 1000 regions from those identified in Table 8.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 8. At least about 5% of the genomic regions of the selector set may be regions identified in Table 8. At least about 10% of the genomic regions of the selector set may be regions identified in Table 8. At least about 20% of the genomic regions of the selector set may be regions identified in Table 8. At least about 30% of the genomic regions of the selector set may be regions identified in Table 8. At least about 40% of the genomic regions of the selector set may be regions identified in Table 8.

The genomic regions of the selector set may comprise at least 2, 3, 4, 5, 6, 7, 8, 9, 10, 11, 12, 13, 14, 15, 16, 17, 18, 19, 20 or more regions from those identified in Table 9. The genomic regions of the selector set may comprise at least 25, 30, 35, 40, 45, 50, 55, 60, 65, 70, 75, 80, 85, 90, 95, 100 regions from those identified in Table 9. The genomic regions of the selector set may comprise at least 250, 300, 350, 400, 450, 500, 550, 600, 650, 700, 750, 800, 850, 900, 950, 1000, 1100, 1200, 1300, 1400, or 1500 regions from those identified in Table 9. The genomic regions of the selector set may comprise at least 2 regions from those identified in Table 9. The genomic regions of the selector set may comprise at least 20 regions from those identified in Table 9. The genomic regions of the selector set may comprise at least 60 regions from those identified in Table 9. The genomic regions of the selector set may comprise at least 100 regions from those identified in Table 9. The genomic regions of the selector set may comprise at least 300 regions from those identified in Table 9. The genomic regions of the selector set may comprise at least 500 regions from those identified in Table 9. The genomic regions of the selector set may comprise at least 1000 regions from those identified in Table 9. The genomic regions of the selector set may comprise at least 1300 regions from those identified in Table 9.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 9. At least about 5% of the genomic regions of the selector set may be regions identified in Table 9. At least about 10% of the genomic regions of the selector set may be regions identified in Table 9. At least about 20% of the genomic regions of the selector set may be regions identified in Table 9. At least about 30% of the genomic regions of the selector set may be regions identified in Table 9. At least about 40% of the genomic regions of the selector set may be regions identified in Table 9.

The genomic regions of the selector set may comprise at least 2, 3, 4, 5, 6, 7, 8, 9, 10, 11, 12, 13, 14, 15, 16, 17, 18, 19, 20 or more regions from those identified in Table 10. The genomic regions of the selector set may comprise at least 25, 30, 35, 40, 45, 50, 55, 60, 65, 70, 75, 80, 85, 90, 95, 100 regions from those identified in Table 10. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, or 330 regions from those identified in Table 10. The genomic regions of the selector set may comprise at least 2 regions from those identified in Table 10. The genomic regions of the selector set may comprise at least 20 regions from those identified in Table 10. The genomic regions of the selector set may comprise at least 60 regions from those identified in Table 10.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 10. At least about 5% of the genomic regions of the selector set may be regions identified in Table 10. At least about 10% of the genomic regions of the selector set may be regions identified in Table 10. At least about 20% of the genomic regions of the selector set may be regions identified in Table 10. At least about 30% of the genomic regions of the selector set may be regions identified in Table 10. At least about 40% of the genomic regions of the selector set may be regions identified in Table 10.

The genomic regions of the selector set may comprise at least 2, 3, 4, 5, 6, 7, 8, 9, 10, 11, 12, 13, 14, 15, 16, 17, 18, 19, 20 or more regions from those identified in Table 11. The genomic regions of the selector set may comprise at least 25, 30, 35, 40, 45, 50, 55, 60, 65, 70, 75, 80, 85, 90, 95, 100 regions from those identified in Table 11. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, or 460 regions from those identified in Table 11. The genomic regions of the selector set may comprise at least 2 regions from those identified in Table 11. The genomic regions of the selector set may comprise at least 20 regions from those identified in Table 11. The genomic regions of the selector set may comprise at least 60 regions from those identified in Table 11. The genomic regions of the selector set may comprise at least 100 regions from those identified in Table 11. The genomic regions of the selector set may comprise at least 200 regions from those identified in Table 11. The genomic regions of the selector set may comprise at least 300 regions from those identified in Table 11. The genomic regions of the selector set may comprise at least 400 regions from those identified in Table 11.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 11. At least about 5% of the genomic regions of the selector set may be regions identified in Table 11. At least about 10% of the genomic regions of the selector set may be regions identified in Table 11. At least about 20% of the genomic regions of the selector set may be regions identified in Table 11. At least about 30% of the genomic regions of the selector set may be regions identified in Table 11. At least about 40% of the genomic regions of the selector set may be regions identified in Table 11.

The genomic regions of the selector set may comprise at least 2, 3, 4, 5, 6, 7, 8, 9, 10, 11, 12, 13, 14, 15, 16, 17, 18, 19, 20 or more regions from those identified in Table 12. The genomic regions of the selector set may comprise at least 25, 30, 35, 40, 45, 50, 55, 60, 65, 70, 75, 80, 85, 90, 95, 100 regions from those identified in Table 12. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480 or 500 regions from those identified in Table 12. The genomic regions of the selector set may comprise at least 2 regions from those identified in Table 12. The genomic regions of the selector set may comprise at least 20 regions from those identified in Table 12. The genomic regions of the selector set may comprise at least 60 regions from those identified in Table 12. The genomic regions of the selector set may comprise at least 100 regions from those identified in Table 12. The genomic regions of the selector set may comprise at least 200 regions from those identified in Table 12. The genomic regions of the selector set may comprise at least 300 regions from those identified in Table 12. The genomic regions of the selector set may comprise at least 400 regions from those identified in Table 12. The genomic regions of the selector set may comprise at least 500 regions from those identified in Table 12.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 12. At least about 5% of the genomic regions of the selector set may be regions identified in Table 12. At least about 10% of the genomic regions of the selector set may be regions identified in Table 12. At least about 20% of the genomic regions of the selector set may be regions identified in Table 12. At least about 30% of the genomic regions of the selector set may be regions identified in Table 12. At least about 40% of the genomic regions of the selector set may be regions identified in Table 12.

The genomic regions of the selector set may comprise at least 2, 3, 4, 5, 6, 7, 8, 9, 10, 11, 12, 13, 14, 15, 16, 17, 18, 19, 20 or more regions from those identified in Table 13. The genomic regions of the selector set may comprise at least 25, 30, 35, 40, 45, 50, 55, 60, 65, 70, 75, 80, 85, 90, 95, 100 regions from those identified in Table 13. The genomic regions of the selector set may comprise at least 250, 300, 350, 400, 450, 500, 550, 600, 650, 700, 750, 800, 850, 900, 950, 1000, 1050, 1100, 1150, 1200, 1250, 1300, 1350, 1400, or 1450 regions from those identified in Table 13. The genomic regions of the selector set may comprise at least 2 regions from those identified in Table 13. The genomic regions of the selector set may comprise at least 20 regions from those identified in Table 13. The genomic regions of the selector set may comprise at least 60 regions from those identified in Table 13. The genomic regions of the selector set may comprise at least 100 regions from those identified in Table 13. The genomic regions of the selector set may comprise at least 300 regions from those identified in Table 13. The genomic regions of the selector set may comprise at least 500 regions from those identified in Table 13. The genomic regions of the selector set may comprise at least 1000 regions from those identified in Table 13. The genomic regions of the selector set may comprise at least 1300 regions from those identified in Table 13.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 13. At least about 5% of the genomic regions of the selector set may be regions identified in Table 13. At least about 10% of the genomic regions of the selector set may be regions identified in Table 13. At least about 20% of the genomic regions of the selector set may be regions identified in Table 13. At least about 30% of the genomic regions of the selector set may be regions identified in Table 13. At least about 40% of the genomic regions of the selector set may be regions identified in Table 13.

The genomic regions of the selector set may comprise at least 2, 3, 4, 5, 6, 7, 8, 9, 10, 11, 12, 13, 14, 15, 16, 17, 18, 19, 20 or more regions from those identified in Table 14. The genomic regions of the selector set may comprise at least 25, 30, 35, 40, 45, 50, 55, 60, 65, 70, 75, 80, 85, 90, 95, 100 regions from those identified in Table 14. The genomic regions of the selector set may comprise at least 250, 300, 350, 400, 450, 500, 550, 600, 650, 700, 750, 800, 850, 900, 950, 1000, 1050, 1100, 1150, 1200, 1210, 1220, 1230, or 1240 regions from those identified in Table 14. The genomic regions of the selector set may comprise at least 2 regions from those identified in Table 14. The genomic regions of the selector set may comprise at least 20 regions from those identified in Table 14. The genomic regions of the selector set may comprise at least 60 regions from those identified in Table 14. The genomic regions of the selector set may comprise at least 100 regions from those identified in Table 14. The genomic regions of the selector set may comprise at least 300 regions from those identified in Table 14. The genomic regions of the selector set may comprise at least 500 regions from those identified in Table 14. The genomic regions of the selector set may comprise at least 1000 regions from those identified in Table 14. The genomic regions of the selector set may comprise at least 1100 regions from those identified in Table 14. The genomic regions of the selector set may comprise at least 1200 regions from those identified in Table 14.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 14. At least about 5% of the genomic regions of the selector set may be regions identified in Table 14. At least about 10% of the genomic regions of the selector set may be regions identified in Table 14. At least about 20% of the genomic regions of the selector set may be regions identified in Table 14. At least about 30% of the genomic regions of the selector set may be regions identified in Table 14. At least about 40% of the genomic regions of the selector set may be regions identified in Table 14.

The genomic regions of the selector set may comprise at least 2, 3, 4, 5, 6, 7, 8, 9, 10, 11, 12, 13, 14, 15, 16, 17, 18, 19, 20 or more regions from those identified in Table 15. The genomic regions of the selector set may comprise at least 25, 30, 35, 40, 45, 50, 55, 60, 65, 70, 75, 80, 85, 90, 95, 100, 110, 120, 130, 140, 150, 160, or 170 regions from those identified in Table 15. The genomic regions of the selector set may comprise at least 2 regions from those identified in Table 15. The genomic regions of the selector set may comprise at least 20 regions from those identified in Table 15. The genomic regions of the selector set may comprise at least 60 regions from those identified in Table 15. The genomic regions of the selector set may comprise at least 100 regions from those identified in Table 15. The genomic regions of the selector set may comprise at least 120 regions from those identified in Table 15. The genomic regions of the selector set may comprise at least 150 regions from those identified in Table 15.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 15. At least about 5% of the genomic regions of the selector set may be regions identified in Table 15. At least about 10% of the genomic regions of the selector set may be regions identified in Table 15. At least about 20% of the genomic regions of the selector set may be regions identified in Table 15. At least about 30% of the genomic regions of the selector set may be regions identified in Table 15. At least about 40% of the genomic regions of the selector set may be regions identified in Table 15.

The genomic regions of the selector set may comprise at least 2, 3, 4, 5, 6, 7, 8, 9, 10, 11, 12, 13, 14, 15, 16, 17, 18, 19, 20 or more regions from those identified in Table 16. The genomic regions of the selector set may comprise at least 25, 30, 35, 40, 45, 50, 55, 60, 65, 70, 75, 80, 85, 90, 95, 100 regions from those identified in Table 16. The genomic regions of the selector set may comprise at least 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or 2050 regions from those identified in Table 16. The genomic regions of the selector set may comprise at least 2 regions from those identified in Table 16. The genomic regions of the selector set may comprise at least 20 regions from those identified in Table 16. The genomic regions of the selector set may comprise at least 60 regions from those identified in Table 16. The genomic regions of the selector set may comprise at least 100 regions from those identified in Table 16. The genomic regions of the selector set may comprise at least 300 regions from those identified in Table 16. The genomic regions of the selector set may comprise at least 500 regions from those identified in Table 16. The genomic regions of the selector set may comprise at least 1000 regions from those identified in Table 16. The genomic regions of the selector set may comprise at least 1200 regions from those identified in Table 16. The genomic regions of the selector set may comprise at least 1500 regions from those identified in Table 16. The genomic regions of the selector set may comprise at least 1700 regions from those identified in Table 16. The genomic regions of the selector set may comprise at least 2000 regions from those identified in Table 16.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 16. At least about 5% of the genomic regions of the selector set may be regions identified in Table 16. At least about 10% of the genomic regions of the selector set may be regions identified in Table 16. At least about 20% of the genomic regions of the selector set may be regions identified in Table 16. At least about 30% of the genomic regions of the selector set may be regions identified in Table 16. At least about 40% of the genomic regions of the selector set may be regions identified in Table 16.

The genomic regions of the selector set may comprise at least 2, 3, 4, 5, 6, 7, 8, 9, 10, 11, 12, 13, 14, 15, 16, 17, 18, 19, 20 or more regions from those identified in Table 17. The genomic regions of the selector set may comprise at least 25, 30, 35, 40, 45, 50, 55, 60, 65, 70, 75, 80, 85, 90, 95, 100 regions from those identified in Table 17. The genomic regions of the selector set may comprise at least 250, 300, 350, 400, 450, 500, 550, 600, 650, 700, 750, 800, 850, 900, 950, 1000, 1010, 1020, 1030, 1040, 1050, 1060, 1070, or 1080 regions from those identified in Table 17. The genomic regions of the selector set may comprise at least 2 regions from those identified in Table 17. The genomic regions of the selector set may comprise at least 20 regions from those identified in Table 17. The genomic regions of the selector set may comprise at least 60 regions from those identified in Table 17. The genomic regions of the selector set may comprise at least 100 regions from those identified in Table 17. The genomic regions of the selector set may comprise at least 300 regions from those identified in Table 17. The genomic regions of the selector set may comprise at least 500 regions from those identified in Table 17. The genomic regions of the selector set may comprise at least 1000 regions from those identified in Table 17. The genomic regions of the selector set may comprise at least 1050 regions from those identified in Table 17.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 17. At least about 5% of the genomic regions of the selector set may be regions identified in Table 17. At least about 10% of the genomic regions of the selector set may be regions identified in Table 17. At least about 20% of the genomic regions of the selector set may be regions identified in Table 17. At least about 30% of the genomic regions of the selector set may be regions identified in Table 17. At least about 40% of the genomic regions of the selector set may be regions identified in Table 17.

The genomic regions of the selector set may comprise at least 2, 3, 4, 5, 6, 7, 8, 9, 10, 11, 12, 13, 14, 15, 16, 17, 18, 19, 20 or more regions from those identified in Table 18. The genomic regions of the selector set may comprise at least 25, 30, 35, 40, 45, 50, 55, 60, 65, 70, 75, 80, 85, 90, 95, 100 regions from those identified in Table 18. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480, 500, 520, 540, or 555 regions from those identified in Table 18. The genomic regions of the selector set may comprise at least 2 regions from those identified in Table 18. The genomic regions of the selector set may comprise at least 20 regions from those identified in Table 18. The genomic regions of the selector set may comprise at least 60 regions from those identified in Table 18. The genomic regions of the selector set may comprise at least 100 regions from those identified in Table 18. The genomic regions of the selector set may comprise at least 200 regions from those identified in Table 18. The genomic regions of the selector set may comprise at least 300 regions from those identified in Table 18. The genomic regions of the selector set may comprise at least 400 regions from those identified in Table 18. The genomic regions of the selector set may comprise at least 500 regions from those identified in Table 18.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 18. At least about 5% of the genomic regions of the selector set may be regions identified in Table 18. At least about 10% of the genomic regions of the selector set may be regions identified in Table 18. At least about 20% of the genomic regions of the selector set may be regions identified in Table 18. At least about 30% of the genomic regions of the selector set may be regions identified in Table 18. At least about 40% of the genomic regions of the selector set may be regions identified in Table 18.

The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer. The plurality of genomic regions may comprise one or more mutations present in at least 60% or more of a population of subjects suffering from the cancer. The plurality of genomic regions may comprise one or more mutations present in at least 72% or more of a population of subjects suffering from the cancer. The plurality of genomic regions may comprise one or more mutations present in at least 80% or more of a population of subjects suffering from the cancer.

The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may comprise less than 1.5 Mb of a genome. The total size of the plurality of genomic regions of the selector set may comprise less than 1 Mb of a genome. The total size of the plurality of genomic regions of the selector set may comprise less than 500 kb of a genome. The total size of the plurality of genomic regions of the selector set may comprise less than 300 kb of a genome. The total size of the plurality of genomic regions of the selector set may comprise less than 100, 90, 80, 70, 60, 50, 40, 30, 20, 10 or 5 kb of a genome. The total size of the plurality of genomic regions of the selector set may comprise less than 100 kb of a genome. The total size of the plurality of genomic regions of the selector set may comprise less than 75 kb of a genome. The total size of the plurality of genomic regions of the selector set may comprise less than 50 kb of a genome.

The total size of the plurality of genomic regions of the selector set may be between 100 kb to 1000 kb of a genome. The total size of the plurality of genomic regions of the selector set may be between 100 kb to 500 kb of a genome. The total size of the plurality of genomic regions of the selector set may be between 100 kb to 300 kb of a genome. The total size of the plurality of genomic regions of the selector set may be between 5 kb to 500 kb of a genome. The total size of the plurality of genomic regions of the selector set may be between 5 kb to 300 kb of a genome. The total size of the plurality of genomic regions of the selector set may be between 5 kb to 200 kb of a genome. The total size of the plurality of genomic regions of the selector set may be between 1 kb to 100 kb of a genome. The total size of the plurality of genomic regions of the selector set may be between 1 kb to 50 kb of a genome.

Further disclosed herein are methods of preparing a library for sequencing. The method may comprise (a) conducting an amplification reaction on cell-free DNA (cfDNA) derived from a sample to produce a plurality of amplicons, wherein the amplification reaction may comprise 20 or fewer amplification cycles; and (b) producing a library for sequencing, the library comprising the plurality of amplicons.

The amplification reaction may comprise 19, 18, 17, 16, 15, 14, 13, 12, 11, or 10 or fewer amplification cycles. The amplification reaction may comprise 15 or fewer amplification cycles.

The method may further comprise attaching adaptors to one or more ends of the cfDNA. The adaptor may comprise a plurality of oligonucleotides. The adaptor may comprise one or more deoxyribonucleotides. The adaptor may comprise ribonucleotides. The adaptor may be single-stranded. The adaptor may be double-stranded. The adaptor may comprise double-stranded and single-stranded portions. For example, the adaptor may be a Y-shaped adaptor. The adaptor may be a linear adaptor. The adaptor may be a circular adaptor. The adaptor may comprise a molecular barcode, sample index, primer sequence, linker sequence or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

The adaptor may comprise a molecular barcode. The molecular barcode may comprise a random sequence. The molecular barcode may comprise a predetermined sequence. Two or more adaptors may comprise two or more different molecular barcodes. The molecular barcodes may be optimized to minimize dimerization. The molecular barcodes may be optimized to enable identification even with amplification or sequencing errors. For examples, amplification of a first molecular barcode may introduce a single base error. The first molecular barcode may comprise greater than a single base difference from the other molecular barcodes. Thus, the first molecular barcode with the single base error may still be identified as the first molecular barcode. The molecular barcode may comprise at least 2, 3, 4, 5, 6, 7, 8, 9, 10 or more nucleotides. The molecular barcode may comprise at least 3 nucleotides. The molecular barcode may comprise at least 4 nucleotides. The molecular barcode may comprise less than 20, 19, 18, 17, 16, or 15 nucleotides. The molecular barcode may comprise less than 10 nucleotides. The molecular barcode may comprise less than 8 nucleotides. The molecular barcode may comprise less than 6 nucleotides. The molecular barcode may comprise 2 to 15 nucleotides. The molecular barcode may comprise 2 to 12 nucleotides. The molecular barcode may comprise 3 to 10 nucleotides. The molecular barcode may comprise 3 to 8 nucleotides. The molecular barcode may comprise 4 to 8 nucleotides. The molecular barcode may comprise 4 to 6 nucleotides.

The adaptor may comprise a sample index. The sample index may comprise a random sequence. The sample index may comprise a predetermined sequence. Two or more sets of adaptors may comprise two or more different sample indexes. Adaptors within a set of adaptors may comprise identical sample indexes. The sample indexes may be optimized to minimize dimerization. The sample indexes may be optimized to enable identification even with amplification or sequencing errors. For examples, amplification of a first sample index may introduce a single base error. The first sample index may comprise greater than a single base difference from the other sample indexes. Thus, the first sample index with the single base error may still be identified as the first molecular barcode. The sample index may comprise at least 2, 3, 4, 5, 6, 7, 8, 9, 10 or more nucleotides. The sample index may comprise at least 3 nucleotides. The sample index may comprise at least 4 nucleotides. The sample index may comprise less than 20, 19, 18, 17, 16, or 15 nucleotides. The sample index may comprise less than 10 nucleotides. The sample index may comprise less than 8 nucleotides. The sample index may comprise less than 6 nucleotides. The sample index may comprise 2 to 15 nucleotides. The sample index may comprise 2 to 12 nucleotides. The sample index may comprise 3 to 10 nucleotides. The sample index may comprise 3 to 8 nucleotides. The sample index may comprise 4 to 8 nucleotides. The sample index may comprise 4 to 6 nucleotides.

The adaptor may comprise a primer sequence. The primer sequence may be a PCR primer sequence. The primer sequence may be a sequencing primer.

Adaptors may be attached to one end of a nucleic acid from a sample. The nucleic acids may be DNA. The DNA may be cell-free DNA (cfDNA). The DNA may be circulating tumor DNA (ctDNA). The nucleic acids may be RNA. Adaptors may be attached to both ends of the nucleic acid. Adaptors may be attached to one or more ends of a single-stranded nucleic acid. Adaptors may be attached to one or more ends of a double-stranded nucleic acid.

Adaptors may be attached to the nucleic acid by ligation. Ligation may be blunt end ligation. Ligation may be sticky end ligation. Adaptors may be attached to the nucleic acid by primer extension. Adaptors may be attached to the nucleic acid by reverse transcription. Adaptors may be attached to the nucleic acids by hybridization. Adaptors may comprise a sequence that is at least partially complementary to the nucleic acid. Alternatively, in some instances, adaptors do not comprise a sequence that is complementary to the nucleic acid.

The method may further comprise fragmenting the cfDNA. The method may further comprise end-repairing the cfDNA. The method may further comprise A-tailing the cfDNA.

Further disclosed herein are methods of determining a statistical significance of a selector set. The method may comprise (a) detecting a presence of one or more mutations in one or more samples from a subject, wherein the one or more mutations may be based on a selector set comprising genomic regions comprising the one or more mutations; (b) determining a mutation type of the one or more mutations present in the sample; and (c) determining a statistical significance of the selector set by calculating a ctDNA detection index based on a p-value of the mutation type of mutations present in the one or more samples.

In some instances, if a rearrangement is observed in two or more samples from the subject, then the ctDNA detection index is 0. At least one of the two or more samples may be a plasma sample. At least one of the two or more samples may be a tumor sample. The rearrangement may be a fusion or a breakpoint.

In some instances, if one type of mutation is present, then the ctDNA detection index is the p-value of the one type of mutation.

In some instances, if (i) two or more types of mutations are present in the sample; (ii) the p-values of the two or more types mutations are less than 0.1; and (iii) a rearrangement is not one of the types of mutations, then the ctDNA detection is calculated based on the combined p-values of the two or more mutations. The p-values of the two or more mutations may be combined according to Fisher's method. One of the two or more types of mutations may be a SNV. The p-value of the SNV may be determined by Monte Carlo sampling. One of the two or more types of mutations may be an indel.

In some instances, if (i) two or more types of mutations are present in the sample; (ii) a p-value of at least one of the two or more types of mutations are greater than 0.1; and (iii) a rearrangement is not one of the types of mutations, then the ctDNA detection is calculated based on the p-value of one of the two or more types mutations. One of the two or more types of mutations may be a SNV. The ctDNA detection index may be calculated based on the p-value of the SNV. One of the two or more types of mutations may be an indel.

Further disclosed herein are methods of identifying rearrangements in one or more nucleic acids. The method may comprise (a) obtaining sequencing information pertaining to a plurality of genomic regions; (b) producing a list of genomic regions, wherein the genomic regions may be adjacent to one or more candidate rearrangement sites or the genomic regions may comprise one or more candidate rearrangement sites; and (c) applying an algorithm to the list of genomic regions to validate candidate rearrangement sites, thereby identifying rearrangements.

The sequencing information may comprise an alignment file. The alignment file may comprise an alignment file of pair-end reads, exon coordinates, and a reference genome.

The sequencing information may be obtained from a database. The database may comprise sequencing information pertaining to a population of subjects suffering from a disease or condition. The disease or condition may be a cancer.

The sequencing information may be obtained from one or more samples from one or more subjects.

Producing the list of genomic regions may comprise identifying discordant read pairs based on the sequencing information. The discordant read-pair may refer to a read and its mate, where: (i) the insert size may be not equal to the expected distribution of the dataset; or (ii) the mapping orientation of the reads may be unexpected.

Producing the list of genomic regions may comprise classifying the discordant read pairs based on the sequencing information. Producing the list of genomic regions further may comprise ranking the genomic regions. The genomic regions may be ranked in decreasing order of discordant read depth.

Producing the list of genomic regions may comprise selecting genomic regions with a minimum user-defined read depth.

The minimum user-defined read depth may be at least 2×, 3×, 4×, 5×, 6×, 7×, 8×, 9×, 10× or more.

The method may further comprise eliminating duplicate fragments.

Producing the list of genomic regions may comprise use of one or more algorithms. The algorithm may analyze properly paired reads in which one of the paired reads may be truncated to produce a soft-clipped read. The algorithm may analyze the soft-clipped reads based on a pattern. The pattern may be based on x number of skipped bases (Sx) and on y number of contiguous mapped bases (My). The pattern may be MySx or SxMy.

Applying the algorithm to validate the candidate rearrangement sites may comprise deleting candidate rearrangements with a read frequency of less than 2. Applying the algorithm to validate the candidate rearrangement sites may comprise ranking the candidate rearrangements based on their read frequency.

Applying the algorithm to validate the candidate rearrangement sites may comprise comparing two or more reads of the candidate rearrangement. Applying the algorithm to validate the candidate rearrangement sites may comprise identifying the candidate rearrangement as a rearrangement if the two or more reads have a sequence alignment.

Applying the algorithm to validate the candidate rearrangement sites may comprise evaluating inter-read concordance. Evaluating inter-read concordance may comprise dividing a first sequencing read of the candidate rearrangement site into a plurality of subsequences of length. Evaluating inter-read concordance may comprise dividing a second sequencing read of the candidate rearrangement site into a plurality of subsequences of length l. Evaluating inter-read concordance may comprise comparing the subsequences of the first sequencing read to the subsequences of the second sequencing read. The first and second sequencing reads may be considered concordant if a minimum matching threshold may be achieved.

Applying the algorithm to validate the candidate rearrangement sites may comprise in silico validation of the candidate rearrangement sites. In silico validation may comprise aligning sequencing reads of the candidate rearrangement site to a reference rearrangement sequence. The reference rearrangement sequence may be obtained from a reference genome. The candidate rearrangement site may be identified as a rearrangement if the reads map to the reference rearrangement sequence with an identity of at least 70%, 75%, 80%, 85%, 90%, 95%, 97% or more.

The candidate rearrangement site may be identified as a rearrangement if the length of the aligned sequences may be at least 70%, 75%, 80%, 85%, 90%, or 95% or more of the read length of the candidate rearrangement site.

Further disclosed herein are methods of identifying tumor-derived single nucleotide variations (SNVs). The method may comprise (a) obtaining a sample from a subject suffering from a cancer or suspected of suffering from a cancer; (b) conducting a sequencing reaction on the sample to produce sequencing information; (c) applying an algorithm to the sequencing information to produce a list of candidate tumor alleles based on the sequencing information from step (b), wherein a candidate tumor allele may comprise a non-dominant base that may be not a germline SNP; and (d) identifying tumor-derived SNVs based on the list of candidate tumor alleles.

Producing the list of candidate tumor alleles may comprise ranking the tumor alleles by their fractional abundance. Producing the list of candidate tumor alleles may comprise selecting tumor alleles with a fractional abundance in the top $70^{th}$, $75^{th}$, $80^{th}$, $85^{th}$, $87^{th}$, $90^{th}$, $92^{nd}$, $95^{th}$, or $97^{th}$ percentile. Producing the list of candidate tumor alleles may comprise selecting tumor alleles with a fractional abundance of less than 1%, 0.9%, 0.8%, 0.7%, 0.6%, 0.5%, 0.4%, 0.3%, 0.2%, 0.1% of the total alleles in the sample from the subject.

Producing the list of candidate tumor alleles may comprise ranking the tumor alleles based on their sequencing depth. Producing the list of candidate tumor alleles may comprise selecting tumor alleles that meet a minimum sequencing depth. The minimum sequencing depth may be at least 100×, 200×, 300×, 400×, 500×, 600×, 700×, 800×, 900×, 1000× or more.

Producing the list of candidate tumor alleles may comprise calculating a strand bias percentage of a tumor allele. Producing the list of candidate tumor alleles may comprise ranking the tumor alleles based on their strand bias percentage. Producing the list of candidate tumor alleles may comprise selecting tumor alleles with a user-defined strand bias percentage. The user-defined strand bias percentage may be less than or equal to 60%, 65%, 70%, 75%, 80%, 85%, 90%, 95%, or 97%.

Producing the list of candidate tumor alleles may comprise comparing the sequence of the tumor allele to a reference tumor allele. Producing the list of candidate tumor alleles further may comprise identifying tumor alleles that are different from the reference tumor allele.

Identifying the tumor alleles that are different from the reference tumor allele may comprise use of one or more statistical analyses. The one or more statistical analyses may comprise using Bonferroni correction to calculate a Bonferroni-adjusted binomial probability for the tumor allele.

Producing the list of candidate tumor alleles may comprise selecting tumor alleles based on the Bonferroni-adjusted binomial probability. The Bonferroni-adjusted binomial probability of a candidate tumor allele may be less than or equal to $3\times10^{-8}$, $2.9\times10^{-8}$, $2.8\times10^{-8}$, $2.7\times10^{-8}$, $2.6\times10^{-8}$, $2.5\times10^{-8}$, $2.3\times10^{-8}$, $2.2\times10^{8}$, $2.1\times10^{-8}$, $2.09\times10^{-8}$, $2.08\times10^{-8}$, $2.07\times10^{-8}$, $2.06\times10^{-8}$, $2.05\times10^{-8}$, $2.04\times10^{-8}$, $2.03\times10^{-8}$, $2.02\times10^{-8}$, $2.01\times10^{-8}$ or $2\times10^{-8}$. The Bonferroni-adjusted binomial probability of a candidate tumor allele may be less than or equal to $2.08\times10^{-8}$.

Identifying the tumor alleles that are different from the reference tumor allele further may comprise applying a Z-test to the Bonferroni-adjusted binomial probability to produce a Bonferroni-adjusted single-tailed Z-score for the tumor allele. A tumor allele with a Bonferroni-adjusted single-tailed Z-score of greater than or equal to 6, 5.9, 5.8, 5.7, 5.6, 5.5, 5.4, 5.3, 5.2, 5.1, or 5.0 may be considered to be different from the reference tumor allele.

The sample may be a blood sample. The sample may be a paired sample.

Further disclosed herein are methods of producing a selector set. The method may comprise (a) obtaining sequencing information of a tumor sample from a subject suffering from a cancer; (b) comparing the sequencing information of the tumor sample to sequencing information from a non-tumor sample from the subject to identify one or more mutations specific to the sequencing information of the tumor sample; and (c) producing a selector set comprising one or more genomic regions comprising the one or more mutations specific to the sequencing information of the tumor sample.

The selector set may comprise sequencing information pertaining to the one or more genomic regions. The selector set may comprise genomic coordinates pertaining to the one or more genomic regions.

The selector set may be used to produce a plurality of oligonucleotides that selectively hybridize the one or more genomic regions. The plurality of oligonucleotides may be biotinylated.

The one or more mutations may comprise SNVs. The one or more mutations may comprise indels. The one or more mutations may comprise rearrangements.

Producing the selector set may comprise identifying tumor-derived SNVs using the methods disclosed herein.

Producing the selector set may comprise identifying tumor-derived rearrangements using the method disclosed herein.

BRIEF DESCRIPTION OF THE DRAWINGS

(FIG. 1A) Schematic depicting design of CAPP-Seq selectors and their application for assessing circulating tumor DNA. (FIG. 1B) Multi-phase design of the NSCLC selector. Phase 1: Genomic regions harboring known/suspected driver mutations in NSCLC are captured. Phases 2-4: Addition of exons containing recurrent SNVs using WES data from lung adenocarcinomas and squamous cell carcinomas from TCGA (n=407). Regions were selected iteratively to maximize the number of mutations per tumor while minimizing selector size. Recurrence index=total unique patients with mutations covered per kb of exon. Phases 5-6: Exons of predicted NSCLC drivers and introns/exons harboring breakpoints in rearrangements involving ALK, ROS1, and RET were added. Bottom: increase of selector length during each design phase. (FIG. 1C) Analysis of the number of SNVs per lung adenocarcinoma covered by the NSCLC selector in the TCGA WES cohort (Training; n=229) and an independent lung adenocarcinoma WES data set (Validation; n=183). Results are compared to selectors randomly sampled from the exome ($P<1.0\times10^{-6}$ for the difference between random selectors and the NSCLC selector). (FIG. 1D) Number of SNVs per patient identified by the NSCLC selector in WES data from three adenocarcinomas from TCGA, colon (COAD), rectal (READ), and endometrioid (UCEC) cancers.

FIG. 2A-2I: Analytical performance. (FIG. 2A-2C) Quality parameters from a representative CAPP-Seq analysis of plasma cfDNA, including length distribution of sequenced cfDNA fragments (FIG. 2A), and depth of sequencing coverage across all genomic regions in the selector] FIG. 2B). (FIG. 2C) Variation in sequencing depth across cfDNA samples from 4 patients. Orange envelope represents s.e.m. (FIG. 2D) Analysis of background rate for 40 plasma cfDNA samples collected from 13 NSCLC patients and 5 healthy individuals. (FIG. 2E) Analysis of biological background in d focusing on 107 recurrent somatic mutations from a previously reported SNAPshot panel. Mutations found in a given patient's tumor were excluded. The mean frequency over all subjects was ~0.01%. A single outlier mutation (TP53 R175H) is indicated by an orange diamond. (FIG. 2F) Individual mutations from e ranked by most to least recurrent, according to mean frequency across the 40 cfDNA samples. The p-value threshold of 0.01 (horizontal line) corresponds to the 99$^{th}$ percentile of global selector background in d. (FIG. 2G) Dilution series analysis of expected versus observed frequencies of mutant alleles using CAPP-Seq. Dilution series were generated by spiking fragmented HCC78 DNA into control cfDNA. (FIG. 2H) Analysis of the effect of the number of SNVs considered on the estimates of fractional abundance (95% confidence intervals shown in gray). (FIG. 2I) Analysis of the effect of the number of SNVs considered on the mean correlation coefficient between expected and observed cancer fractions (blue dashed line) using data from panel h. 95% confidence intervals are shown for e-f. Statistical variation for g is shown as s.e.m.

(FIG. 3A) Receiver Operating Characteristic (ROC) analysis of cfDNA samples from pre-treatment samples and healthy controls, divided into all stages (n=13 patients) and stages II-IV (n=9 patients). Area Under the Curve (AUC) values are significant at P<0.0001. Sn, sensitivity; Sp, specificity. (FIG. 3B) Raw data related to a. TP, true positive; FP, false positive; TN, true negative; FN, false negative. (FIG. 3C) Concordance between tumor volume, measured by CT or PET/CT, and pg per mL of ctDNA from pretreatment samples (n=9), measured by CAPP-Seq. Patients P6 and P9 were excluded due to inability to accurately assess tumor volume and differences related to the capture of fusions, respectively. Of note, linear regression was performed in non-log space; the log-log axes and dashed diagonal line are for display purposes only.

FIG. 4A-4I: Noninvasive detection and monitoring of circulating tumor DNA. (FIG. 4A-4H) Disease monitoring using CAPP-Seq. (FIG. 4A-4B) Disease burden changes in response to treatment in a stage III NSCLC patient using SNVs and an indel (FIG. 4A), and a stage IV NSCLC patient using three rearrangement breakpoints (FIG. 4B). (FIG. 4C) Concordance between different reporters (SNVs and a fusion) in a stage IV NSCLC patient. (FIG. 4D) Detection of a subclonal EGFR T790M resistance mutation in a patient with stage IV NSCLC. The fractional abundance of the dominant clone and T790M-containing clone are shown in the primary tumor (left) and plasma samples (right). (FIG. 4E-4F) CAPP-Seq results from post-treatment cfDNA samples are predictive of clinical outcomes in a stage IIB NSCLC patient FIG. 4E and Stage IIIB NSCLC patient (FIG. 4F). (FIG. 4G-4H) Monitoring of tumor burden following complete tumor resection (FIG. 4G) and Stereotactic Ablative Radiotherapy (SABR) (FIG. 4H) for two stage IB NSCLC patients. (FIG. 4I) Exploratory analysis of the potential application of CAPP-Seq for biopsy-free tumor genotyping or cancer screening. All plasma cfDNA samples from patients in Table 1 were examined for the presence of mutant allele outliers without knowledge of the primary tumor mutations; samples with detectable mutations are shown, along with two samples determined to be cancer-negative (P1-2 and P16-3) and a sample without tumor-derived SNVs (P9-5; see Table 1). The lowest mutant allele fraction detected was ~0.5% (dashed horizontal line). Error bars in d represent s.e.m. Tu, tumor; Ef, pleural effusion; SD, stable disease; PD, progressive disease; PR, partial response; CR, complete response; DOD, dead of disease.

(FIG. 5A) Analytical modeling of CAPP-Seq, WES, and WGS for different detection limits of tumor cfDNA in plasma. Calculations are based on the median number of mutations detected per NSCLC for CAPP-Seq (e.g., 4) and the reported number of mutations in NSCLC exomes and genomes. The vertical dotted line represents the median fraction of tumor-derived cfDNA in plasma from NSCLC patients in this study (see below). (FIG. 5B) Costs for WES and WGS to achieve the same theoretical detection limit as CAPP-Seq (shown as a dark solid line in FIG. 5A).

(FIG. 7A Known/suspected NSCLC drivers are highly enriched at RI≥30 (inset), comprising 1.8% (n=861) of analyzed exons. (FIG. 7B) Known/suspected NSCLC drivers are highly enriched at ≥3 patients with mutations per exon (inset), encompassing 16% of analyzed exons.

FIG. 8A-8E: FACTERA analytical pipeline for breakpoint mapping. Major steps used by FACTERA to precisely identify genomic breakpoints from aligned paired-end sequencing data are anecdotally illustrated using two hypothetical genes, w and v. (FIG. 8A) Improperly paired, or "discordant," reads (indicated in yellow) are used to locate genes involved in a potential fusion (in this case, w and v). (FIG. 8B) Because truncated (e.g., soft-clipped) reads may indicate a fusion breakpoint, any such reads within genomic regions delineated by w and v are also further analyzed. (FIG. 8C) Consider soft-clipped reads, R1 and R2, whose non-clipped segments map to w and v, respectively. If R1 and R2 derive from a fragment encompassing a true fusion between w and v, then the mapped portion of R1 should match the soft-clipped portion of R2, and vice versa. This is assessed by FACTERA using fast k-mer indexing and comparison. SEQ ID NO:33 is shown. (FIG. 8D) Four possible orientations of R1 and R2 are depicted. However, only Cases 1a and 2a can generate valid fusions. Thus, prior to k-mer comparison (FIG. 8C), the reverse complement of R1 is taken for Cases 1b and 2b, respectively, converting them into Cases 1a and 2a. (FIG. 8E) In some cases, short sequences immediately flanking the breakpoint are identical, preventing unambiguous determination of the breakpoint. Let iterators i and j denote the first matching sequence positions between R1 and R2. To reconcile sequence overlap, FACTERA arbitrarily adjusts the breakpoint in R2 (e.g., bp2) to match R1 (e.g., bp1) using the sequence offset determined by differences in distance between bp2 and i, and bp1 and j. Two cases are illustrated, corresponding to sequence orientations described in FIG. 8D.

(FIG. 9A) Pile-up of a subset of soft-clipped reads mapping to the EMLA-ALK fusion identified in NCI-H3122 along with the corresponding Sanger chromatogram (from top to bottom SEQ ID NOs: 1-11; and SEQ ID NOs: 34-42). (FIG. 9B) Same as a, but for the SLC34A2-ROS1 translocation identified in HCC78 (from top to bottom SEQ ID NOs: 12-22 and SEQ ID NO:43-51).

(FIG. 11A) Sixteen hour ligation at 16° C. increases ligation efficiency and reporter recovery. (FIG. 11B) Adapter ligation volume did not have a significant effect on ligation efficiency and reporter recovery. (FIG. 11C) Performing enzymatic reactions "with-bead" to minimize tube transfer steps increases reporter recovery. (FIG. 11D) Increasing adapter concentration during ligation increases ligation efficiency and reporter recovery. Reporter recovery is also higher when using KAPA HiFi DNA polymerase compared to Phusion DNA polymerase (FIG. 11E) and when using the KAPA Library Preparation Kit with the modifications in a-d compared to the NuGEN SP Ovation Ultralow Library System with automation on a Mondrian SP Workstation (FIG. 11F). Relative reporter abundance was determined by qPCR using the $2^{-\Delta Ct}$ method. A two-sided t test with equal variance was used to test the statistical significance between groups. All values are presented as means±s.d. N.S., not significant. Based on these results, we estimate that combining the methodological modifications in FIG. 11A and FIG. 11C-11E-improves yield in NGS libraries by 3.3-fold.

(FIG. 12A) Length of the captured cfDNA fragments sequenced. (FIG. 12B) Depth of sequencing coverage across all genomic regions in the selector (pre-duplicate removal). (FIG. 12C) Sequence mapping and capture statistics. As expected, more input cfDNA mass correlates with more unique fragments sequenced.

(FIG. 13A) The expected proportion of additional library complexity present in post-duplicate reads is plotted for all patient and control samples, including plasma cfDNA (n=40) and paired tumor/PBL specimens (n=17 each). Because of the highly stereotyped size of cfDNA fragments occurring naturally in blood plasma, when compared with genomic DNA shorn by sonication, any two fragments of DNA circulating in plasma are inherently more likely by chance to have arisen from different original molecules, whether considering tumor or non-tumor cells as the source of this cfDNA. To estimate this "missing" complexity, we reasoned that two DNA fragments (e.g., paired end reads) with identical start/end coordinates that differ by a single a priori defined germline variant (e.g. one maternal and one paternal allele) represent two unique and independent starting molecules rather than technical artifacts (e.g. PCR duplicates). Therefore, the number of fragments sharing identical start/end coordinates with both maternal and paternal germline alleles of heterozygous SNPs were used to estimate additional library complexity. Library complexity estimates updated to factor in these data are also provided in Tables 3, 20 and 21 and determined as described herein. (FIG. 13B) Empirical assessment of molecule recovery in cfDNA (n=40) by determination of the mass of DNA produced compared to the expected library yield based on mass input, number of PCR cycles, and efficiency (mean=46%). (FIG. 13A-13B) Values are presented as means±95% confidence intervals.

FIG. 5*a*) (e.g., 0.06×0.1=0.006% of a given sample would on average represent contamination from ctDNA of another sample). Of note, to minimize the risk of inter-sample contamination, we use aerosol barrier tips, work in hoods, and do not multiplex tumor and plasma libraries in the same lane.

(FIG. 16A) Expected and observed (by CAPP-Seq) fractions of NCI-H3122 DNA spiked into control HCC78 DNA are linear for all fractions tested (0.1%, 1%, and 10%; $R^2$=1). Using data from FIG. 16B, analysis of the effect of the number of SNVs considered on the estimates of fractional abundance (95% confidence intervals shown in gray). (FIG. 16C) Analysis of the effect of the number of SNVs considered on the mean correlation coefficient and coefficient of variation between expected and observed cancer fractions (blue dashed line) using data from panel a. (FIG. 16D) Expected and observed fractions of the EML4-ALK fusion present in HCC78 are linear ($R^{2=0.995}$) over all spiking concentrations tested (see FIG. 9B for breakpoint verification). The observed EML4-ALK fractions were normalized based on the relative abundance of the fusion in 100% H3122 DNA. Moreover, both a single heterozygous insertion ('Indel'; chr7: 107416855, +T) and a 4.9 kb homozygous deletion ('Deletion', chr17: 29422259-29592392) in NCI-H3122 were concordant with defined concentrations. Values in a are presented as means±s.e.m.

FIG. 17A-17B: Base-pair resolution breakpoint mapping for all patients and cell lines enumerated by FACTERA. Gene fusions involving ALK (FIG. 17A) and ROS1 (FIG. 17B) are graphically depicted. Schematics in the top panels indicate the exact genomic positions (HG19 NCBI Build 37.1/GRCh37) of the breakpoints in ALK, ROS1, EML4, KIF5B, SLC34A2, CD74, MKX, and FYN. Bottom panels depict exons flanking the predicted gene fusions with notation indicating the 5' fusion partner gene and last fused exon followed by the 3' fusion partner gene and first fused exon. For example, in S13del37; $R^{34}$ exons 1-13 of SLC34A2 (excluding the 3' 37 nucleotides of exon 13) are fused to exons 34-43 of ROS1. Exons in FYN are from its 5'UTR and precede the first coding exon. The green dotted line in the predicted FYN-ROS1 fusion indicates the first in-frame methionine in ROS1 exon 33, which preserves an open reading frame encoding the ROS1 kinase domain. All rearrangements were each independently confirmed by PCR and/or FISH.

FIG. 19A-19D. Receiver Operating Curve (ROC) analysis of CAPP-Seq performance including both pre- and post-treatment samples. Comparison of sensitivity and specificity achieved for non-deduped (FIGS. 19A and 19C) and deduped (post PCR duplicate removal) data (FIGS. 19B and 19D). In addition, all stages (FIG. 19A-19B) are compared with intermediate to advanced stages (stages II-IV, FIGS. 19C and 19D). Finally, for all ROC analyses, the effect of the indel/fusion filter on sensitivity/specificity is shown. Reporter fractions for both non-deduped and deduped cfDNA samples are provided in Table 4.

(FIG. 21A) Steps to identify candidate SNVs in plasma cfDNA demonstrated using a patient sample with NSCLC (P6, see Table 4). Following stepwise filtration, outlier detection is applied. (FIG. 21B) Same as a, but using a plasma cfDNA sample from a patient who had their tumor surgically removed. No SNVs are identified, as expected. (FIG. 21C, 21D) Three additional representative samples applying retrospective screening to patients analyzed in this study. P2 and P5 samples have confirmed tumor-derived SNVs, while P9 is cancer positive but lacks tumor-derived SNVs. Red points, confirmed tumor-derived SNVs; Green points, background noise.

DETAILED DESCRIPTION OF THE INVENTION

Figure 1A:
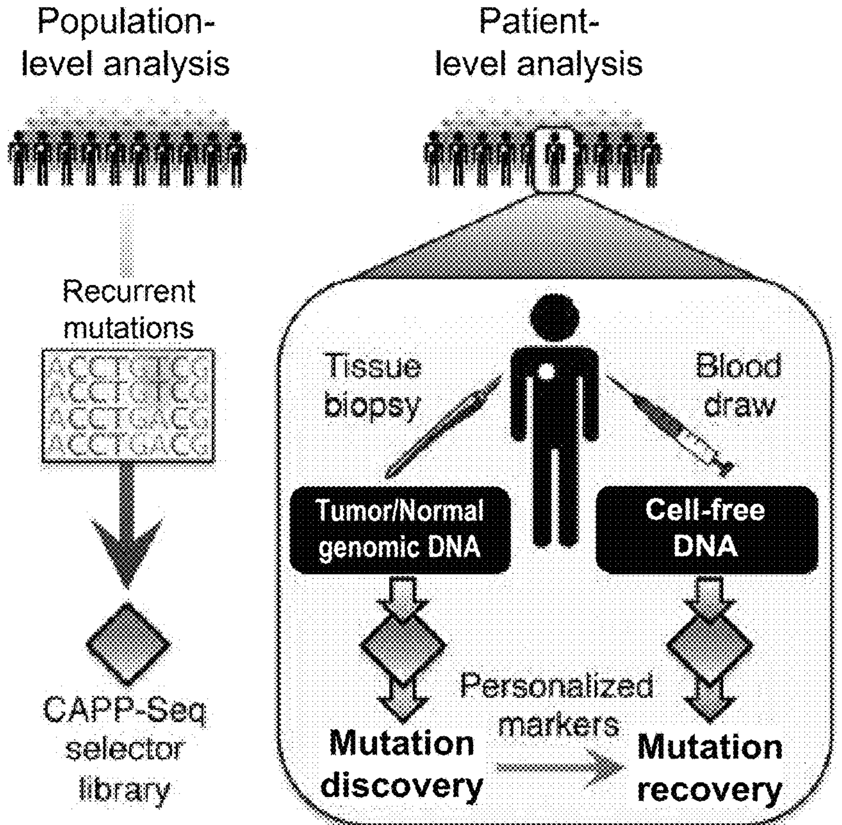
FIG. 1A-1D: Development of CAncer Personalized Profiling by Deep Sequencing (CAPP-Seq).

It is characteristic of cancer cells that due to somatic mutation the genome sequence of the cancer cell is changed from the genome sequence of the individual from which it is derived. Most human cancers are relatively heterogeneous for somatic mutations in individual genes. Specifically, in most human tumors, recurrent somatic alterations of single genes account for a minority of patients, and only a minority of tumor types can be defined using a small number of recurrent mutations at predefined positions. The present invention solves this problem by use of enrichment of tumor-derived nucleic acid molecules from total genomic nucleic acids with a selector set. The design of the selector is vital because (1) it dictates which mutations can be detected in with high probability for a patient with a given cancer, and (2) the selector size (in kb) directly impacts the cost and depth of sequence coverage.

While the specific genetic changes differ from individual to individual and between types of cancer, there are regions of the genome that show recurrent changes. In those regions there is an increased probability that any given individual cancer will show genetic variation. The genetic changes in cancer cells provide a means by which cancer cells can be distinguished from normal (e.g., non-cancer) cells. Cell-free DNA, for example the DNA fragments found in blood samples, can be analyzed for the presence of genetic variation distinctive of tumor cells. However, the absolute levels of tumor DNA in such samples is often small, and the genetic variation may represent only a very small portion of the entire genome. The present invention addresses this issue by providing methods for selective detection of mutated regions associated with cancer, thereby allowing accurate detection of cancer cell DNA or RNA from the background of normal cell DNA or RNA. Although the methods disclosed herein may specifically refer to DNA (e.g., cell-free DNA, circulating tumor DNA), it should be understood that the methods, compositions, and systems disclosed herein are applicable to all types of nucleic acids (e.g., RNA, DNA, RNA/DNA hybrids).

Provided herein are methods for the ultrasensitive detection of a minority nucleic acid in a heterogeneous sample. The method may comprise (a) obtaining sequence information of a cell-free DNA (cfDNA) sample derived from a subject; and (b) using sequence information derived from (a) to detect cell-free minority nucleic acids in the sample, wherein the method is capable of detecting a percentage of the cell-free minority nucleic acids that is less than 2% of total cfDNA. The minority nucleic acid may refer to a nucleic acid that originated from a cell or tissue that is different from a normal cell or tissue from the subject. For example, the subject may be infected with a pathogen such as a bacteria and the minority nucleic acid may be a nucleic acid from the pathogen. In another example, the subject is a recipient of a cell, tissue or organ from a donor and the minority nucleic acid may be a nucleic acid originating from the cell, tissue or organ from the donor. In another example, the subject is a pregnant subject and the minority nucleic acid may be a nucleic acid originating from a fetus. The method may comprise using the sequence information to detect one or more somatic mutations in the fetus. The method may comprise using the sequence information to detect one or more post-zygotic mutations in the fetus. Alternatively, the subject may be suffering from a cancer and the minority nucleic acid may be a nucleic acid originating from a cancer cell.

Provided herein are methods for the ultrasensitive detection of circulating tumor DNA in a sample. The method may be called CAncer Personalized Profiling by Deep Sequencing (CAPP-Seq). The method may comprise (a) obtaining sequence information of a cell-free DNA (cfDNA) sample derived from a subject; and (b) using sequence information derived from (a) to detect cell-free tumor DNA (ctDNA) in the sample, wherein the method is capable of detecting a percentage of ctDNA that is less than 2% of total cfDNA. CAPP-Seq may accurately quantify cell-free tumor DNA from early and advanced stage tumors. CAPP-Seq may identify mutant alleles down to 0.025% with a detection limit of <0.01%. Tumor-derived DNA levels often paralleled clinical responses to diverse therapies and CAPP-Seq may identify actionable mutations. CAPP-Seq may be routinely applied to noninvasively detect and monitor tumors, thus facilitating personalized cancer therapy.

Disclosed herein are methods for determining a quantity of circulating tumor DNA (ctDNA) in a sample. The method may comprise (a) ligating one or more adaptors to cell-free DNA (cfDNA) derived from a sample from a subject to produce one or more adaptor-ligated cfDNA; (b) performing sequencing on the one or more adaptor-ligated cfDNA, wherein the adaptor-ligated cfDNA to be sequenced is based on a selector set comprising a plurality of genomic regions; and (c) using a computer readable medium to determine a quantity of cfDNA originating from a tumor based on the sequencing information obtained from the adaptor-ligated cfDNA.

Further disclosed herein are methods of detecting, diagnosing, or prognosing a status or outcome of a cancer in a subject. The method may comprise (a) obtaining sequence information of a cell-free DNA (cfDNA) sample derived from the subject; (b) using sequence information derived from (a) to detect cell-free tumor DNA (ctDNA) in the sample wherein the method is capable of detecting a percentage of ctDNA that is less than 2% of total cfDNA.

Further disclosed herein are methods of diagnosing a status or outcome of a cancer in a subject. The method may comprise (a) obtaining sequence information of cell-free genomic DNA derived from a sample from a subject, wherein the sequence information is derived from genomic regions that are mutated in at least 80% of a population of subjects afflicted with a cancer; and (b) diagnosing a cancer selected from a group consisting of lung cancer, breast cancer, colorectal cancer and prostate cancer in the subject based on the sequence information, wherein the method has a sensitivity of 80%.

Further disclosed herein are methods of prognosing a status or outcome of a cancer in a subject. The method may comprise (a) obtaining sequence information of cell-free genomic DNA derived from a sample from a subject, wherein the sequence information is derived from regions that are mutated in at least 80% of a population of subjects afflicted with a condition; and (b) determining a prognosis of a condition in the subject based on the sequence information.

Further disclosed herein are methods of selecting a therapy for a subject suffering from a cancer. The method may comprise (a) obtaining sequence information of a cell-free DNA (cfDNA) sample derived from the subject; (b) using sequence information derived from (a) to detect cell-free tumor DNA (ctDNA) in the sample wherein the method is capable of detecting a percentage of ctDNA that is less than 2% of total cfDNA.

Alternatively, the method may comprise (a) obtaining sequence information of cell-free genomic DNA derived from a sample from a subject, wherein the sequence information is derived from regions that are mutated in at least 80% of a population of subjects afflicted with a condition; and (b) determining a therapeutic regimen of a condition in the subject based on the sequence information.

Further disclosed herein are methods for diagnosing, prognosing, or determining a therapeutic regimen for a subject afflicted with or suspected of having a cancer. The method may comprise (a) obtaining sequence information for selected regions of genomic DNA from a cell-free DNA sample from the subject; (b) using the sequence information to determine the presence or absence of one or more mutations in the selected regions, wherein at least 70% of a population of subjects afflicted with the cancer have mutation(s) in the regions; and (c) providing a report with a diagnosis, prognosis or treatment regimen to the subject, based on the presence or absence of the one or more mutations.

Further disclosed herein are methods for assessing tumor burden in a subject. The method may comprise (a) obtaining sequence information on cell-free nucleic acids derived from a sample from the subject; (b) using a computer readable medium to determine quantities of circulating tumor DNA (ctDNA) in the sample; (c) assessing tumor burden based on the quantities of ctDNA; and (d) reporting the tumor burden to the subject or a representative of the subject.

Further disclosed herein are methods for determining a disease state of a cancer in a subject. The method may comprise (a) obtaining a quantity of circulating tumor DNA (ctDNA) in a sample from the subject; (b) obtaining a volume of a tumor in the subject; and (c) determining a disease state of a cancer in the subject based on a ratio of the quantity of ctDNA to the volume of the tumor.

Disclosed herein are methods for detecting at least 50% of stage I cancer with a specificity of greater than 90%. The method may comprise (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage I cancer in the sample based on the quantity of the cell-free DNA.

Disclosed herein are methods for detecting at least 60% of stage II cancer with a specificity of greater than 90% comprising (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage II cancer in the sample based on the quantity of the cell-free DNA.

Disclosed herein are methods for detecting at least 60% of stage III cancer with a specificity of greater than 90% comprising (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage III cancer in the sample based on the quantity of the cell-free DNA.

Disclosed herein are methods for detecting at least 60% of stage IV cancer with a specificity of greater than 90% comprising (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage IV cancer in the sample based on the quantity of the cell-free DNA.

Also provided are selector sets for use in the methods disclosed herein. The selector set may comprise a plurality of genomic regions comprising one or more mutations present in a population of subjects suffering from a cancer. The selector set may be a library of recurrently mutated genomic regions used in the CAPP-Seq methods. The targeting of recurrently mutated genomic regions may allow a distinction between tumor cell DNA and normal DNA. In addition, the targeting of recurrently mutated genomic region may provide for simultaneous detection of point mutations, copy number variation, insertions/deletions, and rearrangements.

The selector set may be a computer readable medium. The computer readable medium may comprise nucleic acid sequence information for two or more genomic DNA regions wherein (a) the genomic regions comprise one or more mutations in >80% of tumors from a population of subjects afflicted with a cancer; (b) the genomic DNA regions represent less than 1.5 Mb of the genome; and (c) one or more of the following: (i) the condition is not hairy cell leukemia, ovarian cancer, Waldenstrom's macroglobulinemia; (ii) each of the genomic DNA regions comprises at least one mutation in at least one subject afflicted with the cancer; (iii) the cancer includes two or more different types of cancer; (iv) the two or more genomic regions are derived from two or more different genes; (v) the genomic regions comprise two or more mutations; or (vi) the two or more genomic regions comprise at least 10 kb.

The selector set may provide, for example, oligonucleotides useful in selective amplification of tumor-derived nucleic acids. The selector set may provide, for example, oligonucleotides useful in selective capture or enrichment of tumor-derived nucleic acids. Disclosed herein are compositions comprising a set of oligonucleotides based on the selector set. The composition may comprise a set of oligonucleotides that selectively hybridize to a plurality of genomic DNA regions, wherein (a) >80% of tumors from a population of cancer subjects include one or more mutations in the genomic DNA regions; (b) the plurality of genomic DNA regions represent less than 1.5 Mb of the genome; and (c) the set of oligonucleotides comprise 5 or more different oligonucleotides that selectively hybridize to the plurality of genomic DNA regions.

The composition may comprise oligonucleotides that selectively hybridize to a plurality of genomic regions, wherein the genomic regions comprise a plurality of mutations present in >60% of a population of subjects suffering from a cancer.

Further disclosed herein is an array comprising a plurality of oligonucleotides to selectively capture genomic regions, wherein the genomic regions comprise a plurality of mutations present in >60% of a population of subjects suffering from a cancer.

Further disclosed herein are methods of producing a selector set for a cancer. The method of producing a selector set for a cancer may comprise (a) identifying recurrently mutated genomic DNA regions of the selected cancer; and (b) prioritizing regions using one or more of the following criteria (i) a Recurrence Index (RI) for the genomic region(s), wherein the RI is the number of unique patients or tumors with somatic mutations per length of a genomic region; and (ii) a minimum number of unique patients or tumors with mutations in a length of genomic region.

Disclosed herein are methods of enriching for circulating tumor DNA from a sample. The method may comprise contacting cell-free nucleic acids from a sample with a plurality of oligonucleotides, wherein the plurality of oligonucleotides selectively hybridize to a plurality of genomic regions comprising a plurality of mutations present in >60% of a population of subjects suffering from a cancer.

Alternatively, the method may comprise contacting cell-free nucleic acids from a sample with a set of oligonucleotides, wherein the set of oligonucleotides selectively hybridize to a plurality of genomic regions, wherein (a) >80% of tumors from a population of cancer subjects include one or more mutations in the genomic regions; (b) the plurality of genomic regions represent less than 1.5 Mb of the genome; and (c) the set of oligonucleotides comprise 5 or more different oligonucleotides that selectively hybridize to the plurality of genomic regions.

Further disclosed herein are methods of preparing a nucleic acid sample for sequencing. The method may comprise (a) conducting an amplification reaction on cell-free DNA (cfDNA) derived from a sample to produce a plurality of amplicons, wherein the amplification reaction comprises 20 or fewer amplification cycles; and (b) producing a library for sequencing, the library comprising the plurality of amplicons.

Figure 23:
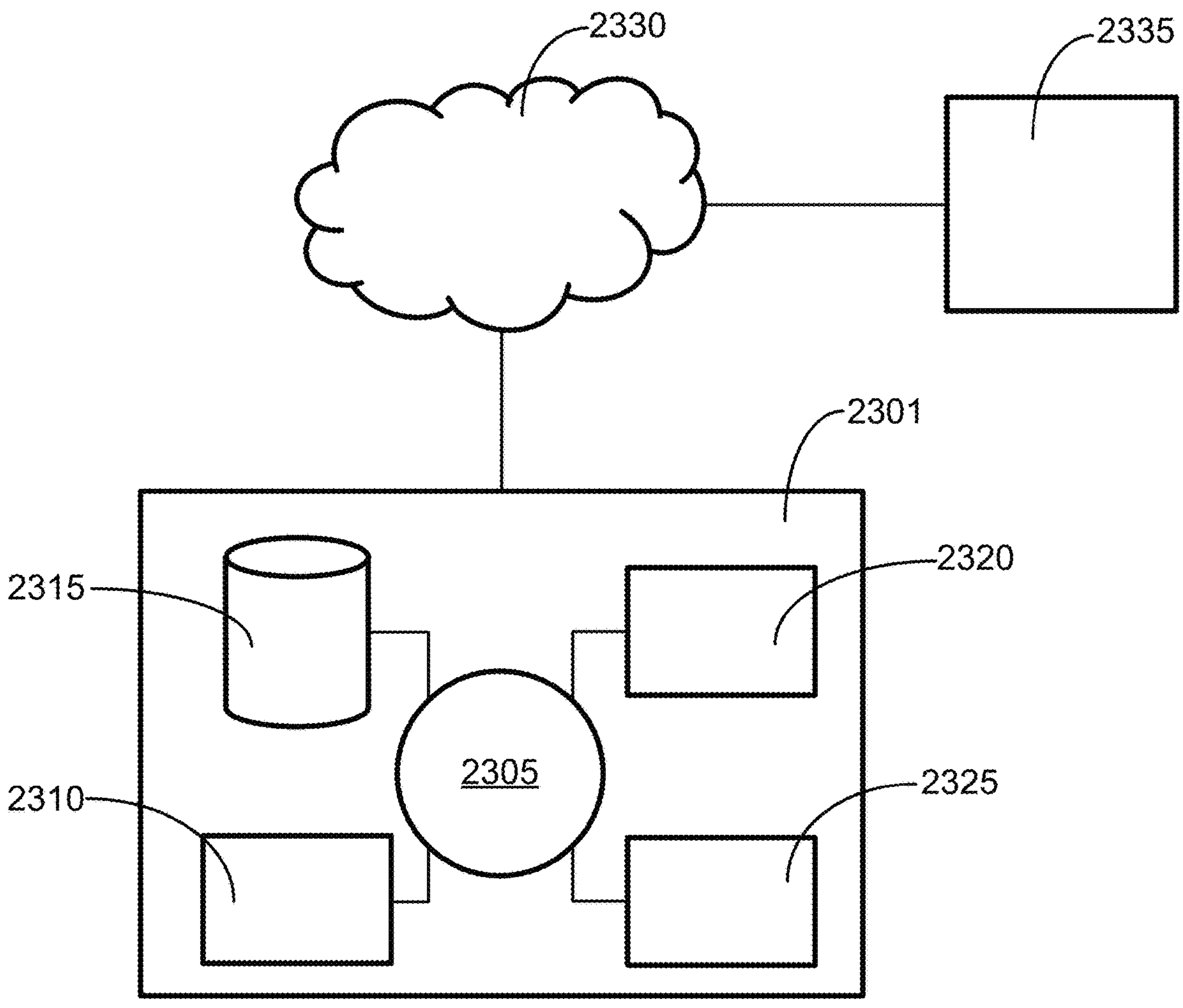
FIG. 23. shows a system for implementing the methods of the disclosure.

Further disclosed herein are systems for implementing one or more of the methods or steps of the methods disclosed herein. FIG. 23 shows a computer system (also "system" herein) 2301 programmed or otherwise configured for implementing the methods of the disclosure, such as producing a selector set and/or data analysis. The system 2301 includes a central processing unit (CPU, also "processor" and "computer processor" herein) 2305, which can be a single core or multi core processor, or a plurality of processors for parallel processing. The system 2301 also includes memory 2310 (e.g., random-access memory, read-only memory, flash memory), electronic storage unit 2315 (e.g., hard disk), communications interface 2320 (e.g., network adapter) for communicating with one or more other systems, and peripheral devices 2325, such as cache, other memory, data storage and/or electronic display adapters. The memory 2310, storage unit 2315, interface 2320 and peripheral devices 2325 are in communication with the CPU 2305 through a communications bus (solid lines), such as a motherboard. The storage unit 2315 can be a data storage unit (or data repository) for storing data. The system 2301 is operatively coupled to a computer network ("network") 2330 with the aid of the communications interface 2320. The network 2330 can be the Internet, an internet and/or extranet, or an intranet and/or extranet that is in communication with the Internet. The network 2330 in some cases is a telecommunication and/or data network. The network 2330 can include one or more computer servers, which can enable distributed computing, such as cloud computing. The network 2330 in some cases, with the aid of the system 2301, can implement a peer-to-peer network, which may enable devices coupled to the system 2301 to behave as a client or a server.

The system 2301 is in communication with a processing system 2335. The processing system 2335 can be configured to implement the methods disclosed herein. In some examples, the processing system 2335 is a nucleic acid sequencing system, such as, for example, a next generation sequencing system (e.g., Illumina sequencer, Ion Torrent sequencer, Pacific Biosciences sequencer). The processing system 2335 can be in communication with the system 2301 through the network 2330, or by direct (e.g., wired, wireless) connection. The processing system 2335 can be configured for analysis, such as nucleic acid sequence analysis.

Methods as described herein can be implemented by way of machine (or computer processor) executable code (or software) stored on an electronic storage location of the system 2301, such as, for example, on the memory 2310 or electronic storage unit 2315. During use, the code can be executed by the processor 2305. In some examples, the code can be retrieved from the storage unit 2315 and stored on the memory 2310 for ready access by the processor 2305. In some situations, the electronic storage unit 2315 can be precluded, and machine-executable instructions are stored on memory 2310.

Disclosed herein is a computer-implemented system for calculating a recurrence index for one or more genomic regions. The computer-implemented system may comprise (a) a digital processing device comprising an operating system configured to perform executable instructions and a memory device; and (b) a computer program including instructions executable by the digital processing device to create a recurrence index, the computer program comprising (i) a first software module configured to receive data pertaining to a plurality of mutations; (ii) a second software module configured to relate the plurality of mutations to one or more genomic regions and/or one or more subjects; and (iii) a third software module configured to calculate a recurrence index of one or more genomic regions, wherein the recurrence index is based on a number of mutations per subject per kilobase of nucleotide sequence.

Selector Set

The methods, kits, and systems disclosed herein may comprise one or more selector sets or uses thereof. A selector set may be a bioinformatics construct comprising the sequence information for regions of the genome (e.g., genomic regions) associated with one or more cancers of interest. A selector set may be a bioinformatics construct comprising genomic coordinates for one or more genomic regions. The genomic regions may comprise one or more recurrently mutated regions. The genomic regions may comprise one or more mutations associated with one or more cancers of interest.

The number of genomic regions in a selector set may vary depending on the nature of the cancer. The inclusion of larger numbers of genomic regions may generally increase the likelihood that a unique somatic mutation will be identified. Including too many genomic regions in the library is not without a cost, however, since the number of genomic regions is directly related to the length of nucleic acids that must be sequenced in the analysis. At the extreme, the entire genome of a tumor sample and a genomic sample could be sequenced, and the resulting sequences could be compared to note any differences.

The selector sets of the invention may address this problem by identifying genomic regions that are recurrently mutated in a particular cancer, and then ranking those regions to maximize the likelihood that the region will include a distinguishing somatic mutation in a particular tumor. The library of recurrently mutated genomic regions, or "selector set", can be used across an entire population for a given cancer or class of cancers, and does not need to be optimized for each subject.

The selector set may comprise at least about 2, 3, 4, 5, 6, 7, 8, or 9 different genomic regions. The selector set may comprise at least about 10 different genomic regions; at least about 25, at least about 50, at least about 100, at least about 150, at least about 200, at least about 250, at least about 300, at least about 350, at least about 400, at least about 500, at least about 600, at least about 700, at least about 800, at least about 900, at least about 1000 or more different genomic regions.

The selector set may comprise between about 10 to about 1000 different genomic regions. The selector set may comprise between about 10 to about 900 different genomic regions. The selector set may comprise between about 10 to about 800 different genomic regions. The selector set may comprise between about 10 to about 700 different genomic regions. The selector set may comprise between about 20 to about 600 different genomic regions. The selector set may comprise between about 20 to about 500 different genomic regions. The selector set may comprise between about 20 to about 400 different genomic regions. The selector set may comprise between about 50 to about 500 different genomic regions. The selector set may comprise between about 50 to about 400 different genomic regions. The selector set may comprise between about 50 to about 300 different genomic regions.

The selector set may comprise a plurality of genomic regions. The plurality of genomic regions may comprise at most 5000 different genomic regions. In some embodiments, the plurality of genomic regions comprises at most 2000 different genomic regions. In some embodiments, the plurality of genomic regions comprises at most 1000 different genomic regions. In some embodiments, the plurality of genomic regions comprises at most 500 different genomic regions. In some embodiments, the plurality of genomic regions comprises at most 400 different genomic regions. In some embodiments, the plurality of genomic regions comprises at most 300 different genomic regions. In some embodiments, the plurality of genomic regions comprises at most 200 different genomic regions. In some embodiments, the plurality of genomic regions comprises at most 150 different genomic regions. In some embodiments, the plurality of genomic regions comprises at most 100 different genomic regions. In some embodiments, the plurality of genomic regions comprises at most 50 different genomic regions or even fewer.

A genomic region may comprise a protein-coding region, or portion thereof. A protein-coding region may refer to a region of the genome that encodes for a protein. A protein-coding region may comprise an intron, exon, and/or untranslated region (UTR). A genomic region may comprise two or more protein-coding regions, or portions thereof. For example, a genomic region may comprise a portion of an exon and a portion of an intron. A genomic region may comprise three or more protein-coding regions, or portions thereof. For example, a genomic region may comprise a portion of a first exon, a portion of an intron, and a portion of a second exon. Alternatively, or additionally, a genomic region may comprise a portion of an exon, a portion of an intron, and a portion of an untranslated region.

A genomic region may comprise a gene. A genomic region may comprise only a portion of a gene. A genomic region may comprise an exon of a gene. A genomic region may comprise an intron of a gene. A genomic region may comprise an untranslated region (UTR) of a gene. In some instances, a genomic region does not comprise an entire gene. A genomic region may comprise less than 90%, 85%, 80%, 75%, 70%, 65%, 60%, 55%, 50%, 45%, 40%, 35%, 30%, 25%, 20%, 15%, 10%, or 5% of a gene. A genomic region may comprise less than 60% of a gene.

A genomic region may comprise a nonprotein-coding region. A nonprotein-coding region may also be referred to as a noncoding region. A nonprotein-coding region may refer to a region of the genome that does not encode for a protein. A nonprotein-coding region may be transcribed into a noncoding RNA (ncRNA). The noncoding RNA may have a known function. For example, the noncoding RNA may be a transfer RNA (tRNA), ribosomal RNA (rRNA), and/or regulatory RNA. The noncoding RNA may have an unknown function. Examples of ncRNA include, but are not limited to, tRNA, rRNA, small nuclear RNA (snRNA), small nucleolar RNA (snoRNA), microRNA, small interfering RNA (siRNAs), Piwi-interacting RNA (piRNA), and long ncRNA (e.g., Xist, HOTAIR). A genomic region may comprise a pseudogene, transposon and/or retrotransposon.

A genomic region may comprise a recurrently mutated region. A recurrently mutated region may refer to a region of the genome, usually the human genome, in which there is an increased probability of genetic mutation in a cancer of interest, relative to the genome as a whole. A recurrently mutation region may refer to a region of the genome that contains one or more mutations that is recurrent in the population. For example, a recurrently mutation region may refer to a region of the genome that contains a mutation that is present in two or more subjects in a population. A recurrently mutated region may be characterized by a "Recurrence Index" (RI). The RI generally refers to the number of individual subjects (e.g., cancer patients) with a mutation that occurs within a given kilobase of genomic sequence (e.g., number of patients with mutations/genomic region length in kb). A genomic region may also be characterized by the number of patients with a mutation per exon. Thresholds for each metric (e.g. RI and patients per exon or genomic region) may be selected to statistically enrich for known/suspected drivers of the cancer of interest. A known/suspected driver of the cancer of interest may be a gene. In non-small cell lung carcinoma (NSCLC), these metrics may enrich for known/suspected drivers (see genes listed in Table 2). Thresholds can also be selected by arbitrarily choosing the top percentile for each metric.

A selector set may comprise a genomic region comprising a mutation that is not recurrent in the population. For example, a genomic region may comprise one or more mutations that are present in a given subject. In some instances, a genomic region that comprises one or more mutations in a subject may be used to produce a personalized selector set for the subject.

The term "mutation" may refer to a genetic alteration in the genome of an organism. For the purposes of the invention, mutations of interest are typically changes relative to the germline sequence, e.g. cancer cell specific changes. Mutations may include single nucleotide variants (SNV), copy number variants (CNV), insertions, deletions and rearrangements (e.g., fusions). The selector set may comprise one or more genomic regions comprising one or more mutations selected from a group consisting of SNV, CNV, insertions, deletions, and rearrangements. The selector set may comprise a plurality of genomic regions comprising two or more mutations selected from a group consisting of SNV, CNV, insertions, deletions, and rearrangements. The selector set may comprise a plurality of genomic regions comprising three or more mutations selected from a group consisting of SNV, CNV, insertions, deletions, and rearrangements. The selector set may comprise a plurality of genomic regions comprising four or more mutations selected from a group consisting of SNV, CNV, insertions, deletions, and rearrangements. The selector set may comprise a plurality of genomic regions comprising five or more mutations selected from a group consisting of SNV, CNV, insertions, deletions, and rearrangements. The selector set may comprise a plurality of genomic regions comprising at least one SNV, insertion, and deletion. The selector set may comprise a plurality of genomic regions comprising at least one SNV and rearrangement. The selector set may comprise a plurality of genomic regions comprising at least one insertion, deletion, and rearrangement. The selector set may comprise a plurality of genomic regions comprising at least one deletion and rearrangement. The selector set may comprise a plurality of genomic regions comprising at least one insertion and rearrangement. The selector set may comprise a plurality of genomic regions comprising at least one SNV, insertion, deletion, and rearrangement. The selector set may comprise a plurality of genomic regions comprising at least one rearrangement and at least one mutation selected from a group consisting of SNV, insertion, and deletion. The selector set may comprise a plurality of genomic regions comprising at least one rearrangement and at least one mutation selected from a group consisting of SNV, CNV, insertion, and deletion.

A selector set may comprise a mutation in a genomic region known to be associated with a cancer. The mutation in a genomic region known to be associated with a cancer may be referred to as a "known somatic mutation." A known somatic mutation may be a mutation located in one or more genes known to be associated with a cancer. A known somatic mutation may be a mutation located in one or more oncogenes. For example, known somatic mutations may include one or more mutations located in p53, EGFR, KRAS and/or BRCA1.

A selector set may comprise a mutation in a genomic region predicted to be associated with a cancer. A selector set may comprise a mutation in a genomic region that has not been reported to be associated with a cancer.

A genomic region may comprise a sequence of the human genome of sufficient size to capture one or more recurrent mutations. The methods of the invention may be directed at cfDNA, which is generally less than about 200 bp in length, and thus a genomic region may be generally less than about 10 kb. The length of genomics region in a selector set may be on average around about 100 bp, about 125 bp, about 150 bp, 175 bp, about 200 bp, about 225 bp, about 250 bp, about 275 bp, or around about 300 bp. Generally the genomic region for a SNV can be quite short, from about 45 to about 500 bp in length, while the genomic region for a fusion or other genomic rearrangement may be longer, from around about 1 Kbp to about 10 Kbp in length. A genomic region in a selector set may be less than about 10 Kbp, 9 Kbp, 8 Kbp, 7 Kbp, 6 Kbp, 5 Kbp, 4 Kbp, 3 Kbp, 2 Kbp, or 1 Kbp in length. A genomic region in a selector set may be less than about 1000 bp, 900 bp, 800 bp, 700 bp, 600 bp, 500 bp, 400 bp, 300 bp, 200 bp, or 100 bp. A genomic region may be said to "identify" a mutation when the mutation is within the sequence of that genomic region.

In some embodiments, the total sequence covered by the selector set is less than about 1.5 megabase pairs (Mbp), 1.4 Mbp, 1.3 Mbp, 1.2 Mbp, 1.1 Mbp, 1 Mbp. The total sequence covered by the selector set may be less than about 1000 kb, less than about 900 kb, less than about 800 kb, less than about 700 kb, less than about 600 kb, less than about 500 kb, less than about 400 kb, less than about 350 kb, less than about 300 kb, less than about 250 kb, less than about 200 kb, or less than about 150 kb. The total sequence covered by the selector set may be between about 100 kb to 500 kb. The total sequence covered by the selector set may be between about 100 kb to 350 kb. The total sequence covered by the selector set may be between about 100 kb to 150 kb.

The selector set may comprise 2, 3, 4, 5, 6, 7, 8, 9, 10, 11, 12, 13, 14, 15, 16, 17, 18, 19, 20 or more mutations in a plurality of genomic regions. The selector set may comprise 25, 30, 35, 40, 45, 50, 55, 60, 65, 70, 75, 80, 85, 90, 95, 100 or more mutations in a plurality of genomic regions. The selector set may comprise 125, 150, 175, 200, 250, 300, 350, 400, 450, 500, 550, 600, 650, 700, 750, 800, 850, 900, 950, 1000 or more mutations in a plurality of genomic regions.

At least a portion of the mutations may be within the same genomic region. At least about 2, 3, 4, 5, 6, 7, 8, 9, 10 or more mutations may be within the same genomic region. At least about 2 mutations may be within the same genomic region. At least about 3 mutations may be within the same genomic region.

At least a portion of the mutations may be within different genomic regions. At least about 2, 3, 4, 5, 6, 7, 8, 9, 10 or more mutations may be within two or more different genomic regions. At least about 2 mutations may be within two or more different genomic regions. At least about 3 mutations may be within two or more different genomic regions.

Two or more mutations may be in two or more different genomic regions of the same noncoding region. Two or more mutations may be in two or more different genomic regions of the same protein-coding region. Two or more mutations may be in two or more different genomic regions of the same gene. For example, a first mutation may be located in a first genomic region comprising a first exon of a first gene and a second mutation may be located in a second genomic region comprising a second exon of the first gene. In another example, a first mutation may be located in a first genomic region comprising a first portion of a first long noncoding RNA and a second mutation may be located in a second genomic region comprising a second portion of the first long noncoding RNA.

Alternatively, or additionally, two or more mutations may be in two or more different genomic regions of two or more different noncoding regions, protein-coding regions, and/or genes. For example, a first mutation may be located in a first genomic region comprising a first exon of a first gene and a second mutation may be located in a second genomic region comprising a second exon of a second gene. In another example, a first mutation may be located in a first genomic region comprising a first exon of a first gene and a second mutation may be located in a second genomic region comprising a portion of a microRNA.

The selector set may identify a median of at least 2, usually at least 3, and preferably at least 4 different mutations per individual subject. The selector set may identify a median of at least 5, 6, 7, 8, 9, 10, 11, 12, 13 or more different mutations per individual subject. The different mutations may be in one or more genomic regions. The different mutations may be in 1, 2, 3, 4, 5, 6, 7, 8, 9, 10, 11, 12, 13, 14, 15 or more genomic regions. The different mutations may be in 1, 2, 3, 4, 5, 6, 7, 8, 9, 10, 11, 12, 13, 14, 15 or more recurrently mutated regions.

The median number of mutations identified by the selector set may be determined in a population of up to 10, up to 25, up to 25, up to 50, up to 87, up to 100 or more subjects. The median number of mutations identified by the selector set may be determined in a population of up to 125, 150, 175, 200, 225, 250, 275, 300, 325, 350, 375, 400 or more subjects. In such a population, a selector set of interest may identify one or more mutations in at least 60%, at least 65%, at least 70%, at least 75%, at least 80%, at least 82%, at least 85%, at least 87%, at least 90%, at least 92%, at least 95% or more of the subjects.

The total mutations identified by the selector set may be present in at least 60%, at least 65%, at least 70%, at least 75%, at least 80%, at least 82%, at least 85%, at least 87%, at least 90%, at least 92%, at least 95% or more of subjects in a population. For example, the selector set may identify a first mutation present in 20% of the subjects and second mutation in 80% of the subjects, thus the total mutations identified by the selector set may be present in 80% to 100% of the subjects in the population.

In addition to a bioinformatics construct, a selector set can be used to generate an oligonucleotide or set of oligonucleotides for specific capture, sequencing and/or amplification of cfDNA corresponding to a genomic region. The set of oligonucleotides may include at least one oligonucleotide for each genomic region that is to be targeted. Oligonucleotides may have the general characteristic of sufficient length to uniquely identify the genomic region, e.g. usually at least about 15 nucleotides, at least about 16, 17, 18, 19, 20 nucleotides in length. An oligonucleotide may further comprise an adapter for the sequencing system; a tag for sorting; a specific binding tag, e.g. biotin, FITC, etc. Oligonucleotides for amplification may comprise a pair of sequences flanking the region of interest, and of opposite orientation. The oligonucleotide may comprise a primer sequence. The oligonucleotide may comprise a sequence that is complementary to at least a portion of the genomic region.

The methods set forth herein may generate a bioinformatics construct comprising the selector set sequence information. In order to use the selector set for patient diagnostic and prognostic methods, a set of selector probes may be generated from the selector set library. The set of selector probes may comprise a sequence from at least about 20 genomic regions, at least about 30 genomic regions, at least about 40 genomic regions, at least about 50 genomic regions, at least about 60 genomic regions, at least about 70 genomic regions, at least about 80 genomic regions, at least about 90 genomic regions, at least about 100 genomic regions, at least about 200 genomic regions, at least about 300 genomic regions, at least about 400 genomic regions, or at least about 500 genomic regions. The genomic regions may be selected from the genomic regions set forth in any one of Tables 2 and 6-18. The selection may be based on bioinformatics criteria, including the additional value provided by the region, the RI, etc. In some embodiments a pre-set coverage of patients is used as a cut-off, for example where at least 90% have one or more of the SNV, where at least 95% have one or more of the SNV, where at least 98% have one or more of the SNV.

The selector set may comprise one or more genomic regions identified by Table 2. The genomic regions of the selector set may comprise at least 2, 3, 4, 5, 6, 7, 8, 9, 10, 11, 12, 13, 14, 15, 16, 17, 18, 19, 20 or more regions from those identified in Table 2. The genomic regions of the selector set may comprise at least 25, 30, 35, 40, 45, 50, 55, 60, 65, 70, 75, 80, 85, 90, 95, 100, 150, 200, 250, 300, 350, 400, 450, 500, or 525 regions from those identified in Table 2. The genomic regions of the selector set may comprise at least 2 regions from those identified in Table 2. The genomic regions of the selector set may comprise at least 20 regions from those identified in Table 2. The genomic regions of the selector set may comprise at least 60 regions from those identified in Table 2. The genomic regions of the selector set may comprise at least 100 regions from those identified in Table 2. The genomic regions of the selector set may comprise at least 300 regions from those identified in Table 2. The genomic regions of the selector set may comprise at least 400 regions from those identified in Table 2. The genomic regions of the selector set may comprise at least 500 regions from those identified in Table 2.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 2. At least about 5% of the genomic regions of the selector set may be regions identified in Table 2. At least about 10% of the genomic regions of the selector set may be regions identified in Table 2. At least about 20% of the genomic regions of the selector set may be regions identified in Table 2. At least about 30% of the genomic regions of the selector set may be regions identified in Table 2. At least about 40% of the genomic regions of the selector set may be regions identified in Table 2.

The selector set may comprise one or more genomic regions identified by Table 6. The genomic regions of the selector set may comprise at least 2, 3, 4, 5, 6, 7, 8, 9, 10, 11, 12, 13, 14, 15, 16, 17, 18, 19, 20 or more regions from those identified in Table 6. The genomic regions of the selector set may comprise at least 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, or 830 regions from those identified in Table 6. The genomic regions of the selector set may comprise at least 2 regions from those identified in Table 6. The genomic regions of the selector set may comprise at least 20 regions from those identified in Table 6. The genomic regions of the selector set may comprise at least 60 regions from those identified in Table 6. The genomic regions of the selector set may comprise at least 100 regions from those identified in Table 6. The genomic regions of the selector set may comprise at least 300 regions from those identified in Table 6. The genomic regions of the selector set may comprise at least 600 regions from those identified in Table 6. The genomic regions of the selector set may comprise at least 800 regions from those identified in Table 6.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 6. At least about 5% of the genomic regions of the selector set may be regions identified in Table 6. At least about 10% of the genomic regions of the selector set may be regions identified in Table 6. At least about 20% of the genomic regions of the selector set may be regions identified in Table 6. At least about 30% of the genomic regions of the selector set may be regions identified in Table 6. At least about 40% of the genomic regions of the selector set may be regions identified in Table 6.

The selector set may comprise one or more genomic regions identified by Table 7. The genomic regions of the selector set may comprise at least 2, 3, 4, 5, 6, 7, 8, 9, 10, 11, 12, 13, 14, 15, 16, 17, 18, 19, 20 or more regions from those identified in Table 7. The genomic regions of the selector set may comprise at least 25, 30, 35, 40, 45, 50, 55, 60, 65, 70, 75, 80, 85, 90, 95, 100, 125, 150, 175, 200, 225, 250, 275, 300, 325, 350, 375, 400, 425, or 450 regions from those identified in Table 7. The genomic regions of the selector set may comprise at least 2 regions from those identified in Table 7. The genomic regions of the selector set may comprise at least 20 regions from those identified in Table 7. The genomic regions of the selector set may comprise at least 60 regions from those identified in Table 7. The genomic regions of the selector set may comprise at least 100 regions from those identified in Table 7. The genomic regions of the selector set may comprise at least 200 regions from those identified in Table 7. The genomic regions of the selector set may comprise at least 300 regions from those identified in Table 7. The genomic regions of the selector set may comprise at least 400 regions from those identified in Table 7.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 7. At least about 5% of the genomic regions of the selector set may be regions identified in Table 7. At least about 10% of the genomic regions of the selector set may be regions identified in Table 7. At least about 20% of the genomic regions of the selector set may be regions identified in Table 7. At least about 30% of the genomic regions of the selector set may be regions identified in Table 7. At least about 40% of the genomic regions of the selector set may be regions identified in Table 7.

The selector set may comprise one or more genomic regions identified by Table 8. The genomic regions of the selector set may comprise at least 2, 3, 4, 5, 6, 7, 8, 9, 10, 11, 12, 13, 14, 15, 16, 17, 18, 19, 20 or more regions from those identified in Table 8. The genomic regions of the selector set may comprise at least 25, 30, 35, 40, 45, 50, 55, 60, 65, 70, 75, 80, 85, 90, 95, 100 regions from those identified in Table 8. The genomic regions of the selector set may comprise at least 250, 300, 350, 400, 450, 500, 550, 600, 650, 700, 750, 800, 850, 900, 950, 1000, or 1050 regions from those identified in Table 8. The genomic regions of the selector set may comprise at least 2 regions from those identified in Table 8. The genomic regions of the selector set may comprise at least 20 regions from those identified in Table 8. The genomic regions of the selector set may comprise at least 60 regions from those identified in Table 8. The genomic regions of the selector set may comprise at least 100 regions from those identified in Table 8. The genomic regions of the selector set may comprise at least 300 regions from those identified in Table 8. The genomic regions of the selector set may comprise at least 600 regions from those identified in Table 8. The genomic regions of the selector set may comprise at least 800 regions from those identified in Table 8. The genomic regions of the selector set may comprise at least 1000 regions from those identified in Table 8.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 8. At least about 5% of the genomic regions of the selector set may be regions identified in Table 8. At least about 10% of the genomic regions of the selector set may be regions identified in Table 8. At least about 20% of the genomic regions of the selector set may be regions identified in Table 8. At least about 30% of the genomic regions of the selector set may be regions identified in Table 8. At least about 40% of the genomic regions of the selector set may be regions identified in Table 8.

The selector set may comprise one or more genomic regions identified by Table 9. The genomic regions of the selector set may comprise at least 2, 3, 4, 5, 6, 7, 8, 9, 10, 11, 12, 13, 14, 15, 16, 17, 18, 19, 20 or more regions from those identified in Table 9. The genomic regions of the selector set may comprise at least 25, 30, 35, 40, 45, 50, 55, 60, 65, 70, 75, 80, 85, 90, 95, 100 regions from those identified in Table 9. The genomic regions of the selector set may comprise at least 250, 300, 350, 400, 450, 500, 550, 600, 650, 700, 750, 800, 850, 900, 950, 1000, 1100, 1200, 1300, 1400, or 1500 regions from those identified in Table 9. The genomic regions of the selector set may comprise at least 2 regions from those identified in Table 9. The genomic regions of the selector set may comprise at least 20 regions from those identified in Table 9. The genomic regions of the selector set may comprise at least 60 regions from those identified in Table 9. The genomic regions of the selector set may comprise at least 100 regions from those identified in Table 9. The genomic regions of the selector set may comprise at least 300 regions from those identified in Table 9. The genomic regions of the selector set may comprise at least 500 regions from those identified in Table 9. The genomic regions of the selector set may comprise at least 1000 regions from those identified in Table 9. The genomic regions of the selector set may comprise at least 1300 regions from those identified in Table 9.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 9. At least about 5% of the genomic regions of the selector set may be regions identified in Table 9. At least about 10% of the genomic regions of the selector set may be regions identified in Table 9. At least about 20% of the genomic regions of the selector set may be regions identified in Table 9. At least about 30% of the genomic regions of the selector set may be regions identified in Table 9. At least about 40% of the genomic regions of the selector set may be regions identified in Table 9.

The selector set may comprise one or more genomic regions identified by Table 10. The genomic regions of the selector set may comprise at least 2, 3, 4, 5, 6, 7, 8, 9, 10, 11, 12, 13, 14, 15, 16, 17, 18, 19, 20 or more regions from those identified in Table 10. The genomic regions of the selector set may comprise at least 25, 30, 35, 40, 45, 50, 55, 60, 65, 70, 75, 80, 85, 90, 95, 100 regions from those identified in Table 10. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, or 330 regions from those identified in Table 10. The genomic regions of the selector set may comprise at least 2 regions from those identified in Table 10. The genomic regions of the selector set may comprise at least 20 regions from those identified in Table 10. The genomic regions of the selector set may comprise at least 60 regions from those identified in Table 10.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 10. At least about 5% of the genomic regions of the selector set may be regions identified in Table 10. At least about 10% of the genomic regions of the selector set may be regions identified in Table 10. At least about 20% of the genomic regions of the selector set may be regions identified in Table 10. At least about 30% of the genomic regions of the selector set may be regions identified in Table 10. At least about 40% of the genomic regions of the selector set may be regions identified in Table 10.

The selector set may comprise one or more genomic regions identified by Table 11. The genomic regions of the selector set may comprise at least 2, 3, 4, 5, 6, 7, 8, 9, 10, 11, 12, 13, 14, 15, 16, 17, 18, 19, 20 or more regions from those identified in Table 11. The genomic regions of the selector set may comprise at least 25, 30, 35, 40, 45, 50, 55, 60, 65, 70, 75, 80, 85, 90, 95, 100 regions from those identified in Table 11. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, or 460 regions from those identified in Table 11. The genomic regions of the selector set may comprise at least 2 regions from those identified in Table 11. The genomic regions of the selector set may comprise at least 20 regions from those identified in Table 11. The genomic regions of the selector set may comprise at least 60 regions from those identified in Table 11. The genomic regions of the selector set may comprise at least 100 regions from those identified in Table 11. The genomic regions of the selector set may comprise at least 200 regions from those identified in Table 11. The genomic regions of the selector set may comprise at least 300 regions from those identified in Table 11. The genomic regions of the selector set may comprise at least 400 regions from those identified in Table 11.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 11. At least about 5% of the genomic regions of the selector set may be regions identified in Table 11. At least about 10% of the genomic regions of the selector set may be regions identified in Table 11. At least about 20% of the genomic regions of the selector set may be regions identified in Table 11. At least about 30% of the genomic regions of the selector set may be regions identified in Table 11. At least about 40% of the genomic regions of the selector set may be regions identified in Table 11.

The selector set may comprise one or more genomic regions identified by Table 12. The genomic regions of the selector set may comprise at least 2, 3, 4, 5, 6, 7, 8, 9, 10, 11, 12, 13, 14, 15, 16, 17, 18, 19, 20 or more regions from those identified in Table 12. The genomic regions of the selector set may comprise at least 25, 30, 35, 40, 45, 50, 55, 60, 65, 70, 75, 80, 85, 90, 95, 100 regions from those identified in Table 12. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480 or 500 regions from those identified in Table 12. The genomic regions of the selector set may comprise at least 2 regions from those identified in Table 12. The genomic regions of the selector set may comprise at least 20 regions from those identified in Table 12. The genomic regions of the selector set may comprise at least 60 regions from those identified in Table 12. The genomic regions of the selector set may comprise at least 100 regions from those identified in Table 12. The genomic regions of the selector set may comprise at least 200 regions from those identified in Table 12. The genomic regions of the selector set may comprise at least 300 regions from those identified in Table 12. The genomic regions of the selector set may comprise at least 400 regions from those identified in Table 12. The genomic regions of the selector set may comprise at least 500 regions from those identified in Table 12.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 12. At least about 5% of the genomic regions of the selector set may be regions identified in Table 12. At least about 10% of the genomic regions of the selector set may be regions identified in Table 12. At least about 20% of the genomic regions of the selector set may be regions identified in Table 12. At least about 30% of the genomic regions of the selector set may be regions identified in Table 12. At least about 40% of the genomic regions of the selector set may be regions identified in Table 12.

The selector set may comprise one or more genomic regions identified by Table 13. The genomic regions of the selector set may comprise at least 2, 3, 4, 5, 6, 7, 8, 9, 10, 11, 12, 13, 14, 15, 16, 17, 18, 19, 20 or more regions from those identified in Table 13. The genomic regions of the selector set may comprise at least 25, 30, 35, 40, 45, 50, 55, 60, 65, 70, 75, 80, 85, 90, 95, 100 regions from those identified in Table 13. The genomic regions of the selector set may comprise at least 250, 300, 350, 400, 450, 500, 550, 600, 650, 700, 750, 800, 850, 900, 950, 1000, 1050, 1100, 1150, 1200, 1250, 1300, 1350, 1400, or 1450 regions from those identified in Table 13. The genomic regions of the selector set may comprise at least 2 regions from those identified in Table 13. The genomic regions of the selector set may comprise at least 20 regions from those identified in Table 13. The genomic regions of the selector set may comprise at least 60 regions from those identified in Table 13. The genomic regions of the selector set may comprise at least 100 regions from those identified in Table 13. The genomic regions of the selector set may comprise at least 300 regions from those identified in Table 13. The genomic regions of the selector set may comprise at least 500 regions from those identified in Table 13. The genomic regions of the selector set may comprise at least 1000 regions from those identified in Table 13. The genomic regions of the selector set may comprise at least 1300 regions from those identified in Table 13.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 13. At least about 5% of the genomic regions of the selector set may be regions identified in Table 13. At least about 10% of the genomic regions of the selector set may be regions identified in Table 13. At least about 20% of the genomic regions of the selector set may be regions identified in Table 13. At least about 30% of the genomic regions of the selector set may be regions identified in Table 13. At least about 40% of the genomic regions of the selector set may be regions identified in Table 13.

The selector set may comprise one or more genomic regions identified by Table 14. The genomic regions of the selector set may comprise at least 2, 3, 4, 5, 6, 7, 8, 9, 10, 11, 12, 13, 14, 15, 16, 17, 18, 19, 20 or more regions from those identified in Table 14. The genomic regions of the selector set may comprise at least 25, 30, 35, 40, 45, 50, 55, 60, 65, 70, 75, 80, 85, 90, 95, 100 regions from those identified in Table 14. The genomic regions of the selector set may comprise at least 250, 300, 350, 400, 450, 500, 550, 600, 650, 700, 750, 800, 850, 900, 950, 1000, 1050, 1100, 1150, 1200, 1210, 1220, 1230, or 1240 regions from those identified in Table 14. The genomic regions of the selector set may comprise at least 2 regions from those identified in Table 14. The genomic regions of the selector set may comprise at least 20 regions from those identified in Table 14. The genomic regions of the selector set may comprise at least 60 regions from those identified in Table 14. The genomic regions of the selector set may comprise at least 100 regions from those identified in Table 14. The genomic regions of the selector set may comprise at least 300 regions from those identified in Table 14. The genomic regions of the selector set may comprise at least 500 regions from those identified in Table 14. The genomic regions of the selector set may comprise at least 1000 regions from those identified in Table 14. The genomic regions of the selector set may comprise at least 1100 regions from those identified in Table 14. The genomic regions of the selector set may comprise at least 1200 regions from those identified in Table 14.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 14. At least about 5% of the genomic regions of the selector set may be regions identified in Table 14. At least about 10% of the genomic regions of the selector set may be regions identified in Table 14. At least about 20% of the genomic regions of the selector set may be regions identified in Table 14. At least about 30% of the genomic regions of the selector set may be regions identified in Table 14. At least about 40% of the genomic regions of the selector set may be regions identified in Table 14.

The selector set may comprise one or more genomic regions identified by Table 15. The genomic regions of the selector set may comprise at least 2, 3, 4, 5, 6, 7, 8, 9, 10, 11, 12, 13, 14, 15, 16, 17, 18, 19, 20 or more regions from those identified in Table 15. The genomic regions of the selector set may comprise at least 25, 30, 35, 40, 45, 50, 55, 60, 65, 70, 75, 80, 85, 90, 95, 100, 110, 120, 130, 140, 150, 160, or 170 regions from those identified in Table 15. The genomic regions of the selector set may comprise at least 2 regions from those identified in Table 15. The genomic regions of the selector set may comprise at least 20 regions from those identified in Table 15. The genomic regions of the selector set may comprise at least 60 regions from those identified in Table 15. The genomic regions of the selector set may comprise at least 100 regions from those identified in Table 15. The genomic regions of the selector set may comprise at least 120 regions from those identified in Table 15. The genomic regions of the selector set may comprise at least 150 regions from those identified in Table 15.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 15. At least about 5% of the genomic regions of the selector set may be regions identified in Table 15. At least about 10% of the genomic regions of the selector set may be regions identified in Table 15. At least about 20% of the genomic regions of the selector set may be regions identified in Table 15. At least about 30% of the genomic regions of the selector set may be regions identified in Table 15. At least about 40% of the genomic regions of the selector set may be regions identified in Table 15.

The selector set may comprise one or more genomic regions identified by Table 16. The genomic regions of the selector set may comprise at least 2, 3, 4, 5, 6, 7, 8, 9, 10, 11, 12, 13, 14, 15, 16, 17, 18, 19, 20 or more regions from those identified in Table 16. The genomic regions of the selector set may comprise at least 25, 30, 35, 40, 45, 50, 55, 60, 65, 70, 75, 80, 85, 90, 95, 100 regions from those identified in Table 16. The genomic regions of the selector set may comprise at least 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or 2050 regions from those identified in Table 16. The genomic regions of the selector set may comprise at least 2 regions from those identified in Table 16. The genomic regions of the selector set may comprise at least 20 regions from those identified in Table 16. The genomic regions of the selector set may comprise at least 60 regions from those identified in Table 16. The genomic regions of the selector set may comprise at least 100 regions from those identified in Table 16. The genomic regions of the selector set may comprise at least 300 regions from those identified in Table 16. The genomic regions of the selector set may comprise at least 500 regions from those identified in Table 16. The genomic regions of the selector set may comprise at least 1000 regions from those identified in Table 16. The genomic regions of the selector set may comprise at least 1200 regions from those identified in Table 16. The genomic regions of the selector set may comprise at least 1500 regions from those identified in Table 16. The genomic regions of the selector set may comprise at least 1700 regions from those identified in Table 16. The genomic regions of the selector set may comprise at least 2000 regions from those identified in Table 16.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 16. At least about 5% of the genomic regions of the selector set may be regions identified in Table 16. At least about 10% of the genomic regions of the selector set may be regions identified in Table 16. At least about 20% of the genomic regions of the selector set may be regions identified in Table 16. At least about 30% of the genomic regions of the selector set may be regions identified in Table 16. At least about 40% of the genomic regions of the selector set may be regions identified in Table 16.

The selector set may comprise one or more genomic regions identified by Table 17. The genomic regions of the selector set may comprise at least 2, 3, 4, 5, 6, 7, 8, 9, 10, 11, 12, 13, 14, 15, 16, 17, 18, 19, 20 or more regions from those identified in Table 17. The genomic regions of the selector set may comprise at least 25, 30, 35, 40, 45, 50, 55, 60, 65, 70, 75, 80, 85, 90, 95, 100 regions from those identified in Table 17. The genomic regions of the selector set may comprise at least 250, 300, 350, 400, 450, 500, 550, 600, 650, 700, 750, 800, 850, 900, 950, 1000, 1010, 1020, 1030, 1040, 1050, 1060, 1070, or 1080 regions from those identified in Table 17. The genomic regions of the selector set may comprise at least 2 regions from those identified in Table 17. The genomic regions of the selector set may comprise at least 20 regions from those identified in Table 17. The genomic regions of the selector set may comprise at least 60 regions from those identified in Table 17. The genomic regions of the selector set may comprise at least 100 regions from those identified in Table 17. The genomic regions of the selector set may comprise at least 300 regions from those identified in Table 17. The genomic regions of the selector set may comprise at least 500 regions from those identified in Table 17. The genomic regions of the selector set may comprise at least 1000 regions from those identified in Table 17. The genomic regions of the selector set may comprise at least 1050 regions from those identified in Table 17.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 17. At least about 5% of the genomic regions of the selector set may be regions identified in Table 17. At least about 10% of the genomic regions of the selector set may be regions identified in Table 17. At least about 20% of the genomic regions of the selector set may be regions identified in Table 17. At least about 30% of the genomic regions of the selector set may be regions identified in Table 17. At least about 40% of the genomic regions of the selector set may be regions identified in Table 17.

The selector set may comprise one or more genomic regions identified by Table 18. The genomic regions of the selector set may comprise at least 2, 3, 4, 5, 6, 7, 8, 9, 10, 11, 12, 13, 14, 15, 16, 17, 18, 19, 20 or more regions from those identified in Table 18. The genomic regions of the selector set may comprise at least 25, 30, 35, 40, 45, 50, 55, 60, 65, 70, 75, 80, 85, 90, 95, 100 regions from those identified in Table 18. The genomic regions of the selector set may comprise at least 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 375, 400, 420, 440, 460, 480, 500, 520, 540, or 555 regions from those identified in Table 18. The genomic regions of the selector set may comprise at least 2 regions from those identified in Table 18. The genomic regions of the selector set may comprise at least 20 regions from those identified in Table 18. The genomic regions of the selector set may comprise at least 60 regions from those identified in Table 18. The genomic regions of the selector set may comprise at least 100 regions from those identified in Table 18. The genomic regions of the selector set may comprise at least 200 regions from those identified in Table 18. The genomic regions of the selector set may comprise at least 300 regions from those identified in Table 18. The genomic regions of the selector set may comprise at least 400 regions from those identified in Table 18. The genomic regions of the selector set may comprise at least 500 regions from those identified in Table 18.

At least about 5%, 10%, 15%, 20%, 25%, 30%, 35%, 40%, 45%, 50%, 55%, 60%, 65%, 70%, 75%, 80%, 85%, 90%, or 95% of the genomic regions of the selector set may be regions identified in Table 18. At least about 5% of the genomic regions of the selector set may be regions identified in Table 18. At least about 10% of the genomic regions of the selector set may be regions identified in Table 18. At least about 20% of the genomic regions of the selector set may be regions identified in Table 18. At least about 30% of the genomic regions of the selector set may be regions identified in Table 18. At least about 40% of the genomic regions of the selector set may be regions identified in Table 18.

Selector set probes may be at least about 15, 20, 25, 30, 35, 40, 45, 50, 55, 60, 65, 70, 75, 80, 85, 90, 95 or 100 nucleotides in length. Selector set probes may be at least about 20 nucleotides in length. Selector set probes may be at least about 30 nucleotides in length. Selector set probes may be at least about 40 nucleotides in length. Selector set probes may be at least about 50 nucleotides in length.

Selector probes may be of about 15 to about 250 nucleotides in length. Selector set probes may be about 15 to about 200 nucleotides in length. Selector set probes may be about 15 to about 170 nucleotides in length. Selector set probes may be about 15 to about 150 nucleotides in length. Selector set probes may be about 25 to about 200 nucleotides in length. Selector set probes may be about 25 to about 150 nucleotides in length. Selector set probes may be about 50 to about 150 nucleotides in length. Selector set probes may be about 50 to about 125 nucleotides in length.

1, 2, 3, 4, 5, 6, 7, 8, 9, 10 or more selector set probes may correspond to one genomic region. Two or more selector set probes may correspond to one genomic region. Three or more selector set probes may correspond to one genomic region. A set of selector set probes therefore may have the complexity of the selector set from which it is obtained. Selector probes may be synthesized using conventional methods, or generated by any other suitable molecular biology approach. Selector probes may be hybridized to cfDNA for hybrid capture, as described herein. Selector probes may comprise a binding moiety that allows capture of the hybrid. Various binding moieties (e.g., tags) useful for this purpose are known in the art, including without limitation biotin, HIS tags, MYC tags, FITC, and the like.

Exemplary selector sets are provided in Tables 2, and 6-18. The selector set comprising one or more genomic regions identified in Table 2 may be useful for non-small cell lung carcinoma (NSCLC). The selector set comprising one or more genomic regions identified in Table 6 may be useful for breast cancer. The selector set comprising one or more genomic regions identified in Table 7 may be useful for colorectal cancer. The selector set comprising one or more genomic regions identified in Table 8 may be useful for diffuse large B-cell lymphoma (DLBCL). The selector set comprising one or more genomic regions identified in Table 9 may be useful for Ehrlich ascites carcinoma (EAC). The selector set comprising one or more genomic regions identified in Table 10 may be useful for follicular lymphoma (FL). The selector set comprising one or more genomic regions identified in Table 11 may be useful for head and Neck squamous cell carcinoma (HNSC). The selector set comprising one or more genomic regions identified in Table 12 may be useful for NSCLC. The selector set comprising one or more genomic regions identified in Table 13 may be useful for NSCLC. The selector set comprising one or more genomic regions identified in Table 14 may be useful for ovarian cancer. The selector set comprising one or more genomic regions identified in Table 15 may be useful for ovarian cancer. The selector set comprising one or more genomic regions identified in Table 16 may be useful for pancreatic cancer. The selector set comprising one or more genomic regions identified in Table 17 may be useful for prostate adenocarcinoma. The selector set comprising one or more genomic regions identified in Table 18 may be useful for skin cutaneous melanoma. The selector set of any one of Tables 2 and 6-18 may be useful for carcinomas and sub-generically for adenocarcinomas or squamous cell carcinomas.

Methods for Producing a Selector Set

Disclosed herein are methods of producing a selector set. One objective in designing a selector set may comprise maximizing the fraction of patients covered and the number of mutations per patient covered while minimizing selector size. Evaluating all possible combinations of genomic regions to build such a selector set may be an exponentially large problem (e.g., $2^n$ possible exon combinations given n exons), rendering the use of an approximation algorithm critical. Thus, a heuristic strategy may be used to produce a selector set.

Figures 5A, 5B:
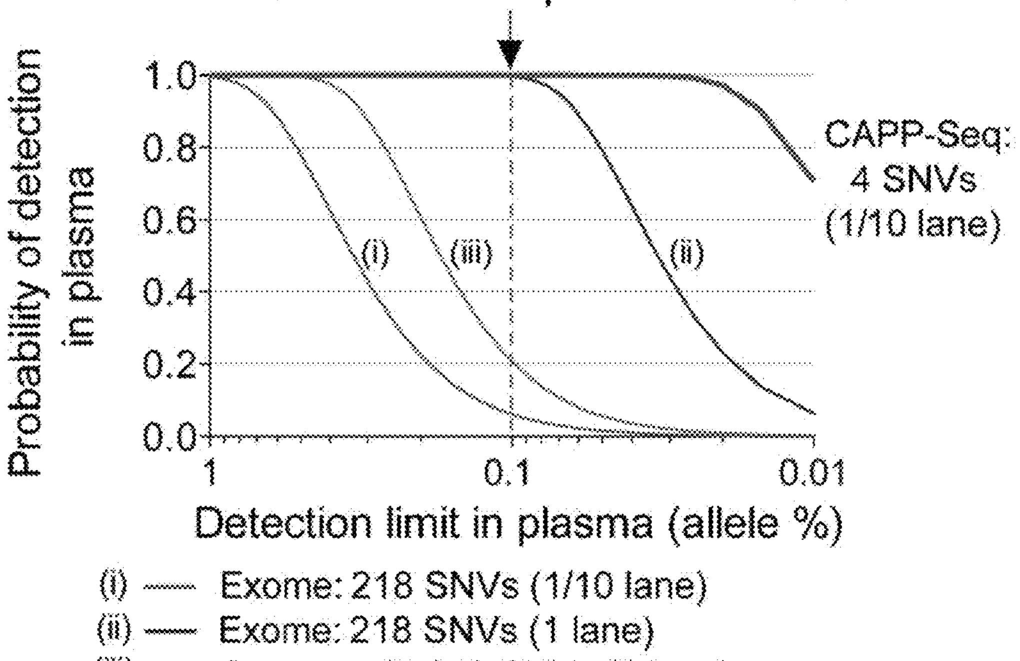
FIG. 5A-5B: Comparison to other methods for detection of ctDNA in plasma.
Figure 6:
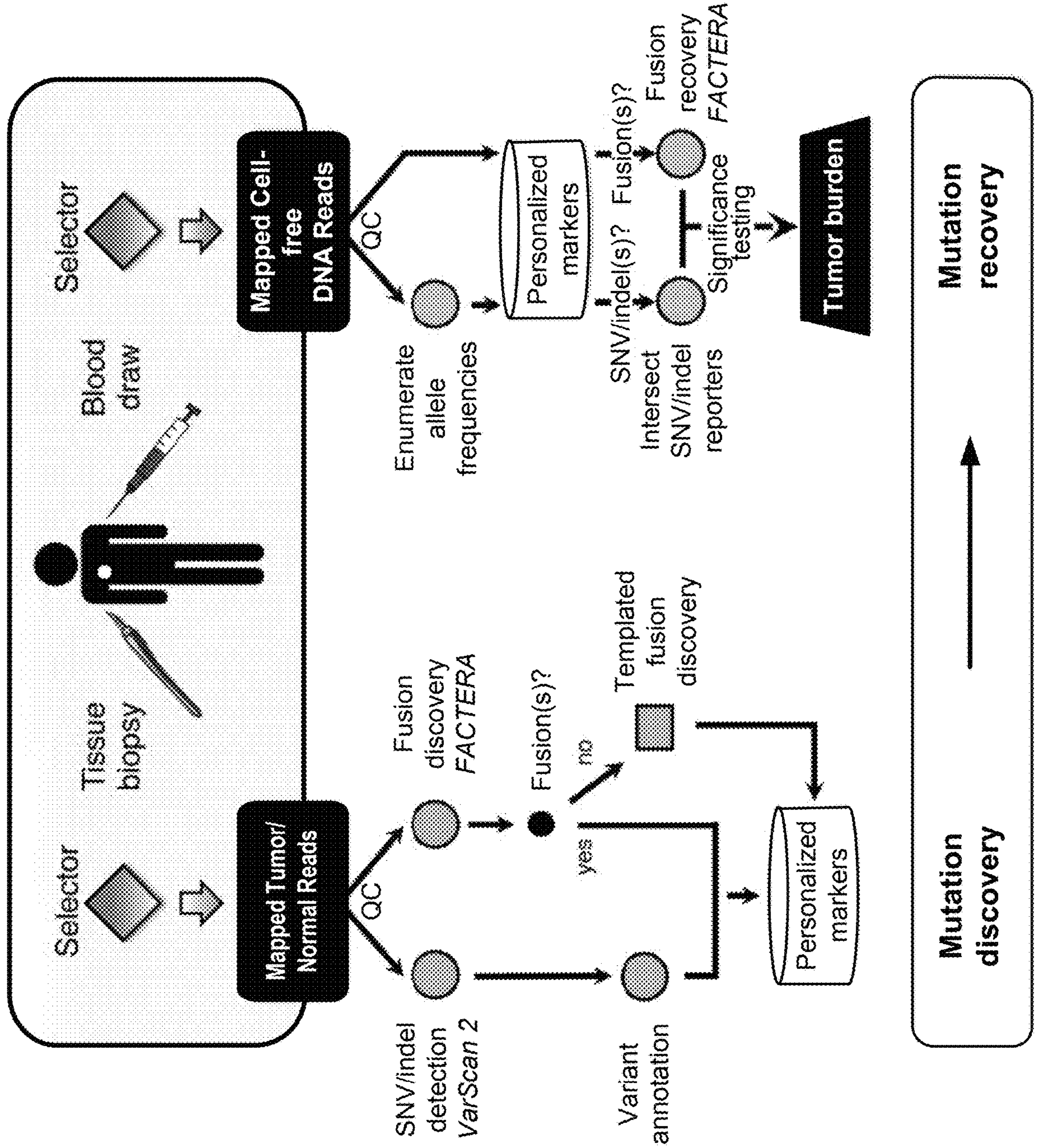
FIG. 6: CAPP-Seq computational pipeline. Major steps of the bioinformatics pipeline for mutation discovery and quantitation in plasma are schematically illustrated.

The selector sets disclosed herein may be rationally designed for a given ctDNA detection limit, sequencing cost, and/or DNA input mass. Such a selector set may be designed using a selector design calculator. A selector design calculator may be based on the following analytical model: the probability P of recovering at least 1 read of a single mutant allele in plasma for a given sequencing read depth and detection limit of ctDNA in plasma may be modeled by a binomial distribution. Given P, the probability of detecting all identified tumor mutations in plasma may be modeled by a geometric distribution. With this design calculator, one can first estimate how many tumor reporters will be needed to achieve a desired sensitivity, and can then target a selector size that balances this number with considerations of cost and DNA mass input. FIG. 5*a* shows a graphical representation of the probability P of detecting ctDNA in plasma for different detection limits of ctDNA in plasma for CAPP-Seq (dark, thick line), whole exome sequence (i and ii), and whole genome sequence (iii).

The method of producing a selector set may comprise (a) calculating a recurrence index of a genomic region of a plurality of genomic regions by dividing a number of subjects that have one or more mutations in the genomic region by a length of the genomic region; and (b) producing a selector set comprising one or more genomic regions of the plurality of genomic regions by selecting genomic regions based on the recurrence index. For example, 10 subjects may contain one or more mutations in a genomic region comprising 100 bases. The recurrence index could be calculated by dividing the number of subjects containing mutations in the one or more genomic regions by the length of the genomic region. In this example, the recurrence index for this genomic region would be 10 subjects divided by 100 bases, which equals 0.1 subjects per base.

The method may further comprise ranking genomic regions of the plurality of genomic regions by the recurrence index. Producing the selector set based on the recurrence index may comprise selecting genomic regions that have a recurrence index in the top $70^{th}$, $75^{th}$, $80^{th}$, $85^{th}$, $90^{th}$, or $95^{th}$ or greater percentile. Producing the selector set based on the recurrence index may comprise selecting genomic regions that has a recurrence index in the top $90^{th}$ percentile. For example, a first genomic region may have a recurrence index in the top $80^{th}$ percentile and a second genomic region may have a recurrence index in the bottom $20^{th}$ percentile. The selector set based on genomic regions with a recurrence index in the top $75^{th}$ percentile may comprise the first genomic region, but not the second genomic region.

The method may further comprise ranking the genomic regions by the number of subjects having one or more mutations in the genomic region. Producing the selector set may further comprise selecting genomic regions in the top $70^{th}$, $75^{th}$, $80^{th}$, $85^{th}$, $90^{th}$, or $95^{th}$ or greater percentile of number of subjects having one or more mutations in the genomic region. Producing the selector set may further comprise selecting genomic regions in the top $90^{th}$ or greater percentile of number of subjects having one or more mutations in the genomic region.

The length of the genomic region may be in kilobases. The length of the genomic region may be in bases. For genomic regions containing known somatic mutations associated with a cancer, the length of the genomic region may consist essentially on the subsequence of the known mutation. For genomic regions containing known somatic mutations associated with a cancer, the length of the genomic region may consist essentially on the subsequence of the known mutation and one or more bases flanking the subsequence of the known mutation. For genomic regions containing known somatic mutations associated with a cancer, the length of the genomic region may consist essentially on the subsequence of the known mutation and 1 to 5 bases flanking the subsequence of the known mutation. For genomic regions containing known somatic mutations associated with a cancer, the length of the genomic region may consist essentially on the subsequence of the known mutation and 5 or fewer bases flanking the subsequence of the known mutation. The recurrence index for a genomic region comprising a known somatic mutation may be recalculated based on the length of the subsequence of the known mutation or the length of the subsequence of the known mutation with additional bases flanking the subsequence of the known mutation. For example, a genomic region may comprise 200 bases and the known somatic mutation within the genomic region may comprise 100 bases. The recurrence index may be calculated by dividing the number of subjects containing one or more mutations in the genomic region divided by the length of the somatic mutation with the genomic region (e.g., 100 bases).

Further disclosed herein is a method of producing a selector set comprising (a) identifying, with the aid of a computer processor, a plurality of genomic regions comprising one or more mutations by analyzing data pertaining to the plurality of genomic regions from a population of subjects suffering from a cancer; and (b) applying an algorithm to the data to produce a selector set comprising two or more genomic regions of the plurality of genomic regions, wherein the algorithm is used to maximize a median number of mutations in the genomic regions of the selector set in the population of subjects.

Identifying the plurality of genomic regions may comprise calculating a recurrence index of one or more genomic regions of the plurality of genomic regions. The algorithm may be applied to the data pertaining to genomic regions with a recurrence index in the top $40^{th}$, $45^{th}$, $50^{th}$, $55^{th}$, $57^{th}$, $60^{th}$, $63^{rd}$, or $65^{th}$ or higher percentile. The algorithm may be applied to data pertaining to genomic regions having a recurrence index of at least about 15, 20, 25, 30, 35, 40, 45, or 50 or more.

Identifying the plurality of genomic regions may comprise determining a number of subjects having one or more mutations in a genomic region. The algorithm may be applied to the data pertaining to genomic regions in the top $40^{th}$, $45^{th}$, $50^{th}$, $55^{th}$, $57^{th}$, $60^{th}$, $63^{rd}$, or $65^{th}$ or greater percentile of number of subjects having one or more mutations in the genomic region.

The algorithm may maximize the median number of mutations by identifying genomic regions that result in the largest reduction in subjects with one mutation in the genomic region. Producing the selector set may comprise selecting genomic regions that result in the largest reduction in subjects with one mutation in the genomic region.

The algorithm may be applied to the data pertaining to genomic regions meeting a minimum threshold. The minimum threshold may pertain to the recurrence index. For example, the algorithm may be applied to genomic regions having a recurrence index in the top 60th percentile. In another example, the algorithm may be applied to genomic regions that have a recurrence index of greater than or equal to 30. Alternatively, or additionally, the minimum threshold may pertain to genomic regions in the top $60^{th}$ percentile of the number of subjects having one or more mutations in the genomic region.

The algorithm may be applied 1, 2, 3, 4, 5, 6, 7, 8, 9, 10 or more times. The algorithm may be applied one or more times. The algorithm may be applied two or more times. The algorithm may be applied to a first set of genomic regions meeting a first minimum threshold. For example, the algorithm may be applied to a first set of genomic regions in the top 60th percentile of the recurrence index and the top $60^{th}$ percentile of the number of subjects having one or more mutations in the genomic region. The algorithm may be applied a second set of genomic regions meeting a second minimum threshold. For example, the algorithm may be applied to a second set of genomic regions having a recurrence index of greater than or equal to 20.

The median number of mutations in the genomic regions in the population of subjects may be at least about 2, 3, 4, 5, 6, 7, 8, 9, 10 or more mutations. The median number of mutations in the genomic regions in the population of subjects may be at least about 2, 3, or 4 or more mutations.

The algorithm may further be used to maximize a number of subjects containing one or more mutations within the genomic regions in the selector set. The algorithm may further be used to maximize a percentage of subjects from the population containing the one or more mutations within the genomic regions in the selector set. The percentage of subjects from the population containing the one or more mutations within the genomic regions may be at least about 60%, 65%, 70%, 75%, 80%, 85%, 87%, 90%, 92%, 95%, or 97% or more.

Alternatively, the method of producing a selector set may comprise (a) obtaining data pertaining to a plurality of genomic regions from a population of subjects suffering from a cancer; and (b) applying an algorithm to the data to produce a selector set comprising two or more genomic regions of the plurality of genomic regions, wherein the algorithm is used to maximize a number of subjects containing one or more mutations within the genomic regions in the selector.

The algorithm may maximize the number of subjects containing the one or more mutations by calculating a recurrence index of the genomic regions. Producing the selector set may comprise selecting one or more genomic regions based on the recurrence index.

The algorithm may maximize the number of subjects containing the one or more mutations by identifying genomic regions comprising one or more mutations found in 2, 3, 4, 5, 6, 7, 8, 9, 10 or more subjects. The algorithm may maximize the number of subjects containing the one or more mutations by identifying genomic regions comprising one or more mutations found in 5 or more subjects. Producing the selector set may comprise selecting one or more genomic regions based on a frequency of the mutation within the genomic region in the population of subjects.

Producing the selector set may comprise iterative addition of the genomic regions to the selector set. Producing the selector set may comprise selecting one or more genomic regions that identify mutations in at least one new subject from the population of subjects. For example, a selector set may comprise genomic regions A, B, and C, which contain mutations observed in subjects 1, 2, 3, 4, 5, 6, 7 and 8. Genomic region D may contain a mutation observed in subjects 1-4 and 10. Genomic region E may contain a mutation observed in subjects 1-5. Genomic region D identified at least one additional subject (e.g., subject 10) and may be added to the selector set, whereas genomic region E did not identify an additional subject and is not added to the selector set.

Producing the selector set may comprise selecting one or more genomic regions based on minimizing overlap of subjects already identified by the selector. For example, a selector set may comprise genomic regions A, B, C, and D, which contain mutations observed in subjects 1, 2, 3, 4, 5, 6, 7, 8, 9, and 10. Genomic region E may contain a mutation observed in subjects 1-5, 11, and 13. Genomic region F may contain a mutation observed in subjects 12 and 15. Genomic region E had 5 subjects in common with the selector set, whereas genomic region F had no subjects in common with the selector set. Thus, genomic region F may be added to the selector set.

The algorithm may be used to maximize a percentage of subjects from the population containing the one or more mutations within the genomic regions in the selector. The percentage of subjects from the population containing the one or more mutations within the genomic regions may be at least about 60%, 65%, 70%, 75%, 80%, 85%, 87%, 90%, 92%, 95%, or 97% or more.

The algorithm may further be used to maximize a median number of mutations in the genomic regions in a subject of the population of subjects. The median number of mutations in the genomic regions in the subject may be at least about 2, 3, 4, 5, 6, 7, 8, 9, 10 or more mutations. The median number of mutations in the genomic regions in the subject may be at least about 2, 3, or 4 or more mutations.

Producing the selector set may further comprise adding genomic regions comprising one or more mutations known to be associated with a cancer. Producing the selector set may further comprise adding genomic regions comprising one or more mutations predicted to be associated with a cancer. Producing the selector set may further comprise adding genomic regions comprising one or more rearrangements. Producing the selector set may further comprise adding genomic regions comprising one or more fusions.

The method may further comprise identifying one or more genomic regions that contain one or more recurrent mutations in a cancer. The identification of these recurrent mutations may benefit greatly from the availability of databases such as, for example, The Cancer Genome Atlas (TCGA) and its subsets. Such databases may serve as the starting point for identifying the recurrently mutated genomic regions of the selector sets. The databases may also provide a sample of mutations occurring within a given percentage of subjects with a specific cancer.

The method of producing a selector set may comprise (a) identifying a plurality of genomic regions; (b) prioritizing the plurality of genomic regions; and (c) selecting one or more genomic regions for inclusion in a selector set. The following design strategy can be used to identify and prioritize genomic regions for inclusion in a selector set. Three phases may incorporate known and suspected driver genes, as well as genomic regions known to participate in clinically actionable fusions, while another three phases may employ an algorithmic approach to maximize both the number of patients covered and SNVs per patient, utilizing the "Recurrence Index" (RI) as described herein. The strategy may utilize an initial patient database to evaluate the utility of including genomic regions in the selector set. A typical database for this purpose may include sequence information from at least 25, at least 50, at least 100, at least 200, at least 300 or more individual tumors. The method for producing a selector set may comprise one or more of the following phases:

Phase 1 (Known drivers). Genes known to be drivers in the cancer of interest are selected based on the pattern of SNVs previously identified in tumors.

Phase 2 (Maximize coverage). To maximize coverage, for each exon with SNVs covering ≥5 cancer patients in the starting database, select the exon with highest RI that identified at least 1 new patient when compared to the prior phase. Among exons with equally high RI, add the exon with minimum overlap among patients already captured by the selector. Repeat until no further exons met these criteria.

Phase 3 (RI≥30). For each remaining exon with an RI≥30 and with SNVs covering ≥3 patients in the relevant database, identify the exon that results in the largest reduction in patients with only 1 SNV. To break ties among equally best exons, the exon with highest RI was chosen. This was repeated until no additional exons satisfied these criteria.

Phase 4 (RI≥20). Repeat the procedure in Phase 3, but using RI≥20.

Phase 5 (Predicted drivers). Add in all exons from additional genes previously predicted to harbor driver mutations in the cancer of interest.

Phase 6 (Add fusions). Add in for known recurrent rearrangements the introns most frequently implicated in the fusion event and the flanking exons.

It should be understood, however, that the addition of known drivers, predicted drivers and fusions can be performed independently and in any order.

A method of producing a selector set may comprise (a) calculating a recurrence index for a plurality of genomic regions from a population of subjects suffering from a cancer by dividing a number of subjects containing one or more mutations in a genomic region of the plurality of genomic regions by a size of the genomic region; and (b) ranking the plurality of genomic regions based on their recurrence index.

A method of producing a selector set may comprise (a) calculating a recurrence index for a plurality of genomic regions from a population of subjects suffering from a cancer by dividing a number of subjects containing one or more mutations in a genomic region of the plurality of genomic regions by a size of the genomic region; and (b) producing a selector set comprising two or more genomic regions of the plurality of genomic regions by (i) using the recurrence index to maximize coverage of the selector set for the population of subjects; and/or (ii) using the recurrence index to maximize a median number of mutations per subject in the population of subjects.

Maximizing subject coverage may comprise use of a metric termed "Recurrence Index" (RI). The RI may refer to the number of subjects that harbor mutations (e.g., SNVs/indels) in a given kilobase of genomic sequence. This metric can be further normalized by the number of subjects per study to allow comparison of different studies and distinct cancers. A similar approach was used to produce a selector set for non-small cell lung cancer (NSCLC) (see FIG. 1*b*). For one exemplary NSCLC selector set, exons were the primary genomic unit and indels were not considered. A portion of an exon may contain known somatic mutations. In this case, the algorithm only includes the subsequence of the portion of the exon containing known lesions flanked by a user-defined buffer (by default, =1 base). RI may be recalculated for each exon following this adjustment. The algorithm may rank genomic regions by decreasing RI. The algorithm may consider a subset of the genomic regions. For example, the algorithm may only consider genomic regions in the top P percentile of both RI and/or the number of subjects per exon (P=$90^{th}$ percentile by default, but is user modifiable). Selector design may proceed by iteratively traversing the list of ranked genomic regions, selecting each genomic region that adds additional subject coverage with minimal additional space. This may continue until all genomic regions satisfying percentile filters have been evaluated and/or a user-defined maximum selector size has been reached.

Producing the selector set may comprise maximizing the median number of mutations per subject. Maximizing the median number of mutations per subject may comprise use of one or more algorithms. Maximizing the median number of mutations per subject may comprise use of one or more thresholds or filters to evaluate the genomic regions for inclusion in the selector set. The thresholds or filters may be based on the recurrence index. For example, the filter may be a percentile filter of the recurrence index. The percentile filters may be relaxed to permit the assessment of additional genomic regions for inclusion in the selector set. The percentile filter may be set at (⅔)×P, where P is a top percentile of RI. The threshold may be user-defined. The threshold may be greater than or equal to ⅔. Alternatively, the threshold is less than or equal to ⅔. P may also be user-defined. The algorithm may proceed through the list of genomic regions ranked by decreasing RI, iteratively adding regions that maximally increase the median number of mutations per subject. The process may terminate after assessing all genomic regions that pass percentile filters, and/or if the desired selector size endpoint is reached. This process may be repeated for a third round or more by continuing to relax the percentile threshold. Maximizing the median number of mutations per subject may comprise (i) ranking two or more genomic regions based on their recurrence index; (ii) producing a list of genomic regions comprising a subset of the genomic regions, wherein the genomic regions in the list have a recurrence index in the top $60^{th}$ percentile; and (iii) producing a preliminary selector set by adding genomic regions to the preliminary selector set and calculating a median number of mutations per subject in the preliminary selector set.

Further disclosed herein is a method of producing a selector set comprising (a) obtaining data pertaining to one or more genomic regions; (b) applying an algorithm to the data to determine for a genomic region: (i) a presence of one or more mutations in the genomic region; (ii) a number of subjects with mutations in that genomic region; and (iii) a recurrence index (RI), wherein the RI is determined by dividing the number of subjects with mutations in the genomic region by the size of genomic region; and (c) producing a selector set comprising one or more genomic regions based on the recurrence index of the one or more genomic regions.

The method may further comprise recalculating the recurrence index for one or more genomic regions comprising known mutations. The size of the known mutation may be less than the size of the genomic region. Recalculating the recurrence index may comprise dividing the number of subjects with known mutations in the genomic region by the size of the known mutation. For example, the size of a genomic region may be 200 basepairs and the size of the known mutation within the genomic region may be 100 basepairs. The recurrence index for the genomic region may be determined by dividing the number of subjects with the known mutation in the genomic region by the size of the known mutation (e.g., 100 base pairs) rather than dividing by the size of the entire genomic region (e.g., 200 base pairs).

The method may further comprise ranking the two or more genomic regions based on the recurrence index. The list of ranked genomic regions may comprise a subset of the genomic regions ranked by the recurrence index. The list of ranked genomic regions may comprise a subset of the genomic regions that satisfy one or more criteria. The one or more criteria may be based on the recurrence index. For example, the list of ranked genomic regions may comprise a subset of genomic regions that have a recurrence index in the top $90^{th}$ percentile. Producing the selector set may comprise selecting the one or more genomic regions based on the recurrence index. Producing the selector set may comprise selecting the one or more genomic regions based on the rank of the two or more genomic regions. The two or more genomic regions may be ranked with the aid of an algorithm. The algorithm used to rank the two or more genomic regions based on the recurrence may be the same algorithm used to determine the recurrence index of the one or more genomic regions. The algorithm may be a different from the algorithm used to determine the recurrence index.

The method may further comprise iteratively traversing a list of ranked genomic regions and selecting genomic regions that provide additional subject coverage with minimal addition to the total size of the genomic regions of a proposed selector set. For example, a first genomic region may add two new subjects to the proposed selector set and the size of the proposed selector set may increase by 10 base pairs, whereas a second genomic region may add two new subjects to the proposed selector set and the size of the proposed selector set may increase by 100 base pairs. The first genomic region may be selected over the second genomic region for inclusion in the proposed selector set. The entire list of ranked genomic regions may be traversed. Alternatively, a portion of the list of ranked genomic regions may be traversed. For example, the traversal and selection of genomic regions may be based on a user-defined maximum selector size. Once the maximum selector size has been reached, the step of traversing the list of ranked genomic regions and selecting genomic regions may be terminated. An algorithm may be used to traverse the list of ranked genomic regions and to select genomic regions for inclusion in the selector set. The algorithm may be the same algorithm used to determine the recurrence index. The algorithm may be a different from the algorithm used to determine the recurrence index.

The method may further comprise iteratively traversing a list of ranked genomic regions and selecting genomic regions that maximize the median number of mutations per subject in the population of subjects of the selector set. The median number of mutations per subject for a proposed selector set may be determined by (a) counting a number of mutations N in each subject across all genomic regions for the proposed selector set; and (b) applying an algorithm to identify the median number of mutations by sorting the subjects by the number of mutations. For example, a proposed selector set may comprise 10 genomic regions comprising 20 mutations in a population of 9 subjects. A first subject may have 4 mutations, a second subject may have 2 mutations, a third subject may have 3 mutations, a fourth subject may have 6 mutations, a fifth subject have May 8 mutations, a sixth subject may have 6 mutations, a seventh subject may have eight mutations, an eighth subject may have 4 mutations, and a ninth subject may have two mutations. The median of {2, 2, 3, 4, 4, 6, 8, 8} is 4. A genomic region may be selected for inclusion in the selector set if the inclusion of the genomic region increases the median number of mutations per subject in the population of subjects in the selector set. For example, a first genomic region may contain one mutation present in two of the ten subjects and second genomic region may contain one mutation present in three of the ten subjects. The second genomic region may be selected for inclusion into the selector set over the first genomic region because addition of the second genomic region to the selector set would result in a greater increase the median number of mutations per subject than addition of the first genomic region. The entire list of ranked genomic regions may be traversed. Alternatively, a portion of the list of ranked genomic regions may be traversed. For example, the traversal and selection of genomic regions may be based on a user-defined maximum selector size. Once the maximum selector size has been reached, the step of traversing the list of ranked genomic regions and selecting genomic regions may be terminated.

Methods of producing a selector set may comprise: (a) obtaining sequencing information of a tumor sample from a subject suffering from a cancer; (b) comparing the sequencing information of the tumor sample to sequencing information from a non-tumor sample from the subject to identify one or more mutations specific to the sequencing information of the tumor sample; and (c) producing a selector set comprising one or more genomic regions comprising the one or more mutations specific to the sequencing information of the tumor sample. The selector set may comprise sequencing information pertaining to the one or more genomic regions. The selector set may comprise genomic coordinates pertaining to the one or more genomic regions. The selector set may comprise a plurality of oligonucleotides that selectively hybridize the one or more genomic regions. The plurality of oligonucleotides may be biotinylated. The one or more mutations comprise SNVs. The one or more mutations comprise indels. The one or more mutations comprise rearrangements. Producing the selector set may comprise identifying tumor-derived SNVs based on the methods disclosed herein. Producing the selector set may comprise identifying tumor-derived rearrangements based on the methods disclosed herein.

Application of the approaches described herein for mutated genomic regions in non-small cell lung cancer may result in the selector set shown in Table 2. The selector set created according to the methods of the invention may identify genomic regions that are highly likely to include identifiable mutations in tumor sequences. This selector set may include a relatively small total number of genomic regions and thus a relatively short cumulative length of genomic regions and yet may provide a high overall coverage of likely mutations in a population. The selector set does not, therefore, need to be optimized on a patient-by-patient basis. The relatively short cumulative length of genomic regions also means that the analysis of cancer-derived cell-free DNA using these libraries may be highly sensitive. The relatively short cumulative length of genomic regions may allow the sequencing of cell-free DNA to a great depth.

The selector sets comprising recurrently mutated genomic regions created according to the instant methods may enable the identification of patient-specific mutations and/or tumor-specific mutations within the genomic regions in a high percentage of subjects. Specifically, in these selector sets, at least one mutation within the plurality of genomic regions may be present in at least 60% of a population of subjects with the specific cancer. In some embodiments, at least two mutations within the plurality of genomic regions are present in at least 60% of a population of subjects with the specific cancer. In specific embodiments, at least three mutations, or even more, within the plurality of genomic regions are present in at least 60% of a population of subjects with the specific cancer.

The methods for creating a selector set, as disclosed herein, may be implemented by a programmed computer system. Therefore, according to another aspect, the instant disclosure provides computer systems for creating a selector set (e.g., library of recurrently mutated genomic regions). Such systems may comprise at least one processor and a non-transitory computer-readable medium storing computer-executable instructions that, when executed by the at least one processor, cause the computer system to carry out the methods described herein for creating a selector set (e.g., library).

ctDNA Detection Index

The methods, kits and systems disclosed herein may comprise a ctDNA detection index or use thereof. Generally, the ctDNA detection index is based on a p-value of one or more types of mutations present in a sample from a subject. The ctDNA detection index may comprise an integration of information content across a plurality of mutations and classes of somatic mutations. The ctDNA detection index may be analogous to a false positive rate. The ctDNA detection index may be based on a decision tree in which fusion breakpoints take precedence due to their nonexistent background and/or in which p-values from multiple classes of mutations may be integrated. The classes of mutations may include, but are not limited to, SNVs, indels, copy number variants, and rearrangements.

The ctDNA detection index may be used to assess the statistical significance of a selector set comprising genomic regions comprising multiple classes of mutations. For example, the ctDNA detection index may be used to assess the statistical significance of a selector set comprising genomic regions comprising SNVs and indels. In another example, the ctDNA detection index may be used to assess the statistical significance of a selector set comprising genomic regions comprising SNVs and rearrangements. In another example, the ctDNA detection index may be used to assess the statistical significance of a selector set comprising genomic regions comprising rearrangements and indels. In another example, the ctDNA detection index may be used to assess the statistical significance of a selector set comprising genomic regions comprising SNVs, indels, copy number variants, and rearrangements. The calculation of the ctDNA detection index may be based on the types (e.g., classes) of mutations within the genomic region of a selector set that are detected in a subject. For example, a selector set may comprise genomic regions comprising SNVs, indels, copy number variants, and rearrangements, however, the types of mutations for the selector that are detected in a subject may be SNVs and indels. The ctDNA detection index may be determined by combining a p-value of the SNVs and a p-value of the indels. Any method that is suitable for combining independent, partial tests may be used to combine the p-value of the SNVs and indels. Combining the p-values of the SNVs and indels may be based on Fisher's method.

A method of determining a ctDNA detection index may comprise (a) detecting a presence of one or more mutations in one or more samples from a subject, wherein the one or more mutations are based on a selector set comprising genomic regions comprising the one or more mutations; (b) determining a mutation type of the one or more mutations present in the sample; and (c) calculating a ctDNA detection index based on a p-value of the mutation type of mutations present in the one or more samples.

For instances in which a single type of mutation is present in the sample from the subject, the ctDNA detection index is based on the p-value of the single type of mutation. The p-value of the single type of mutation may be estimated by Monte Carlo sampling. Monte Carlo sampling may use a broad class of computational algorithms that rely on repeated random sampling to obtain a p-value. The ctDNA detection index may be equivalent to the p-value of the single type of mutation.

For instances in which a rearrangement (e.g., fusion) is detected in a tumor sample and a plasma sample from the subject, the ctDNA detection index is based on the p-value of the rearrangement. The p-value of the rearrangement may be 0. Thus, the ctDNA detection index is the p-value of the rearrangement, which is 0.

For instances in which a rearrangement (e.g., fusion) is detected in only a tumor sample from the subject and not in a plasma sample from the subject, the ctDNA detection index is based on the p-value of the other types of mutations.

For instances in which (a) a SNV and indel are detected in a sample from the subject; (b) a p-value of the SNV is less than 0.1 and a p-value of the indel is less than 0.1; and (c) a rearrangement is not detected in a plasma sample from the subject, the ctDNA detection index is calculated based on the combined p-values of the SNV and indel. Any method that is suitable for combining independent, partial tests may be used to combine the p-value of the SNVs and indels. The p-values of the SNV and indel may be combined according to Fisher's method. Thus, the ctDNA detection index is the combined p-value of the SNV and indel.

For instances in which (a) a SNV and indel are detected in a sample from the subject; (b) a p-value of the SNV is not less than 0.1 or a p-value of the indel is not less than 0.1; and (c) a rearrangement is not detected in a plasma sample from the subject, the ctDNA detection index is based on the p-value of the SNV. Thus, the ctDNA detection index is the p-value of the SNV.

A ctDNA detection index may be significant if the ctDNA detection index is less than or equal to 0.10, 0.09, 0.08, 0.07, 0.06, 0.05, 0.04, 0.03, 0.02, or 0.01. A ctDNA detection index may be significant if the ctDNA detection index is less than or equal to 0.05. A ctDNA detection index may be significant if the ctDNA detection index is less than or equal to a false positive rate (FPR).

A ctDNA detection index may be calculated for a subject based on his or her array of reporters (e.g., mutations) using the following rules, executed in any order:

(i) For cases where only a single reporter type is present in a patient's tumor, the corresponding p-value is used (estimated by Monte Carlo sampling).

(ii) If SNV and indel reporters are detected, and if each independently has a p-value $<0.1$, their respective p-values are combined using Fisher's method. Otherwise, given the prioritization of SNVs in the selector design, the SNV p-value is used.

(iii) If a fusion breakpoint identified in a tumor sample (e.g., involving ROS1, ALK, or RET) is recovered in plasma DNA from the same patient, it trumps all other mutation types, and its p-value (~0) is used.

(iv) If a fusion detected in the tumor is not found in corresponding plasma (potentially due to hybridization inefficiency), the p-value for any remaining mutation type(s) is used.

The ctDNA detection index may be considered significant if the ctDNA detection index is $\leq 0.05$ ($\approx$false positive rate (FPR) $\leq 5\%$), which is the threshold that maximized CAPP-Seq sensitivity and specificity in ROC analyses (determined by Euclidean distance to a perfect classifier; e.g., true positive report (TPR)=1 and FPR=0).

Calculating a ctDNA detection index may comprise determining a significance of SNVs. In some embodiments, to evaluate the significance SNVs, the strategy integrates cfDNA fractions across all somatic SNVs, performs a position-specific background adjustment, and evaluates statistical significance by Monte Carlo sampling of background alleles across the selector. This allows the quantitation of low levels of ctDNA with potentially high rates of allelic drop out. The method for evaluating the significance of SNVs may utilize the following steps:

adjusting the allelic fraction f for each of n SNVs from patient P for a given cfDNA sample $\theta$ by the operation $f^*=\max\{0, f-(e-\mu)\}$, where f is the raw allelic fraction in cfDNA, e is the position-specific error rate for the given allele across all cfDNA samples, and $\mu$ denotes the mean selector-wide background rate;

comparing with Monte Carlo simulation the adjusted mean SNV fraction $F^*(=(\Sigma f^*)/n)$ against the null distribution of background alleles across the selector;

determining a SNV p-value for patient P as the percentile of $F^*$ with respect to the null distribution of background alleles in $\theta$.

Calculating a ctDNA detection index may comprise determining a significance of rearrangements. The recovery of a tumor-derived genomic fusion (rearrangement) can be assigned a p-value of ~0, due to the very low error rate.

Calculating a ctDNA detection index may comprise determining a significance of indels. The analysis of insertions and deletions (indels) may be separately evaluated utilizing the following steps:

For each indel in patient P compare its fraction in a given cfDNA sample θ against its fraction in every cfDNA sample in a cohort (excluding cfDNA samples from the same patient P) with a Z-test; where each read strand is optionally assessed separately and combined into a single Z-score;

if patient P has more than 1 indel, all indel-specific Z-scores are combined into a final Z statistic.

The p-values of the different mutation types may be integrated to estimate the statistical significance (e.g., p-value) of tumor burden quantitation. Thus, the ctDNA detection index, which integrates the p-values of different mutation types, may be used to estimate the statistical significance of tumor burden quantitation. For each sample, a ctDNA detection index may be calculated based on p-value integration from the plurality of somatic mutations that are detected. The ctDNA detection index may be determined based on the methods disclosed herein. For cases where only a single somatic mutation is present in a sample, the corresponding p-value may be used. If a fusion breakpoint identified in a tumor sample is recovered in cfDNA from the same patient, the p-value of the fusion breakpoint may be used. If SNV and indel somatic mutations are detected, and if each independently has a p-value <0.1, their respective p-values may be combined and the resulting p-value is used. If the ctDNA detection index is determined to be 0.05, then the p-value of the tumor burden quantitation is 0.05. A ctDNA detection index of ≤0.05 may suggest that a subject's mutations are significantly detectable in a sample from the subject. A ctDNA detection index that is less than the false positive rate (FPR) may suggest that a subject's mutations are significantly detectable in a sample from the subject.

Selector Set Sensitivity and Specificity

The selector set may be chosen to provide a desired sensitivity and/or specificity. As is known in the art, the relative sensitivity and/or specificity of a predictive model can be "tuned" to favor either the selectivity metric or the sensitivity metric, where the two metrics have an inverse relationship. One or both of sensitivity and specificity can be at least about at least about 0.6, at least about 0.65, at least about 0.7, at least about 0.75, at least about 0.8, at least about 0.85, at least about 0.9, or higher.

The sensitivity and specificity may be statistical measures of the performance of selector set to perform a function. For example, the sensitivity of the selector set may be used to assess the use of the selector set to correctly diagnose or prognosticate a status or outcome of a cancer in a subject. The sensitivity of the selector set may measure the proportion of subjects which are correctly identified as suffering from a cancer. The sensitivity of the selector set may also measure the use of the selector set to correctly screen for a cancer in a subject. The sensitivity of the selector set may also measure the use of the selector set to correctly diagnose a cancer in a subject. The sensitivity of the selector set may also measure the use of the selector set to correctly prognosticate a cancer in a subject. The sensitivity of the selector set may also measure the use of the selector set to correctly identify a subject as a responder to a therapeutic regimen. The sensitivity may be at least about 60%, 61%, 62%, 63%, 64%, 65%, 66%, 67%, 68%, 69%, 70% or greater. The sensitivity may be at least about 72%, 75%, 77%, 80%, 82%, 85%, 87%, 90%, 92%, 95%, 97% or greater.

Sensitivity may vary according to the tumor stage. The sensitivity may be at least about 50%, at least about 52%, at least about 55%, at least about 57%, at least about 60%, at least about 62%, at least about 65%, at least about 67%, at least about 70%, at least about 72%, at least about 75%, at least about 77%, at least about 80%, at least about 85%, at least about 87%, at least about 90%, at least about 92%, at least about 95%, at least about 98%, at least about 99% or more for tumors at stage I. The sensitivity may be at least about 50% for tumors at stage I. The sensitivity may be at least about 65% for tumors at stage I. The sensitivity may be at least about 72% for tumors at stage I. The sensitivity may be at least about 75% for tumors at stage I The sensitivity may be at least about 85% for tumors at stage I The sensitivity may be at least about 92% for tumors at stage I.

The sensitivity may be at least about 50%, at least about 52%, at least about 55%, at least about 57%, at least about 60%, at least about 62%, at least about 65%, at least about 67%, at least about 70%, at least about 72%, at least about 75%, at least about 77%, at least about 80%, at least about 85%, at least about 87%, at least about 90%, at least about 92%, at least about 95%, at least about 98%, at least about 99% or more for tumors at stage II. The sensitivity may be at least about 60% for tumors at stage II. The sensitivity may be at least about 75% for tumors at stage II. The sensitivity may be at least about 85% for tumors at stage II. The sensitivity may be at least about 92% for tumors at stage II.

The sensitivity may be at least about 50%, at least about 52%, at least about 55%, at least about 57%, at least about 60%, at least about 62%, at least about 65%, at least about 67%, at least about 70%, at least about 72%, at least about 75%, at least about 77%, at least about 80%, at least about 85%, at least about 87%, at least about 90%, at least about 92%, at least about 95%, at least about 98%, at least about 99% or more for tumors at stage III. The sensitivity may be at least about 60% for tumors at stage III. The sensitivity may be at least about 75% for tumors at stage III. The sensitivity may be at least about 85% for tumors at stage III. The sensitivity may be at least about 92% for tumors at stage III.

The sensitivity may be at least about 50%, at least about 52%, at least about 55%, at least about 57%, at least about 60%, at least about 62%, at least about 65%, at least about 67%, at least about 70%, at least about 72%, at least about 75%, at least about 77%, at least about 80%, at least about 85%, at least about 87%, at least about 90%, at least about 92%, at least about 95%, at least about 98%, at least about 99% or more for tumors at stage IV. The sensitivity may be at least about 60% for tumors at stage IV. The sensitivity may be at least about 75% for tumors at stage IV. The sensitivity may be at least about 85% for tumors at stage IV. The sensitivity may be at least about 92% for tumors at stage IV.

The sensitivity may be at least about and may be at least about 60%, at least about 65%, at least about 70%, at least about 75%, at least about 80%, at least about 85%, at least about 87%, at least about 90%, at least about 92%, at least about 95%, at least about 98%, at least about 99% or more with healthy controls.

The AUC value may also vary according to tumor stage. The AUC value may be at least about 0.50, at least about 0.52, at least about 0.55, at least about 0.57, at least about 0.60, at least about 0.62, at least about 0.65, at least about 0.67, at least about 0.70, at least about 0.72, at least about 0.75, at least about 0.77, at least about 0.80, at least about 0.82, at least about 0.85, at least about 0.87, at least about 0.90, at least about 0.92, at least about 0.95, at least about 0.97 or more for stage I cancer. The AUC value may be at least about 0.50 for stage I cancer. The AUC value may be at least about 0.55 for stage I cancer. The AUC value may be at least about 0.60 for stage I cancer. The AUC value may be at least about 0.70 for stage I cancer. The AUC value may be at least about 0.75 for stage I cancer. The AUC value may be at least about 0.80 for stage I cancer.

The AUC value may be at least about 0.50, at least about 0.52, at least about 0.55, at least about 0.57, at least about 0.60, at least about 0.62, at least about 0.65, at least about 0.67, at least about 0.70, at least about 0.72, at least about 0.75, at least about 0.77, at least about 0.80, at least about 0.82, at least about 0.85, at least about 0.87, at least about 0.90, at least about 0.92, at least about 0.95, at least about 0.97 or more for stage II cancer. The AUC value may be at least about 0.50 for stage II cancer. The AUC value may be at least about 0.55 for stage II cancer. The AUC value may be at least about 0.60 for stage II cancer. The AUC value may be at least about 0.70 for stage II cancer. The AUC value may be at least about 0.75 for stage II cancer. The AUC value may be at least about 0.80 for stage II cancer. The AUC value may be at least about 0.90 for stage II cancer. The AUC value may be at least about 0.95 for stage II cancer.

The AUC value may be at least about 0.50, at least about 0.52, at least about 0.55, at least about 0.57, at least about 0.60, at least about 0.62, at least about 0.65, at least about 0.67, at least about 0.70, at least about 0.72, at least about 0.75, at least about 0.77, at least about 0.80, at least about 0.82, at least about 0.85, at least about 0.87, at least about 0.90, at least about 0.92, at least about 0.95, at least about 0.97 or more for stage III cancer. The AUC value may be at least about 0.50 for stage III cancer. The AUC value may be at least about 0.55 for stage III cancer. The AUC value may be at least about 0.60 for stage III cancer. The AUC value may be at least about 0.70 for stage III cancer. The AUC value may be at least about 0.75 for stage III cancer. The AUC value may be at least about 0.80 for stage III cancer. The AUC value may be at least about 0.90 for stage III cancer. The AUC value may be at least about 0.95 for stage III cancer.

The AUC value may be at least about 0.50, at least about 0.52, at least about 0.55, at least about 0.57, at least about 0.60, at least about 0.62, at least about 0.65, at least about 0.67, at least about 0.70, at least about 0.72, at least about 0.75, at least about 0.77, at least about 0.80, at least about 0.82, at least about 0.85, at least about 0.87, at least about 0.90, at least about 0.92, at least about 0.95, at least about 0.97 or more for stage IV cancer. The AUC value may be at least about 0.50 for stage IV cancer. The AUC value may be at least about 0.55 for stage IV cancer. The AUC value may be at least about 0.60 for stage IV cancer. The AUC value may be at least about 0.70 for stage IV cancer. The AUC value may be at least about 0.75 for stage IV cancer. The AUC value may be at least about 0.80 for stage IV cancer. The AUC value may be at least about 0.90 for stage IV cancer. The AUC value may be at least about 0.95 for stage IV cancer.

The AUC values may be at least about 0.70, at least about 0.75, at least about 0.80, at least about 0.85, at least about 0.90, at least about 0.95 for healthy controls.

The specificity of the selector may measure the proportion of subjects which are correctly identified as not suffering from a cancer. The specificity of the selector set may also measure the use of the selector set to correctly make a diagnosis of no cancer in a subject. The specificity of the selector set may also measure the use of the selector set to correctly identify a subject as a non-responder to a therapeutic regimen. The specificity may be at least about 60%, 61%, 62%, 63%, 64%, 65%, 66%, 67%, 68%, 69%, 70% or greater. The specificity may be at least about 72%, 75%, 77%, 80%, 82%, 85%, 87%, 90%, 92%, 95%, 97% or greater.

The selector set may be used to detect, diagnose, and/or prognosticate a status or outcome of a cancer in a subject based on the detection of one or more mutations within one or more genomic regions in the selector set in a sample from the subject. The sensitivity and/or specificity of the selector set to detect, diagnose, and/or prognosticate the status or outcome of the cancer in the subject may be tuned (e.g., adjusted/modified) by the ctDNA detection index. The ctDNA detection index may be used to assess the significance of classes of mutations detected in the sample from the subject by the selector set. The ctDNA detection index may be used to determine whether the detection of one or more classes of mutations by the selector set is significant. For example, the ctDNA detection index may determine that the classes of mutations detected by the selector set in a first subject is statistically significant, which may result in a diagnosis of cancer in the first subject. The ctDNA detection index may determine that the classes of mutations detected by the selector set in a second subject is not statistically significant, which may result in a diagnosis of no cancer in the second subject. As such, the ctDNA detection index may affect the analysis of the specificity and/or sensitivity of the selector set to detect, diagnose, and/or prognosticate the status or outcome of the cancer in the subject.

Identification of Rearrangements

Further disclosed herein are methods of identifying rearrangements. The rearrangement may be a genomic fusion event and/or breakpoint. The method may be used for de novo analysis of cfDNA samples. Alternatively, the method may be used for analysis of known tumor/germline DNA samples. The method may comprise a heuristic approach. Generally, the method may comprise (a) obtaining an alignment file of pair-end reads, exon coordinates, a reference genome, or a combination thereof; and (b) applying an algorithm to information from the alignment file to identify one or more rearrangements. The algorithm may be applied to information pertaining to one or more genomic regions. The algorithm may be applied to information that overlaps with one or more genomic regions.

The method may be termed FACTERA (FACile Translocation Enumeration and Recovery Algorithm). As input, FACTERA may use an alignment file of paired-end reads, exon coordinates, and a reference genome. In addition, the analysis can be optionally restricted to reads that overlap particular genomic regions. FACTERA may process the input in three sequential phases: identification of discordant reads, detection of breakpoints at base pair-resolution, and in silico validation of candidate fusions.

Further disclosed herein is a method of identifying rearrangements comprising (a) obtaining sequencing information pertaining to a plurality of genomic regions; (b) producing a list of genomic regions adjacent to one or more candidate rearrangement sites; (c) applying an algorithm to validate candidate rearrangement sites, thereby identifying rearrangements.

The sequencing information may comprise an alignment file. The alignment file may comprise an alignment file of pair-end reads, exon coordinates, and a reference genome. The sequencing information may be obtained from a database. The database may comprise sequencing information pertaining to a population of subjects suffering from a disease or condition. The database may be a pharmacogenomics database. The sequencing information may be obtained from one or more samples from one or more subjects.

Producing the list of genomic regions adjacent to the one or more candidate rearrangement sites may comprise identifying discordant read pairs based on the sequencing information. A discordant read-pair may refer to a read and its mate, where the insert size is not equal to (e.g., greater or less than) the expected distribution of the dataset, or where the mapping orientation of the reads is unexpected (e.g. both on the same strand). Producing the list of genomic regions adjacent to the one or more candidate rearrangement sites may comprise classifying the discordant read pairs based on the sequencing information.

Discordant read pairs may be introduced by NGS library preparation and/or sequencing artifacts (e.g., jumping PCR). However, they are also likely to flank the breakpoints of bona fide fusion events. Producing a list of genomic regions adjacent to the one or more candidate rearrangement sites may further comprise ranking the genomic regions. The genomic regions may be ranked in decreasing order of discordant read depth. The method may further comprise eliminating duplicate fragments. Producing a list of genomic regions adjacent to the one or more candidate rearrangement sites may comprise selecting genomic regions with a minimum user-defined read depth. The read depth may be at least 2×, 3×, 4×, 5×, 6×, 7×, 8×, 9×, 10× or more. The read depth may be at least about 2×.

Producing the list of genomic regions adjacent to the one or more candidate fusion sites may comprise use of one or more algorithms. The algorithm may analyze properly paired reads in which one of the two reads is "soft-clipped," or truncated. Soft-clipping may refer to truncating one or more ends of the paired reads. Soft-clipping may truncate the one or more ends by removing less than or equal to 10, 9, 8, 7, 6, 5, 4, 3, 2, 1 base or base pair from the paired reads. Soft-clipping may comprise removing at least one base or base pair from the paired reads. Soft-clipping may comprise removing at least one base or base pair from one end of the paired reads. Soft-clipping may comprise removing at least one base or base pair from both ends of the paired reads. Soft-clipped reads may allow for precise breakpoint determination. The precise breakpoint may be identified by parsing the CIGAR string associated with each mapped read, which compactly specifies the alignment operation used on each base (e.g. My=y contiguous bases were mapped, Sx=x bases were skipped). The algorithm may analyze soft-clipped reads with a specific pattern. For example, the algorithm may analyze soft-clipped reads with the following patterns, SxMy or MySx. The number of skipped bases x may have a minimum requirement. By setting a minimum requirement for the number of skipped bases x, the impact of non-specific sequence alignments may be reduced. The number of skipped bases may be at least 10, 11, 12, 13, 14, 15, 16, 17, 18, 19, 20, 21, 22, 23, 24, 25 or more. The number of skipped bases may be at least 16. The number of skipped bases may be user-defined. The number of contiguous bases y may also be used-defined.

An algorithm may be used to validate candidate rearrangement sites. The algorithm may determine the read frequency for the candidate rearrangement sites. The algorithm may eliminate candidate rearrangement sites that do not meet a minimum read frequency. The minimum read frequency may be user-defined. The minimum read frequency may be at least about 2, 3, 4, 5, 6, 7, 8, 9, 10 or more reads. The minimum read frequency may be at least about 2 reads. The algorithm may rank the candidate rearrangement sites based on the read frequency. A candidate rearrangement site may contain multiple soft-clipped reads. The algorithm may select a representative soft-clipped read for a candidate rearrangement site. Selection of the representative soft-clipped read may be based on selecting a soft-clipped read that has a length that is closest to half the read length. If the mapped region of the representative soft-clipped read matches the mapped region of another soft-clipped read of the candidate rearrangement site, the algorithm may annotate the candidate rearrangement site as a rearrangement event. If the mapped region of the representative soft-clipped read matches the mapped region of another soft-clipped read of the candidate rearrangement site, the algorithm may identify the candidate rearrangement site as a rearrangement. If the mapped region of the representative soft-clipped read matches the mapped region of another soft-clipped read of the candidate rearrangement site, the algorithm may annotate the candidate rearrangement site as a fusion event. Applying the algorithm to validate the candidate rearrangements may comprise identifying the candidate rearrangement as a rearrangement if the two or more reads have a sequence alignment.

Validating the candidate rearrangement sites may further comprise using an algorithm to assess inter-read concordance. The algorithm may assess inter-read concordance by dividing a first sequence read of a soft-clipped sequence of a candidate rearrangement site into multiple possible subsequences of a user-defined length k. A second sequence read of the soft-clipped sequence may be divided into subsequences of length k. Subsequences of size k of the second sequence read may be compared to the first sequencing read, and the concordance of the two reads may be determined. For example, the soft-clipped sequence of a candidate fusion may be 100 bases and the soft-clipped sequence may be subdivided into a user-defined length of 10 bases. The subsequences with a length of 10 may be extracted from the first read and stored. A second read may be compared to the first read by selecting subsequences of 10 bases in the second read. The user-defined lengths may allow parts of the second read to be merged with the soft-clipped (e.g., non-mapping) parts of the first read into a composite sequence which is then assessed for improved mapping properties. Validating the candidate rearrangement may comprise dividing a first read into subsequences of k-mers. A second read may be divided into k-mers in order to rapidly compare it to the first read. If any k-mers overlap the first read, they are counted and used to assess sequence similarity. The two reads may be considered concordant if a minimum matching threshold is achieved. The minimum matching threshold may be a user-defined value. The minimum matching threshold may be 50% of the shortest length of the two sequences being compared. For example, the first sequence read may be 100 bases and the second sequence read may be 130 bases. The minimum matching threshold may be 50 bases (e.g., 100 bases times 0.50). The minimum matching threshold may be at least 10%, 20%, 25%, 30%, 35%, 40%, 45%, 50%, 55%, 60%, 65%, 70%, 75%, or 80% of the shortest length of the two sequences being compared. The algorithm may process 100, 200, 300, 400, 500, 600, 700, 800, 900, 1000, 1500, 2000 or more putative breakpoint pairs for each discordant gene (or genomic region) pair. The number of putative breakpoint pairs that the algorithm processes may be user-defined. Moreover, for a gene pair, the algorithm may compare reads whose orientations are compatible with valid fusions. Such reads may have soft-clipped sequences facing opposite directions. When this condition is not satisfied, the algorithm may use the reverse complement of read 1 for k-mer analysis.

In some instances, genomic subsequences flanking the true breakpoint may be nearly or completely identical, causing the aligned portions of soft-clipped reads to overlap. This may prevent an unambiguous determination of the breakpoint. As such, an algorithm may be used to adjust the breakpoint in one read (e.g., read 2) to match the other (e.g., read 1). For a read, the algorithm may calculate the distance between the breakpoint and the read coordinate corresponding to the first k-mer match between reads. For example, let x be defined as the distance between the breakpoint coordinate of read 1 and the index of the first matching k-mer, j, and y be defined as the corresponding distance for read 2. Then, the offset is estimated as the difference in distances (x, y) between the two reads. Thus, for instances in which a fusion event cannot be unambiguously determined based on the sequence reads, an algorithm is used to determine a fusion site.

The method may further comprise in silico validation of candidate rearrangement sites. An algorithm may perform a local realignment of reads of the candidate rearrangement sites against a reference rearrangement sequence. The reference rearrangement sequence may be obtained from a reference genome. The local alignment may be of sequences flanking the candidate rearrangement site. The local alignment may be of sequences within 100, 200, 300, 400, 500, 600, 700, 800, 900, or 1000 or more base pairs of the candidate rearrangement site. The local alignment may be of sequences within 500 base pairs of the candidate rearrangement site. BLAST may be used align the sequences. A BLAST database may be constructed by collecting reads that map to a candidate fusion sequence, including discordant reads and soft-clipped reads, as well as unmapped reads in the original input file. Reads that map to the reference rearrangement sequence with a user-defined identity (e.g., at least 95%) and/or a length of the aligned sequences is a user-defined percentage (e.g., 90%) of the input read length. The reads that span or flank the breakpoint may be counted. The user-defined identity may be at least about 70%, 75%, 80%, 85%, 90%, 95%, 97% or more. The length of the aligned sequences may be at least about 70%, 75%, 80%, 85%, 90%, or 95% or more of the input read length (e.g., read length of the candidate rearrangement sequence). The output redundancies may be minimized by removing fusion sequences within an interval of at least 20 base pairs or more of a fusion sequence with greater read support and with the same sequence orientation (to avoid removing reciprocal fusions).

The method may further comprise producing an output pertaining to the rearrangement. The output may comprise one or more of the following gene pair, genomic coordinates of the rearrangement, the orientation of the rearrangement (e.g., forward-forward or forward-reverse), genomic sequences within 50 bp of the rearrangement, and depth statistics for reads spanning and flanking the rearrangement.

The method may further comprise enumerating a fusion allele frequency. For example, fusion allele frequency in sequenced cfDNA may be enumerated as described herein and in Example 1. The fusion allele frequency may be calculated as $\alpha/\beta$, where $\alpha$ is the number of breakpoint-spanning reads, and $\beta$ is the mean overall depth within a genomic region at a predefined distance around the breakpoint. Thus, the fusion allele frequency may be calculated by dividing the number of rearrangement-spanning reads by the mean overall depth within a genomic region at a predefined distance around the breakpoint.

The method of identifying rearrangements may be applied to whole genome sequencing data or other suitable next-generation sequencing datasets. The genomic regions comprising the rearrangements identified from this data may be used to design a selector set.

The method of identifying rearrangements may be applied to sequencing data from a subject. The method may identify subject-specific breakpoints in tumor genomic DNA captured by a selector set. The method may be used to determine whether the subject-specific breakpoints are present in corresponding plasma DNA sample from the subject.

Identification of Tumor-Derived SNVs

Further disclosed herein are non-invasive methods of identifying tumor-derived SNVs. The tumor-derived SNVs may be identified without prior knowledge of somatic variants identified in a corresponding tumor biopsy sample. In some embodiments of the invention, cfDNA is analyzed without comparison to a known tumor DNA sample from the patient. In such embodiments, the presence of ctDNA utilizes iterative models for (i) background noise in paired germline DNA, (ii) base-pair resolution background frequencies in cfDNA across the selector set, and (iii) sequencing error in cfDNA. These methods may utilize the following steps, which can be iterated through data point to automatically call tumor-derived SNVs:

- taking allele frequencies from a single cfDNA sample and selecting high quality data;
- testing whether a given input cfDNA allele is significantly different from the corresponding paired germline allele;
- assembling a database of cfDNA background allele frequencies;
- testing whether a given input allele differs significantly from cfDNA background at the same position, and selecting those with an average background frequency of a predetermined threshold, e.g. 5% or greater; 2.5% or greater, etc.
- distinguishing tumor-derived SNVs from remaining background noise by outlier analysis.

The non-invasive method of identifying tumor-derived SNVs may comprise (a) obtaining a sample from a subject suffering from a cancer or suspected of suffering from a cancer; (b) conducting a sequencing reaction on the sample to produce sequencing information; (c) applying an algorithm to the sequencing information to produce a list of candidate tumor alleles based on the sequencing information from step (b), wherein a candidate tumor allele comprises a non-dominant base that is not a germline SNP; and (d) identifying tumor-derived SNVs based on the list of candidate tumor alleles. The candidate tumor allele may refer to a genomic region comprising a candidate SNV.

The candidate tumor allele may be a high quality candidate tumor allele. A high quality background allele may refer to the non-dominant base with the highest fractional abundance, excluding germline SNPs. The fractional abundance of a candidate tumor allele may be calculated by dividing a number of supporting reads by a total sequencing depth at that genomic position. For example, for a candidate mutation in a first genomic region, twenty sequence reads may contain a first sequence with the candidate mutation and 100 sequence reads may contain a second sequence without the candidate mutation. The candidate tumor allele may be the first sequence containing the candidate mutation. Based on this example, the fractional abundance of the candidate tumor allele would be 20 divided by 120, which is ~17%. Producing the list of candidate tumor alleles may comprise ranking the tumor alleles based on their fractional abundance. Producing the list of candidate tumor alleles may comprise selecting tumor alleles with the highest fractional abundance. Producing the list of candidate tumor alleles may comprise selecting tumor alleles with a fractional abundance in the top $70^{th}$, $75^{th}$, $80^{th}$, $85^{th}$, $87^{th}$, $90^{th}$, $92^{nd}$, $95^{th}$, or $97^{th}$ percentile. A candidate tumor allele may have a fractional abundance of less than 35%, 30%, 27%, 25%, 20%, 18%, 15%, 13%, 10%, 9%, 8%, 7%, 6.5%, 6%, 5.5%, 5%, 4.5%, 4%, 3.5%, 3%, 2.5%, 2%, 1.75%, 1.50%, 1.25%, or 1% of the total alleles pertaining to the candidate tumor allele in the sample from the subject. A candidate tumor allele may have a fractional abundance of less than 1%, 0.9%, 0.8%, 0.7%, 0.6%, 0.5%, 0.4%, 0.3%, 0.2%, or 0.1% of the total alleles pertaining to the candidate tumor allele in the sample from the subject. The candidate tumor allele may have a fractional abundance of less than 0.5% of the total alleles in the sample from the subject. The sample may comprise paired samples from the subject. Thus, the fractional abundance may be based on paired samples from the subject. The paired samples may comprise a sample containing suspected tumor-derived nucleic acids and a sample containing non-tumor-derived nucleic acids. For example, the paired samples may comprise a plasma sample and a sample containing peripheral blood lymphocytes (PBLs) or peripheral blood mononuclear cells (PBMCs).

The candidate tumor allele may have a minimum sequencing depth. Producing the list of candidate tumor alleles may comprise ranking the tumor alleles based on their sequencing depth. Producing the list of candidate tumor alleles may comprise selecting tumor alleles that meet a minimum sequencing depth. The minimum sequencing depth may be at least 100×, 200×, 300×, 400×, 500×, 600×, 700×, 800×, 900×, 1000× or more. The minimum sequencing depth may be at least about 500×. The minimum sequencing depth may be user-defined.

The candidate tumor allele may have a strand bias percentage. Producing the list of candidate tumor alleles may comprise calculating the strand bias percentage of a tumor allele. Producing the list of candidate tumor alleles may comprise ranking the tumor alleles based on their strand bias percentage. Producing the list of candidate tumor alleles may comprise selecting tumor alleles with a strand bias percentage of less than or equal to 60%, 65%, 70%, 75%, 80%, 85%, 90%, 95%, or 97%. Producing the list of candidate tumor alleles may comprise selecting tumor alleles with a strand bias percentage of less than or equal to 90%. The strand bias percentage may be user-defined.

Producing the list of candidate tumor alleles may comprise comparing the sequence of the tumor allele to a reference tumor allele. The reference tumor allele may be a germline allele. Producing the list of candidate tumor alleles may comprise determining whether the candidate tumor allele is different from a reference tumor allele. Producing the list of candidate tumor alleles may comprise selecting tumor alleles that are different from the reference tumor allele.

Determining whether the tumor allele is different from the reference tumor allele may comprise use of one or more statistical analyses. The statistical analysis may comprise using Bonferroni correction to calculate a Bonferroni-adjusted binomial probability for a tumor allele. The Bonferroni-adjusted binomial probability may be calculated by dividing a desired p-value cutoff (alpha) by the number of hypotheses tested. The number of hypotheses tested may be calculated by multiplying the number of bases in a selector by the number of possible base changes. The Bonferroni-adjusted binomial probability may be calculated by dividing the desired p-value cutoff (alpha) by the number of bases in a selector multiplied by the number of possible base changes. The Bonferroni-adjusted binomial probability may be used to determine whether the tumor allele occurred by chance. Producing the list of candidate tumor alleles may comprise selecting tumor alleles based on the Bonferroni-adjusted binomial probability. A candidate tumor allele may have a Bonferroni-adjusted binomial probability of less than or equal to $3\times10^{-8}$, $2.9\times10^{-8}$, $2.8\times10^{-8}$, $2.7\times10^{-8}$, $2.6\times10^{-8}$, $2.5\times10^{-8}$, $2.3\times10^{-8}$, $2.2\times10^{-8}$, $2.1\times10^{-8}$, $2.09\times10^{-8}$, $2.08\times10^{-8}$, $2.07\times10^{-8}$, $2.06\times10^{-8}$, $2.05\times10^{-8}$, $2.04\times10^{-8}$, $2.03\times10^{-8}$, $2.02\times10^{-8}$, $2.01\times10^{-8}$ or $2\times10^{-8}$. A candidate tumor allele may have a Bonferroni-adjusted binomial probability of less than or equal to $2.08\times10^{-8}$.

Determining whether the tumor allele is different from the reference tumor allele may comprise use of a binomial distribution. The binomial distribution may be used to assemble a database of candidate tumor allele frequencies. An algorithm, such as a Z-test, may be used to determine whether a candidate tumor allele differs significantly from a typical circulating allele at the same position. A significant difference may refer to a difference that is unlikely to have occurred by chance. The Z-test may be applied to the Bonferroni-adjusted bionomial probability of the tumor alleles to produce a Bonferroni-adjusted single-tailed Z-score. The Bonferroni-adjusted single-tailed Z-score may be determined by using a normal distribution. A tumor allele with a Bonferroni-adjusted single-tailed Z-score of greater than or equal to 6, 5.9, 5.8, 5.7, 5.6, 5.5, 5.4, 5.3, 5.2, 5.1, or 5.0 is considered to be different from the reference tumor allele. Producing the list of candidate tumor alleles may comprise selecting tumor alleles with a Bonferroni-adjusted single-tailed Z-score of greater than or equal to 6, 5.9, 5.8, 5.7, 5.6, 5.5, 5.4, 5.3, 5.2, 5.1, or 5.0. Producing the list of candidate tumor alleles may comprise selecting tumor alleles with a Bonferroni-adjusted single-tailed Z-score of greater than 5.6.

Candidate tumor alleles may be based on genomic regions from a selector set. The list of candidate tumor alleles may comprise candidate tumor alleles with a frequency of less than or equal to 10%, 9%, 8%, 7%, 6.5%, 6%, 5.5%, 5%, 4.5%, 4%, 3.5%, or 3%. The list of candidate tumor alleles may comprise candidate tumor alleles with a frequency of less than 5%.

Identifying tumor-derived SNVs based on the list of candidate tumor alleles may comprise testing the candidate tumor alleles from the list of candidate tumor alleles for sequencing errors. Testing the candidate tumor alleles for sequencing errors may be based on the duplication rate of the candidate tumor allele. The duplication rate may be determined by comparing the number of supporting reads for a candidate tumor allele for nondeduped data (e.g., all fragments meeting quality control criteria) and deduped data (e.g., unique fragments meeting quality control criteria). The candidate tumor alleles may be ranked based on their duplication rate. A tumor-derived SNV may be in a candidate tumor allele with a low duplication rate.

Identifying tumor-derived SNVs may further comprise use of an outlier analysis. The outlier analysis may be used to distinguish candidate tumor-derived SNVs from the remaining background noise. The outlier analysis may comprise comparing the square root of the robust distance Rd (Mahalanobis distance) to the square root of the quantiles of a chi-squared distribution Cs. Tumor-derived SNVs may be identified from the outliers in the outlier analysis.

The sequencing information may pertain to regions flanking one or more genomic regions from a selector set. The sequencing information may pertain to regions flanking genomic coordinates from a selector set. The sequencing information may pertain to regions within 100, 200, 300, 400, 500, 600, 700, 800, 900, 1000 or more base pairs of a genomic region from a selector set. The sequencing information may pertain to regions within 500 base pairs of a genomic region from a selector set. The sequencing information may pertain to regions within 100, 200, 300, 400, 500, 600, 700, 800, 900, 1000 or more base pairs of a genomic coordinate from a selector set. The sequencing information may pertain to regions within 500 base pairs of a genomic coordinate from a selector set.

Computer Program

The methods described herein may be performed by a computer program product that comprises a computer executable logic that is recorded on a computer readable medium. For example, the computer program can execute some or all of the following functions: (i) controlling isolation of nucleic acids from a sample, (ii) pre-amplifying nucleic acids from the sample or (iii) selecting, amplifying, sequencing or arraying specific regions in the sample, (iv) identifying and quantifying somatic mutations in a sample, (v) comparing data on somatic mutations detected from the sample with a predetermined threshold, (vi) determining the tumor load based on the presence of somatic mutations in the cfDNA, and (vii) declaring an assessment of tumor load, residual disease, response to therapy, or initial diagnosis. The computer program may calculate a recurrence index. The computer program may rank genomic regions by the recurrence index. The computer program may select one or more genomic regions based on the recurrence index. The computer program may produce a selector set. The computer program may add genomic regions to the selector set. The computer program may maximize subject coverage of the selector set. The computer program may maximize a median number of mutations per subject in a population. The computer program may calculate a ctDNA detection index. The computer program may calculate a p-value of one or more types of mutations. The computer program may identify genomic regions comprising one or more mutations present in one or more subjects suffering from a cancer. The computer program may identify novel mutations present in one or more subjects suffering from a cancer. The computer program may identify novel fusions present in one or more subjects suffering from a cancer.

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of evaluating the presence of tumor cells in an individual by accessing data that reflects the sequence of the selected cfDNA from the individual, and/or the quantitation of one or more nucleic acids from the cfDNA in the circulation of the individual. The one or more nucleic acids from the cfDNA in the circulation to be quantified may be based on genomic regions or genomic coordinates provided by a selector set.

In one embodiment, the computer executing the computer logic of the invention may also include a digital input device such as a scanner. The digital input device can provide information on a nucleic acid, e.g., polymorphism levels/quantity.

In some embodiments, the invention provides a computer readable medium comprising a set of instructions recorded thereon to cause a computer to perform the steps of (i) receiving data from one or more nucleic acids detected in a sample; and (ii) diagnosing or predicting tumor load, residual disease, response to therapy, or initial diagnosis based on the quantitation.

Sequencing

Genotyping ctDNA and/or detection, identification and/or quantitation of the ctDNA can utilize sequencing. Sequencing can be accomplished using high-throughput systems. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read. Sequencing can be performed using nucleic acids described herein such as genomic DNA, cDNA derived from RNA transcripts or RNA as a template. Sequencing may comprise massively parallel sequencing.

In some embodiments, high-throughput sequencing involves the use of technology available by Helicos BioSciences Corporation (Cambridge, Massachusetts) such as the Single Molecule Sequencing by Synthesis (SMSS) method. In some embodiments, high-throughput sequencing involves the use of technology available by 454 Lifesciences, Inc. (Branford, Connecticut) such as the Pico Titer Plate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication application Nos. 200401061 30; 20030064398; 20030022207; and Constans, A, The Scientist 2003, 17 (13): 36.

In some embodiments, high-throughput sequencing of RNA or DNA can take place using AnyDot.chips (Genovoxx, Germany), which allows for the monitoring of biological processes (e.g., miRNA expression or allele variability (SNP detection). In particular, the AnyDot-chips allow for 10×-50× enhancement of nucleotide fluorescence signal detection. Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication application No. 20030044781 and 2006/0078937. The growing of the nucleic acid strand and identifying the added nucleotide analog may be repeated so that the nucleic acid strand is further extended and the sequence of the target nucleic acid is determined.

The methods disclosed herein may comprise conducting a sequencing reaction based on one or more genomic regions from a selector set. The selector set may comprise one or more genomic regions from Table 2. A sequencing reaction may be performed on 10, 20, 30, 40, 50, 60, 70, 80, 90, 100 or more genomic regions from a selector set based on Table 2. A sequencing reaction may be performed on 5%, 10%, 15%, 20%, 25%, 30%, 35%, 40%, 45%, 50%, 55%, 60%, 65%, 70%, 75%, 80%, 85%, 90%, or 95% or more of the genomic regions from a selector set based on Table 2.

A sequencing reaction may be performed on a subset of genomic regions from a selector set. A sequencing reaction may be performed on 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more genomic regions from a selector set. A sequencing reaction may be performed on 325, 350, 375, 400, 425, 450, 475, 500 or more genomic regions from a selector set.

A sequencing reaction may be performed on all of the genomic regions from a selector set. Alternatively, a sequencing reaction may be performed on 5%, 10%, 15%, 20%, 25%, 30%, 35%, 40%, 45%, 50%, 55%, 60%, 65%, 70%, 75%, 80%, 85%, 90%, 95% or more of the genomic regions from a selector set. A sequencing reaction may be performed on at least 10% of the genomic regions from a selector set. A sequencing reaction may be performed on at least 30% of the genomic regions from a selector set. A sequencing reaction may be performed on at least 50% of the genomic regions from a selector set.

A sequencing reaction may be performed on less than 5%, 10%, 15%, 20%, 25%, 30%, 35%, 40%, 45%, 50%, 55%, 60%, 65%, 70%, 75%, 80%, 85%, 90%, 95% of the genomic regions from a selector set. A sequencing reaction may be performed on less than 10% of the genomic regions from a selector set. A sequencing reaction may be performed on less than 30% of the genomic regions from a selector set. A sequencing reaction may be performed on less than 50% of the genomic regions from a selector set.

The methods disclosed herein may comprise obtaining sequencing information for one or more genomic regions from a selector set. Sequencing information may be obtained for 10, 20, 30, 40, 50, 60, 70, 80, 90, 100 or more genomic regions from a selector set based on Table 2. Sequencing information may be obtained for 5%, 10%, 15%, 20%, 25%, 30%, 35%, 40%, 45%, 50%, 55%, 60%, 65%, 70%, 75%, 80%, 85%, 90%, or 95% or more of the genomic regions from a selector set based on Table 2.

Sequencing information may be obtained for a subset of genomic regions from a selector set. Sequencing information may be obtained for 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more genomic regions from a selector set. Sequencing information may be obtained for 325, 350, 375, 400, 425, 450, 475, 500 or more genomic regions from a selector set.

Sequencing information may be obtained for all of the genomic regions from a selector set. Alternatively, sequencing information may be obtained for 5%, 10%, 15%, 20%, 25%, 30%, 35%, 40%, 45%, 50%, 55%, 60%, 65%, 70%, 75%, 80%, 85%, 90%, or 95% or more of the genomic regions from a selector set. Sequencing information may be obtained for at least 10% of the genomic regions from a selector set. Sequencing information may be obtained for at least 30% of the genomic regions from a selector set.

Sequencing information may be obtained for less than 5%, 10%, 15%, 20%, 25%, 30%, 35%, 40%, 45%, 50%, 55%, 60%, 65%, 70%, 75%, 80%, 85%, 90%, or 95% of the genomic regions from a selector set. Sequencing information may be obtained for less than 10% of the genomic regions from a selector set. Sequencing information may be obtained for less than 30% of the genomic regions from a selector set. Sequencing information may be obtained for less than 50% of the genomic regions from a selector set. Sequencing information may be obtained for less than 70% of the genomic regions from a selector set.

Amplification

The methods disclosed herein may comprise amplification of cell-free DNA (cfDNA) and/or of circulating tumor DNA (ctDNA). Amplification may comprise PCR-based amplification. Alternatively, amplification may comprise nonPCR-based amplification.

Amplification of cfDNA and/or ctDNA may comprise using bead amplification followed by fiber optics detection as described in Marguiles et al. "Genome sequencing in microfabricated high-density pricolitre reactors", Nature, doi: 10.1038/nature03959; and well as in US Publication Application Nos. 200200 12930; 20030058629; 20030 1001 02; 20030 148344; 20040248 161; 200500795 10,20050 124022; and 20060078909.

Amplification of the nucleic acid may comprise use of one or more polymerases. The polymerase may be a DNA polymerase. The polymerase may be a RNA polymerase. The polymerase may be a high fidelity polymerase. The polymerase may be KAPA HiFi DNA polymerase. The polymerase may be Phusion DNA polymerase.

Amplification may comprise 20 or fewer amplification cycles. Amplification may comprise 20, 19, 18, 17, 16, 15, 14, 13, 12, 11, 10, or 9 or fewer amplification cycles. Amplification may comprise 18 or fewer amplification cycles. Amplification may comprise 16 or fewer amplification cycles. Amplification may comprise 15 or fewer amplification cycles.

Sample

The methods, kits, and systems disclosed herein may comprise one or more samples or uses thereof. A "sample" may refer to any biological sample that is isolated from a subject. A sample can include, without limitation, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" may also encompass the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. The sample may be from a bodily fluid. The sample may be a plasma sample. The sample may be a serum sample. The sample may be a tumor sample. Samples can be obtained from a subject by means including but not limited to venipuncture, excretion, ejaculation, massage, biopsy, needle aspirate, lavage, scraping, surgical incision, or intervention or other means known in the art.

Samples useful for the methods of the invention may comprise cell-free DNA (cfDNA), e.g., DNA in a sample that is not contained within a cell. Typically such DNA may be fragmented, and may be on average about 170 nucleotides in length, which may coincide with the length of DNA around a single nucleosome. cfDNA may generally be a heterogeneous mixture of DNA from normal and tumor cells, and an initial sample of cfDNA may generally not be enriched for recurrently mutated regions of a cancer cell genome. The terms ctDNA, cell-free tumor DNA or "circulating tumor" DNA may be used to refer to the fraction of cfDNA in a sample that is derived from a tumor. One of skill in the art will understand that germline sequences may not be distinguished between a tumor source and a normal cell source, but sequences containing somatic mutations have a high probability of being derived from tumor DNA. A sample may be a control germline DNA sample. A sample may be a known tumor DNA sample. A sample may be cfDNA obtained from an individual suspected of having ctDNA in the sample.

The methods disclosed herein may comprise obtaining one or more samples from a subject. The one or more samples may be a tumor nucleic acid sample. Alternatively, or additionally, the one or more samples may be a genomic nucleic acid sample. It should be understood that the step of obtaining a tumor nucleic acid sample and a genomic nucleic acid sample from a subject with a specific cancer may occur in a single step. Alternatively, the step of obtaining a tumor nucleic acid sample and a genomic nucleic acid sample from a subject with a specific cancer may occur in separate steps. For example, it may be possible to obtain a single tissue sample from a patient, for example from a biopsy sample, which includes both tumor nucleic acids and genomic nucleic acids. It is also within the scope of this step to obtain the tumor nucleic acid sample and the genomic nucleic acid sample from the subject in separate samples, in separate tissues, or even at separate times.

The sample may comprise nucleic acids. The nucleic acids may be cell-free nucleic acids. The nucleic acids may be circulating nucleic acids. The nucleic acids may be from a tumor. The nucleic acids may be circulating tumor DNA (ctDNA). The nucleic acids may be cell-free DNA (cfDNA). The nucleic acids may be genomic nucleic acids. The nucleic acids may be tumor nucleic acids.

The step of obtaining a tumor nucleic acid sample and a genomic nucleic acid sample from a subject with a specific cancer may also include the process of extracting a biological fluid or tissue sample from the subject with the specific cancer. These particular steps are well understood by those of ordinary skill in the medical arts, particularly by those working in the medical laboratory arts.

The step of obtaining a tumor nucleic acid sample and a genomic nucleic acid sample from a subject with a specific cancer may additionally include procedures to improve the yield or recovery of the nucleic acids in the sample. For example, the step may include laboratory procedures to separate the nucleic acids from other cellular components and contaminants that may be present in the biological fluid or tissue sample. As noted, such steps may improve the yield and/or may facilitate the sequencing reactions.

It should also be understood that the step of obtaining a tumor nucleic acid sample and a genomic nucleic acid sample from a subject with a specific cancer may be performed by a commercial laboratory that does not even have direct contact with the subject. For example, the commercial laboratory may obtain the nucleic acid samples from a hospital or other clinical facility where, for example, a biopsy or other procedure is performed to obtain tissue from a subject. The commercial laboratory may thus carry out all the steps of the instantly-disclosed methods at the request of, or under the instructions of, the facility where the subject is being treated or diagnosed.

A sample may be selected for DNA corresponding to regions of recurrent mutations, utilizing a selector set as described herein. In some embodiments, the selection process comprises the following method. DNA obtained from cellular sources may be fragmented to approximate the size of cfDNA, e.g. of from about 50 to about 1 KB in length. The DNA may then be denatured, and hybridized to a population of selector set probes comprising a specific binding member, e.g. biotin, etc. The composition of hybridized DNA may then be applied to a complementary binding member, e.g. avidin, streptavidin, an antibody specific for a tag, etc., and the unbound DNA washed free. The selected DNA population may then be washed free of the unbound DNA.

The captured DNA may then be sequenced by any suitable protocol. In some embodiments, the captured DNA is amplified prior to sequencing, where the amplification primers may utilize primers or oligonucleotides suitable for high throughput sequencing. The resulting product may be a set of DNA sequences enriched for sequences corresponding to regions of the genome that have recurrent mutations in the cancer of interest. The remaining analysis may utilize bioinformatics methods, which can vary with the type of somatic mutation, e.g. SNV, SNV, fusion, etc.

Further disclosed herein are methods of preparing a next-generation sequencing (NGS) library. The method may comprise (a) attaching adaptors to a plurality of nucleic acids to produce a plurality of adaptor-modified nucleic acids; and (b) amplifying the plurality of adaptor-modified nucleic acids, thereby producing a NGS library, wherein amplifying comprises 1 to 20 amplification cycles.

The methods disclosed herein may comprise attaching adaptors to nucleic acids. Attaching adaptors to nucleic acids may comprise ligating adaptors to nucleic acids. Attaching adaptors to nucleic acids may comprise hybridizing adaptors to nucleic acids. Attaching adaptors to nucleic acids may comprise primer extension.

The plurality of nucleic acids may be from a sample. Attaching the adaptors to the plurality of nucleic acids may comprise contacting the sample with the adaptors.

Attaching the adaptors to the nucleic acids may comprise incubating the adaptors and nucleic acids at a specific temperature or temperature range. Attaching the adaptors to the nucleic acids may comprise incubating the adaptors and nucleic acids at 20° C. Attaching the adaptors to the nucleic acids may comprise incubating the adaptors and nucleic acids at less 20° C. Attaching the adaptors to the nucleic acids may comprise incubating the adaptors and nucleic acids at 19° C., 18° C., 17° C., 16° C. or less. Alternatively, attaching the adaptors to the nucleic acids may comprise incubating the adaptors and nucleic acids at varying temperatures. For example, attaching the adaptors to the nucleic acids may comprise temperature cycling. Attaching the adaptors to the nucleic acids may comprise may comprise incubating the nucleic acids and adaptors at a first temperature for a first period of time, followed by incubation at one or more additional temperatures for one or more additional periods of time. The one or more additional temperatures may be greater than the first temperature or preceding temperature. Alternatively, or additionally, the one or more additional temperatures may be less than the first temperature or preceding temperature. For example, the nucleic acids and adaptors may be incubated at 10° C. for 30 second, followed by incubation at 30° C. for 30 seconds. The temperature cycling of 10° C. for 30 seconds and 30° C. for 30 second may be repeated multiple times. For example, attaching the adaptors to the nucleic acids by temperature cycling may comprise alternating the temperature from 10° C. to 30° C. in 30 second increments for a total time period of 12 to 16 hours.

The adaptors and nucleic acids may be incubated at a specified temperature or temperature range for a period of time. The adaptors and nucleic acid may be incubated at a specific temperature or temperature range for at least about 15 minutes. The adaptors and nucleic acid may be incubated at a specific temperature or temperature range for at least about 30 minutes, 60 minutes, 90 minutes, 120 minutes or more. The adaptors and nucleic acid may be incubated at a specific temperature or temperature range for at least about 1 hour, 2 hours, 3 hours, 4 hours, 5 hours, 6 hours, 7 hours, 8 hours, 9 hours, 10 hours, 12 hours, 14 hours, 16 hours, or more. The adaptors and nucleic acid may be incubated at a specific temperature or temperature range for at least about 16 hours.

The adaptors may be attached to the nucleic acid by incubating the nucleic acids and the adaptors at a temperature less than or equal to 20° C. for at least about 20, 30, 40, 50, 60, 70, 80, 90, 100 or more minutes. The adaptors may be attached to the nucleic acid by incubating the nucleic acids and the adaptors at a temperature less than or equal to 20, 19, 18, 17, 16° C. for at least about 1 hour. The adaptors may be attached to the nucleic acid by incubating the nucleic acids and the adaptors at a temperature less than or equal to 18° C. for at least about 1, 2, 3, 4, 5, 6, 7, 8, 9, 10, 11, 12, 13, 14, 15, 16 or more hours. The adaptors may be attached to the nucleic acid by incubating the nucleic acids and the adaptors at a temperature less than or equal to 20, 19, 18, 17, 16° C. for at least about 5 hours. The adaptors may be attached to the nucleic acid by incubating the nucleic acids and the adaptors at a temperature less than or equal to 16° C. for at least about 5 hours.

Attaching the adaptors to the nucleic acids may comprise use of one or more enzymes. The enzyme may be a ligase. The ligase may be a DNA ligase. The DNA ligase may be a T4 DNA ligase, *E. coli* DNA ligase, mammalian ligase, or a combination thereof. The mammalian ligase may be DNA ligase I, DNA ligase III, or DNA ligase IV. The ligase may be a thermostable ligase.

The adaptor may comprise a universal primer binding sequence. The adaptor may comprise a primer sequence. The primer sequence may enable sequencing of the adaptor-modified nucleic acids. The primer sequence may enable amplification of the adaptor-modified nucleic acids. The adaptor may comprise a barcode. The barcode may enable differentiation of two or more molecules of the same molecular species. The barcode may enable quantification of one or more molecules.

The method may further comprise contacting the plurality of nucleic acids with a plurality of beads to produce a plurality of bead-conjugated nucleic acids. The plurality of nucleic acids may be contacted with the plurality of beads after attaching the adaptors to the nucleic acids. Alternatively, or additionally, the plurality of nucleic acids may be contacted with the plurality of beads before amplification of the adaptor-modified nucleic acids. Alternatively, or additionally, the plurality of nucleic acids may be contacted with the plurality of beads after amplification of the adaptor-modified nucleic acids.

The beads may be magnetic beads. The beads may be coated beads. The beads may be antibody-coated beads. The beads may be protein-coated beads. The beads may be coated with one or more functional groups. The beads may be coated with one or more oligonucleotides.

Amplifying the plurality of adaptor-modified nucleic acids may comprise any method known in the art. For example, amplifying may comprise PCR-based amplification. Alternatively, amplifying may comprise nonPCR-based amplification. Amplifying may comprise any of the amplification methods disclosed herein.

Amplifying the plurality of adaptor-modified nucleic acids may comprise amplifying a product or derivative of the adaptor-modified nucleic acids. A product or derivative of the adaptor-ligated nucleic acids may comprise bead-conjugated nucleic acids, enriched-nucleic acids, fragmented nucleic acids, end-repaired nucleic acids, A-tailed nucleic acids, barcoded nucleic acids, or a combination thereof.

Amplifying the adaptor-modified nucleic acids may comprise 1 to 20 amplification cycles. Amplifying the adaptor-modified nucleic acids may comprise 1 to 18 amplification cycles. Amplifying the adaptor-modified nucleic acids may comprise 1 to 17 amplification cycles. Amplifying the adaptor-modified nucleic acids may comprise 1 to 16 amplification cycles. Amplifying the adaptor-modified nucleic acids may comprise 2 to 20 amplification cycles. Amplifying the adaptor-modified nucleic acids may comprise 2 to 18 amplification cycles. Amplifying the adaptor-modified nucleic acids may comprise 2 to 16 amplification cycles. Amplifying the adaptor-modified nucleic acids may comprise 3 to 20 amplification cycles. Amplifying the adaptor-modified nucleic acids may comprise 3 to 19 amplification cycles. Amplifying the adaptor-modified nucleic acids may comprise 3 to 17 amplification cycles. Amplifying the adaptor-modified nucleic acids may comprise 4 to 20 amplification cycles. Amplifying the adaptor-modified nucleic acids may comprise 4 to 18 amplification cycles. Amplifying the adaptor-modified nucleic acids may comprise 4 to 16 amplification cycles. Amplifying the adaptor-modified nucleic acids may comprise 5 to 20 amplification cycles. Amplifying the adaptor-modified nucleic acids may comprise 5 to 19 amplification cycles. Amplifying the adaptor-modified nucleic acids may comprise 5 to 18 amplification cycles. Amplifying the adaptor-modified nucleic acids may comprise 5 to 17 amplification cycles. Amplifying the adaptor-modified nucleic acids may comprise 5 to 16 amplification cycles. Amplifying the adaptor-modified nucleic acids may comprise 5 to 15 amplification cycles.

Amplifying the adaptor-modified nucleic acids may comprise 20, 19, 18, 17, 16, 15, 14, 13, 12, 11, 10, 9, 8, 7, 6, 5, 4, 3, or 2 or fewer amplification cycles. Amplifying the adaptor-modified nucleic acids may comprise 20 or fewer amplification cycles. Amplifying the adaptor-modified nucleic acids may comprise 18 or fewer amplification cycles. Amplifying the adaptor-modified nucleic acids may comprise 16 or fewer amplification cycles. Amplifying the adaptor-modified nucleic acids may comprise 15 or fewer amplification cycles.

The method may further comprise fragmenting the plurality of nucleic acids to produce a plurality of fragmented nucleic acids. The plurality of nucleic acids may be fragmented prior to attaching the adaptors to the plurality of nucleic acids. The plurality of nucleic acids may be fragmented after attachment of the adaptors to the plurality of nucleic acids. The plurality of nucleic acids may be fragmented prior to amplification of the adaptor-modified nucleic acids. The plurality of nucleic acids may be fragmented after amplification of the adaptor-modified nucleic acids. Fragmenting the plurality of nucleic acids may comprise use of one or more restriction enzymes. Fragmenting the plurality of nucleic acids may comprise use of a sonicator. Fragmenting the plurality of nucleic acids may comprise shearing the nucleic acids.

The method may further comprise conducting an end repair reaction on the plurality of nucleic acids to produce a plurality of end repaired nucleic acids. The end repair reaction may be conducted prior to attaching the adaptors to the plurality of nucleic acids. The end repair reaction may be conducted after attaching the adaptors to the plurality of nucleic acids. The end repair reaction may be conducted prior to amplification of the adaptor-modified nucleic acids. The end repair reaction may be conducted after amplification of the adaptor-modified nucleic acids. The end repair reaction may be conducted prior to fragmenting the plurality of nucleic acids. The end repair reaction may be conducted after fragmenting the plurality of nucleic acids. Conducting the end repair reaction may comprise use of one or more end repair enzymes.

The method may further comprise conducting an A-tailing reaction on the plurality of nucleic acids to produce a plurality of A-tailed nucleic acids. The A-tailing reaction may be conducted prior to attaching the adaptors to the plurality of nucleic acids. The A-tailing reaction may be conducted after attaching the adaptors to the plurality of nucleic acids. The A-tailing reaction may be conducted prior to amplification of the adaptor-modified nucleic acids. The A-tailing reaction may be conducted after amplification of the adaptor-modified nucleic acids. The A-tailing reaction may be conducted prior to fragmenting the plurality of nucleic acids. The A-tailing reaction may be conducted after fragmenting the plurality of nucleic acids. The A-tailing reaction may be conducted prior to end repair of the plurality of nucleic acids. The A-tailing reaction may be conducted after end repair of the plurality of nucleic acids. Conducting the A-tailing reaction may comprise use of one or more A-tailing enzymes.

The method may further comprise contacting the plurality of nucleic acids with a plurality of molecular barcodes to produce a plurality of barcoded nucleic acids. Producing the plurality of barcoded nucleic acids may occur prior to attaching the adaptors to the plurality of nucleic acids. Producing the plurality of barcoded nucleic acids may occur after attaching the adaptors to the plurality of nucleic acids. Producing the plurality of barcoded nucleic acids may occur prior to amplification of the adaptor-modified nucleic acids. Producing the plurality of barcoded nucleic acids may occur after amplification of the adaptor-modified nucleic acids. Producing the plurality of barcoded nucleic acids may occur prior to fragmenting the plurality of nucleic acids. Producing the plurality of barcoded nucleic acids may occur after fragmenting the plurality of nucleic acids. Producing the plurality of barcoded nucleic acids may occur prior to end repair of the plurality of nucleic acids. Producing the plurality of barcoded nucleic acids may occur after end repair the plurality of nucleic acids. Producing the plurality of barcoded nucleic acids may occur prior to A-tailing of the plurality of nucleic acids. Producing the plurality of barcoded nucleic acids may occur after A-tailing of the plurality of nucleic acids. The barcode may enable differentiation of two or more molecules of the same molecular species. The barcode may enable quantification of one or more molecules. The barcode may be a molecular barcode. The molecular barcode may be used to differentiate two or more molecules of the same molecular species. The molecular barcode may be used to differentiate two or more molecules of the same genomic region. The barcode may be a sample index. The sample index may be used to identify a sample from which the molecule (e.g., nucleic acid) originated from. For example, molecules from a first sample may be associated with a first sample index, whereas molecules from a second sample may be associated with a second sample index. The sample index from two or more samples may be different. The two or more samples may be from the same subject. The two or more samples may be from two or more subjects. The two or more samples may be obtained at the same time. Alternatively, or additionally, the two or more samples may be obtained at two or more time points.

The method may further comprise contacting the plurality of nucleic acids with a plurality of sequencing adaptors to produce a plurality of sequencer-adapted nucleic acids. Producing the plurality of sequencer-adapted nucleic acids may occur prior to attaching the adaptors to the plurality of nucleic acids. Producing the plurality of sequencer-adapted nucleic acids may occur after attaching the adaptors to the plurality of nucleic acids. Producing the plurality of sequencer-adapted nucleic acids may occur prior to amplification of the adaptor-modified nucleic acids. Producing the plurality of sequencer-adapted nucleic acids may occur after amplification of the adaptor-modified nucleic acids. Producing the plurality of sequencer-adapted nucleic acids may occur prior to fragmenting the plurality of nucleic acids. Producing the plurality of sequencer-adapted nucleic acids may occur after fragmenting the plurality of nucleic acids. Producing the plurality of sequencer-adapted nucleic acids may occur prior to end repair of the plurality of nucleic acids. Producing the plurality of sequencer-adapted nucleic acids may occur after end repair the plurality of nucleic acids. Producing the plurality of sequencer-adapted nucleic acids may occur prior to A-tailing of the plurality of nucleic acids. Producing the plurality of sequencer-adapted nucleic acids may occur after A-tailing of the plurality of nucleic acids. Producing the plurality of sequencer-adapted nucleic acids may occur prior to producing the barcoded nucleic acids. Producing the plurality of sequencer-adapted nucleic acids may occur after producing the barcoded nucleic acids. The sequencing adaptor may enable sequencing of the nucleic acids.

The method may further comprise contacting the plurality of nucleic acids with a plurality of primer adaptors to produce a plurality of primer-adapted nucleic acids. Producing the plurality of primer-adapted nucleic acids may occur prior to attaching the adaptors to the plurality of nucleic acids. Producing the plurality of primer-adapted nucleic acids may occur after attaching the adaptors to the plurality of nucleic acids. Producing the plurality of primer-adapted nucleic acids may occur prior to amplification of the adaptor-modified nucleic acids. Producing the plurality of primer-adapted nucleic acids may occur after amplification of the adaptor-modified nucleic acids. Producing the plurality of primer-adapted nucleic acids may occur prior to fragmenting the plurality of nucleic acids. Producing the plurality of primer-adapted nucleic acids may occur after fragmenting the plurality of nucleic acids. Producing the plurality of primer-adapted nucleic acids may occur prior to end repair of the plurality of nucleic acids. Producing the plurality of primer-adapted nucleic acids may occur after end repair the plurality of nucleic acids. Producing the plurality of primer-adapted nucleic acids may occur prior to A-tailing of the plurality of nucleic acids. Producing the plurality of primer-adapted nucleic acids may occur after A-tailing of the plurality of nucleic acids. Producing the plurality of primer-adapted nucleic acids may occur prior to producing the barcoded nucleic acids. Producing the plurality of primer-adapted nucleic acids may occur after producing the barcoded nucleic acids. Producing the plurality of primer-adapted nucleic acids may occur prior to producing the sequencer-adapted nucleic acids. Producing the plurality of primer-adapted nucleic acids may occur after producing the sequencer-adapted nucleic acids. Producing the plurality of primer-adapted nucleic acids may comprise ligating the primer adaptors to the nucleic acids. The primer adaptor may enable sequencing of the nucleic acids. The primer adaptor may enable amplification of the nucleic acids.

The method may further comprise conducting a hybridization reaction. The hybridization reaction may comprise use of a solid support. The hybridization reaction may comprise hybridizing the plurality of nucleic acids to the solid support. The hybridization reaction may comprise use of a plurality of beads. The hybridization reaction may comprise hybridizing the plurality of nucleic acids to the plurality of beads. The method may further comprise conducting a hybridization reaction after an enzymatic reaction. The enzymatic reaction may comprise a ligation reaction. The enzymatic reaction may comprise a fragmentation reaction. The enzymatic reaction may comprise an end repair reaction. The enzymatic reaction may comprise an A-tailing reaction. The enzymatic reaction may comprise an amplification reaction. The method may further comprise conducting a hybridization reaction after one or more reactions selected from a group consisting of a ligation reaction, fragmentation reaction, end repair reaction, A-tailing reaction, and amplification reaction. The method may further comprise conducting a hybridization reaction after two or more reactions selected from a group consisting of a ligation reaction, fragmentation reaction, end repair reaction, A-tailing reaction, and amplification reaction. The method may further comprise conducting a hybridization reaction after three or more reactions selected from a group consisting of a ligation reaction, fragmentation reaction, end repair reaction, A-tailing reaction, and amplification reaction. The method may further comprise conducting a hybridization reaction after four or more reactions selected from a group consisting of a ligation reaction, fragmentation reaction, end repair reaction, A-tailing reaction, and amplification reaction. The hybridization reaction may be conducted after each reaction selected from a group consisting of ligation reaction, fragmentation reaction, end repair reaction, A-tailing reaction, and amplification reaction.

Nucleic Acid Detection Methods

Provided herein are methods for the ultrasensitive detection of a minority nucleic acid in a heterogeneous sample. The method may comprise (a) obtaining sequence information of a cell-free DNA (cfDNA) sample derived from a subject; and (b) using sequence information derived from (a) to detect cell-free minority nucleic acids in the sample, wherein the method is capable of detecting a percentage of the cell-free minority nucleic acids that is less than 2% of total cfDNA. The minority nucleic acid may refer to a nucleic acid that originated from a cell or tissue that is different from a normal cell or tissue from the subject. For example, the subject may be infected with a pathogen such as a bacteria and the minority nucleic acid may be a nucleic acid from the pathogen. In another example, the subject is a recipient of a cell, tissue or organ from a donor and the minority nucleic acid may be a nucleic acid originating from the cell, tissue or organ from the donor. In another example, the subject is a pregnant subject and the minority nucleic acid may be a nucleic acid originating from a fetus. The method may comprise using the sequence information to detect one or more somatic mutations in the fetus. The method may comprise using the sequence information to detect one or more post-zygotic mutations in the fetus. Alternatively, the subject may be suffering from a cancer and the minority nucleic acid may be a nucleic acid originating from a cancer cell.

Provided herein are methods for the ultrasensitive detection of circulating tumor DNA in a sample. The method may be called CAncer Personalized Profiling by Deep Sequencing (CAPP-Seq). The method may comprise (a) obtaining sequence information of a cell-free DNA (cfDNA) sample derived from a subject; and (b) using sequence information derived from (a) to detect cell-free tumor DNA (ctDNA) in the sample, wherein the method is capable of detecting a percentage of ctDNA that is less than 2% of total cfDNA. CAPP-Seq may accurately quantify cell-free tumor DNA from early and advanced stage tumors. CAPP-Seq may identify mutant alleles down to 0.025% with a detection limit of <0.01%. Tumor-derived DNA levels often paralleled clinical responses to diverse therapies and CAPP-Seq may identify actionable mutations. CAPP-Seq may be routinely applied to noninvasively detect and monitor tumors, thus facilitating personalized cancer therapy.

Disclosed herein are methods for determining a quantity of circulating tumor DNA (ctDNA) in a sample. The method may comprise (a) ligating one or more adaptors to cell-free DNA (cfDNA) derived from a sample from a subject to produce one or more adaptor-ligated cfDNA; (b) performing sequencing on the one or more adaptor-ligated cfDNA, wherein the adaptor-ligated cfDNA to be sequenced is based on a selector set comprising a plurality of genomic regions; and (c) using a computer readable medium to determine a quantity of cfDNA originating from a tumor based on the sequencing information obtained from the adaptor-ligated cfDNA. cfDNA originating from the tumor may be referred to as cell-free tumor DNA or circulating tumor DNA (ctDNA). The quantity of ctDNA may be a percentage. Determining the quantity of the ctDNA may comprise determining the sequence of one or more genomic regions from the selector set. Determining the quantity of the ctDNA may comprise determining a number of sequence reads that contain a sequence a mutation corresponding to one or more mutations in the one or more genomic regions based on the selector set. Determining the quantity of ctDNA may comprise determining a number of sequence reads that contain a sequence that does not contain a mutation corresponding to one or more mutations in the one or more genomic regions based on the selector set. Determining the quantity of ctDNA may comprise calculating a percentage of sequence reads that contain sequences with one or more mutations corresponding to one or more mutations in the one or more genomic regions based on the selector set. For example, a selector set may be used to obtain sequencing information for a first genomic region. The sequence information may comprise twenty sequencing reads pertaining to the first genomic region. Analysis of the sequencing information may determine that two of the sequencing reads contain a mutation corresponding to a first mutation in the first genomic region based on the selector set and eighteen of the sequencing reads do not contain a mutation corresponding to a mutation in the first genomic region based on the selector set. Thus, the quantity of the ctDNA may be equal to the percentage of sequencing reads with the mutation corresponding to a mutation in the first genomic region, which would be 10% (e.g., 2 reads divided by 20 reads times 100%). For sequence information pertaining to two or more genomic regions based on the selector set, determining the quantity of ctDNA may comprise calculating an average of the percentages the two or more genomic regions. For example, the percentage of sequencing reads containing a mutation corresponding to a first mutation in a first genomic region is 20% and the percentage of sequencing reads containing a mutation corresponding to a second mutation in a second genomic region is 40%; the quantity of ctDNA is the average of the percentages of the two genomic regions, which is 30% (e.g., (20%+40%) divided by 2). The quantity of ctDNA may be converted into a mass per unit volume value by multiplying the percentage of the ctDNA by the absolute concentration of the total cell-free DNA per unit volume. For example, the percentage of ctDNA may be 30% and the concentration of the cell free DNA may be 10 nanograms per milliliter (ng/mL); the quantity of ctDNA may be 3 ng/ml (e.g., 0.30 times 10 ng/mL).

Alternatively, or additionally, determining the quantity of ctDNA may comprise use of adaptors comprising a barcode sequence. Two or more adaptors may contain two or more different barcode sequences. The barcode sequence may be a random sequence. A genomic region may be attached to an adaptor containing a barcode sequence. Identical genomic regions may be attached to adaptors containing different barcode sequences. Non-identical genomic regions may be attached to adaptors containing different barcode sequences. The barcode sequences may be used to count a number of occurrences of a genomic region. The quantity of the ctDNA may be based on counting a number of occurrences of genomic regions based on the selector set. Rather than basing the quantity of the ctDNA on the number of sequencing reads, the quantity of the ctDNA may be based on the number of different barcodes associated with one or more genomic regions. For example, ten different barcodes may be associated with sequences containing a mutation corresponding to a mutation in a first genomic region based on the selector set, resulting in a quantity of ctDNA of ten. For two or more genomic regions, the quantity of the ctDNA may be a sum of the quantity of the two or more genomic regions. For example, ten different barcodes may be associated with sequences containing a mutation corresponding to a mutation in a first genomic region and twenty different barcodes may be associated with sequences containing a mutation correspond to a mutation in a second genomic region, resulting in a quantity of ctDNA of 30. The quantity of the ctDNA may be a percentage of the total cell-free DNA. For example, ten different barcodes may be associated with sequences containing a mutation corresponding to a mutation in a first genomic region and forty different barcodes may be associated with sequences that do not contain a mutation corresponding to a mutation in the first genomic region, resulting in a quantity of ctDNA of 20% (e.g., (10 divided by 50) times 100%).

Disclosed herein are methods of enriching for circulating tumor DNA from a sample. The method may comprise contacting cell-free nucleic acids from a sample with a plurality of oligonucleotides, wherein the plurality of oligonucleotides selectively hybridize to a plurality of genomic regions comprising a plurality of mutations present in >60% of a population of subjects suffering from a cancer.

Alternatively, the method may comprise contacting cell-free nucleic acids from a sample with a set of oligonucleotides, wherein the set of oligonucleotides selectively hybridize to a plurality of genomic regions, wherein (a) >80% of tumors from a population of cancer subjects include one or more mutations in the genomic regions; (b) the plurality of genomic regions represent less than 1.5 Mb of the genome; and (c) the set of oligonucleotides comprise 5 or more different oligonucleotides that selectively hybridize to the plurality of genomic regions. The cell-free nucleic acids may be DNA. The cell-free nucleic acids may be RNA.

Applications

The selector sets created according to the methods described herein may be useful in the analysis of genetic alterations, particularly in comparing tumor and genomic sequences in a patient with cancer. As shown in FIG. 2, a tissue biopsy sample from the patient may be used to discover mutations in the tumor by sequencing the genomic regions of the selector library in tumor and genomic nucleic acid samples and comparing the results. The selector sets may be designed to identify mutations in tumors from a large percentage of all patients, thus, it may not be necessary to optimize the library for each patient.

In some methods of the invention, the analysis of cfDNA for somatic mutations is compared to personalized tumor markers in an initial dataset developed from somatic mutations in a known tumor sample from an individual. To develop such a dataset, a sample of tumor cells or known tumor DNA may be obtained, which is compared to a germline sample. Preferably although not necessarily, a germline sample may be from the individual.

To "analyze" may include determining a set of values associated with a sample by determining a DNA sequence, and comparing the sequence against the sequence of a sample or set of samples from the same subject, from a control, from reference values, etc. as known in the art. To "analyze" can include performing a statistical analysis.

Figure 22:
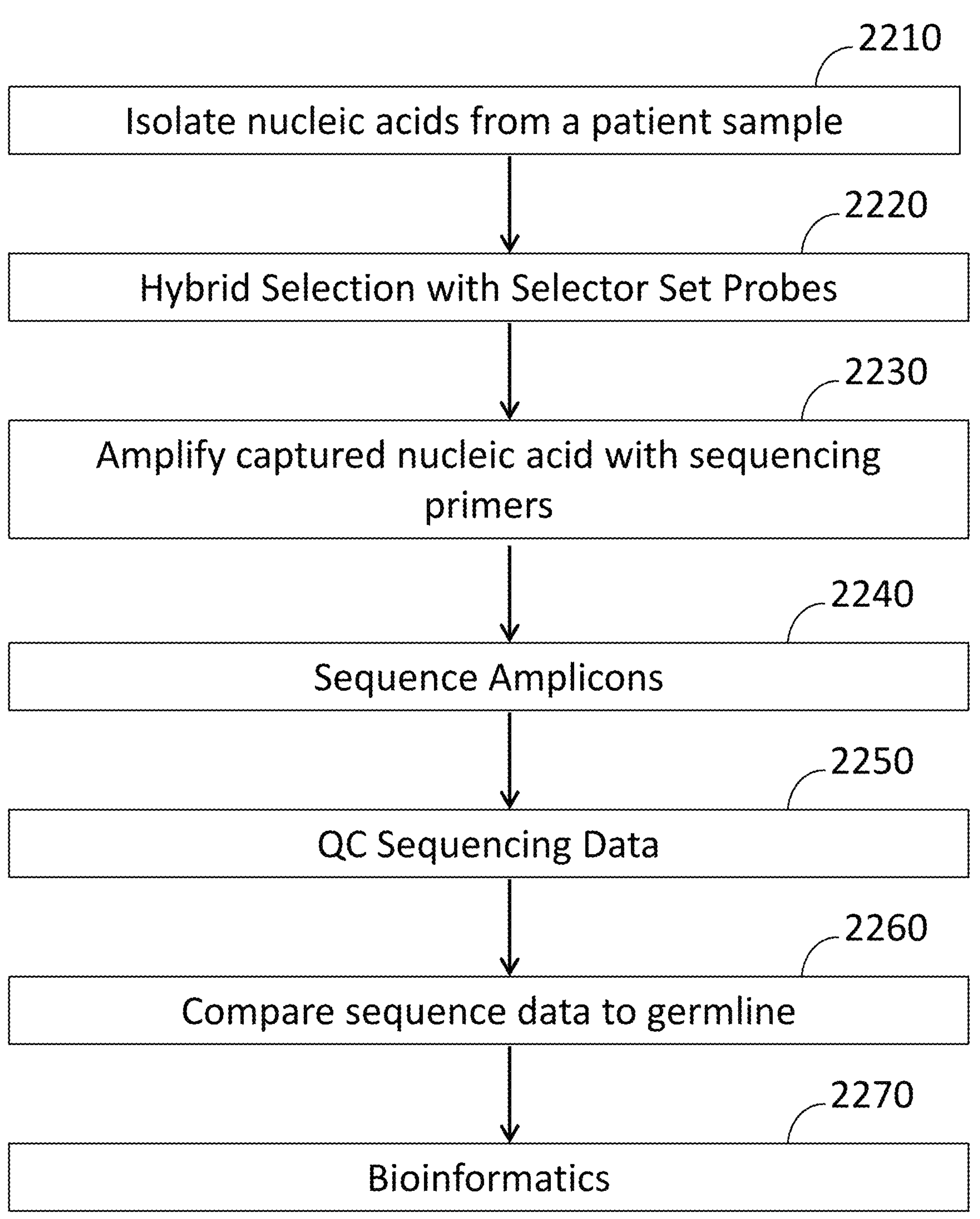
FIG. 22. depicts a flow chart of patient analysis.

CAPP-seq may utilize hybrid selection of cfDNA corresponding to regions of recurrent mutation for diagnosis and monitoring of cancer in an individual patient. In such embodiments the selector set probes are used to enrich, e.g. by hybrid selection, for ctDNA that corresponds to the regions of the genome that are most likely to contain tumor-specific somatic mutations. The "selected" ctDNA is then amplified and sequenced to determine which of the selected genomic regions are mutated in the individual tumor. An initial comparison is optionally made with the individual's germline DNA sequence and/or a tumor biopsy sample from the individual. These somatic mutations provide a means of distinguishing ctDNA from germline DNA, and thus provide useful information about the presence and quantity of tumor cells in the individual. A flow chart for this process is provided in FIG. 22.

In other embodiments, CAPP-seq is used for cancer screening and biopsy-free tumor genotyping, where a patient ctDNA sample is analyzed without reference to a biopsy sample. In some such embodiments, where CAPP-Seq identifies a mutation in a clinically actionable target from a ctDNA sample, the methods include providing a therapy appropriate for the target. Such mutations include, without limitation, rearrangements and other mutations involving oncogenes, receptor tyrosine kinases, etc.

Further disclosed herein is a method of detecting, diagnosing, prognosing, or therapy selection for a cancer subject comprising: (a) obtaining sequence information of a cell-free DNA (cfDNA) sample derived from the subject; and (b) using sequence information derived from (a) to detect cell-free non-germline DNA (cfNG-DNA) in the sample, wherein the method is capable of detecting a percentage of cfNG-DNA that is less than 2% of total cfDNA. The method may be capable of detecting a percentage of ctDNA that is less than 1.5% of the total cfDNA. The method may be capable of detecting a percentage of cfNG-DNA that is less than 1% of the total cfDNA. The method may be capable of detecting a percentage of cfNG-DNA that is less than 0.5% of the total cfDNA. The method may be capable of detecting a percentage of cfNG-DNA that is less than 0.1% of the total cfDNA. The method may be capable of detecting a percentage of cfNG-DNA that is less than 0.01% of the total cfDNA. The method may be capable of detecting a percentage of cfNG-DNA that is less than 0.001% of the total cfDNA. The method may be capable of detecting a percentage of cfNG-DNA that is less than 0.0001% of the total cfDNA. The sample may be a plasma or serum sample. The sample may be a cerebral spinal fluid sample. In some instances, the sample is not a pap smear fluid sample. In some instances, the sample is a cyst fluid sample. In some instances, the sample is a pancreatic fluid sample. The sequence information may comprise information related to at least 10, 20, 30, 40, 100, 200, 300 genomic regions. The genomic regions may comprise genes, exonic regions, intronic regions, untranslated regions, non-coding regions or a combination thereof. The genomic regions may comprise two or more of exonic regions, intronic regions, and untranslated regions. The genomic regions may comprise at least one exonic region and at least one intronic region. At least 5% of the genomic regions may comprise intronic regions. At least about 20% of the genomic regions may comprise exonic regions. The genomic regions may comprise less than 1.5 megabases (Mb) of the genome. The genomic regions may comprise less than 1 Mb of the genome. The genomic regions may comprise less than 500 kilobases (kb) of the genome. The genomic regions may comprise less than 350 kb of the genome. The genomic regions may comprise between 100 kb to 300 kb of the genome. The sequence information may comprise information pertaining to 1, 2, 3, 4, 5, 6, 7, 8, 9, 10, 15, 20 or more genomic regions from a selector set comprising a plurality of genomic regions. The sequence information may comprise information pertaining to 25, 30, 40, 50, 60, 70, 80, 90, 100 or more genomic regions from a selector set comprising a plurality of genomic regions. The sequence information may comprise information pertaining to a plurality of genomic regions. The plurality of genomic regions may be based on a selector set comprising genomic regions comprising one or more mutations present in one or more subjects from a population of cancer subjects. At least about 5%, 10%, 15%, 20%, 25%, 30%, 35%, 40%, 45%, 50%, 55%, 60%, 65%, 70%, 75%, 80%, 85%, 90%, or 95% of the plurality of genomic regions may be based on a selector set comprising genomic regions comprising one or more mutations present in one or more subjects from a population of cancer subjects. The total size of the genomic regions of the selector set may comprise less than 1.5 megabases (Mb), 1 Mb, 500 kilobases (kb), 350 kb, 300 kb, 250 kb, 200 kb, or 150 kb of the genome. The total size of the genomic regions of the selector set may be between 100 kb to 300 kb of the genome. The selector set may comprise 1, 2, 3, 4, 5, 6, 7, 8, 9, 10, 15, 20, 25, 30, 40, 50, 60, 70, 80, 90, 100 or more genomic regions selected from Table 2. In some instances, the subject is not suffering from a pancreatic cancer. Obtaining sequence information may comprise performing massively parallel sequencing. Massively parallel sequencing may be performed on a subset of a genome of cfDNA from the cfDNA sample. The subset of the genome may comprise less than 1.5 megabases (Mb), 1 Mb, 500 kilobases (kb), 350 kb, 300 kb, 250 kb, 200 kb, or 150 kb of the genome. The subset of the genome may comprise between 100 kb to 300 kb of the genome. Obtaining sequence information may comprise using single molecule barcoding. Using single molecule barcoding may comprise attaching barcodes comprising different sequences to nucleic acids from the cfDNA sample. The sequence information may comprise sequence information pertaining to the barcodes. The method may comprise obtaining sequencing information of cell-free DNA samples from two or more samples from the subject. The two or more samples may be the same type of sample. The two or more samples may be two different types of sample. The two or more samples may be obtained from the subject at the same time point. The two or more samples may be obtained from the subject at two or more time points. The method may comprise obtaining sequencing information of cell-free DNA samples from two or more different subjects. The samples from two or more different subjects may be indexed and pooled together prior to obtaining the sequencing information. Using the sequence information may comprise detecting one or more SNVs, indels, fusions, breakpoints, structural variants, variable number of tandem repeats, hypervariable regions, minisatellites, dinucleotide repeats, trinucleotide repeats, tetranucleotide repeats, simple sequence repeats, or a combination thereof in selected regions of the subject's genome. Using the sequence information may comprise detecting one or more of SNVs, indels, copy number variants, and rearrangements in selected regions of the subject's genome. Using the sequence information may comprise detecting two or more of SNVs, indels, copy number variants, and rearrangements in selected regions of the subject's genome. Using the sequence information may comprise detecting at least one SNV, indel, copy number variant, and rearrangement in selected regions of the subject's genome. In some instances, detecting does not involve performing digital PCR (dPCR). Detecting cell-free non-germline DNA may comprise applying an algorithm to the sequence information to determine a quantity of one or more genomic regions from a selector set. The selector set may comprise a plurality of genomic regions comprising one or more mutations present in one or more cancer subjects from a population of cancer subjects. The selector set may comprise a plurality of genomic regions comprising one or more mutations present in at least about 60% of cancer subjects from population of cancer subjects. The cfNG-DNA may be derived from a tumor in the subject. The method may further comprise detecting a cancer in the subject based on the detection of the cfNG-DNA. The method may further comprise diagnosing a cancer in the subject based on the detection of the cfNG-DNA. Diagnosing the cancer may have a sensitivity of at least about 75%, 77%, 80%, 82%, 85%, 87%, 89%, 90%, 91%, 92%, 93%, 94%, 95%, 96%, 97%, or 99%. Diagnosing the cancer may have a specificity of at least about 75%, 77%, 80%, 82%, 85%, 87%, 89%, 90%, 91%, 92%, 93%, 94%, 95%, 96%, 97%, or 99%. The method may further comprise prognosing a cancer in the subject based on the detection of the cfNG-DNA. Prognosing the cancer may have a sensitivity of at least about 75%, 77%, 80%, 82%, 85%, 87%, 89%, 90%, 91%, 92%, 93%, 94%, 95%, 96%, 97%, or 99%. Prognosing the cancer may have a specificity of at least about 75%, 77%, 80%, 82%, 85%, 87%, 89%, 90%, 91%, 92%, 93%, 94%, 95%, 96%, 97%, or 99%. The method may further comprise determining a therapeutic regimen for the subject based on the detection of the cfNG-DNA. The method may further comprise administering an anti-cancer therapy to the subject based on the detection of the cfNG-DNA. The cfNG-DNA may be derived from a fetus in the subject. The method may further comprise diagnosing a disease or condition in the fetus based on the detection of the cfNG-DNA. Diagnosing the disease or condition in the fetus may have a sensitivity of at least about 75%, 77%, 80%, 82%, 85%, 87%, 89%, 90%, 91%, 92%, 93%, 94%, 95%, 96%, 97%, or 99%. Diagnosing the disease or condition in the fetus may have a specificity of at least about 75%, 77%, 80%, 82%, 85%, 87%, 89%, 90%, 91%, 92%, 93%, 94%, 95%, 96%, 97%, or 99%. The cfNG-DNA may be derived from a transplanted organ, cell or tissue in the subject. The method may further comprise diagnosing an organ transplant rejection in the subject based on the detection of the cfNG-DNA. Diagnosing the organ transplant rejection may have a sensitivity of at least about 75%, 77%, 80%, 82%, 85%, 87%, 89%, 90%, 91%, 92%, 93%, 94%, 95%, 96%, 97%, or 99%. Diagnosing the organ transplant rejection may have a specificity of at least about 75%, 77%, 80%, 82%, 85%, 87%, 89%, 90%, 91%, 92%, 93%, 94%, 95%, 96%, 97%, or 99%. The method may further comprise prognosing a risk of organ transplant rejection in the subject based on the detection of the cfNG-DNA. Prognosing the risk of organ transplant rejection may have a sensitivity of at least about 75%, 77%, 80%, 82%, 85%, 87%, 89%, 90%, 91%, 92%, 93%, 94%, 95%, 96%, 97%, or 99%. Prognosing the risk of organ transplant rejection may have a specificity of at least about 75%, 77%, 80%, 82%, 85%, 87%, 89%, 90%, 91%, 92%, 93%, 94%, 95%, 96%, 97%, or 99%. The method may further comprise determining an immunosuppresive therapy for the subject based on the detection of the cfNG-DNA. The method may further comprise administering an immunosuppresive therapy to the subject based on the detection of the cfNG-DNA.

Further disclosed herein are methods of detecting, diagnosing, or prognosing a status or outcome of a cancer in a subject. The method may comprise (a) obtaining sequence information of a cell-free DNA (cfDNA) sample derived from the subject; (b) using sequence information derived from (a) to detect cell-free tumor DNA (ctDNA) in the sample wherein the method is capable of detecting a percentage of ctDNA that is less than 2% of total cfDNA. The method may be capable of detecting a percentage of ctDNA that is less than 1.5% of the total cfDNA. The method may be capable of detecting a percentage of ctDNA that is less than 1% of the total cfDNA. The method may be capable of detecting a percentage of ctDNA that is less than 0.5% of the total cfDNA. The method may be capable of detecting a percentage of ctDNA that is less than 0.1% of the total cfDNA. The method may be capable of detecting a percentage of ctDNA that is less than 0.01% of the total cfDNA. The method may be capable of detecting a percentage of ctDNA that is less than 0.001% of the total cfDNA. The method may be capable of detecting a percentage of ctDNA that is less than 0.0001% of the total cfDNA. The sample may be a plasma or serum sample. The sample may be a cerebral spinal fluid sample. In some instances, the sample is not a pap smear fluid sample. In some instances, the sample is a cyst fluid sample. In some instances, the sample is a pancreatic fluid sample. The sequence information may comprise information related to at least 10, 20, 30, 40, 100, 200, 300 genomic regions. The genomic regions may comprise genes, exonic regions, intronic regions, untranslated regions, non-coding regions or a combination thereof. The genomic regions may comprise two or more of exonic regions, intronic regions, and untranslated regions. The genomic regions may comprise at least one exonic region and at least one intronic region. At least 5% of the genomic regions may comprise intronic regions. At least about 20% of the genomic regions may comprise exonic regions. The genomic regions may comprise less than 1.5 megabases (Mb) of the genome. The genomic regions may comprise less than 1 Mb of the genome. The genomic regions may comprise less than 500 kilobases (kb) of the genome. The genomic regions may comprise less than 350 kb of the genome. The genomic regions may comprise between 100 kb to 300 kb of the genome. The sequence information may comprise information pertaining to 1, 2, 3, 4, 5, 6, 7, 8, 9, 10, 15, 20 or more genomic regions from a selector set comprising a plurality of genomic regions. The sequence information may comprise information pertaining to 25, 30, 40, 50, 60, 70, 80, 90, 100 or more genomic regions from a selector set comprising a plurality of genomic regions. The sequence information may comprise information pertaining to a plurality of genomic regions. The plurality of genomic regions may be based on a selector set comprising genomic regions comprising one or more mutations present in one or more subjects from a population of cancer subjects. At least about 5%, 10%, 15%, 20%, 25%, 30%, 35%, 40%, 45%, 50%, 55%, 60%, 65%, 70%, 75%, 80%, 85%, 90%, or 95% of the plurality of genomic regions may be based on a selector set comprising genomic regions comprising one or more mutations present in one or more subjects from a population of cancer subjects. The total size of the genomic regions of the selector set may comprise less than 1.5 megabases (Mb), 1 Mb, 500 kilobases (kb), 350 kb, 300 kb, 250 kb, 200 kb, or 150 kb of the genome. The total size of the genomic regions of the selector set may be between 100 kb to 300 kb of the genome. The selector set may comprise 1, 2, 3, 4, 5, 6, 7, 8, 9, 10, 15, 20, 25, 30, 40, 50, 60, 70, 80, 90, 100 or more genomic regions selected from Table 2. In some instances, the subject is not suffering from a pancreatic cancer. Obtaining sequence information may comprise performing massively parallel sequencing. Massively parallel sequencing may be performed on a subset of a genome of cfDNA from the cfDNA sample. The subset of the genome may comprise less than 1.5 megabases (Mb), 1 Mb, 500 kilobases (kb), 350 kb, 300 kb, 250 kb, 200 kb, or 150 kb of the genome. The subset of the genome may comprise between 100 kb to 300 kb of the genome. Obtaining sequence information may comprise using single molecule barcoding. Using single molecule barcoding may comprise attaching barcodes comprising different sequences to nucleic acids from the cfDNA sample. The sequence information may comprise sequence information pertaining to the barcodes. The method may comprise obtaining sequencing information of cell-free DNA samples from two or more samples from the subject. The two or more samples may be the same type of sample. The two or more samples may be two different types of sample. The two or more samples may be obtained from the subject at the same time point. The two or more samples may be obtained from the subject at two or more time points. The method may comprise obtaining sequencing information of cell-free DNA samples from two or more different subjects. The samples from two or more different subjects may be indexed and pooled together prior to obtaining the sequencing information. Using the sequence information may comprise detecting one or more SNVs, indels, fusions, breakpoints, structural variants, variable number of tandem repeats, hypervariable regions, minisatellites, dinucleotide repeats, trinucleotide repeats, tetranucleotide repeats, simple sequence repeats, or a combination thereof in selected regions of the subject's genome. Using the sequence information may comprise detecting one or more of SNVs, indels, copy number variants, and rearrangements in selected regions of the subject's genome. Using the sequence information may comprise detecting two or more of SNVs, indels, copy number variants, and rearrangements in selected regions of the subject's genome. Using the sequence information may comprise detecting at least one SNV, indel, copy number variant, and rearrangement in selected regions of the subject's genome. In some instances, detecting does not involve performing digital PCR (dPCR). Detecting ctDNA may comprise applying an algorithm to the sequence information to determine a quantity of one or more genomic regions from a selector set. The selector set may comprise a plurality of genomic regions comprising one or more mutations present in one or more cancer subjects from a population of cancer subjects. The selector set may comprise a plurality of genomic regions comprising one or more mutations present in at least about 60% of cancer subjects from population of cancer subjects. The ctDNA may be derived from a tumor in the subject. The method may further comprise detecting a cancer in the subject based on the detection of the ctDNA. The method may further comprise diagnosing a cancer in the subject based on the detection of the ctDNA. Diagnosing the cancer may have a sensitivity of at least about 75%, 77%, 80%, 82%, 85%, 87%, 89%, 90%, 91%, 92%, 93%, 94%, 95%, 96%, 97%, or 99%. Diagnosing the cancer may have a specificity of at least about 75%, 77%, 80%, 82%, 85%, 87%, 89%, 90%, 91%, 92%, 93%, 94%, 95%, 96%, 97%, or 99%. The method may further comprise prognosing a cancer in the subject based on the detection of the ctDNA. Prognosing the cancer may have a sensitivity of at least about 75%, 77%, 80%, 82%, 85%, 87%, 89%, 90%, 91%, 92%, 93%, 94%, 95%, 96%, 97%, or 99%. Prognosing the cancer may have a specificity of at least about 75%, 77%, 80%, 82%, 85%, 87%, 89%, 90%, 91%, 92%, 93%, 94%, 95%, 96%, 97%, or 99%. The method may further comprise determining a therapeutic regimen for the subject based on the detection of the ctDNA. The method may further comprise administering an anti-cancer therapy to the subject based on the detection of the ctDNA.

Further disclosed herein are methods of diagnosing a status or outcome of a cancer in a subject. The method may comprise (a) obtaining sequence information of cell-free genomic DNA derived from a sample from a subject, wherein the sequence information is derived from genomic regions that are mutated in at least 80% of a population of subjects afflicted with a cancer; and (b) diagnosing a cancer selected from a group consisting of lung cancer, breast cancer, colorectal cancer and prostate cancer in the subject based on the sequence information, wherein the method has a sensitivity of 80%. The regions that are mutated may comprise a total size of less than 1.5 Mb of the genome. The regions that are mutated may comprise a total size of less than 1 Mb of the genome. The regions that are mutated may comprise a total size of less than 500 kb of the genome. The regions that are mutated may comprise a total size of less than 350 kb of the genome. The regions that are mutated may comprise a total size between 100 kb-300 kb of the genome. The sequence information may be derived from 2 or more regions. The sequence may be derived from 10 or more regions. The sequence may be derived from 50 or more regions. The population of subjects afflicted with the cancer may be subjects from one or more databases. The one or more databases may comprise The Cancer Genome Atlas (TCGA). The sequence information may comprise information pertaining to at least one mutation that may be present in at least about 60% of the population of subjects afflicted with the cancer. The sequence information may comprise information pertaining to at least one mutation that may be present in at least about 70% of the population of subjects afflicted with the cancer. The sequence information may comprise information pertaining to at least one mutation that may be present in at least about 80% of the population of subjects afflicted with the cancer. The sequence information may comprise information pertaining to at least one mutation that may be present in at least about 90% of the population of subjects afflicted with the cancer. The sequence information may comprise information pertaining to at least one mutation that may be present in at least about 95% of the population of subjects afflicted with the cancer. The sequence information may comprise information pertaining to at least one mutation that may be present in at least about 99% of the population of subjects afflicted with the cancer. The sequence information may be derived from regions that are mutated in at least 85% of the population of subjects afflicted with the cancer. The sequence information may be derived from regions that are mutated in at least 90% of the population of subjects afflicted with the cancer. The sequence information may be derived from regions that are mutated in at least 95% of the population of subjects afflicted with the cancer. The sequence information may be derived from regions that are mutated in at least 99% of the population of subjects afflicted with the cancer. The obtaining sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof. Obtaining sequence information may comprise sequencing protein coding regions. The protein coding regions may comprise one or more exons, introns, untranslated regions, or a combination thereof. In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1. The method may further comprise detecting mutations in the regions based on the sequencing information. Diagnosing the cancer may be based on the detection of the mutations. The detection of at least 3 mutations may be indicative of the cancer. The detection of one or more mutations in three or more regions may be indicative of the cancer. The breast cancer may be a BRCA1 cancer. The method may have a sensitivity of at least 85%, 87%, 90%, 91%, 92%, 93%, 94%, 95%, 96%, 97%, 98%, or 99%. The method may have a specificity of at least 70%, 72%, 75%, 77%, 80%, 82%, 85%, 87%, 90%, 91%, 92%, 93%, 94%, 95%, 96%, 97%, 98%, or 99%. The method may further comprise providing a computer-generated report comprising the diagnosis of the cancer.

Further disclosed herein are methods of prognosing a status or outcome of a cancer in a subject. The method may comprise (a) obtaining sequence information of cell-free genomic DNA derived from a sample from a subject, wherein the sequence information is derived from regions that are mutated in at least 80% of a population of subjects afflicted with a condition; and (b) determining a prognosis of a condition in the subject based on the sequence information. The regions that are mutated may comprise a total size of less than 1.5 Mb of the genome. The regions that are mutated may comprise a total size of less than 1 Mb of the genome. The regions that are mutated may comprise a total size of less than 500 kb of the genome. The regions that are mutated may comprise a total size of less than 350 kb of the genome. The regions that are mutated may comprise a total size between 100 kb-300 kb of the genome. The sequence information may be derived from 2 or more regions. The sequence may be derived from 10 or more regions. The sequence may be derived from 50 or more regions. The population of subjects afflicted with the condition may be subjects from one or more databases. The one or more databases may comprise The Cancer Genome Atlas (TCGA). The sequence information may comprise information pertaining to at least one mutation that may be present in at least about 60% of the population of subjects afflicted with the condition. The sequence information may comprise information pertaining to at least one mutation that may be present in at least about 70% of the population of subjects afflicted with the condition. The sequence information may comprise information pertaining to at least one mutation that may be present in at least about 80% of the population of subjects afflicted with the condition. The sequence information may comprise information pertaining to at least one mutation that may be present in at least about 90% of the population of subjects afflicted with the condition. The sequence information may comprise information pertaining to at least one mutation that may be present in at least about 95% of the population of subjects afflicted with the condition. The sequence information may comprise information pertaining to at least one mutation that may be present in at least about 99% of the population of subjects afflicted with the condition. The sequence information may be derived from regions that are mutated in at least 85% of the population of subjects afflicted with the condition. The sequence information may be derived from regions that are mutated in at least 90% of the population of subjects afflicted with the condition. The sequence information may be derived from regions that are mutated in at least 95% of the population of subjects afflicted with the condition. The sequence information may be derived from regions that are mutated in at least 99% of the population of subjects afflicted with the condition. Obtaining sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof. Obtaining sequence information may comprise sequencing protein coding regions. The protein coding regions may comprise one or more exons, introns, untranslated regions, or a combination thereof. In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1. The method may further comprise detecting mutations in the regions based on the sequencing information. Prognosing the condition may be based on the detection of the mutations. The detection of at least 3 mutations may be indicative of an outcome of the condition. The detection of one or more mutations in three or more regions may be indicative of an outcome of the condition. The condition may be a cancer. The cancer may be a solid tumor. The solid tumor may be non-small cell lung cancer (NSCLC). The cancer may be a breast cancer. The breast cancer may be a BRCA1 cancer. The cancer may be a lung cancer, colorectal cancer, prostate cancer, ovarian cancer, esophageal cancer, breast cancer, lymphoma, or leukemia. The method may have a sensitivity of at least 75%, 77%, 80%, 82%, 85%, 87%, 90%, 91%, 92%, 93%, 94%, 95%, 96%, 97%, 98%, or 99%. The method may have a specificity of at least 70%, 72%, 75%, 77%, 80%, 82%, 85%, 87%, 90%, 91%, 92%, 93%, 94%, 95%, 96%, 97%, 98%, or 99%. The method may further comprise providing a computer-generated report comprising the prognosis of the condition.

Disclosed herein are methods for detecting at least 50% of stage I cancer with a specificity of greater than 90%. The method may comprise (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage I cancer in the sample based on the quantity of the cell-free DNA. Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR. The quantity of the cell-free DNA may be determined by molecular barcoding of the cell-free DNA (cfDNA). Molecular barcoding of the cfDNA may comprise attaching barcodes to one or more ends of the cfDNA. The barcode may comprise a random sequence. Two or more barcodes may comprise two or more different random sequences. The barcode may comprise an adaptor sequence. Two or more barcodes may comprise the same adaptor sequence. The barcode may comprise a primer sequence. Two or more barcodes may comprise the same primer sequence. The primer sequence may be a PCR primer sequence. The primer sequence may be a sequencing primer. Attaching the barcodes to one or more ends of the ctDNA may comprise ligating the barcodes to the one or more ends of the ctDNA. Sequencing may comprise massively parallel sequencing. The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2. At least 20%, 30%, 35%, 40%, 455, 50%, 55%, 60%, 65%, 70%, 75%, 80%, 85%, 90%, or 95% or more of the genomic regions in the selector set are based on genomic regions from Table 2. The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer. The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may be between 100 kb to 300 kb of a genome. The method may have a sensitivity of at least 75%, 77%, 80%, 82%, 85%, 87%, 90%, 92%, 95%, 97%, or 99% or more. The method may detect at least 52%, 55%, 57%, 60%, 62%, 65%, 70%, 72%, 75%, 77%, 80%, 82%, 85%, 87%, 90%, 92%, 95%, 97% or more of stage I cancer.

Disclosed herein are methods for detecting at least 60% of stage II cancer with a specificity of greater than 90% comprising (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage II cancer in the sample based on the quantity of the cell-free DNA. Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR. The quantity of the cell-free DNA may be determined by molecular barcoding of the cell-free DNA (cfDNA). Molecular barcoding of the cfDNA may comprise attaching barcodes to one or more ends of the cfDNA. The barcode may comprise a random sequence. Two or more barcodes may comprise two or more different random sequences. The barcode may comprise an adaptor sequence. Two or more barcodes may comprise the same adaptor sequence. The barcode may comprise a primer sequence. Two or more barcodes may comprise the same primer sequence. The primer sequence may be a PCR primer sequence. The primer sequence may be a sequencing primer. Attaching the barcodes to one or more ends of the ctDNA may comprise ligating the barcodes to the one or more ends of the ctDNA. Sequencing may comprise massively parallel sequencing. The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2. At least 20%, 30%, 35%, 40%, 455, 50%, 55%, 60%, 65%, 70%, 75%, 80%, 85%, 90%, or 95% or more of the genomic regions in the selector set may be based on genomic regions from Table 2. The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer. The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may be between 100 kb to 300 kb of a genome. The method may have a sensitivity of at least 75%, 77%, 80%, 82%, 85%, 87%, 90%, 92%, 95%, 97%, or 99% or more. The method may detect at least 60%, 62%, 65%, 70%, 72%, 75%, 77%, 80%, 82%, 85%, 87%, 90%, 92%, 95%, 97% or more of stage II cancer.

Disclosed herein are methods for detecting at least 60% of stage III cancer with a specificity of greater than 90% comprising (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage III cancer in the sample based on the quantity of the cell-free DNA. Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR. The quantity of the cell-free DNA may be determined by molecular barcoding of the cell-free DNA (cfDNA). Molecular barcoding of the cfDNA may comprise attaching barcodes to one or more ends of the cfDNA. The barcode may comprise a random sequence. Two or more barcodes may comprise two or more different random sequences. The barcode may comprise an adaptor sequence. Two or more barcodes may comprise the same adaptor sequence. The barcode may comprise a primer sequence. Two or more barcodes may comprise the same primer sequence. The primer sequence may be a PCR primer sequence. The primer sequence may be a sequencing primer. Attaching the barcodes to one or more ends of the ctDNA may comprise ligating the barcodes to the one or more ends of the ctDNA. Sequencing may comprise massively parallel sequencing. The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2. At least 20%, 30%, 35%, 40%, 455, 50%, 55%, 60%, 65%, 70%, 75%, 80%, 85%, 90%, or 95% or more of the genomic regions in the selector set may be based on genomic regions from Table 2. The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer. The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may be between 100 kb to 300 kb of a genome. The method may have a sensitivity of at least 75%, 77%, 80%, 82%, 85%, 87%, 90%, 92%, 95%, 97%, or 99% or more. The method may detect at least 60%, 62%, 65%, 70%, 72%, 75%, 77%, 80%, 82%, 85%, 87%, 90%, 92%, 95%, 97% or more of stage III cancer.

Disclosed herein are methods for detecting at least 60% of stage IV cancer with a specificity of greater than 90% comprising (a) performing sequencing on cell-free DNA derived from a sample, wherein the cell-free DNA to be sequenced is based on a selector set comprising a plurality of genomic regions; (b) using a computer readable medium to determine a quantity of the cell-free DNA based on the sequencing information of the cell-free DNA; and (c) detecting a stage IV cancer in the sample based on the quantity of the cell-free DNA. Determining the quantity of the cell-free DNA may comprise determining absolute quantities of the cell-free DNA. The quantity of the cell-free DNA may be determined by counting sequencing reads pertaining to the cell-free DNA. The quantity of the cell-free DNA may be determined by quantitative PCR. The quantity of the cell-free DNA may be determined by molecular barcoding of the cell-free DNA (cfDNA). Molecular barcoding of the cfDNA may comprise attaching barcodes to one or more ends of the cfDNA. The barcode may comprise a random sequence. Two or more barcodes may comprise two or more different random sequences. The barcode may comprise an adaptor sequence. Two or more barcodes may comprise the same adaptor sequence. The barcode may comprise a primer sequence. Two or more barcodes may comprise the same primer sequence. The primer sequence may be a PCR primer sequence. The primer sequence may be a sequencing primer. Attaching the barcodes to one or more ends of the ctDNA may comprise ligating the barcodes to the one or more ends of the ctDNA. Sequencing may comprise massively parallel sequencing. The selector set may comprise 1, 2, 3, 4, 5, 6, 7, 8, 9, 10, 15, 20, 25, 30, 35, 40, 45, 50, 55, 60, 65, 70, 75, 80, 85, 90, 95, or 100 or more genomic regions from Table 2. At least 20%, 30%, 35%, 40%, 455, 50%, 55%, 60%, 65%, 70%, 75%, 80%, 85%, 90%, or 95% or more of the genomic regions in the selector set may be based on genomic regions from Table 2. The plurality of genomic regions may comprise one or more mutations present in at least 60%, 62%, 65%, 67%, 70%, 72%, 75%, 77%, 80%, 82%, 85%, 87%, 90%, 92%, 95%, 97% or 99% or more of a population of subjects suffering from the cancer. The total size of the plurality of genomic regions of the selector set may comprise less than 1.5 megabases (Mb), 1 Mb, 500 kilobases (kb), 350 kb, 300 kb, 250 kb, 200 kb, or 150 kb of a genome. The total size of the plurality of genomic regions of the selector set may be between 100 kb to 300 kb of a genome. The method may have a sensitivity of at least 75%, 77%, 80%, 82%, 85%, 87%, 90%, 92%, 95%, 97%, or 99% or more. The method may detect at least 60%, 62%, 65%, 70%, 72%, 75%, 77%, 80%, 82%, 85%, 87%, 90%, 92%, 95%, 97% or more of stage IV cancer.

Further disclosed herein are methods of selecting a therapy for a subject suffering from a cancer. The method may comprise (a) obtaining sequence information of a cell-free DNA (cfDNA) sample derived from the subject; (b) using sequence information derived from (a) to detect cell-free tumor DNA (ctDNA) in the sample; and (c) determining a therapy for the subject based on the detection of the ctDNA, wherein the method is capable of detecting a percentage of ctDNA that is less than 2% of total cfDNA. The method may be capable of detecting a percentage of ctDNA that is less than 1.5% of the total cfDNA. The method may be capable of detecting a percentage of ctDNA that is less than 1% of the total cfDNA. The method may be capable of detecting a percentage of ctDNA that is less than 0.5% of the total cfDNA. The method may be capable of detecting a percentage of ctDNA that is less than 0.1% of the total cfDNA. The method may be capable of detecting a percentage of ctDNA that is less than 0.01% of the total cfDNA. The method may be capable of detecting a percentage of ctDNA that is less than 0.001% of the total cfDNA. The method may be capable of detecting a percentage of ctDNA that is less than 0.0001% of the total cfDNA. The sample may be a plasma or serum sample. The sample may be a cerebral spinal fluid sample. In some instances, the sample is not a pap smear fluid sample. In some instances, the sample is a cyst fluid sample. In some instances, the sample is a pancreatic fluid sample. The sequence information may comprise information related to at least 10, 20, 30, 40, 100, 200, 300 genomic regions. The genomic regions may comprise genes, exonic regions, intronic regions, untranslated regions, non-coding regions or a combination thereof. The genomic regions may comprise two or more of exonic regions, intronic regions, and untranslated regions. The genomic regions may comprise at least one exonic region and at least one intronic region. At least 5% of the genomic regions may comprise intronic regions. At least about 20% of the genomic regions may comprise exonic regions. The genomic regions may comprise less than 1.5 megabases (Mb) of the genome. The genomic regions may comprise less than 1 Mb of the genome. The genomic regions may comprise less than 500 kilobases (kb) of the genome. The genomic regions may comprise less than 350 kb of the genome. The genomic regions may comprise between 100 kb to 300 kb of the genome. The sequence information may comprise information pertaining to 1, 2, 3, 4, 5, 6, 7, 8, 9, 10, 15, 20 or more genomic regions from a selector set comprising a plurality of genomic regions. The sequence information may comprise information pertaining to 25, 30, 40, 50, 60, 70, 80, 90, 100 or more genomic regions from a selector set comprising a plurality of genomic regions. The sequence information may comprise information pertaining to a plurality of genomic regions. The plurality of genomic regions may be based on a selector set comprising genomic regions comprising one or more mutations present in one or more subjects from a population of cancer subjects. At least about 5%, 10%, 15%, 20%, 25%, 30%, 35%, 40%, 45%, 50%, 55%, 60%, 65%, 70%, 75%, 80%, 85%, 90%, or 95% of the plurality of genomic regions may be based on a selector set comprising genomic regions comprising one or more mutations present in one or more subjects from a population of cancer subjects. The total size of the genomic regions of the selector set may comprise less than 1.5 megabases (Mb), 1 Mb, 500 kilobases (kb), 350 kb, 300 kb, 250 kb, 200 kb, or 150 kb of the genome. The total size of the genomic regions of the selector set may be between 100 kb to 300 kb of the genome. The selector set may comprise 1, 2, 3, 4, 5, 6, 7, 8, 9, 10, 15, 20, 25, 30, 40, 50, 60, 70, 80, 90, 100 or more genomic regions selected from Table 2. In some instances, the subject is not suffering from a pancreatic cancer. Obtaining sequence information may comprise performing massively parallel sequencing. Massively parallel sequencing may be performed on a subset of a genome of cfDNA from the cfDNA sample. The subset of the genome may comprise less than 1.5 megabases (Mb), 1 Mb, 500 kilobases (kb), 350 kb, 300 kb, 250 kb, 200 kb, or 150 kb of the genome. The subset of the genome may comprise between 100 kb to 300 kb of the genome. Obtaining sequence information may comprise using single molecule barcoding. Using single molecule barcoding may comprise attaching barcodes comprising different sequences to nucleic acids from the cfDNA sample. The sequence information may comprise sequence information pertaining to the barcodes. The method may comprise obtaining sequencing information of cell-free DNA samples from two or more samples from the subject. The two or more samples may be the same type of sample. The two or more samples may be two different types of sample. The two or more samples may be obtained from the subject at the same time point. The two or more samples may be obtained from the subject at two or more time points. The method may comprise obtaining sequencing information of cell-free DNA samples from two or more different subjects. The samples from two or more different subjects may be indexed and pooled together prior to obtaining the sequencing information. Using the sequence information may comprise detecting one or more SNVs, indels, fusions, breakpoints, structural variants, variable number of tandem repeats, hypervariable regions, minisatellites, dinucleotide repeats, trinucleotide repeats, tetranucleotide repeats, simple sequence repeats, or a combination thereof in selected regions of the subject's genome. Using the sequence information may comprise detecting one or more of SNVs, indels, copy number variants, and rearrangements in selected regions of the subject's genome. Using the sequence information may comprise detecting two or more of SNVs, indels, copy number variants, and rearrangements in selected regions of the subject's genome. Using the sequence information may comprise detecting at least one SNV, indel, copy number variant, and rearrangement in selected regions of the subject's genome. In some instances, detecting does not involve performing digital PCR (dPCR). Detecting ctDNA may comprise applying an algorithm to the sequence information to determine a quantity of one or more genomic regions from a selector set. The selector set may comprise a plurality of genomic regions comprising one or more mutations present in one or more cancer subjects from a population of cancer subjects. The selector set may comprise a plurality of genomic regions comprising one or more mutations present in at least about 60% of cancer subjects from population of cancer subjects. The ctDNA may be derived from a tumor in the subject. Determining the therapy may comprise administering a therapy to the subject. Determining the therapy may comprise modifying a therapeutic regimen. Modifying the therapeutic regimen may comprise terminating a therapeutic regimen. Modifying the therapeutic regimen may comprise adjusting a dosage of the therapy. Modifying the therapeutic regimen may comprise adjusting a frequency of the therapy. The therapeutic regimen may be modified based on a change in the quantity of the ctDNA. The dosage of the therapy may be increased in response to an increase in the quantity of the ctDNA. The dosage of the therapy may be decreased in response to a decrease in the quantity of the ctDNA. The frequency of the therapy may be increased in response to an increase in the quantity of the ctDNA. The frequency of the therapy may be decreased in response to a decrease in the quantity of ctDNA.

Alternatively, the method may comprise (a) obtaining sequence information of cell-free genomic DNA derived from a sample from a subject, wherein the sequence information is derived from regions that are mutated in at least 80% of a population of subjects afflicted with a condition; and (b) determining a therapeutic regimen of a condition in the subject based on the sequence information. The regions that are mutated may comprise a total size of less than 1.5 Mb of the genome. The regions that are mutated may comprise a total size of less than 1 Mb of the genome. The regions that are mutated may comprise a total size of less than 500 kb of the genome. The regions that are mutated may comprise a total size of less than 350 kb of the genome. The regions that are mutated may comprise a total size between 100 kb-300 kb of the genome. The sequence information may be derived from 2 or more regions. The sequence may be derived from 10 or more regions. The sequence may be derived from 50 or more regions. The population of subjects afflicted with the condition may be subjects from one or more databases. The one or more databases may comprise The Cancer Genome Atlas (TCGA). The sequence information may comprise information pertaining to at least one mutation that may be present in at least about 60% of the population of subjects afflicted with the condition. The sequence information may comprise information pertaining to at least one mutation that may be present in at least about 70% of the population of subjects afflicted with the condition. The sequence information may comprise information pertaining to at least one mutation that may be present in at least about 80% of the population of subjects afflicted with the condition. The sequence information may comprise information pertaining to at least one mutation that may be present in at least about 90% of the population of subjects afflicted with the condition. The sequence information may comprise information pertaining to at least one mutation that may be present in at least about 95% of the population of subjects afflicted with the condition. The sequence information may comprise information pertaining to at least one mutation that may be present in at least about 99% of the population of subjects afflicted with the condition. The sequence information may be derived from regions that are mutated in at least 85% of the population of subjects afflicted with the condition. The sequence information may be derived from regions that are mutated in at least 90% of the population of subjects afflicted with the condition. The sequence information may be derived from regions that are mutated in at least 95% of the population of subjects afflicted with the condition. The sequence information may be derived from regions that are mutated in at least 99% of the population of subjects afflicted with the condition. Obtaining sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof. Obtaining sequence information may comprise sequencing protein coding regions. The protein coding regions may comprise one or more exons, introns, untranslated regions, or a combination thereof. In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1. The method may further comprise detecting mutations in the regions based on the sequencing information. Determining the therapeutic regimen may be based on the detection of the mutations. The condition may be a cancer. The cancer may be a solid tumor. The solid tumor may be non-small cell lung cancer (NSCLC). The cancer may be a breast cancer. The breast cancer may be a BRCA1 cancer. The cancer may be a lung cancer, colorectal cancer, prostate cancer, ovarian cancer, esophageal cancer, breast cancer, lymphoma, or leukemia.

Further disclosed herein are methods for diagnosing, prognosing, or determining a therapeutic regimen for a subject afflicted with or susceptible of having a cancer. The method may comprise (a) obtaining sequence information for selected regions of genomic DNA from a cell-free DNA sample from the subject; (b) using the sequence information to determine the presence or absence of one or more mutations in the selected regions, wherein at least 70% of a population of subjects afflicted with the cancer have mutation(s) in the regions; and (c) providing a report with a diagnosis, prognosis or treatment regimen to the subject, based on the presence or absence of the one or more mutations. The selected regions may comprise a total size of less than 1.5 Mb of the genome. The selected regions may comprise a total size of less than 1 Mb of the genome. The selected regions may comprise a total size of less than 500 kb of the genome. The selected regions mutated may comprise a total size of less than 350 kb of the genome. The selected regions may comprise a total size between 100 kb-300 kb of the genome. The sequence information may be derived from 2 or more selected regions. The sequence may be derived from 10 or more selected regions. The sequence may be derived from 50 or more selected regions. The population of subjects afflicted with the cancer may be subjects from one or more databases. The one or more databases may comprise The Cancer Genome Atlas (TCGA). The sequence information may comprise information pertaining to at least one mutation that may be present in at least about 60% of the population of subjects afflicted with the cancer. The sequence information may comprise information pertaining to at least one mutation that may be present in at least about 70% of the population of subjects afflicted with the cancer. The sequence information may comprise information pertaining to at least one mutation that may be present in at least about 80% of the population of subjects afflicted with the cancer. The sequence information may comprise information pertaining to at least one mutation that may be present in at least about 90% of the population of subjects afflicted with the cancer. The sequence information may comprise information pertaining to at least one mutation that may be present in at least about 95% of the population of subjects afflicted with the cancer. The sequence information may comprise information pertaining to at least one mutation that may be present in at least about 99% of the population of subjects afflicted with the cancer. The sequence information may be derived from regions that are mutated in at least 85% of the population of subjects afflicted with the cancer. The sequence information may be derived from regions that are mutated in at least 90% of the population of subjects afflicted with the cancer. The sequence information may be derived from regions that are mutated in at least 95% of the population of subjects afflicted with the cancer. The sequence information may be derived from regions that are mutated in at least 99% of the population of subjects afflicted with the cancer. Obtaining sequence information may comprise sequencing noncoding regions. The noncoding regions may comprise one or more lncRNA, snoRNA, siRNA, miRNA, piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, LSINCTs, or a combination thereof. Obtaining sequence information may comprise sequencing protein coding regions. The protein coding regions may comprise one or more exons, introns, untranslated regions, or a combination thereof. In some instances, at least one of the regions does not comprise KRAS or EGFR. In some instances, at least two of the regions do not comprise KRAS and EGFR. In some instances, at least one of the regions does not comprise KRAS, EGFR, p53, PIK3CA, BRAF, EZH2, or BRCA1. In some instances, at least two of the regions do not comprise KRAS, EGFR, p53, PIK3CA, BRAF, EZH2, or BRCA1. In some instances, at least three of the regions do not comprise KRAS, EGFR, p53, PIK3CA, BRAF, EZH2, or BRCA1. In some instances, at least four of the regions do not comprise KRAS, EGFR, p53, PIK3CA, BRAF, EZH2, or BRCA1. The detection of at least 3 mutations may be indicative of an outcome of the cancer. The detection of one or more mutations in three or more regions may be indicative of an outcome of the cancer. The cancer may be non-small cell lung cancer (NSCLC). The cancer may be a breast cancer. The breast cancer may be a BRCA1 cancer. The cancer may be a lung cancer, colorectal cancer, prostate cancer, ovarian cancer, esophageal cancer, breast cancer, lymphoma, or leukemia. The method of diagnosing or prognosing the cancer has a sensitivity of at least 75%, 77%, 80%, 82%, 85%, 87%, 90%, 91%, 92%, 93%, 94%, 95%, 96%, 97%, 98%, or 99%. The method of diagnosing or prognosing the cancer has a specificity of at least 70%, 72%, 75%, 77%, 80%, 82%, 85%, 87%, 90%, 91%, 92%, 93%, 94%, 95%, 96%, 97%, 98%, or 99%. The method may further comprise administering a therapeutic drug to the subject. The method may further comprise modifying a therapeutic regimen. Modifying the therapeutic regimen may comprise terminating the therapeutic regimen. Modifying the therapeutic regimen may comprise increasing a dosage or frequency of the therapeutic regimen. Modifying the therapeutic regimen may comprise decreasing a dosage or frequency of the therapeutic regimen. Modifying the therapeutic regimen may comprise starting the therapeutic regimen.

In some embodiment, the method further comprises selecting a therapeutic regimen based on the analysis. In an embodiment, the method further comprises determining a treatment course for the subject based on the analysis. In such embodiments, the presence of tumor cells in an individual, including an estimation of tumor load, provides information to guide clinical decision making, both in terms of institution of and escalation of therapy as well as in the selection of the therapeutic agent to which the patient is most likely to exhibit a robust response.

The information obtained by CAPP-seq can be used to (a) determine type and level of therapeutic intervention warranted (e.g. more versus less aggressive therapy, monotherapy versus combination therapy, type of combination therapy), and (b) to optimize the selection of therapeutic agents. With this approach, therapeutic regimens can be individualized and tailored according to the specificity data obtained at different times over the course of treatment, thereby providing a regimen that is individually appropriate. In addition, patient samples can be obtained at any point during the treatment process for analysis.

The therapeutic regimen may be selected based on the specific patient situation. Where CAPP-seq is used as an initial diagnosis, a sample having a positive finding for the presence of ctDNA can indicate the need for additional diagnostic tests to confirm the presence of a tumor, and/or initiation of cytoreductive therapy, e.g. administration of chemotherapeutic drugs, administration of radiation therapy, and/or surgical removal of tumor tissue.

Further disclosed herein are methods for assessing tumor burden in a subject. The method may comprise (a) obtaining sequence information on cell-free nucleic acids derived from a sample from the subject; (b) using a computer readable medium to determine quantities of circulating tumor DNA (ctDNA) in the sample; (c) assessing tumor burden based on the quantities of ctDNA; and (d) reporting the tumor burden to the subject or a representative of the subject. Determining quantities of ctDNA may comprise determining absolute quantities of ctDNA. Determining quantities of ctDNA may comprise determining relative quantities of ctDNA. Determining quantities of ctDNA may be performed by counting sequence reads pertaining to the ctDNA. Determining quantities of ctDNA may be performed by quantitative PCR. Determining quantities of ctDNA may be performed by digital PCR. Determining quantities of ctDNA may be performed by molecular barcoding of the ctDNA. Molecular barcoding of the ctDNA may comprise attaching barcodes to one or more ends of the ctDNA. The barcode may comprise a random sequence. Two or more barcodes may comprise two or more different random sequences. The barcode may comprise an adaptor sequence. Two or more barcodes may comprise the same adaptor sequence. The barcode may comprise a primer sequence. Two or more barcodes may comprise the same primer sequence. The primer sequence may be a PCR primer sequence. The primer sequence may be a sequencing primer. Attaching the barcodes to one or more ends of the ctDNA may comprise ligating the barcodes to the one or more ends of the ctDNA. The sequence information may comprise information related to one or more genomic regions. The sequence information may comprise information related to at least 10, 20, 30, 40, 100, 200, 300 genomic regions. The genomic regions may comprise genes, exonic regions, intronic regions, untranslated regions, non-coding regions or a combination thereof. The genomic regions may comprise two or more of exonic regions, intronic regions, and untranslated regions. The genomic regions may comprise at least one exonic region and at least one intronic region. At least 5% of the genomic regions may comprise intronic regions. At least about 20% of the genomic regions may comprise exonic regions. The genomic regions may comprise less than 1.5 megabases (Mb) of the genome. The genomic regions may comprise less than 1 Mb of the genome. The genomic regions may comprise less than 500 kilobases (kb) of the genome. The genomic regions may comprise less than 350 kb of the genome. The genomic regions may comprise between 100 kb to 300 kb of the genome. The sequence information may comprise information pertaining to 1, 2, 3, 4, 5, 6, 7, 8, 9, 10, 15, 20 or more genomic regions from a selector set comprising a plurality of genomic regions. The sequence information may comprise information pertaining to 25, 30, 40, 50, 60, 70, 80, 90, 100 or more genomic regions from a selector set comprising a plurality of genomic regions. The sequence information may comprise information pertaining to a plurality of genomic regions. The plurality of genomic regions may be based on a selector set comprising genomic regions comprising one or more mutations present in one or more subjects from a population of cancer subjects. At least about 5%, 10%, 15%, 20%, 25%, 30%, 35%, 40%, 45%, 50%, 55%, 60%, 65%, 70%, 75%, 80%, 85%, 90%, or 95% of the plurality of genomic regions may be based on a selector set comprising genomic regions comprising one or more mutations present in one or more subjects from a population of cancer subjects. The total size of the genomic regions of the selector set may comprise less than 1.5 megabases (Mb), 1 Mb, 500 kilobases (kb), 350 kb, 300 kb, 250 kb, 200 kb, or 150 kb of the genome. The total size of the genomic regions of the selector set may be between 100 kb to 300 kb of the genome. The selector set may comprise 1, 2, 3, 4, 5, 6, 7, 8, 9, 10, 15, 20, 25, 30, 40, 50, 60, 70, 80, 90, 100 or more genomic regions selected from Table 2. Obtaining sequence information may comprise performing massively parallel sequencing. Massively parallel sequencing may be performed on a subset of a genome of the cell-free nucleic acids from the sample. The subset of the genome may comprise less than 1.5 megabases (Mb), 1 Mb, 500 kilobases (kb), 350 kb, 300 kb, 250 kb, 200 kb, or 150 kb of the genome. The subset of the genome may comprise between 100 kb to 300 kb of the genome. The method may comprise obtaining sequencing information of cell-free DNA samples from two or more samples from the subject. The two or more samples are the same type of sample. The two or more samples are two different types of sample. The two or more samples are obtained from the subject at the same time point. The two or more samples are obtained from the subject at two or more time points. Determining the quantities of ctDNA may comprise detecting one or more SNVs, indels, fusions, breakpoints, structural variants, variable number of tandem repeats, hypervariable regions, minisatellites, dinucleotide repeats, trinucleotide repeats, tetranucleotide repeats, simple sequence repeats, or a combination thereof in selected regions of the subject's genome. Determining the quantities of ctDNA may comprise detecting one or more of SNVs, indels, copy number variants, and rearrangements in selected regions of the subject's genome. Determining the quantities of ctDNA may comprise detecting two or more of SNVs, indels, copy number variants, and rearrangements in selected regions of the subject's genome. Determining the quantities of ctDNA may comprise detecting at least one SNV, indel, copy number variant, and rearrangement in selected regions of the subject's genome. Determining the quantities of ctDNA does not involve performing digital PCR (dPCR). Determining the quantities of ctDNA may comprise applying an algorithm to the sequence information to determine a quantity of one or more genomic regions from a selector set. The selector set may comprise a plurality of genomic regions comprising one or more mutations present in one or more cancer subjects from a population of cancer subjects. The selector set may comprise a plurality of genomic regions comprising one or more mutations present in at least about 60% of cancer subjects from population of cancer subjects. The representative of the subject may be a healthcare provider. The healthcare provider may be a nurse, physician, medical technician, or hospital personnel. The representative of the subject may be a family member of the subject. The representative of the subject may be a legal guardian of the subject.

Further disclosed herein are methods for determining a disease state of a cancer in a subject. The method may comprise (a) obtaining a quantity of circulating tumor DNA (ctDNA) in a sample from the subject; (b) obtaining a volume of a tumor in the subject; and (c) determining a disease state of a cancer in the subject based on a ratio of the quantity of ctDNA to the volume of the tumor. A high ctDNA to volume ratio may be indicative of radiographically occult disease. A low ctDNA to volume ratio may be indicative of non-malignant state. Obtaining the volume of the tumor may comprise obtaining an image of the tumor. Obtaining the volume of the tumor may comprise obtaining a CT scan of the tumor. Obtaining the quantity of ctDNA may comprise digital PCR. Obtaining the quantity of ctDNA may comprise obtaining sequencing information on the ctDNA. The sequencing information may comprise information relating to one or more genomic regions based on a selector set. Obtaining the quantity of ctDNA may comprise hybridization of the ctDNA to an array. The array may comprise a plurality of probes for selective hybridization of one or more genomic regions based on a selector set. The selector set may comprise one or more genomic regions from Table 2. The selector set may comprise one or more genomic regions comprising one or more mutations, wherein the one or more mutations are present in a population of subjects suffering from a cancer. The selector set may comprise a plurality of genomic regions comprising a plurality of mutations, wherein the plurality of mutations are present in at least 60% of a population of subjects suffering from a cancer.

In some embodiments, the ctDNA content in an individual's blood, or blood derivative, sample is determined at one or more time points, optionally in conjunction with a therapeutic regimen. The presence of the ctDNA correlates with tumor burden, and is useful in monitoring response to therapy, monitoring residual disease, monitoring for the presence of metastases, monitoring total tumor burden, and the like. Although not required, for some methods CAPP-Seq may be performed in conjunction with tumor imaging methods, e.g. PET/CT scans and the like. Where CAPP-seq is used to estimate tumor burden or residual disease, increased presence of tumor cells over time indicates a need to increase the therapy by escalating dose, selection of agent, etc. Correspondingly, where CAPP-seq shows no evidence of residual disease, a patient may be taken off therapy, or put on a lowered dose.

CAPP-seq can also be used in clinical trials for new drugs, to determine the efficacy of treatment for a cancer of interest, where a decrease in tumor burden is indicative of efficacy and increased tumor burden is indicative of a lack of efficacy.

The cancer of interest may be specific for a cancer, for example non-small cell carcinoma, endometrioid uterine carcinoma, etc.; or may be generic for a class of cancers, e.g. epithelial cancers (carcinomas); sarcomas; lymphomas; melanomas; gliomas; teratomas; etc.; or subgenus, e.g. adenocarcinoma; squamous cell carcinoma; and the like.

The term "diagnosis" may refer to the identification of a molecular or pathological state, disease or condition, such as the identification of a molecular subtype of breast cancer, prostate cancer, or other type of cancer.

The term "prognosis" may refer to the prediction of the likelihood of cancer-attributable death or progression, including recurrence, metastatic spread, and drug resistance, of a neoplastic disease, such as ovarian cancer. The term "prediction" may refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

The terms "treatment," "treating," and the like, may refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, e.g., arresting its development; and (c) relieving the disease, e.g., causing regression of the disease.

Definitions

A number of terms conventionally used in the field of cell culture are used throughout the disclosure. In order to provide a clear and consistent understanding of the specification and claims, and the scope to be given to such terms, the following definitions are provided.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" may include a plurality of such cells and reference to "the culture" may include reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

"Measuring" or "measurement" in the context of the present teachings may refer to determining the presence, absence, quantity, amount, or effective amount of a substance in a clinical or subject-derived sample, including the presence, absence, or concentration levels of such substances, and/or evaluating the values or categorization of a subject's clinical parameters based on a control.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure may be available from commercial vendors such as BioRad, Stratagene, Invitrogen, Sigma-Aldrich, and ClonTech.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

The terms "subject," "individual," and "patient" are used interchangeably herein and may refer to a mammal being assessed for treatment and/or being treated. In an embodiment, the mammal is a human. The terms "subject," "individual," and "patient" may encompass, without limitation, individuals having cancer or suspected of having cancer. Subjects may be human, but also include other mammals, particularly those mammals useful as laboratory models for human disease, e.g. mouse, rat, etc. Also included are mammals such as domestic and other species of canines, felines, and the like.

The terms "cancer," "neoplasm," and "tumor" are used interchangeably herein and may refer to cells which exhibit autonomous, unregulated growth, such that they exhibit an aberrant growth phenotype characterized by a significant loss of control over cell proliferation. Cells of interest for detection, analysis, or treatment in the present application may include, but are not limited to, precancerous (e.g., benign), malignant, pre-metastatic, metastatic, and non-metastatic cells. Cancers of virtually every tissue are known. The phrase "cancer burden" may refer to the quantum of cancer cells or cancer volume in a subject. Reducing cancer burden accordingly may refer to reducing the number of cancer cells or the cancer volume in a subject. The term "cancer cell" as used herein may refer to any cell that is a cancer cell or is derived from a cancer cell, e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include, but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer may include, but it not limited to, all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, may refer to further growth of neoplastic or cancerous cells after diagnosis of cancer. Particularly, recurrence may occur when further cancerous cell growth occurs in the cancerous tissue.

"Tumor spread," similarly, may occur when the cells of a tumor disseminate into local or distant tissues and organs; therefore tumor spread may encompass tumor metastasis. "Tumor invasion" may occur when the tumor growth spreads out locally to compromise the function of involved tissues by compression, destruction, and/or prevention of normal organ function.

As used herein, the term "metastasis" may refer to the growth of a cancerous tumor in an organ or body part, which is not directly connected to the organ of the original cancerous tumor. Metastasis may include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

As used herein, DNA, RNA, nucleic acids, nucleotides, oligonucleotides, polynucleotides may be used interchangeably. Unless explicitly stated otherwise, the term DNA encompasses any type of nucleic acid (e.g., DNA, RNA, DNA/RNA hybrids, and analogues thereof). In instances in which RNA is used in the methods disclosed herein, the methods may further comprise reverse transcription of the RNA to produce a complementary DNA (cDNA) or DNA copy.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. In another example, due to similarities in DNA and RNA, the methods, compositions, and systems may be equally applicable to all types of nucleic acids (e.g., DNA, RNA, DNA/RNA hybrids, and analogues thereof). Moreover, due to biological functional equivalency considerations, changes can be made in protein structure without affecting the biological action in kind or amount. All such modifications are intended to be included within the scope of the appended claims.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1: An Ultrasensitive Method for Quantitating Circulating Tumor DNA with Broad Patient Coverage Circulating tumor DNA (ctDNA) represents a promising biomarker for noninvasive detection of disease burden and monitoring of recurrence. However, existing ctDNA detection methods are limited by sensitivity, a focus on small numbers of mutations, and/or the need for patient-specific optimization. To address these shortcomings, CAncer Personalized Profiling by Deep Sequencing (CAPP-Seq) was developed, an economical and highly sensitive method for quantifying ctDNA in plasma in nearly every patient. We implemented CAPP-Seq for non-small cell lung cancer (NSCLC) with a design that identified mutations in >95% of tumors, simultaneously detecting point mutations, insertions/deletions, copy number variants, and rearrangements. When tumor mutation profiles were known, we detected ctDNA in 100% of pre-treatment plasma samples from stages II-IV NSCLC and 50% of samples from stage I NSCLC, with a specificity of 95% for mutant allele fractions down to ~0.02%. Absolute quantities of ctDNA were significantly correlated with tumor volume. Furthermore, ctDNA levels in post-treatment samples helped distinguish between residual disease and treatment-related imaging changes and provided earlier response assessment than radiographic approaches. Finally, we explored the utility of this method for biopsy-free tumor genotyping and cancer screening. CAPP-Seq can be routinely applied clinically to detect and monitor diverse malignancies, thus facilitating personalized cancer therapy. Here we demonstrate the technical performance and explore the clinical utility of CAPP-Seq in patients with early and advanced stage NSCLC.

Figure 1B:
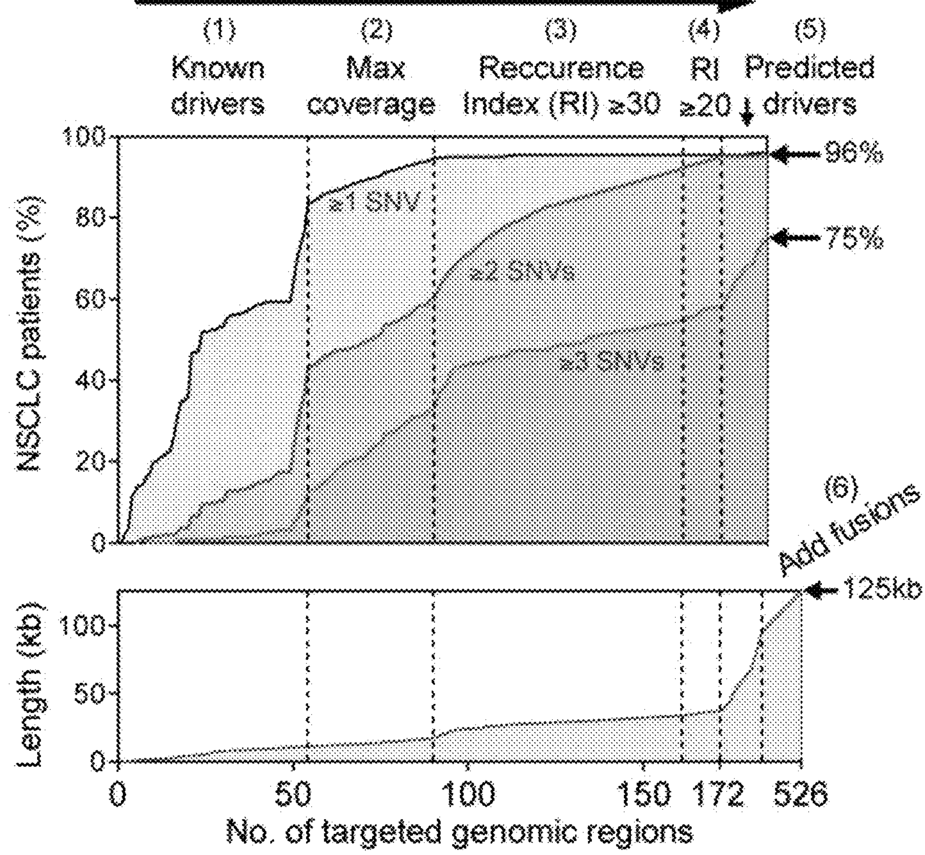
Figure 7A:
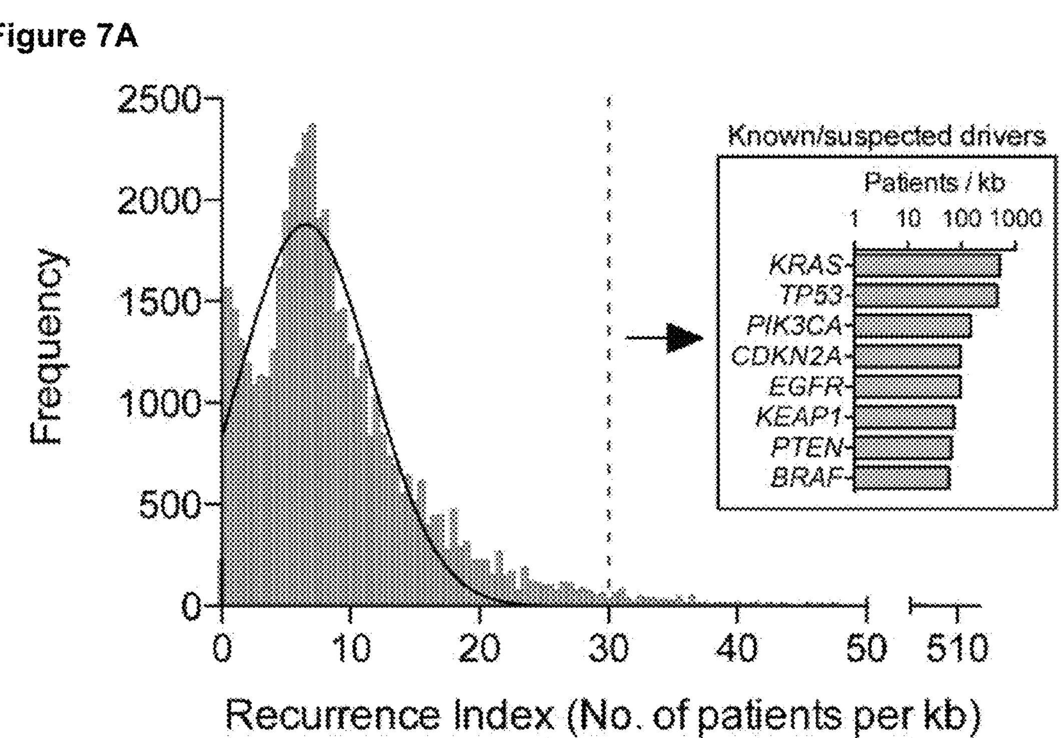
FIG. 7A-7B: Statistical enrichment of recurrently mutated NSCLC exons captures known drivers. We employed two metrics to prioritize exons with recurrent mutations for inclusion in the CAPP-Seq NSCLC selector. The first, termed Recurrence Index (RI), is defined as the number of unique patients (e.g. tumors) with somatic mutations per kilobase of a given exon and the second metric is based on the minimum number of unique patients (e.g. tumors) with mutations in a given kb of exon. We analyzed exons containing at least one non-silent SNV genotyped by TCGA (n=47,769) in a combined cohort of 407 lung adenocarcinoma (LUAD) and squamous cell carcinoma (SCC) patients.
Figure 7B:
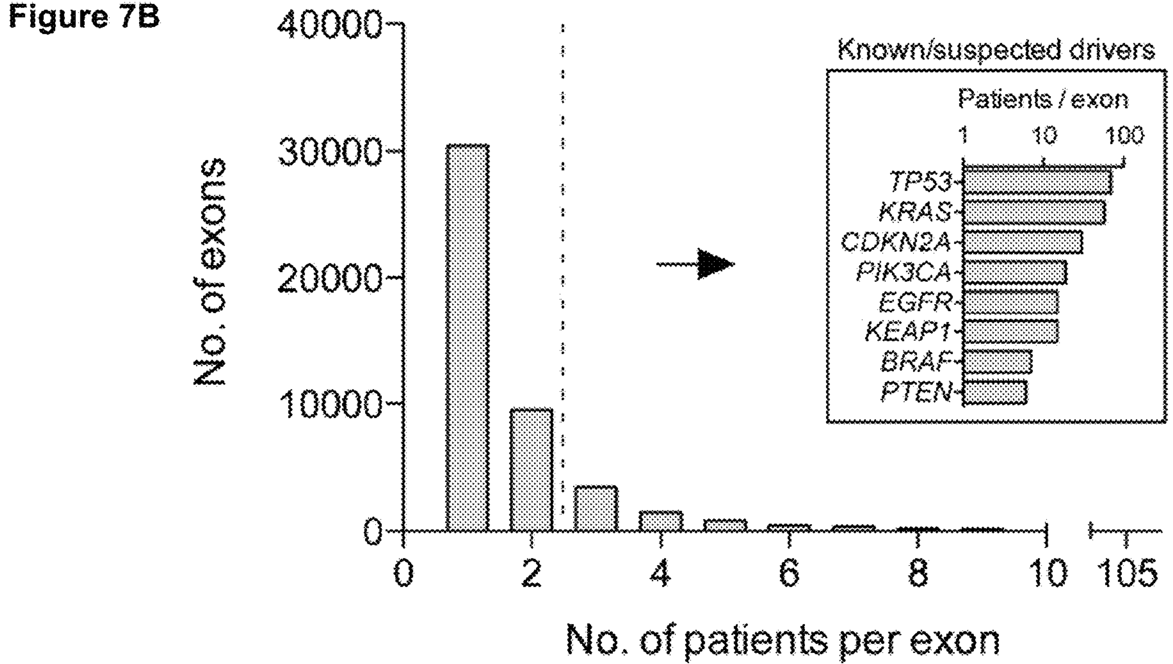

Design of a CAPP-Seq selector for NSCLC. For the initial implementation of CAPP-Seq we focused on NSCLC, although our approach can be used for any cancer for which recurrent mutations have been identified. We employed a multi-phase approach to design an NSCLC-specific selector, aiming to identify genomic regions recurrently mutated in this disease (FIG. 1*b*, Table 1). We began by including exons covering recurrent mutations in potential driver genes from the Catalogue of Somatic Mutations in Cancer (COSMIC) database as well as other sources (e.g. KRAS, EGFR, TP53). Next, using whole exome sequencing (WES) data from 407 NSCLC patients profiled by The Cancer Genome Atlas (TCGA), we applied an iterative algorithm to maximize the number of missense mutations per patient while minimizing selector size. Our approach relied on a recurrence index that identified known driver mutations as well as uncharacterized genes that are frequently mutated and are therefore likely to be involved in NSCLC pathogenesis (FIG. 7 and Table 2).

Approximately 8% of NSCLCs harbor clinically actionable rearrangements involving the receptor tyrosine kinases, ALK, ROS1 and RET. These structural aberrations, which are clinically actionable because they are targets of pharmacologic inhibitors, tend to disproportionately occur in younger patients with significantly less smoking history and whose tumors harbor fewer somatic alterations than most other patients with NSCLC. To utilize the personalized nature and lower false detection rate inherent in the unique junctional sequences of structural rearrangements, we included the introns and exons spanning recurrent fusion breakpoints in these genes in the final design phase (FIG. 1*b*). To detect fusions in tumor and plasma DNA, we developed a breakpoint-mapping algorithm called FACTERA (FIG. 8). Application of FACTERA to next generation sequencing (NGS) data from 2 NSCLC cell lines known to harbor fusions with previously uncharacterized breakpoints readily identified the breakpoints at nucleotide resolution and these were independently confirmed in both cases (FIG. 9).

Figure 1C:
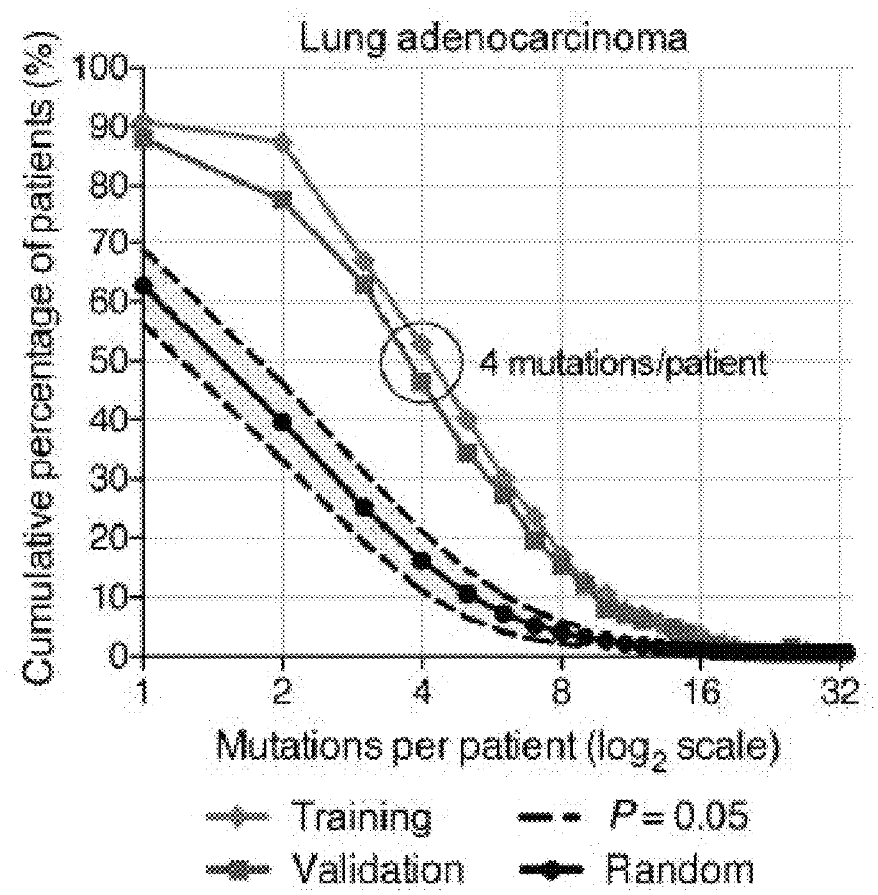
Figure 1D:
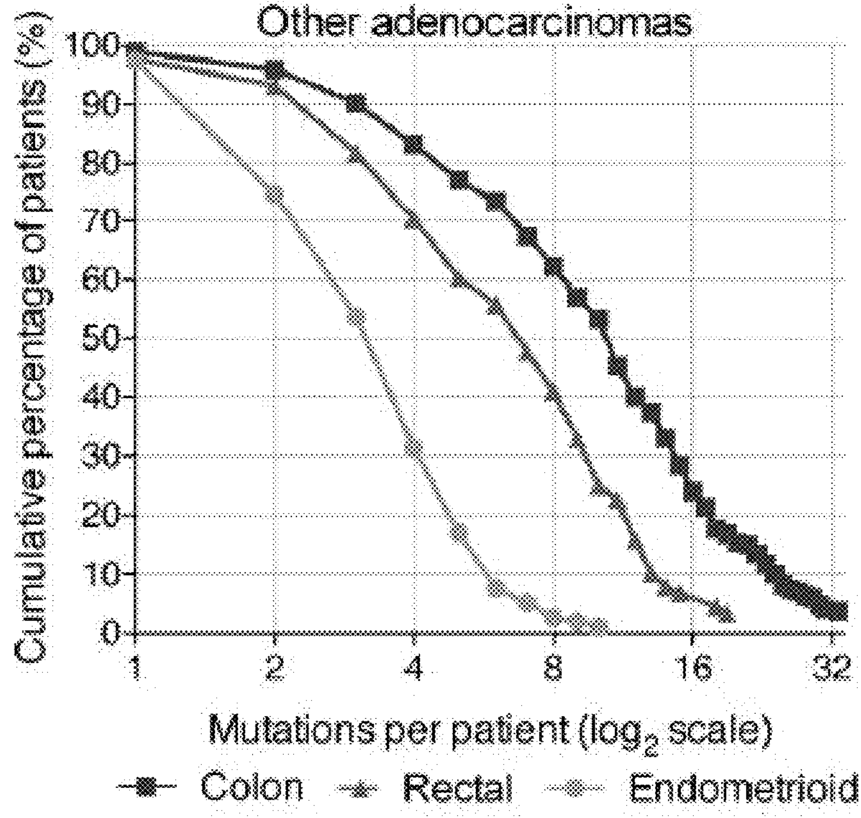

Collectively, the NSCLC selector design targets 521 exons and 13 introns from 139 recurrently mutated genes, in total covering ~125 kb (FIG. 1*b*). Within this small target (0.004% of the human genome), the selector identifies a median of 4 point mutations and covers 96% of patients with lung adenocarcinoma or squamous cell carcinoma. To validate the number of mutations covered per tumor, we examined the selector region in WES data from an independent cohort of 183 lung adenocarcinoma patients. The selector covered 88% of patients with a median of 4 SNVs per patient, thus validating our selector design algorithm ($P<1.0\times10^{-6}$; FIG. 1*c*). When compared to randomly sampling the exome, regions targeted by the NSCLC selector captured ~4-fold more mutations per patient (at the median, FIG. 1*c*). Due to similarities in key oncogenic machinery across cancers, the NSCLC selector performs favorably on other carcinomas. Indeed, the selector successfully captured 99% of colon, 98% of rectal, and 97% of endometrioid uterine carcinomas, with a median of 12, 7, and 3 mutations per patient, respectively (FIG. 1*d*). This demonstrates the value of targeting hundreds of recurrently mutated genomic regions and shows that a single selector can be designed to simultaneously cover recurrent mutations for multiple malignancies.

Methodological optimization and performance assessment. We performed deep sequencing with the NSCLC selector to achieve ~10,000× coverage (pre-duplication removal, ~10-12 samples per lane), and profiled a total of 90 samples, including 2 NSCLC cell lines, 17 primary tumor biopsies and matched peripheral blood leukocyte (PBL) specimens, and 40 plasma samples from 18 human subjects, including 5 healthy adults and 13 patients with NSCLC before and after various cancer therapies (Tables 3, 20 and 21). To assess and optimize selector performance, we first applied it to cfDNA purified from healthy control plasma, observing efficient and uniform capture of genomic DNA (Tables 3, 20 and 21). Sequenced cfDNA fragments had a median length of ~170 bp (FIG. 2*a*), closely corresponding to the length of DNA contained within a chromatosome. To optimize library preparation from small quantities of cfDNA we explored a variety of modifications to the ligation and post-ligation amplification steps including temperature, incubation time, DNA polymerase, and PCR purification. The optimized protocol increased recovery efficiency by >300% and decreased bias for libraries constructed from as little as 4 ng of cfDNA (FIGS. 10, 11, and 12). Consequently, fluctuations in sequencing depth were minimal (FIG. 2*b,c*).

Figures 2D, 2E:
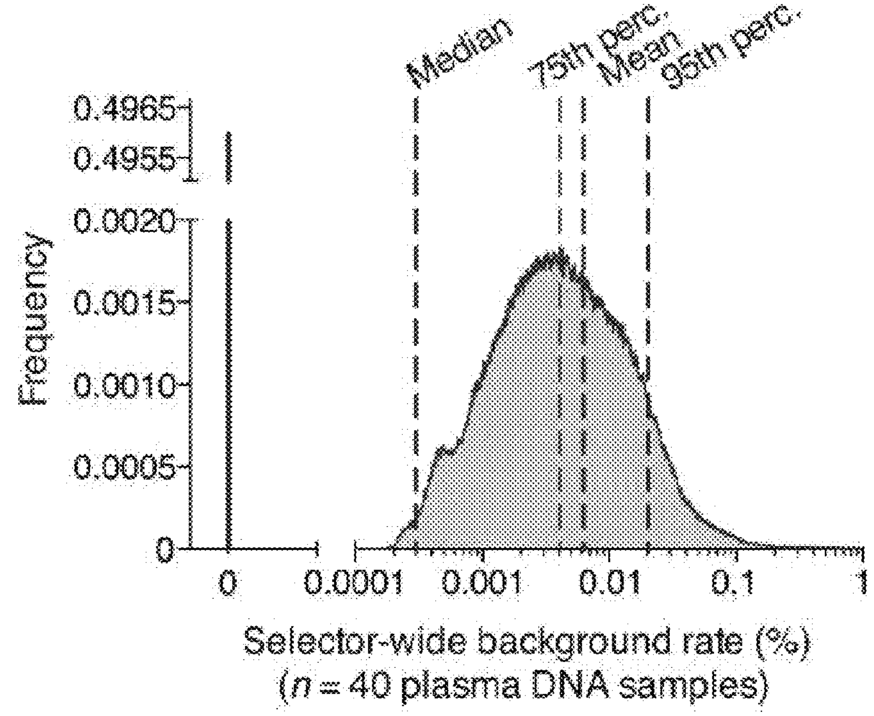
Figure 13A:
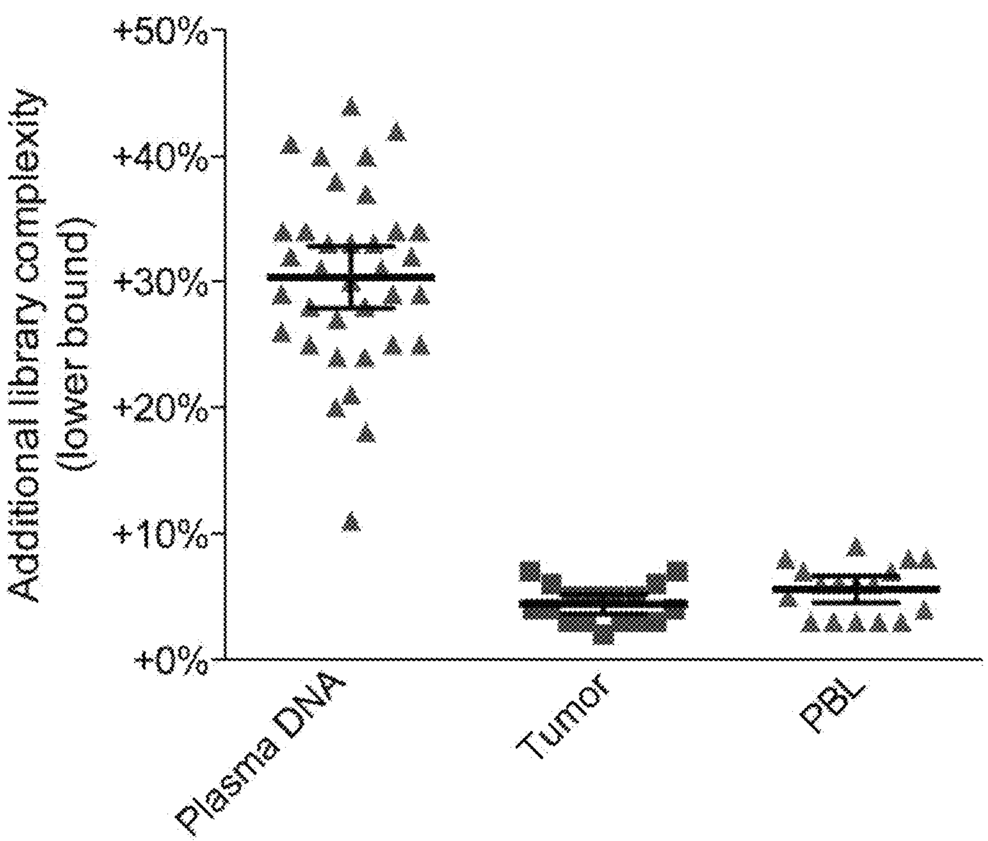
FIG. 13A-13B. Analysis of library complexity and molecule recovery.
Figure 13B:
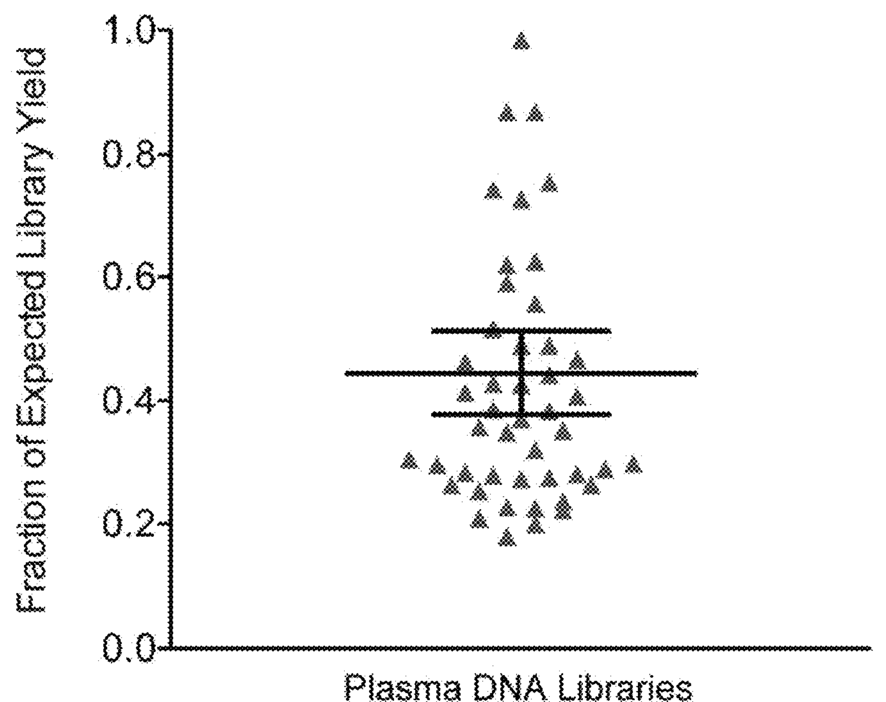
Figure 14:
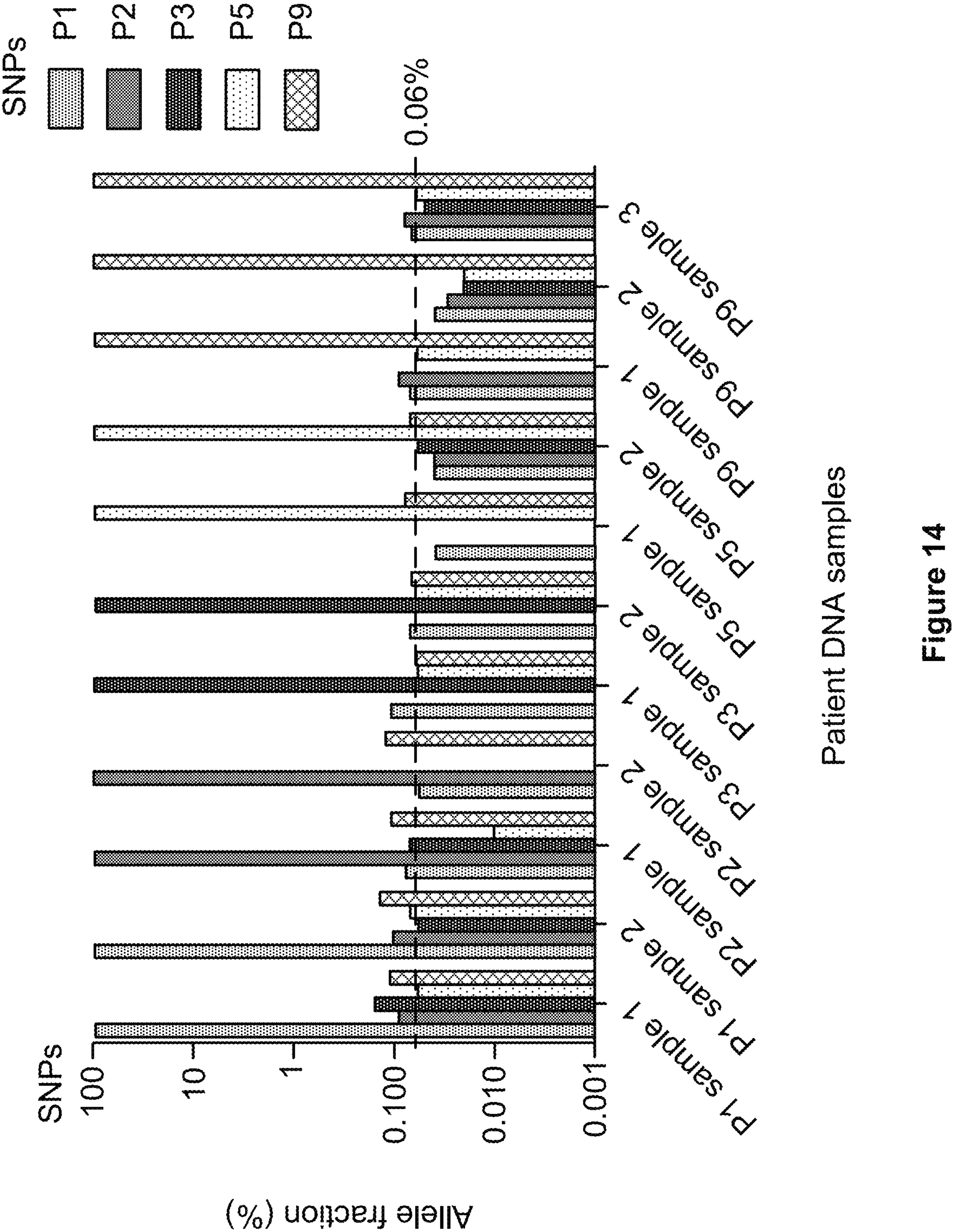
FIG. 14. Analysis of library cross-contamination. Allelic fractions of patient-specific homozygous germline SNPs were assessed in cfDNA samples multiplexed on the same lane. SNPs were called as described in the Methods. The mean "cross-contamination" rate in cfDNA samples was 0.06%, shown by the horizontal dotted line. This level of contamination is too low to affect our estimates of tumor burden given the low fraction of tumor-derived cfDNA in plasma of NSCLC patients (median of ~0.1%.
Figure 15:
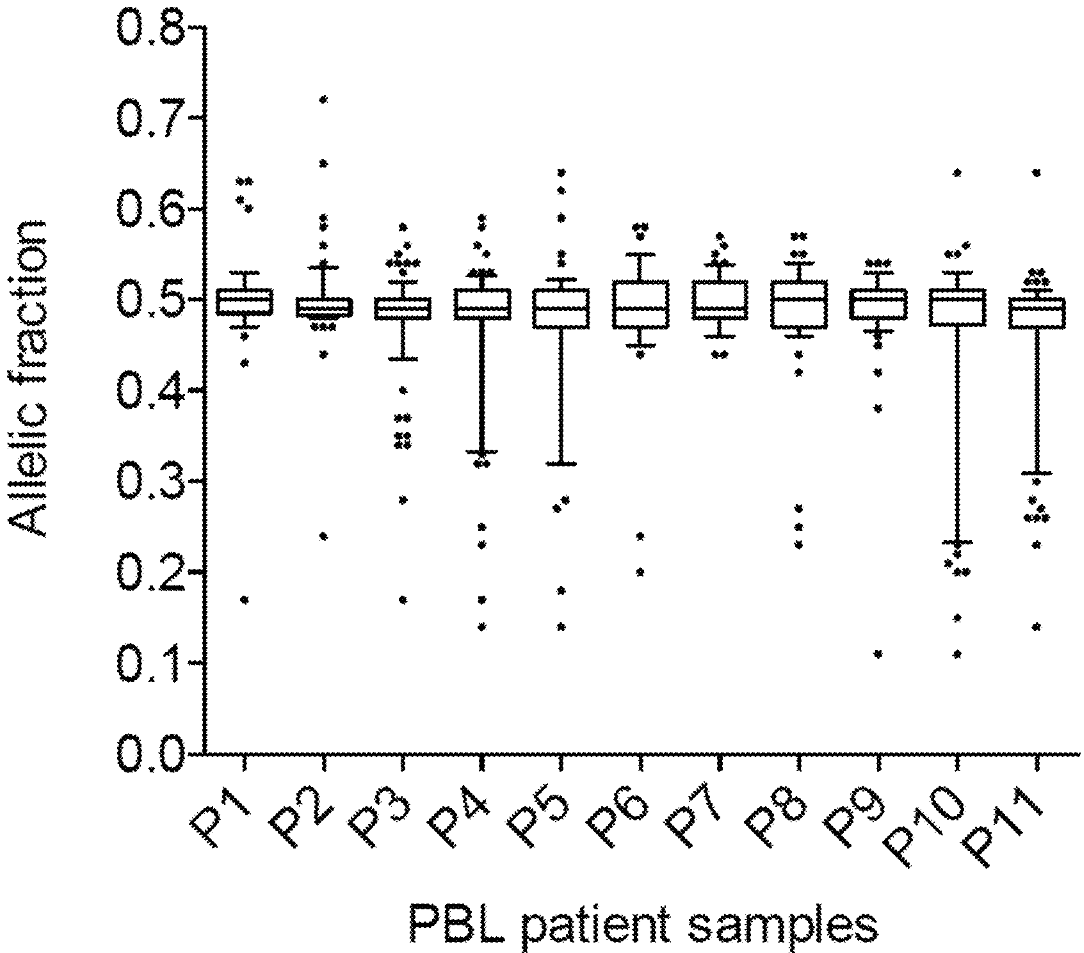
FIG. 15. Analysis of selector-wide bias in captured sequence. Because the NSCLC selector was designed to target the hg19 reference genome, we reasoned that selector bias for SNVs, if any, should be discernable as a systematically lower ratio of non-reference to reference alleles in heterozygous germline SNPs. Therefore, we analyzed high confidence SNPs detected by VarScan in patient PBL samples, where high confidence was defined as variants with a non-reference fraction >10% present in the common SNPs subset of dbSNP (version 137.0). As shown, we detected a very small skew toward reference (8 of 11 samples have a median non-reference allelic frequency of 49%; the remaining 3 samples are unbiased). Importantly, such bias appears too small to significantly affect our results. Boxes represent the interquartile range, and whiskers encapsulate the $10^{th}$ to $90^{th}$ percentiles. Germline SNPs were identified using VarScan 2.

The detection limit of CAPP-Seq is affected by (i) the input number and recovery rate of cfDNA molecules, (ii) sample cross-contamination, (iii) potential allelic bias in the capture reagent, and (iv) PCR or sequencing errors (e.g., "technical" background). We examined each of these elements in turn to better understand their potential impact on CAPP-Seq sensitivity. First, by comparing the number of input DNA molecules per sample with estimates of library complexity (FIG. 13*a*), we calculated a cfDNA molecule recovery rate of ≥49% (Tables 3, 20 and 21). This was in agreement with molecule recovery efficiencies calculated using post-PCR mass yields (FIG. 13*b*). Second, by analyzing patient-specific homozygous SNPs across samples, we found cross-contamination of ~0.06% in multiplexed cfDNA (FIG. 14). While too low to affect ctDNA detection in most applications, we excluded any tumor-derived SNV from further analysis if found as a germline SNP in another profiled patient. To analyze possible capture bias, we next evaluated the allelic skew in heterozygous SNPs (single nucleotide polymorphism) within patient PBL (peripheral blood lymphocyte) samples. We observed a median heterozygous allele fraction of 51% (FIG. 15), indicating minimal bias toward capture of reference alleles. Finally, we analyzed the distribution of non-reference alleles across the selector for the 40 cfDNA samples, excluding tumor-derived SNVs and germline SNPs (FIG. 2*d*). We found mean and median technical background rates of 0.006% and 0.0003%, respectively (FIG. 2*d*), both considerably lower than previously reported NGS-based methods for ctDNA analysis.

Figure 2F:
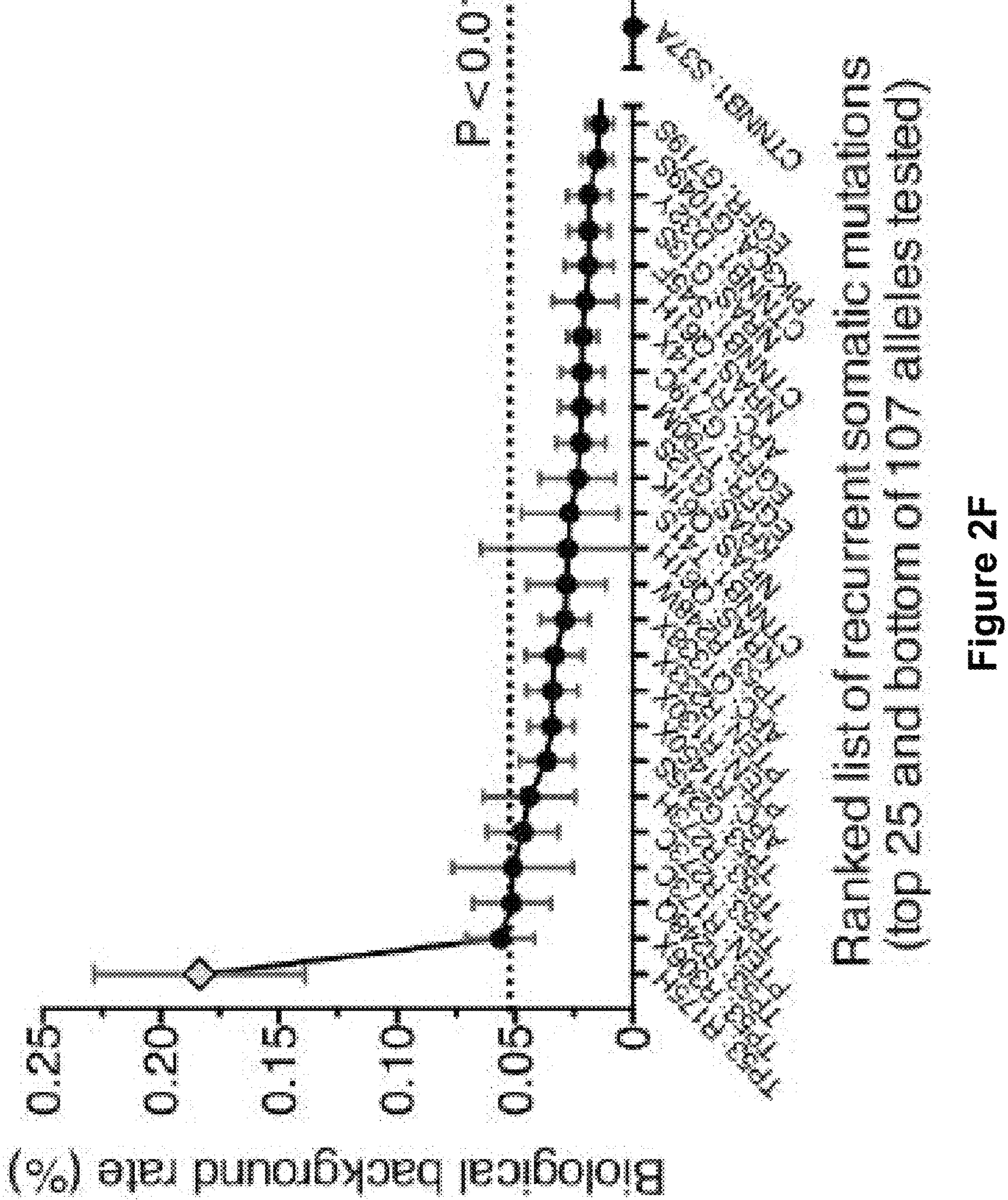

In addition to technical background, mutant cfDNA could be present in the absence of cancer due to contributions from pre-neoplastic cells from diverse tissues, and such "biological" background may impact sensitivity. We hypothesized that biological background, if present, would be particularly high for recurrently mutated positions in known cancer driver genes and therefore analyzed mutation rates of 107 selected cancer-associated SNVs in all 40 plasma samples, excluding somatic mutations found in a patient's tumor. Though the median fractional abundance was comparable to the global selector background (~0%), the mean was marginally higher at ~0.01% (FIG. 2*e*). Strikingly, one mutation (TP53 $R^{175}H$) was detected at a median frequency of ~0.18% across all cfDNA samples, including patients and healthy subjects (FIG. 2*f*). Since this allele is significantly above global background ($P<0.01$; FIG. 2*f*), we hypothesize that it reflects true biological background and thus excluded it as a potential reporter. To address background more generally, we also normalized for allele-specific differences in background rate when assessing the significance of ctDNA detection. As a result, we found that biological background is not a significant factor for ctDNA quantitation at detection limits above ~0.01%.

Figure 16A:
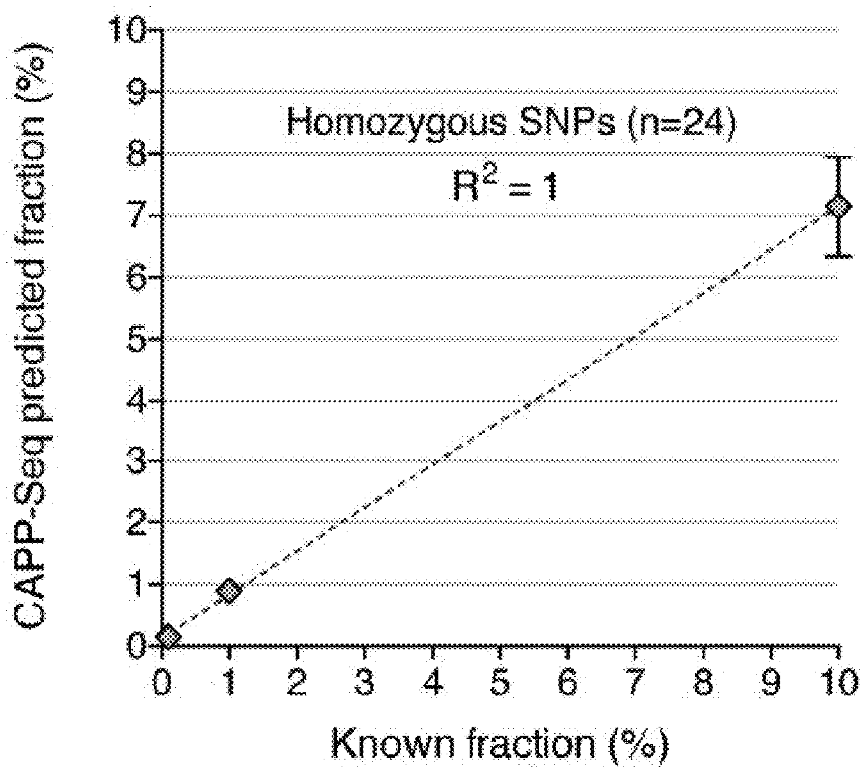
FIG. 16A-16D: Empirical spiking analysis of CAPP-Seq using two NSCLC cell lines.
Figure 16B:
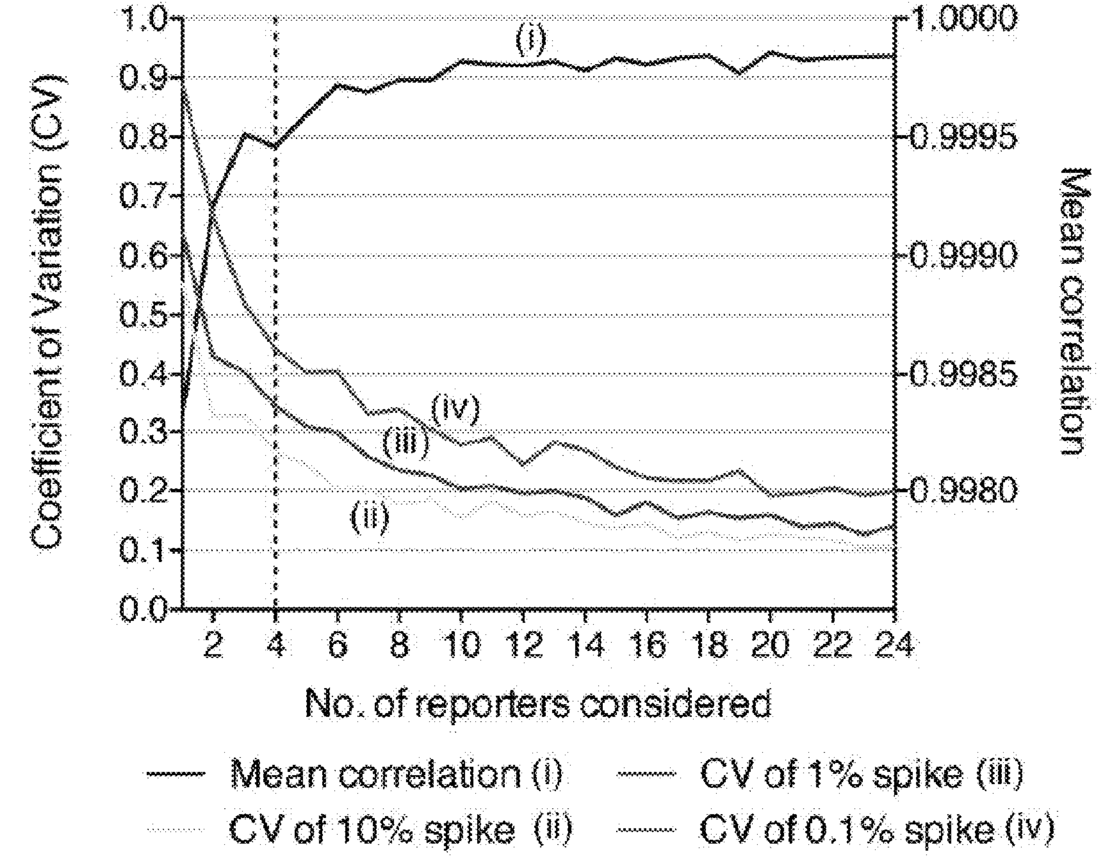
Figure 16C:
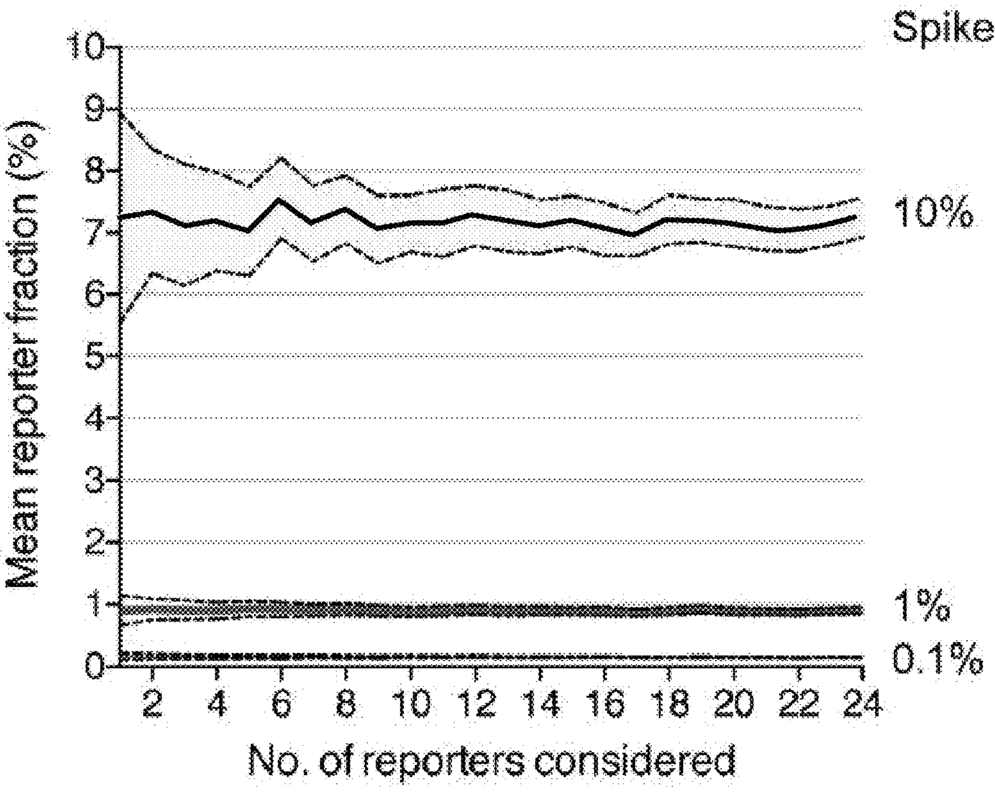
Figure 16D:
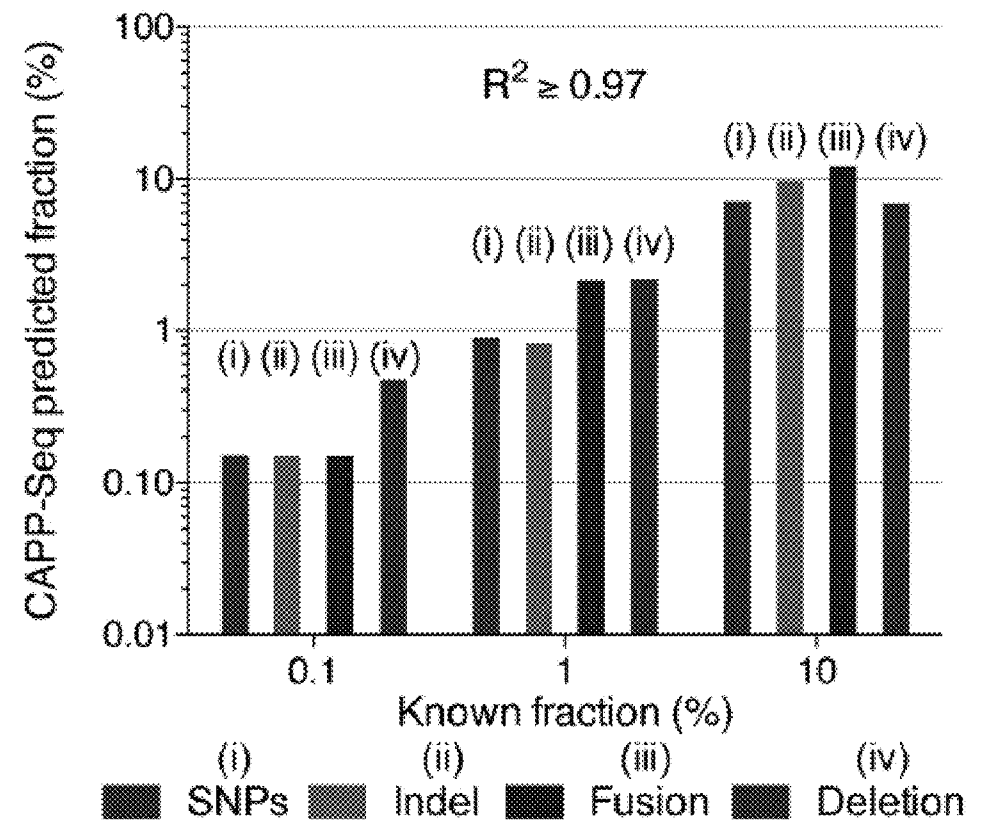

Next, we empirically benchmarked the allele frequency detection limit and linearity of CAPP-Seq by spiking defined concentrations of fragmented genomic DNA from a NSCLC cell line into cfDNA from a healthy individual (FIG. 2*g*) or into genomic DNA from a second NSCLC line (FIG. 16*a*). Defined inputs of NSCLC DNA were accurately detected at fractional abundances between 0.025% and 10% with high linearity ($R^2\geq0.994$). Analyses of the influence of the number of SNP reporters on error metrics showed only marginal improvements above a threshold of 4 reporters (FIG. 2*h,i*, FIG. 16*b,c*), equivalent to the median number of SNVs per NSCLC tumor identified by the selector. We also tested whether fusion breakpoints, indels, and CNVs could serve as linear reporters and found that the fractional abundance of these mutation types correlated highly with expected concentrations ($R^2\geq0.97$; FIG. 16*d*).

Figure 17B:
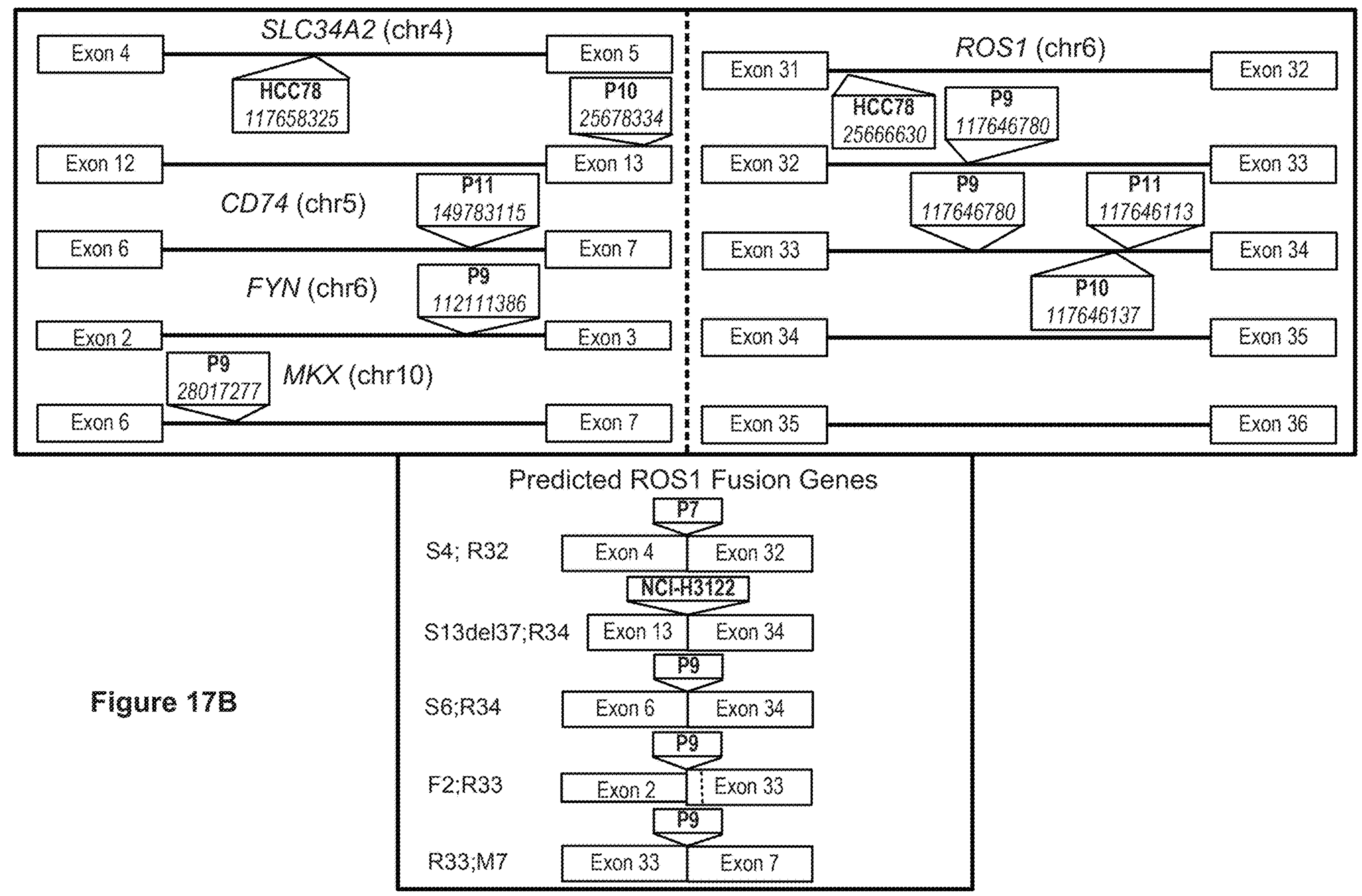
Figure 18:
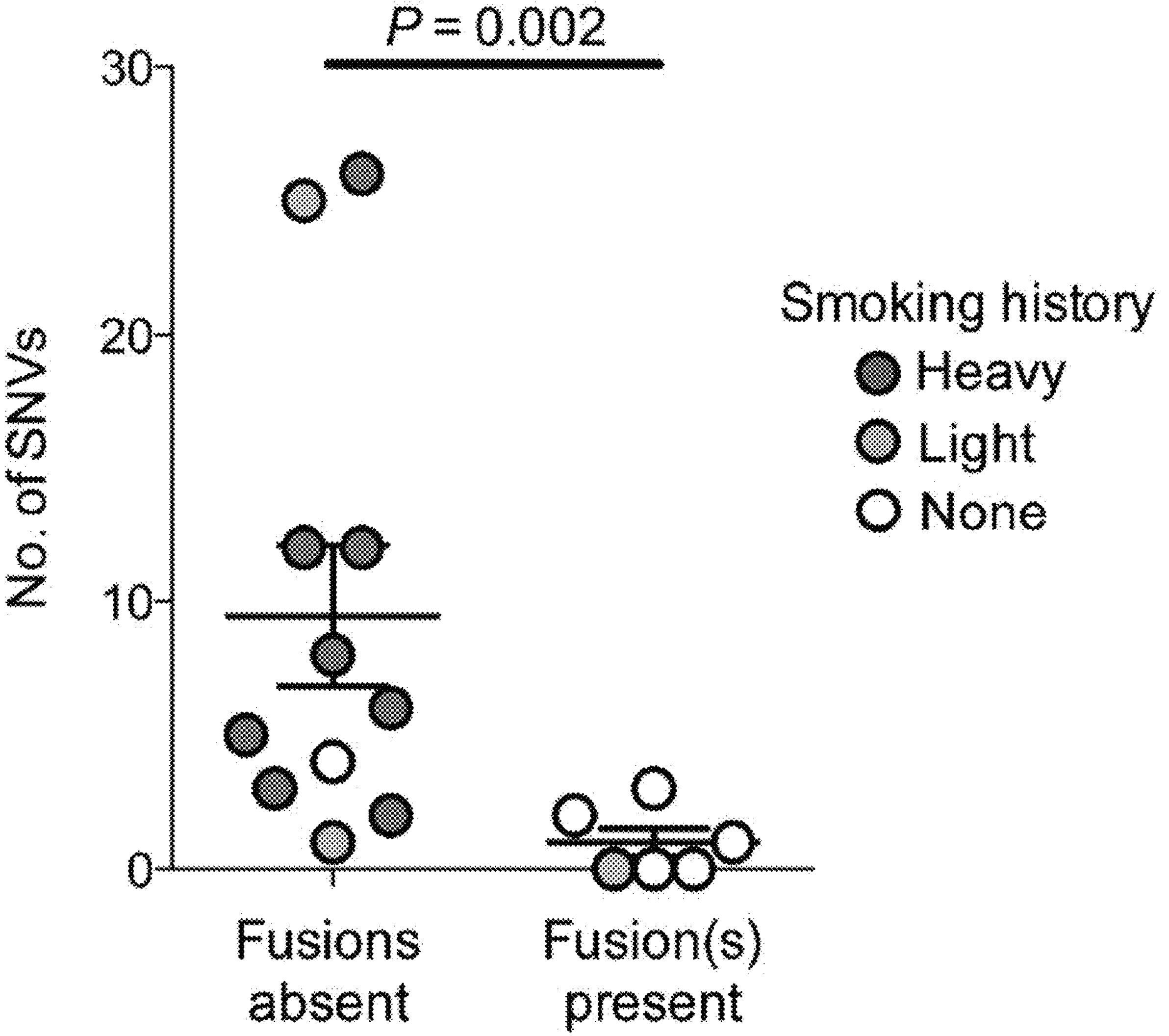
FIG. 18: Presence of fusions is inversely related to the number of SNVs detected by CAPP-Seq. For each patient listed in Table 1 the number of identified SNVs versus the presence (n=11) or absence (n=6) of detected genomic fusions is plotted. Statistical significance was determined using a two-sided Wilcoxon rank sum test, and summarized values are presented as means±s.e.m.

Identification of somatic mutations in NSCLC patients. Having designed, optimized, and assessed the technical performance of CAPP-Seq, we applied it to the discovery of somatic mutations in tumors collected from a diverse group of 17 NSCLC patients (Table 1 and Table 19). To test the utility of CAPP-Seq for identifying structural rearrangements, which are more frequently seen in tumors from nonsmokers, we included 6 patients with clinically confirmed fusions. These translocations served as positive controls, along with SNVs in other tumors previously identified by clinical assays (Table 19). Tumor samples included formalin fixed surgical or biopsy specimens and pleural fluid containing malignant cells. At a mean sequencing depth of ~5,000× (pre-duplicate removal) in tumor and paired germline samples (Tables 3, 20 and 21), we detected 100% of previously identified SNVs and fusions (7 and 8, respectively) and discovered many additional somatic variants (Table 1 and Table 19). Moreover, partner genes and base-pair resolution breakpoints were characterized for each of the 8 rearrangements (FIG. 17). Tumors containing fusions were almost exclusively from never smokers and, as expected, contained fewer SNVs than those lacking fusions (FIG. 18). Excluding patients with fusions (<10% of the TCGA design cohort), we identified a median of 6 SNVs (3 missense) per patient (Table 1), in line with our selector design-stage predictions (FIG. 1*b-c*).

Figure 3A:
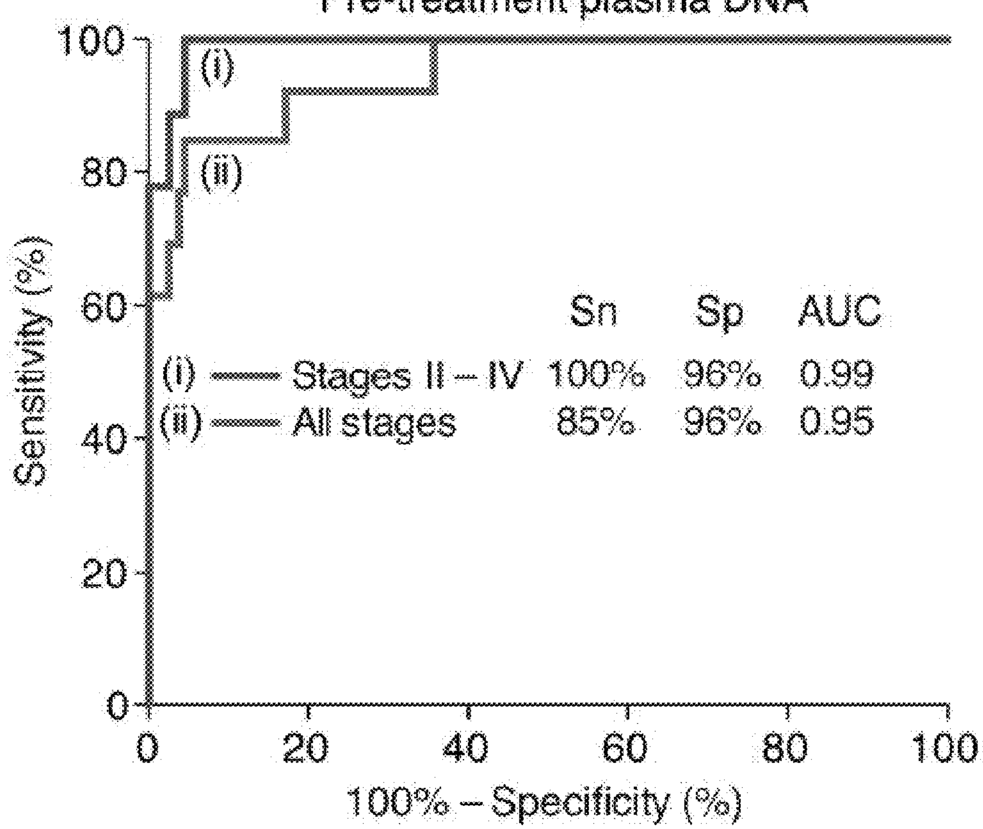
FIG. 3A-3C: Sensitivity and specificity analysis.
Figure 3B:
Figure 3B:
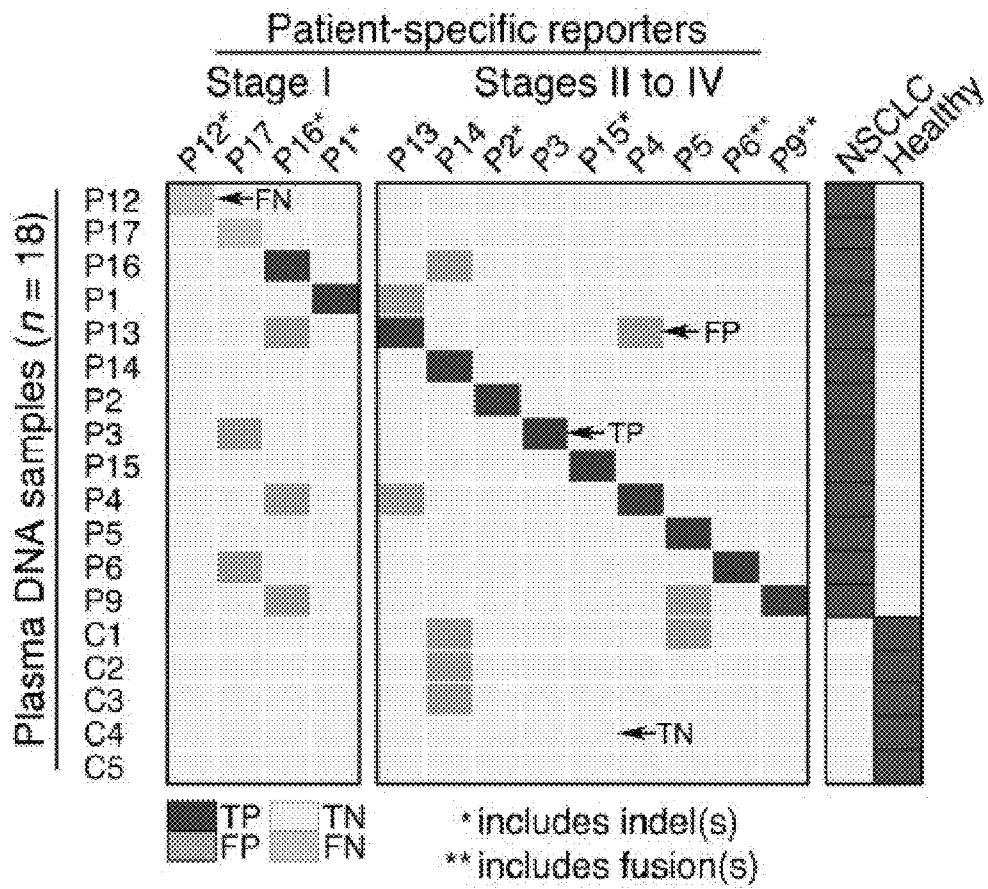
Figure 19C:
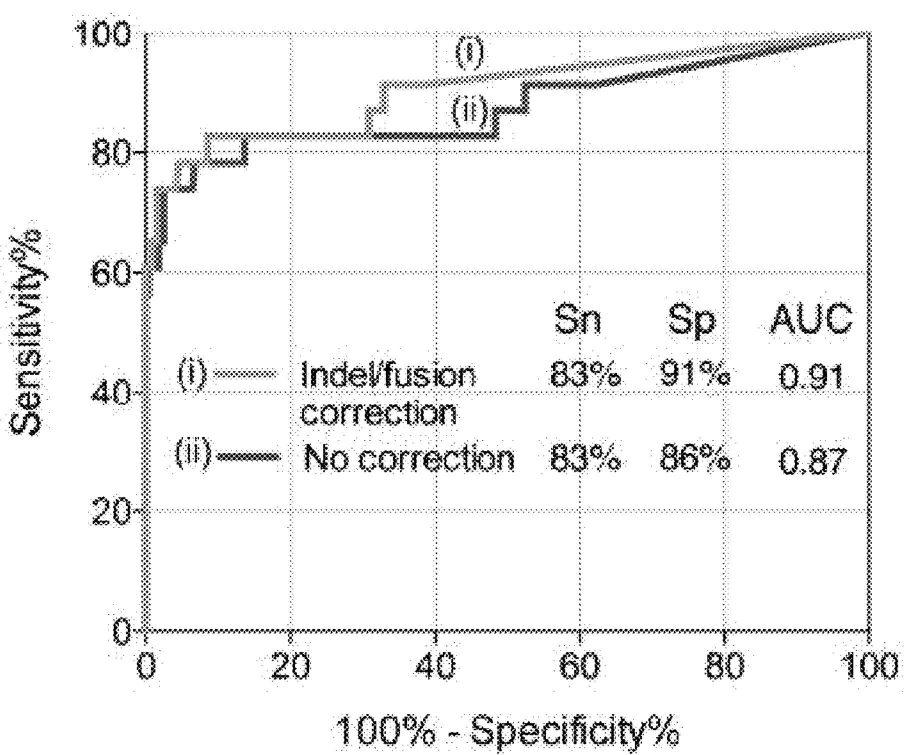
Figure 19D:
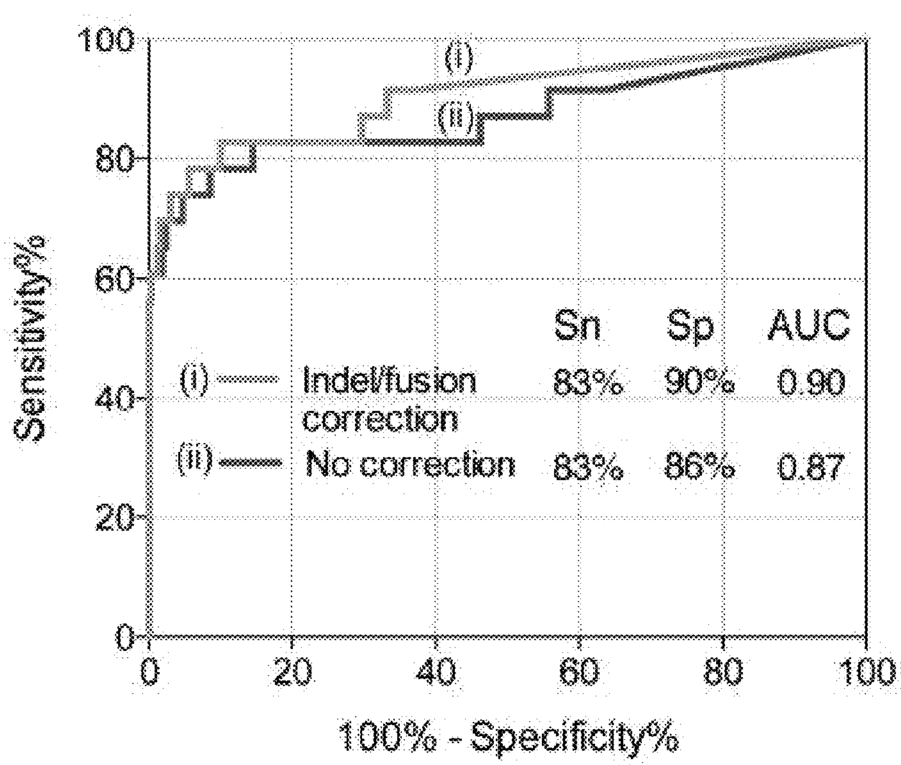
Figure 20:
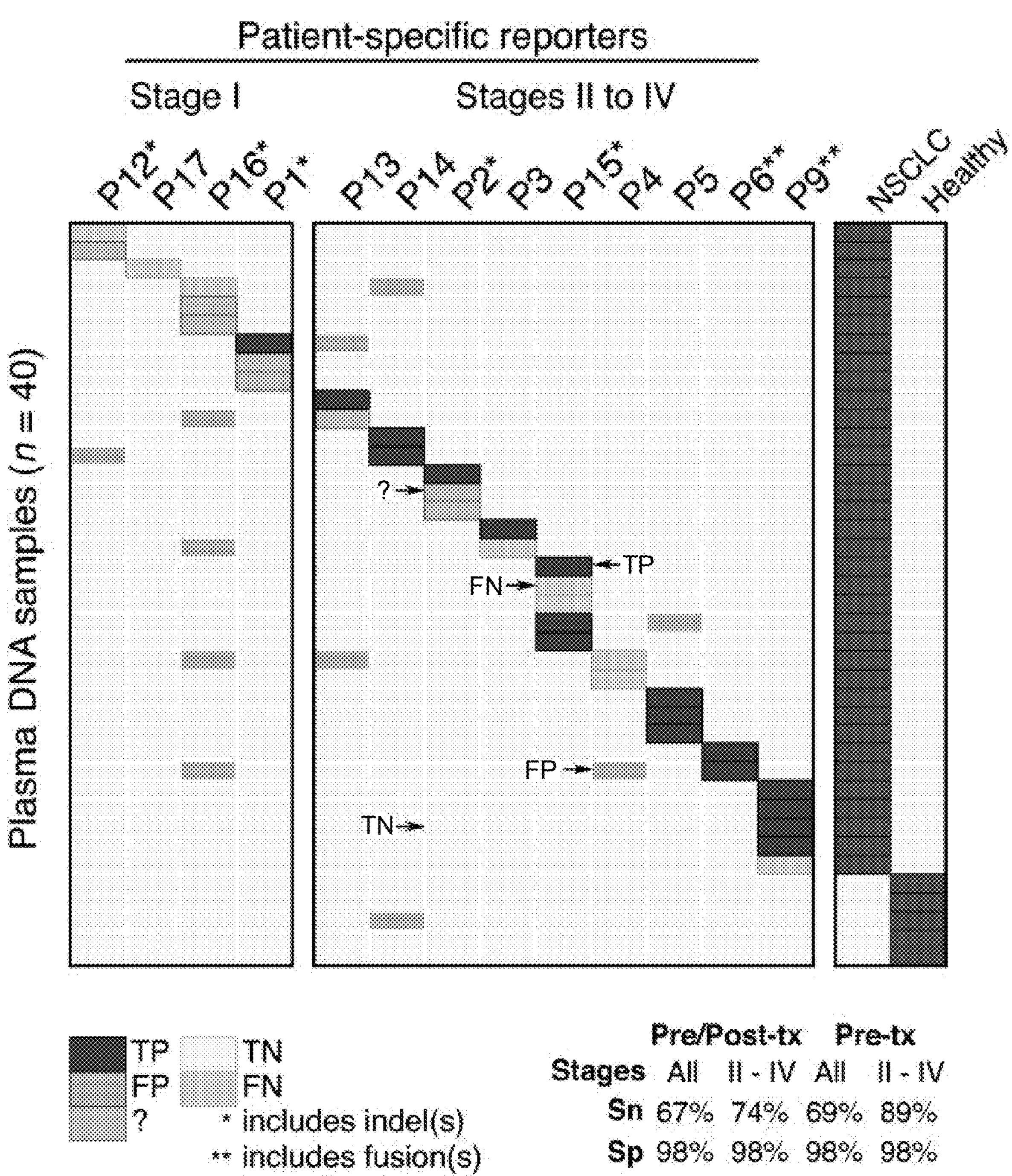
FIG. 20. CAPP-Seq sensitivity and specificity over all patient reporters and sequenced plasma cfDNA samples. All values shown reflect a ctDNA detection index of 0.03. See Methods for details on detection metrics, and determination of cancer-positive, cancer-negative, and unknown categories.

Sensitivity and specificity. Next, we assessed the sensitivity and specificity of CAPP-Seq for disease monitoring and minimal residual disease detection, using plasma samples from 5 healthy controls and 35 serial samples collected from 13 NSCLC patients, all but one of whom had pre- and post-treatment samples available (Table 1; Table 5). CAPP-Seq was used to measure tumor burden across the entire grid of plasma cfDNA samples (13 patient-specific sets of somatic reporters across 40 plasma samples, or 520 pairs), with an approach that integrates information content across multiple instances and classes of somatic mutations to increase sensitivity and specificity. Using ROC analysis, we achieved a maximal sensitivity and specificity of 85% and 95% (AUC=0.95), respectively, for all pre-treated tumors and healthy controls. Sensitivity among stage I tumors was 50% and among stage II-IV patients was 100% with a specificity of 96% (FIG. 3*a,b*). Moreover, when considering both pre and post-treatment samples in an ROC analysis, CAPP-Seq exhibited robust performance, with AUC values of 0.89 for all stages and 0.91 for stages II-IV (P<0.0001; FIG. 19). Furthermore, by adjusting the ctDNA detection index, we could increase specificity up to 98% while still capturing ⅔ of all cancer-positive samples and ¾ of stage II-IV cancer-positive samples (FIG. 20). This indicates that our approach could be tuned to deliver a desired sensitivity and specificity depending on the application in question and that CAPP-Seq can achieve robust assessment of tumor burden in NSCLC patients.

Figure 3C:
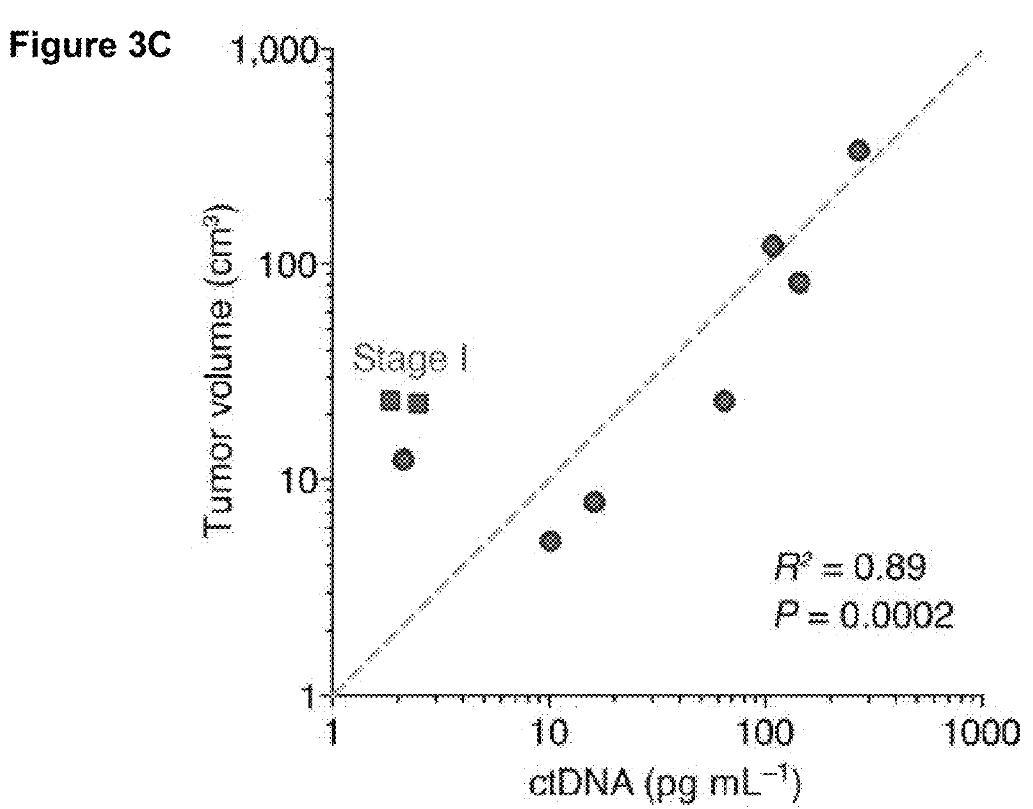

Monitoring of NSCLC tumor burden in plasma samples. We next asked whether significantly detectable levels of ctDNA correlate with radiographically measured tumor volume and clinical response to therapy. Fractions of tumor-derived DNA detected in plasma by SNV and/or indel reporters ranged from ~0.02% to 3.2% (Table 1), with a median of ~0.1% in pre-treatment samples. Moreover, absolute levels of ctDNA in pre-treatment plasma were significantly correlated with tumor volume as measured by computed tomography (CT) and positron emission tomography (PET) imaging ($R^2$=0.89, P=0.0002; FIG. 3*c*).

Figure 4A:
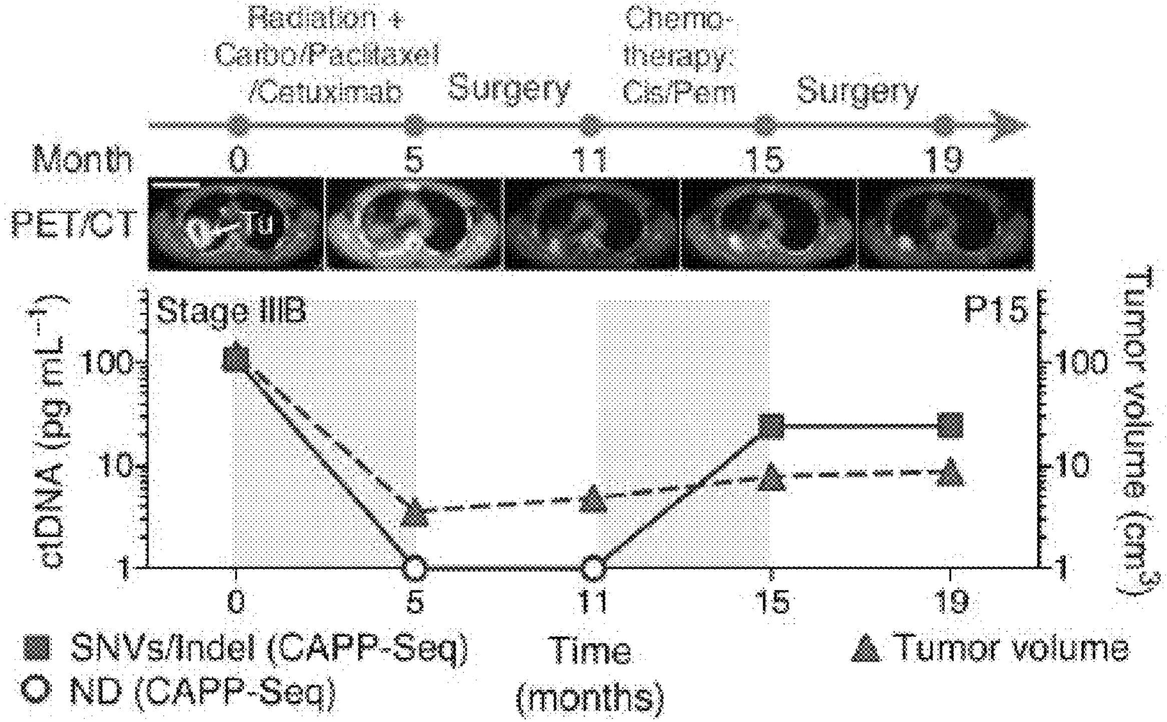
Figure 4B:
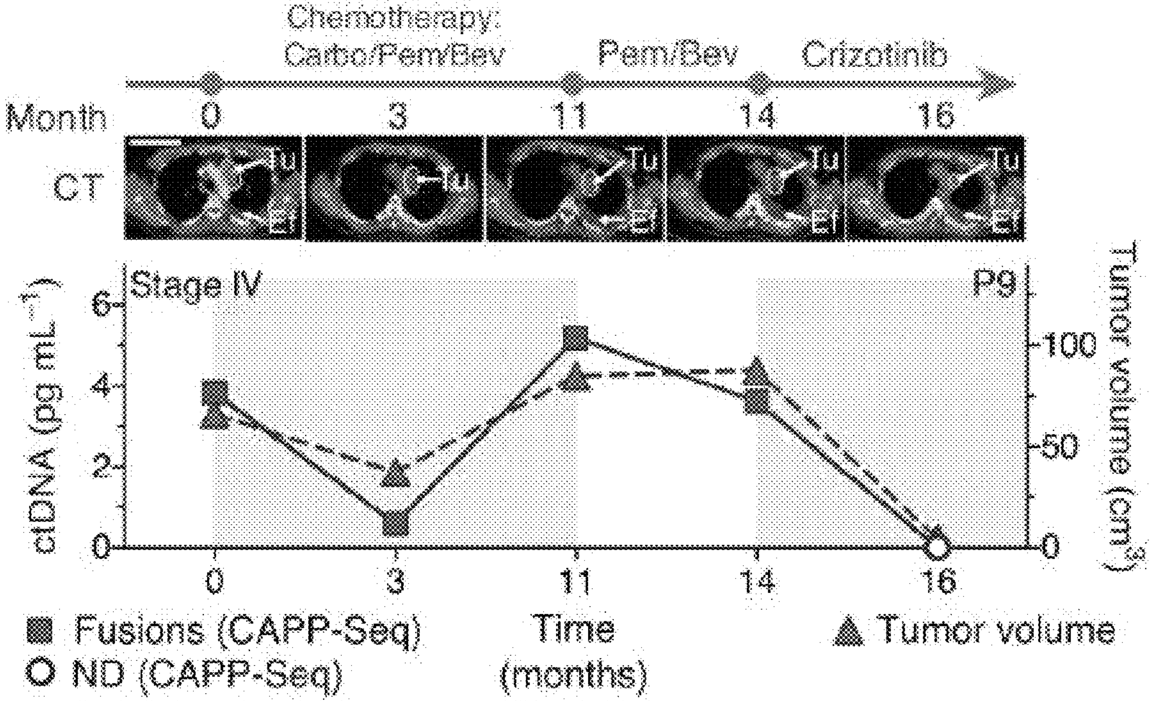
Figures 4C, 4D:
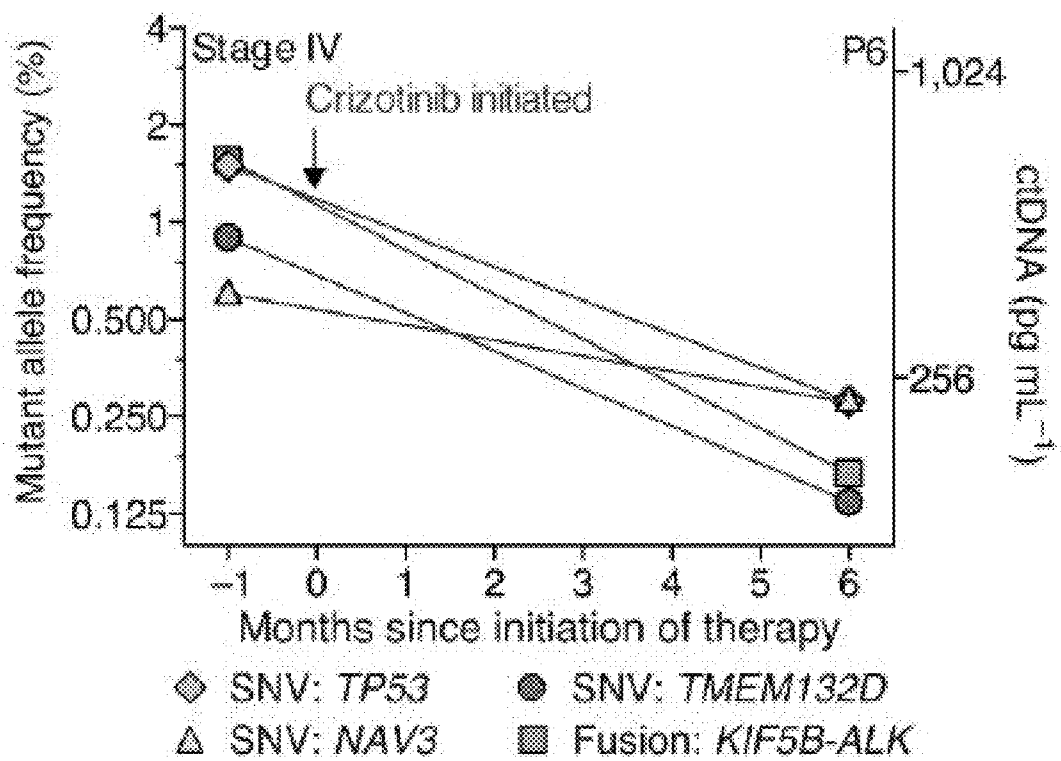

To determine whether ctDNA concentrations reflect disease burden in longitudinal samples, we analyzed plasma cfDNA from three patients with high disease burden who underwent several rounds of therapy for metastatic NSCLC, including surgery, radiotherapy, chemotherapy, and tyrosine kinase inhibitors (FIG. 4*a-c*). As in pre-treatment samples, ctDNA levels were highly correlated with tumor volumes during therapy ($R^{2=0.95}$ for P15; $R^{2=0.85}$ for P9). In a never-smoker (P6), we detected 3 SNVs and a KIF5B-ALK fusion, and both mutation types were simultaneously detectable in plasma cfDNA and behaved comparably in response to Crizotinib therapy (FIG. 4*c*). In all 3 patients, this behavior was observed whether the mutation type measured was a collection of SNVs and an indel (P15, FIG. 4*a*), multiple fusions (P9, FIG. 4*b*), or SNVs and a fusion (P6, FIG. 4*c*), validating the utility of diverse tumor-derived somatic lesions. Of note, in one patient (P9) we identified both a classic EML4-ALK fusion and two previously unreported fusions involving ROS1: FYN-ROS1 and ROS1-MKX (FIG. 17). All fusions were confirmed by qPCR amplification of genomic DNA and were independently recovered in plasma samples (Table 5). While the potential function of these novel ROS1 fusions is unknown, to the best of our knowledge this is the first observation of ROS1 and ALK fusions in the same NSCLC patient.

The NSCLC selector was designed to detect multiple SNVs per tumor and if present, more than 1 type of mutation per tumor. In one patient's tumor (P5), this design allowed us to identify a dominant clone with an activating EGFR mutation as well as a subclone with an EGFR T790M "gatekeeper" mutation. The ratio between clones was identical in a tumor biopsy and simultaneously sampled plasma (FIG. 4*d*), demonstrating that by detecting multiple reporters per tumor, our method is useful for detecting and quantifying clinically relevant subclones.

Figures 4E, 4F:
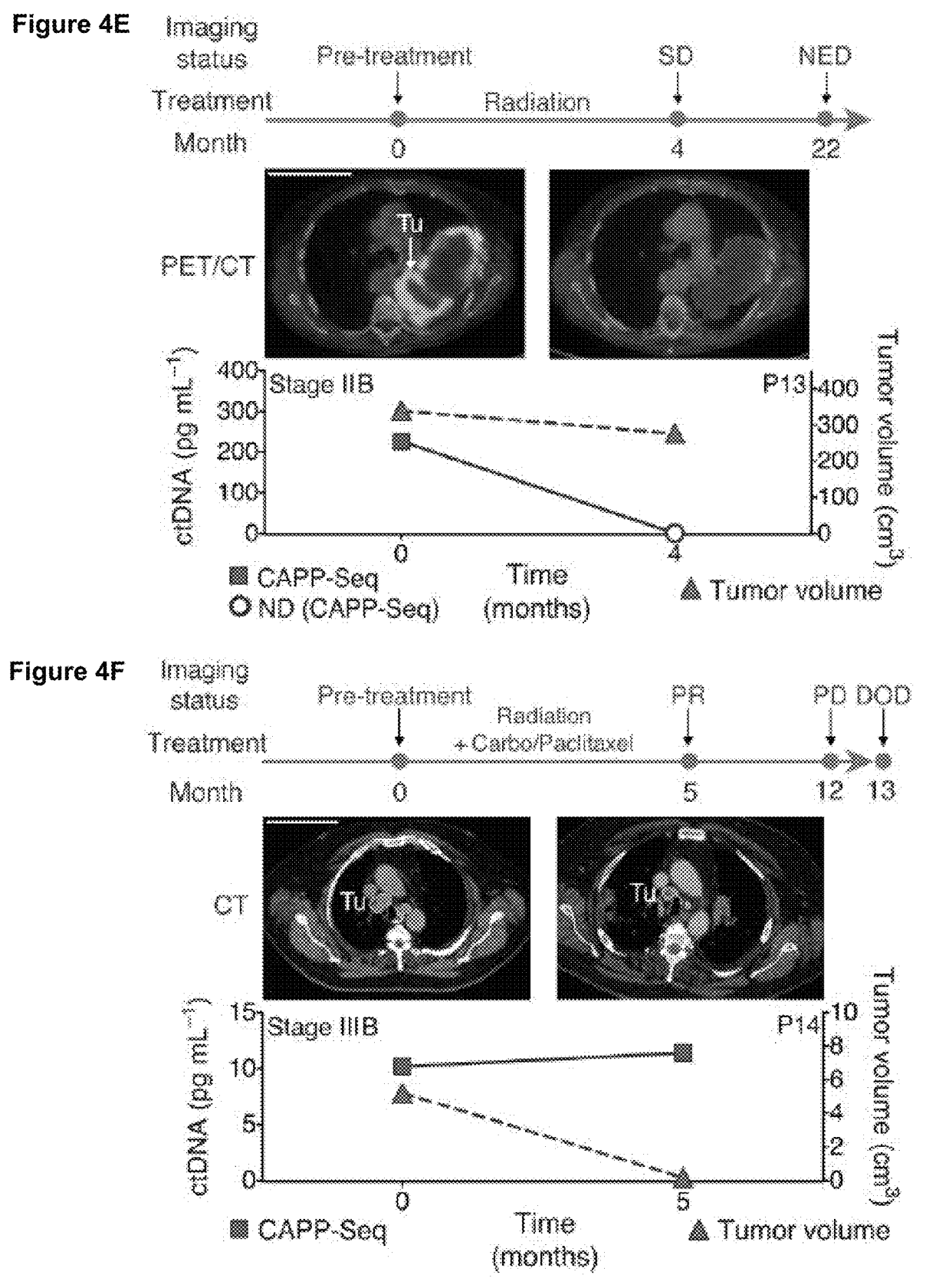

Having validated the performance of CAPP-Seq on advanced stage patients, we next examined other clinical scenarios in which ctDNA biomarkers could be useful. Stage II-III NSCLC patients who undergo definitive radiotherapy with curative intent often have surveillance CT and/or PET/CT scans that are difficult to interpret due to radiation-induced inflammatory and fibrotic changes in the lung and surrounding tissues. These can delay diagnosis of recurrence or lead to unnecessary biopsies and patient anxiety. To compare the results of ctDNA quantitation to routine surveillance imaging, we analyzed pre- and post-radiotherapy plasma cfDNA in 2 patients. For patient P13, who was treated with radiotherapy alone for stage IIB NSCLC, follow-up imaging showed a large mass that was felt to represent residual disease. However, ctDNA at the same time point was undetectable (FIG. 4*e*) and the patient remained disease free 22 months later, supporting the ctDNA result. The second patient (P14) was treated with concurrent chemoradiotherapy for stage IIIB NSCLC and follow-up imaging revealed a near complete response in the thorax (FIG. 4*f*). However, the ctDNA concentration slightly increased compared to pre-treatment, suggesting progression of occult microscopic disease. Indeed, progression was detected clinically 7 months later and the patient ultimately succumbed to NSCLC. These data highlight the use of cfDNA analysis as a complementary modality to imaging studies and as a method for early diagnosis of recurrence.

Figure 4G:
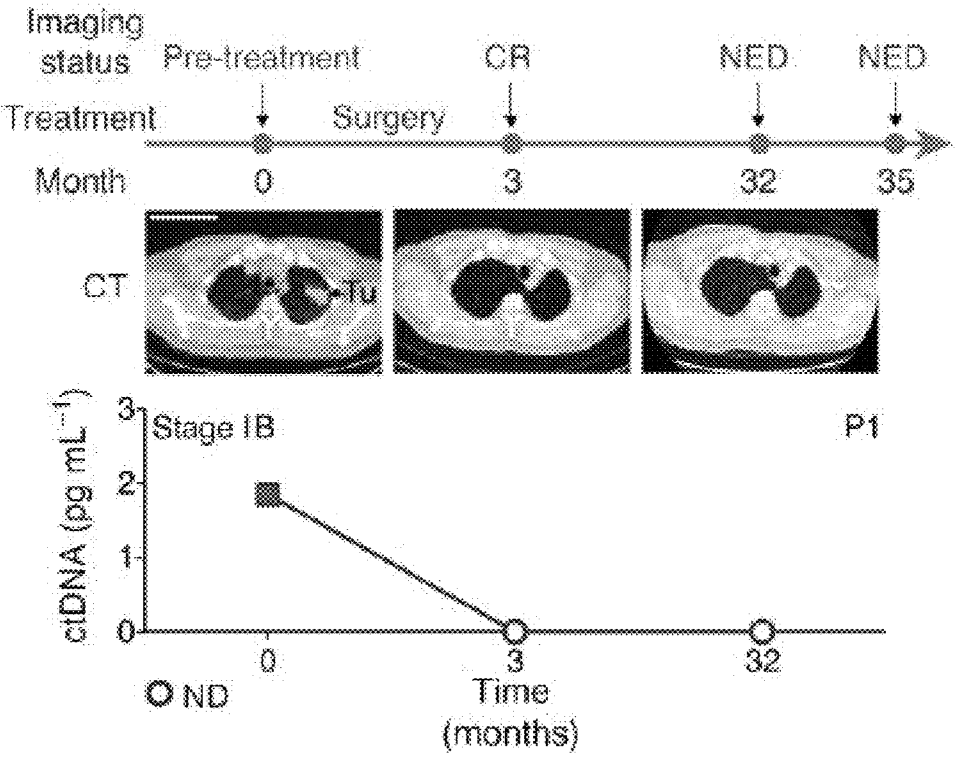
Figure 4H:
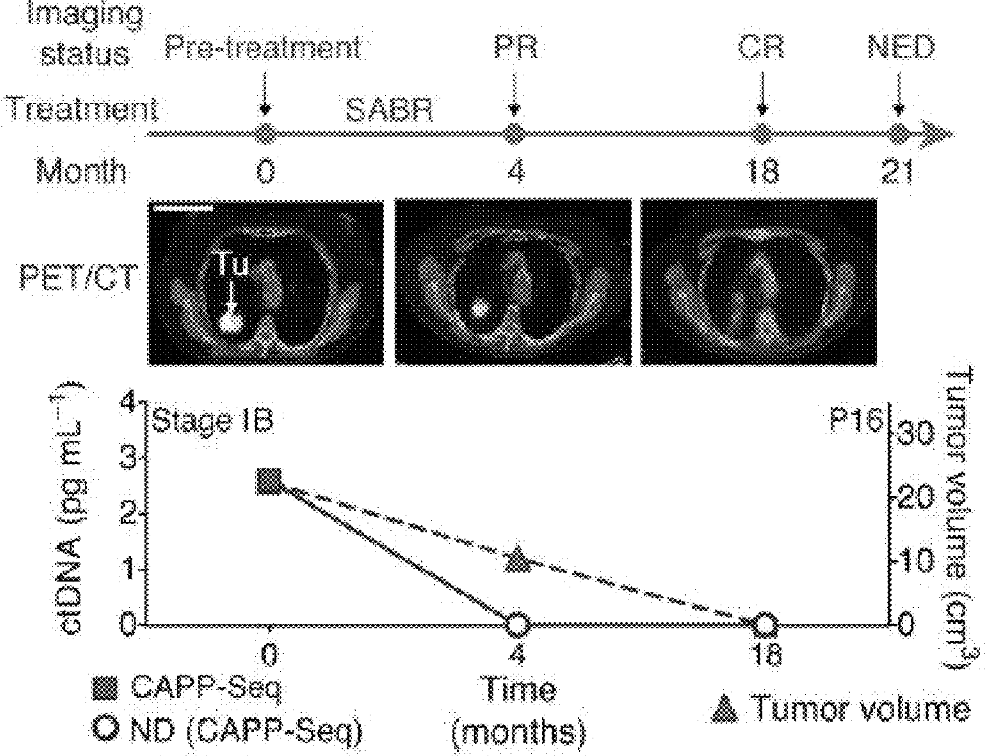

We next asked whether the low detection limit of CAPP-Seq would allow monitoring of response to treatment in early stage NSCLC. Approximately 60-70% of stage I NSCLCs are curable with surgery or stereotactic ablative radiotherapy (SABR). Patients P1 (FIG. 4*g*) and P16 (FIG. 4*h*) underwent surgery and SABR, respectively, for stage IB NSCLC. We detected tumor-derived cfDNA in pre-treatment plasma of P1 but not at 3 or 32 months following surgery, suggesting this patient was free of disease and likely cured. For patient P16, the initial surveillance PET-CT scan following SABR showed a residual mass that was interpreted as representing either residual tumor or post-radiotherapy inflammation. We detected no evidence of residual disease by ctDNA, supporting the latter, and the patient remained free of disease at last follow-up 21 months after therapy. Taken together, these results demonstrate the utility of CAPP-Seq as a noninvasive clinical assay for measuring tumor burden in early and advanced stage NSCLC and for monitoring ctDNA during distinct types of therapy.

Figure 4I:
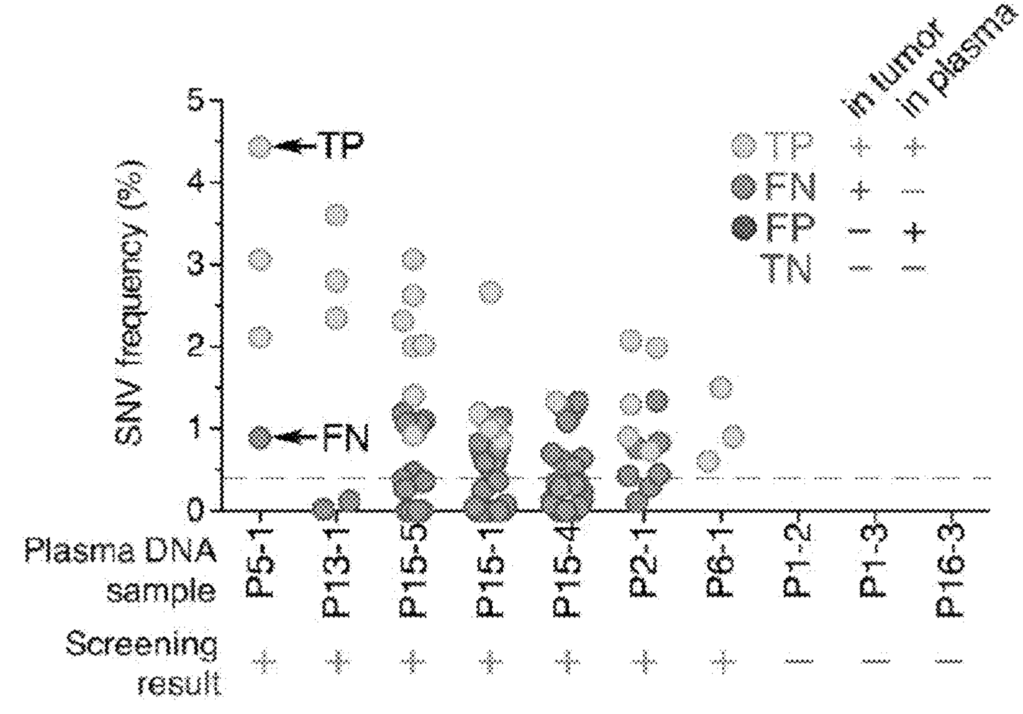

Noninvasive tumor genotyping and cancer screening. Finally, we explored whether CAPP-Seq analysis of cfDNA could potentially be used for non-invasive tumor genotyping and cancer screening (e.g., without prior knowledge of tumor mutations). We blinded ourselves to the mutations present in each patient's tumor and applied a novel statistical method to test for the presence of cancer DNA in each plasma sample in our cohort (FIG. 21). This method identified mutant alleles in all plasma samples containing ctDNA above fractional abundances of 0.4%, with no false positives (FIG. 4*i*). Thus, this approach has utility for non-invasive tumor genotyping in locally advanced or metastatic patients. Since ~95% of nodules identified in patients at high risk for developing NSCLC by low-dose CT are false positives, CAPP-Seq can also serve as a complementary noninvasive screening test.

In this study, we present CAPP-Seq as a new method for ctDNA quantitation. Key features of our approach include high sensitivity and specificity, coverage of nearly all patients with NSCLC, lack of patient-specific optimization, and low cost. By incorporating optimized library construction and bioinformatics methods, CAPP-Seq achieves the lowest background error rate and lowest detection limit of any NGS-based method used for ctDNA analysis to date. Our approach also reduces the potential impact of stochastic noise and biological variability (e.g., mutations near the detection limit or subclonal tumor evolution) on tumor burden quantitation by integrating information content across multiple instances and classes of somatic mutations. These features facilitated the detection of minimal residual disease and the first report of ctDNA quantitation from stage I NSCLC tumors using deep sequencing. Although we focused on NSCLC, our method can be applied to any malignancy for which recurrent mutation data are available.

In many patients, levels of ctDNA are considerably lower than the detection thresholds of previously described sequencing-based methods. For example, pre-treatment ctDNA concentration is <0.5% in the majority of patients with lung and colorectal carcinomas (and likely others), and <0.1% in most early and many advanced stage patients. Following therapy, ctDNA concentrations typically drop, rendering highly sensitive methods, like CAPP-Seq, even more critical. Recently, amplicon-based deep sequencing methods were implemented to detect up to 6 recurrently mutated genes per assay. Such approaches are limited by the number and types of mutations that can be simultaneously interrogated, and the reported allele detection limit of ~2% in plasma precludes ctDNA detection in most NSCLC patients. Several studies have reported application of whole exome or genome sequencing to cfDNA for analysis of somatic SNVs (single nucleotide variant) and CNVs (copy number variant). The sensitivity of SNV detection with these approaches is significantly limited by cost of sequencing, and even with 10-fold greater sequencing depth than we used for CAPP-Seq, would be insufficient to detect ctDNA in most NSCLC patients (FIG. 5*a*). Likewise, quantitation of CNVs in plasma via WGS has a reported detection limit of ~1%, limiting this approach to patients with high tumor burden.

Additional gains in the detection threshold are desirable. Approaches to achieve these gains include using barcoding strategies that suppress PCR errors resulting from library preparation, increasing the amount of plasma used for ctDNA analysis above the average of ~1.5 mL used in this study, further improving ligation and capture efficiency during library preparation, and increasing the size of the selector to increase the number of tumor-specific mutations per patient. A second limitation is the potential for inefficient capture of fusions, which could lead to underestimates of tumor burden (e.g., P9). However, this bias can be analytically addressed when other reporter types are present (e.g., P6; Table 4). Finally, while we found that CAPP-Seq could quantitate CNVs, our current selector design did not prioritize these types of aberrations. Adding coverage for certain CNVs can be useful for monitoring various types of cancers.

In summary, targeted hybrid capture and high-throughput sequencing of cfDNA allows for highly sensitive and non-invasive detection of ctDNA in cancer patients, at low cost. CAPP-Seq can be routinely applied clinically for accelerating the personalized detection, therapy, and monitoring of cancer. CAPP-Seq is valuable in a variety of clinical settings, including the assessment of cancer DNA in alternative biological fluids and specimens with low cancer cell content.

Patient Selection. Between April 2010 and June 2012, patients undergoing treatment for newly diagnosed or recurrent NSCLC were enrolled in a study approved by the Stanford University Institutional Review Board and provided informed consent. Enrolled patients had not received blood transfusions within 3 months of blood collection. Patient characteristics are in Tables 3, 20 and 21. All treatments and radiographic examinations were performed as part of standard clinical care. Volumetric measurements of tumor burden were based on visible tumor on CT and calculated according to the ellipsoid formula: (length/2)*(width^2).

Sample Collection and Processing. Peripheral blood from patients was collected in EDTA Vacutainer tubes (BD). Blood samples were processed within 3 hours of collection. Plasma was separated by centrifugation at 2,500×g for 10 min, transferred to microcentrifuge tubes, and centrifuged at 16,000×g for 10 min to remove cell debris. The cell pellet from the initial spin was used for isolation of germline genomic DNA from PBLs (peripheral blood leukocytes) with the DNeasy Blood & Tissue Kit (Qiagen). Matched tumor DNA was isolated from FFPE specimens or from the cell pellet of pleural effusions. Genomic DNA was quantified by Quant-iT PicoGreen dsDNA Assay Kit (Invitrogen).

Cell-free DNA Purification and Quantification. Cell-free DNA (cfDNA) was isolated from 1-5 mL plasma with the QIAamp Circulating Nucleic Acid Kit (Qiagen). The concentration of purified cfDNA was determined by quantitative PCR (qPCR) using an 81 bp amplicon on chromosome 1 and a dilution series of intact male human genomic DNA (Promega) as a standard curve. Power SYBR Green was used for qPCR on a HT7900 Real Time PCR machine (Applied Biosystems), using standard PCR thermal cycling parameters.

Illumina NGS Library Construction. Indexed Illumina NGS libraries were prepared from cfDNA and shorn tumor, germline, and cell line genomic DNA. For patient cfDNA, 7-32 ng DNA were used for library construction without additional fragmentation. For tumor, germline, and cell line genomic DNA, 69-1000 ng DNA was sheared prior to library construction with a Covaris S2 instrument using the recommended settings for 200 bp fragments. See Table 2 for details.

The NGS libraries were constructed using the KAPA Library Preparation Kit (Kapa Biosystems) employing a DNA Polymerase possessing strong 3'-5' exonuclease (or proofreading) activity and displaying the lowest published error rate (e.g. highest fidelity) of all commercially available B-family DNA polymerases. The manufacturer's protocol was modified to incorporate with-bead enzymatic and cleanup steps using Agencourt AMPure XP beads (Beckman-Coulter). Ligation was performed for 16 hours at 16° C. using 100-fold molar excess of indexed Illumina TruSeq adapters. Single-step size selection was performed by adding 40 μL (0.8×) of PEG buffer to enrich for ligated DNA fragments. The ligated fragments were then amplified using 500 nM Illumina backbone oligonucleotides and 4-9 PCR cycles, depending on input DNA mass. Library purity and concentration was assessed by spectrophotometer (Nano- Drop 2000) and qPCR (KAPA Biosystems), respectively. Fragment length was determined on a 2100 Bioanalyzer using the DNA 1000 Kit (Agilent).

Design of Library for Hybrid Selection. Hybrid selection was performed with a custom SeqCap EZ Choice Library (Roche NimbleGen). This library was designed through the NimbleDesign portal (v1.2.R[1]) using genome build HG19 NCBI Build 37.1/GRCh37 and with Maximum Close Matches set to 1. Input genomic regions were selected according to the most frequently mutated genes and exons in NSCLC. These regions were identified from the COSMIC database, TCGA, and other published sources. Final selector coordinates are provided in Table 1.

Hybrid Selection and High Throughput Sequencing. NimbleGen SeqCap EZ Choice was used according to the manufacturer's protocol with modifications. Between 9 and 12 indexed Illumina libraries were included in a single capture reaction. Following hybrid selection, the captured DNA fragments were amplified with 12 to 14 cycles of PCR using 1×KAPA HiFi Hot Start Ready Mix and 2 μM Illumina backbone oligonucleotides in 4 to 6 separate 50 μL reactions. The reactions were then pooled and processed with the QIAquick PCR Purification Kit (Qiagen). Multiplexed libraries were sequenced using 2×100 bp pared-end runs on an Illumina HiSeq 2000.

Mapping and Quality Control of NGS Data. Paired-end reads were mapped to the hg19 reference genome with BWA 0.6.2 (default parameters), and sorted/indexed with SAMtools. QC was assessed using a custom Perl script to collect a variety of statistics, including mapping characteristics, read quality, and selector on-target rate (e.g., number of unique reads that intersect the selector space divided by all aligned reads), generated respectively by SAMtools flagstat, FastQC, and BEDTools coverageBed, modified to count each read at most once. Plots of fragment length distribution and sequence depth/coverage were automatically generated for visual QC assessment. To mitigate the impact of sequencing errors, analyses not involving fusions were restricted to properly paired reads, and only bases with a Phred quality score ≥30 (≤0.1% probability of a sequencing error) were further analyzed.

Analysis of Detection Thresholds by CAPP-Seq. Two dilution series were performed to assess the linearity and accuracy of CAPP-Seq for quantitating tumor-derived cfDNA. In one experiment, shorn genomic DNA from a NSCLC cell line (HCC78) was spiked into cfDNA from a healthy individual, while in a second experiment, shorn genomic DNA from one NSCLC cell line (NCI-H3122) was spiked into shorn genomic DNA from a second NSCLC line (HCC78). A total of 32 ng DNA was used for library construction. Following mapping and quality control, homozygous reporters were identified as alleles unique to each sample with at least 20× sequencing depth and an allelic fraction >80%. Fourteen such reporters were identified between HCC78 genomic DNA and plasma cfDNA (FIG. 2*g-h*), whereas 24 reporters were found between NCI-H3122 and HCC78 genomic DNA (FIG. 16).

Statistical Analysis. The NSCLC selector was validated in silico using an independent cohort of lung adenocarcinomas (FIG. 1*c*). To assess statistical significance, we analyzed the same cohort using 10,000 random selectors sampled from the exome, each with an identical size distribution to the CAPP-Seq NSCLC selector. The performance of random selectors had a normal distribution, and p-values were calculated accordingly. Note that all identified somatic lesions were considered in this analysis.

Figure 2G:
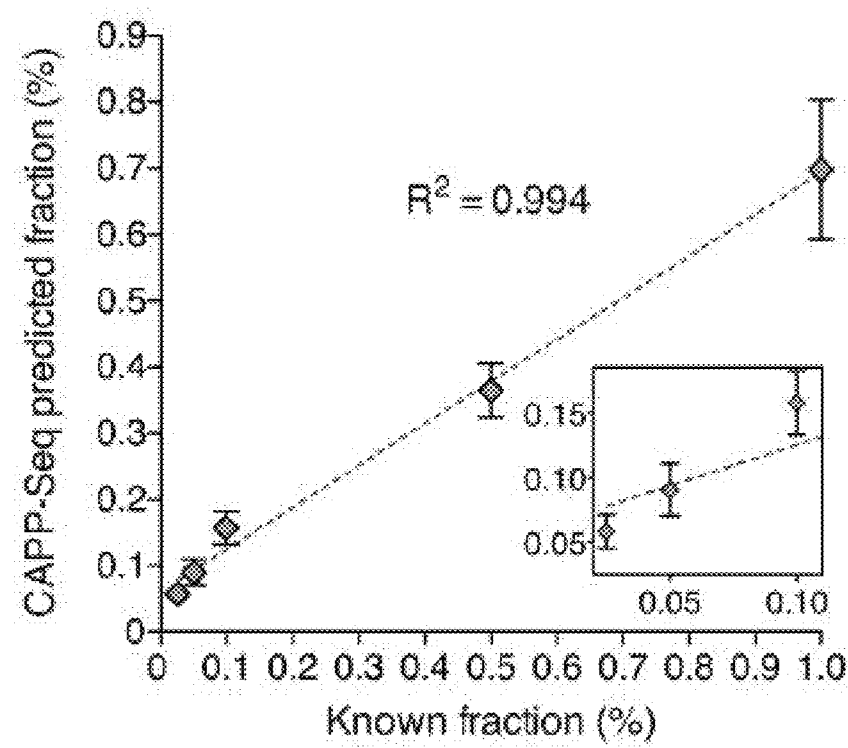
Figure 2H:
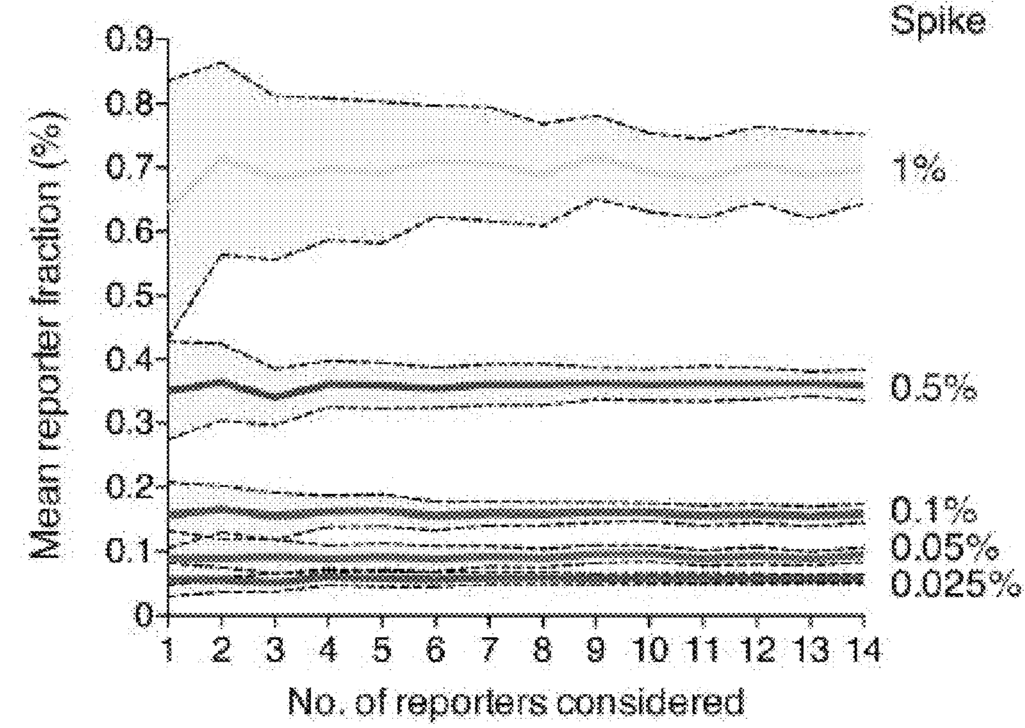
Figure 2I:
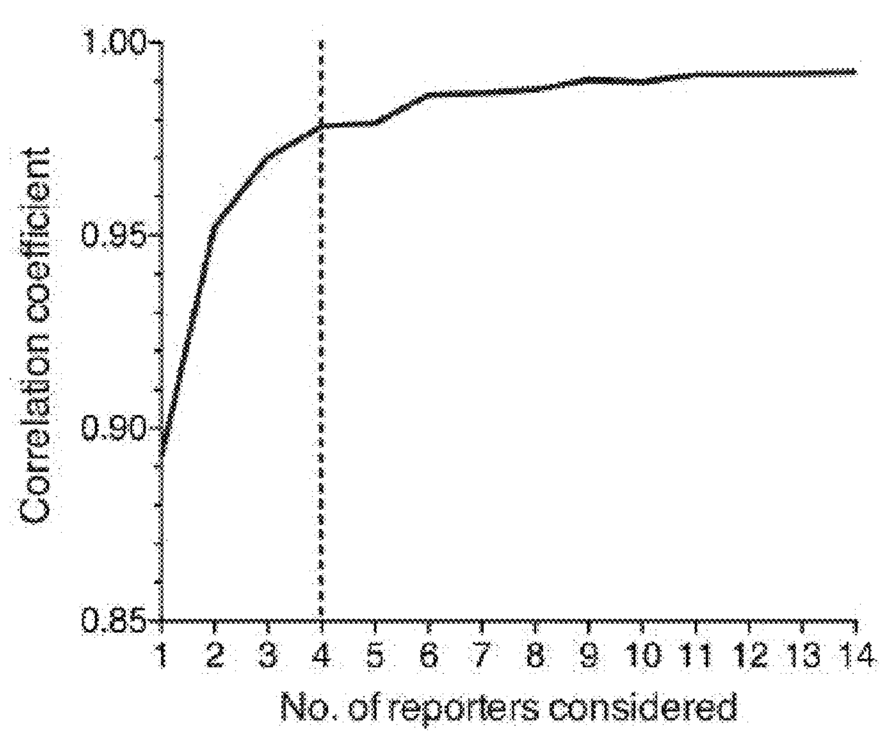

To evaluate the impact of reporter number on tumor burden estimates, we performed Monte Carlo sampling (1,000×), varying the number of reporters available {1, 2, . . . , max n} in two spiking experiments (FIG. 2*g-i*; FIG. 13*b-d*).

To assess the significance of tumor burden estimates in plasma cfDNA, we compared patient-specific SNV frequencies to the null distribution of selector-wide background alleles. Indels were separately analyzed using mutation-specific background rates and Z statistics. Fusion breakpoints were considered significant when present with >0 read support due to their ultra-low false detection rate. p-values from distinct reporter types were integrated into a single ctDNA detection index, and this was considered significant if the metric was ≤0.05 (~FPR≤5%), the threshold that maximized CAPP-Seq sensitivity and specificity in ROC analyses (determined by Euclidean distance to a perfect classifier; e.g., TPR=1 and FPR=0; FIG. 3, FIG. 4, Table 1, Table 4).

Related to FIG. 5, the probability P of recovering at least 2 reads of a single mutant allele in plasma for a given depth and detection limit was modeled by a binomial distribution. Given P, the probability of detecting all identified tumor mutations in plasma (e.g., median of 4 for CAPP-Seq) was modeled by a geometric distribution. Estimates in FIG. 5*a* are based on 250 million 100 bp reads per lane (e.g., using an Illumina HiSeq 2000 platform). Moreover, an on-target rate of 60% was assumed for CAPP-Seq and WES (FIG. 5).

Molecular Biology Methods

Cell Lines. The lung adenocarcinoma cell lines NCI-H3122 and HCC78 were obtained from ATCC and DSMZ, respectively, and grown in RPMI 1640 with L-glutamine (Gibco) supplemented with 10% fetal bovine serum (Gembio) and 1% penicillin/streptomycin cocktail. Cells were maintained in mid-log-phase growth in a 37° C. incubator with 5% $CO_2$. Genomic DNA was purified from freshly harvested cells with the DNeasy Blood & Tissue Kit (Qiagen).

Pleural Fluid Processing and Flow Cytometry, and Cell Sorting. Cells from pleural fluid from patients P9 and P6 were harvested by centrifugation at 300×g for 5 min at 4° C. and washed in FACS staining buffer (HBSS+2% heat-inactivated calf serum [HICS]). Red blood cells were lysed with ACK Lysing Buffer (Invitrogen), and clumps were removed by passing through a 100 μm nylon filter. Filtered cells were spun down and resuspended in staining buffer. While on ice, the cell suspension was blocked for 20 min with 10 μg/mL rat IgG and then stained for 20 min with APC-conjugated mouse anti-human EpCAM (BioLegend, clone 9C4), PerCP-Cy5.5-conjugated mouse anti-human CD45 (eBioscience, clone 2D1), and PerCP-eFluor710-conjugated mouse anti-human CD31 (eBioscience, clone WM59). After staining, cells were washed and resuspended with staining buffer containing 1 μg/mL DAPI, analyzed, and sorted with a FACSAria II cell sorter (BD Biosciences). Cell doublets and DAPI-positive cells were excluded from analysis and sorting. $CD31^-CD45^-EpCAM^+$ cells were sorted into staining buffer, spun down, and flash frozen in liquid nitrogen. DNA was isolated with the QIAamp DNA Micro Kit (Qiagen).

Optimization of NGS Library Preparation from Low Input cfDNA. Protocols for Illumina library construction were compared in a step-wise manner with the goal of (1) optimizing adapter ligation efficiency, (2) reducing the necessary number of PCR cycles following adapter ligation, (3) preserving the naturally occurring size distribution of cfDNA fragments, and (4) minimizing variability in depth of sequencing coverage across all captured genomic regions. Initial optimization was done with NEBNext DNA Library Prep Reagent Set for Illumina (New England BioLabs), which includes reagents for end-repair of the cfDNA fragments, A-tailing, adapter ligation, and amplification of ligated fragments with Phusion High-Fidelity PCR Master Mix. Input was 4 ng cfDNA (obtained from plasma of the same healthy volunteer) for all conditions. Relative allelic abundance in the constructed libraries was assessed by qPCR of 4 genomic loci (Roche NimbleGen: NSC-0237, NSC-0247, NSC-0268, and NSC-0272) and compared by the $2^{-\Delta Ct}$ method.

Ligations were performed at 20° C. for 15 min (as per the manufacturer's protocol), at 16° C. for 16 hours, or with temperature cycling for 16 hours as previously described. Ligation volumes were varied from the standard (50 μL) down to 10 μL while maintaining a constant concentration of DNA ligase, cfDNA fragments, and Illumina adapters. Subsequent optimizations incorporated ligation at 16° C. for 16 hours in 50 μL reaction volumes.

Next, we compared standard SPRI bead processing procedures, in which new AMPure XP beads are added after each enzymatic reaction and DNA is eluted from the beads for the next reaction, to with-bead protocol modifications as previously described[3]. We compared 2 concentrations of Illumina adapters in the ligation reaction: 12 nM (10-fold molar excess to cfDNA fragments) and 120 nM (100-fold molar excess).

Using the optimized library preparation procedures, we next compared the NEBNext DNA Library Prep Reagent Set (with Phusion DNA Polymerase) to the KAPA Library Preparation Kit (with KAPA HiFi DNA Polymerase). The KAPA Library Preparation Kit with our modifications was also compared to the NuGEN SP Ovation Ultralow Library System with automation on Mondrian SP Workstation.

Evaluation of Library Preparation Modifications on CAPP-Seq Performance. We performed CAPP-Seq on 32 ng cfDNA using standard library preparation procedures with the NEBNext kit, or with optimized procedures using either the NEBNext kit or the KAPA Library Preparation Kit. In parallel we performed CAPP-Seq on 4 ng and 128 ng cfDNA using the KAPA kit with our optimized procedures. Indexed libraries were constructed, and hybrid selection was performed in multiplex. The post-capture multiplexed libraries were amplified with Illumina backbone primers for 14 cycles of PCR and then sequenced on a paired-end 100 bp lane of an Illumina HiSeq 2000.

We also evaluated CAPP-Seq on ultralow input following whole genome amplification (WGA). We used SeqPlex DNA Amplification Kit (Sigma-Aldrich), which employs degenerate oligonucleotide primer PCR. Briefly, 1 ng cfDNA was amplified with real-time monitoring with SYBR Green I (Sigma-Aldrich) on a HT7900 Real Time PCR machine (Applied Biosystems). Amplification was terminated after 17 cycles yielding 2.8 μg DNA. The primer removal step yielded ~600 ng DNA, and this entire amount was used for library preparation using the NEBNext kit with optimized procedures as described herein.

Validation of Variants Detected by CAPP-Seq. All structural rearrangements and a subset of tumoral SNVs detected by CAPP-Seq were independently confirmed by qPCR and/or Sanger sequencing of amplified fragments. For HCC78, a 120 bp fragment containing the SLC34A2-ROS1 breakpoint was amplified from genomic DNA using the primers: 5'-AGACGGGAGAAAATAGCACC-3' (SEQ ID NO: 23) and 5'-ACCAAGGGTTGCAGAAATCC-3' (SEQ ID NO: 24). For NCI-H3122, a 143 bp fragment containing the EML4-ALK breakpoint was amplified using the primers: 5'-GAGATGGAGTTTCACTCTTGTTGC-3' (SEQ ID NO: 25) and 5' GAACCTTTCCATCATACTTAGAAATAC-3' (SEQ ID NO: 26). 5 ng genomic DNA was used as template with 250 nM oligos and 1× Phusion PCR Master Mix (NEB) in 50 μL reactions. Products were resolved on 2.5% agarose gel and bands of the expected size were removed. The amplified DNA fragments were purified using the Qiaquick Gel Extraction Kit (Qiagen) and submitted for Sanger sequencing (Elim Biopharm). For P9, genomic DNA breakpoints were confirmed by qPCR using the primers: 5'-TCCATGGAAGCCAGAAC-3' (SEQ ID NO: 27) and 5'-ATGCTAAGATGTGTCTGTCA-3' (SEQ ID NO: 28) for EML4-ALK; 5'-CCTTAACACAGATGGCTCTTGATGC-3' (SEQ ID NO: 29) and 5'-TCCTCTTTCCACCTTGGCTTTCC-3' (SEQ ID NO: 30) for ROS1-MKX; and 5'-GGTTCAGAACTACCAATAACAAG-3' (SEQ ID NO: 31) and 5' ACCTGATGTGTGACCTGATTGATG-3' (SEQ ID NO: 32) for FYN-ROS1. For qPCR, 10 ng of pre-amplified genomic DNA was used as template with 250 nM oligos and 1× Power SyberGreen Master Mix in 10 μL reactions performed in triplicate on a HT7900 Real Time PCR machine (Applied Biosystems). Standard PCR thermal cycling parameters were used. Amplification of amplicons spanning all 3 breakpoints detected in P9 were confirmed in tumor genomic DNA as well as plasma cfDNA, and PBL genomic DNA was used as a negative control.

CAPP-Seq confirmed somatic tumor mutations (SNVs and rearrangements) that were detected by clinical assays as a part of standard clinical care (Tables 3, 20 and 21). Clinical mutation assays were performed on formalin-fixed paraffin-embedded tissues. SNVs were detected by the SNAPshot assay[4]. Rearrangements were detected by fluorescence in situ hybridization (FISH) using separation probes targeting the ALK locus (Abbott) or ROS1 locus (Cytocell).

Bioinformatics and Statistical Methods

CAPP-Seq Detection Threshold Metrics. Selector base-level background. We assessed the base-level background distribution of the NSCLC selector (FIG. 2*d*) using all 40 plasma cfDNA samples collected from NSCLC and healthy individuals analyzed in this work (Table 2). Specifically, for each background base in selector positions having ≥500× overall sequencing depth, the outlier-corrected mean across all cfDNA samples was calculated. Although we tested dedicated outlier detection methods, such as iterative Grubbs' method and ROUT, our empirical analyses indicated that simple removal of the minimum and maximum values worked best. Importantly, to restrict our analysis to background bases, each patient sample was pre-filtered to remove germline, loss of heterozygosity (LOH), and/or somatic variant calls made by VarScan 2[6] (somatic p-value=0.01; otherwise, default parameters).

Significance of SNVs as reporters. To evaluate the significance of tumor-derived SNVs in plasma, we implemented a strategy that integrates cfDNA fractions across all somatic SNVs, performs a position-specific background adjustment, and evaluates statistical significance by Monte Carlo sampling of background alleles across the selector. We note that this approach differs fundamentally from previous methods, where mutations are interrogated individually. Unlike these methods, our strategy dampens the impact of stochastic noise and biological variables (e.g., mutations near the detection limit, or tumor evolution) on tumor burden quantitation, permitting a more robust statistical assessment. In particular, this allows CAPP-Seq to quantitate low levels of ctDNA with potentially high rates of allelic drop out.

For a given plasma cfDNA sample θ, we begin by adjusting the allelic fraction f for each of n SNVs from patient P in order to minimize the influence of selector technical/biological background on significance estimates. Specifically, for each allele, we perform the following simple operation, $f^*=\max\{0, f-(e-\mu)\}$, where f is the raw allelic fraction in plasma cfDNA, e is the position-specific error rate for the given allele across all cfDNA samples (see above), and μ denotes the mean selector-wide background rate (=0.006% in this study, see section B1.1 and FIG. 2*d*). In effect, this adjustment nudges the mean of all n SNVs closer to the global selector mean μ, mitigating the confounding impact of technical/biological background. Using Monte Carlo simulation, we compare the adjusted mean SNV fraction $F^*$ $(=(\Sigma f^*)/n)$ against the null distribution of background alleles across the selector. Specifically, for each of i iterations (=10,000 in this work), n background alleles are randomly sampled from θ, after which their fractions are adjusted using the above formula and averaged. A SNV p-value for patient P is determined as the percentile of $F^*$ with respect to the null distribution of background alleles in θ. Thus, a panel of SNVs from patient P would be assigned a detection p-value of 0.04 if $F^*$ ranks in the $96^{th}$ percentile of adjusted background alleles in θ. We note that background adjustment always improved CAPP-Seq specificity in our ROC analyses.

Significance of indels as reporters. We implemented an approach based on population statistics to assess the significance of indels separately from SNVs. For each indel in patient P, we use the Z-test to compare its fraction in a given plasma cfDNA sample θ against its fraction in every cfDNA sample in our cohort (excluding cfDNA samples from the same patient P). To increase statistical robustness, each read strand (positive or negative orientation) is assessed separately, yielding two Z-scores for each indel. These are combined into a single Z-score by Stouffer's method, an unweighted approach for integrative Z statistics. Finally, if patient P has more than 1 indel, all indel-specific Z-scores are combined by Stouffer's method into a final Z statistic, which is trivially converted to a p-value.

Significance of fusions as reporters. Given the exceedingly low false positive rate associated with the detection of the same NSCLC fusion breakpoint in independent libraries, the recovery of a tumor-derived genomic fusion in plasma cfDNA by CAPP-Seq was (arbitrarily) assigned a p-value of ~0.

Integration of distinct mutation types to estimate significance of tumor burden quantitation. For each patient, we calculate a ctDNA detection index (akin to a false positive rate) based on p-value integration from his or her array of reporters (Table 1 and Table 19). For cases where only a single reporter type is present in a patient's tumor, the corresponding p-value is used. If SNV and indel reporters are detected, and if each independently has a p-value <0.1, we combine their respective p-values by Fisher's method (Fisher, 1925), and the resulting p-value is used. Otherwise, given the prioritization of SNVs in the selector design, the SNV p-value is used. If a fusion breakpoint identified in a tumor sample (e.g., involving ROS1, ALK, or RET) is recovered in plasma cfDNA from the same patient, it trumps all other mutation types, and its p-value (~0) is used. If a fusion detected in the tumor is not found in corresponding plasma (potentially due to hybridization inefficiency; see section C4), the p-value for any remaining mutation type(s) is used. Importantly, as new patients are processed, we cross check reporter types across the growing sample database to improve specificity (described in section B1.6, below) and identify potential red flags.

Indel/fusion correction for sensitivity and specificity assessment. Related to FIG. 3, after calculating a ctDNA detection index for every set of reporters across all cfDNA samples using the methods described herein, we applied an additional step to increase specificity. Namely, to exploit the lower technical background of indels and fusion breakpoints as compared to SNVs, we applied an "indel/fusion correction". Specifically, if indel/fusion reporters found in patient X's tumor could be uniquely detected in patient X's plasma cfDNA (e.g., not detected in any other patient or control cfDNA sample), then the ctDNA detection index corresponding to patient X was set to 1 (e.g., ctDNA not detectable) in every unmatched cfDNA sample. In other words, patient X's reporters would not be called a false positive in another patient. Although we have not yet encountered two patients with the same indel/fusion reporter(s), if this was the case, the correction would not be applied from one patient to the other.

To perform this correction in a blinded manner, as shown for FIG. 3 (panels a and b), we identified germline SNPs in each cfDNA and PBL sample, and assigned each cfDNA sample to the tumor/normal pair with highest SNP concordance (after un-blinding, all cfDNA samples were found to be correctly matched to their corresponding tumor/normal pairs). As shown in FIG. 19, this correction consistently increased CAPP-Seq specificity. Germline SNPs were identified using VarScan 2, with a p-value threshold of 0.01, minimum sequence coverage of 100×, a minimum average quality score of 30 (Phred), and otherwise default parameters.

Sensitivity and Specificity Analysis. We tested CAPP-Seq performance in a blinded fashion by masking all patient identifying information, including disease stage, cfDNA time point, treatment, etc. We then tested our detection metrics described herein for correctly calling tumor burden across the entire grid of de-identified plasma cfDNA samples (13 patient-specific sets of somatic reporters across 40 plasma samples, or 520 pairs). To calculate sensitivity and specificity, we "un-blinded" ourselves and grouped patient samples into cancer-positive (e.g. cancer was present in the patient's body), cancer-negative (e.g. patient was cured), or cancer-unknown (e.g. insufficient data to determine true classification) categories. We considered every time point of patients with radiographic evidence of recurrence and all stage IV patients as cancer-positive, regardless of clinical evaluation at the time point in question. The post-treatment time point of patient 13 (P13; stage IIB NSCLC) was considered cancer-unknown due to "No Evidence of Disease (NED)" status at last follow-up, nearly 2 years from their treatment (FIG. 4*e*). Patient 2 (P2; stage IIIB NSCLC), was classified as NED following complete surgical resections, and was also considered cancer-unknown. All post-treatment stage I NSCLC patient samples were conservatively considered "cancer unknown" rather than true negatives due to limited follow-up.

Analysis of Library Complexity

Library complexity estimation. We estimated the number of haploid genome equivalents per library using 330 genome equivalents per lng of input DNA (Table 2), and calculated overall 'molecule recovery' as the median depth after duplicate removal divided by the smaller of (i) the median depth before duplicate removal and (ii) the estimated number of haploid genome equivalents. Molecule recovery at a given sequencing depth was estimated to be 38% for cfDNA, 37% for tumor DNA, and 48% for PBLs (highest DNA input mass among all samples).

In contrast to genomic DNA, plasma cfDNA is naturally fragmented and has a highly stereotyped size distribution related to nucleosome spacing, with a median length of ~170 bp and very low dispersion (FIG. 2*a*, Tables 3, 20 and 21). As such, we hypothesized that independent input molecules with identical start/end coordinates may inflate the duplication rate of cfDNA, leading to an underestimated molecule recovery rate.

We tested this hypothesis by analyzing heterozygous germline SNPs, reasoning that DNA fragments (e.g., paired end reads) with identical start/end coordinates and differing by a single a priori defined germline variant are more likely to represent independent starting molecules than technical artifacts (e.g., PCR duplicates). Heterozygous SNPs were identified in all ninety samples (Table 2) using VarScan 2 (as described herein), and filtered for variants with an allele frequency between 40% and 60% that are present in the Common SNPs subset of dbSNP (version 137.0). For each heterozygous common SNP, A/B, we counted all fragments with unique start/end coordinates that support A, B, or AB. Among molecules with a given A/B SNP, there is a 50% chance of getting A and B together when randomly sampling two molecules (AB or BA), and there is a combined 50% chance of getting either AA or BB. Since the number of unique start/end positions for AB (denoted N) represents at least twice as many molecules (≥2N), and a combined ≥2N molecules can be assumed missing from unique start/end coordinates that support A or B, a lower bound on total missing library complexity is determined by the formula, 3N/S, where S denotes the sum of unique start/end coordinates covering A, B, and AB. Across SNPs in each input sample, we calculated an average of 30% missing library complexity in cfDNA samples, and 4% and 6% missing library complexity in tumor and PBL genomic DNA, respectively (FIG. 13*a*). Molecule recovery rates adjusted for estimated loss of complexity are provided in Table 2, and indicate a mean molecule recovery of at least 49% in cfDNA, 37% in tumor genomic DNA (mostly FFPE) and 51% in PBL genomic DNA.

Duplication rate. Common deduping tools, such as SAMtools rmdup and Picard tools MarkDuplicates (picard.sourceforge.net), identify and/or collapse reads based on sequence coordinates and quality, not sequence composition. This can result in the removal of tumor-derived reads (representing distinct molecules) that happen to share sequence coordinates with germline reads. This is particularly problematic for cfDNA since for a large fraction of molecules there are other unique molecules with the same start and end (see above). To address this issue, we developed a custom Perl script that ignores bases with low quality (here, Phred Q<30), and collapses only those fragments (read pairs) with 100% sequence identity that also share genomic coordinates. The resulting post-duplicate reads are provided alongside corresponding non-deduped data in Tables 2 and 4, which respectively cover sequencing statistics and cfDNA monitoring results.

Library complexity measured via PCR and mass input. As a separate estimation of library complexity, for each Illumina NGS library constructed from cfDNA, we calculated the fraction of expected library yield from the actual yield and the expected (ideal) yield (FIG. 13*b*). The actual library yield was determined from the molarity and volume of the constructed libraries (prior to hybrid selection). The expected library yield was calculated from the mass of cfDNA used for library preparation and the number of PCR cycles performed, with the assumption that ligation was 100% efficient and PCR was 95% efficient at each cycle. A PCR efficiency of 95% was observed from qPCR performed on serial dilutions of Illumina TruSeq libraries (average of $R^2$>0.999 from 4 independent experiments).

CAPP-Seq Selector Design. Most human cancers are relatively heterogeneous for somatic mutations in individual genes. Specifically, in most human tumors, recurrent somatic alterations of single genes account for a minority of patients, and only a minority of tumor types can be defined using a small number of recurrent mutations (<5-10) at predefined positions. Therefore, the design of the selector is vital to the CAPP-Seq method because (1) it dictates which mutations can be detected in with high probability for a patient with a given cancer, and (2) the selector size (in kb) directly impacts the cost and depth of sequence coverage. For example, the hybrid selection libraries available in current whole exome capture kits range from 51-71 Mb, providing ~40-60 fold maximum theoretical enrichment versus whole genome sequencing. The degree of potential enrichment is inversely proportional to the selector size such that for a ~100 kb selector, >10,000 fold enrichment should be achievable.

We employed a six-phase design strategy to identify and prioritize genomic regions for the CAPP-Seq NSCLC selector as detailed below. Three phases were used to incorporate known and suspected NSCLC driver genes, as well as genomic regions known to participate in clinically actionable fusions (phases 1, 5, 6), while another three phases employed an algorithmic approach to maximize both the number of patients covered and SNVs per patient (phases 2-4). The latter relied upon a metric that we termed "Recurrence Index" (RI), defined for this example as the number of NSCLC patients with SNVs that occur within a given kilobase of exonic sequence (e.g., No. of patients with mutations/exon length in kb). RI thus serves to measure patient-level recurrence frequency at the exon level, while simultaneously normalizing for gene/exon size. As a source of somatic mutation data uniformly genotyped across a large cohort of patients, in phases 2-4, we analyzed non-silent SNVs identified in TCGA whole exome sequencing data from 178 patients in the Lung Squamous Cell Carcinoma dataset (SCC) and from 229 patients in the Lung Adenocarcinoma (LUAD) datasets (TCGA query date was Mar. 13, 2012).

Thresholds for each metric (e.g. RI and patients per exon) were selected to statistically enrich for known/suspected drivers in SCC and LUAD data (FIG. 7). RefSeq exon coordinates (hg19) were obtained via the UCSC Table Browser (query date was Apr. 11, 2012).

The following algorithm was used to design the CAPP-Seq selector (parenthetical descriptions match design phases noted in FIG. 1*b*).

Phase 1 (Known Drivers)

Initial seed genes were chosen based on their frequency of mutation in NSCLCs. Analysis of COSMIC (v57) identified known driver genes that are recurrently mutated in ≥9% of NSCLC (denominator ≥500 cases). Specific exons from these genes were selected based on the pattern of SNVs previously identified in NSCLC. The seed list also included single exons from genes with recurrent mutations that occurred at low frequency but had strong evidence for being driver mutations, such as BRAF exon 15, which harbors V600E mutations in <2% of NSCLC.

Phase 2 (Max. Coverage)

For each exon with SNVs covering ≥5 patients in LUAD and SCC, we selected the exon with highest RI that identified at least 1 new patient when compared to the prior phase. Among exons with equally high RI, we added the exon with minimum overlap among patients already captured by the selector. This was repeated until no further exons met these criteria.

Phase 3 (RI≥30)

For each remaining exon with an RI≥30 and with SNVs covering ≥3 patients in LUAD and SCC, we identified the exon that would result in the largest reduction in patients with only 1 SNV. To break ties among equally best exons, the exon with highest RI was chosen. This was repeated until no additional exons satisfied these criteria.

Phase 4 (RI≥20)

Same procedure as phase 3, but using RI≥20.

Phase 5 (Predicted Drivers)

We included all exons from additional genes previously predicted to harbor driver mutations in NSCLC.

Phase 6 (Add fusions)

For recurrent rearrangements in NSCLC involving the receptor tyrosine kinases ALK, ROS1, and RET, the introns most frequently implicated in the fusion event and the flanking exons were included.

All exons included in the selector, along with their corresponding HUGO gene symbols and genomic coordinates, as well as patient statistics for NSCLC and a variety of other cancers, are provided in Table 1, organized by selector design phase.

CAPP-Seq Computational Pipeline

Mutation Discovery: SNVs/indels. For detection of somatic SNV and insertion/deletion events, we employed VarScan 2 (somatic p-value=0.01, minimum variant frequency=5%, strand filter=true, and otherwise default parameters). Somatic variant calls (SNV or indel) present at less than 0.5% mutant allelic frequency in the paired normal sample (PBLs), but in a position with at least 1000× overall depth in PBLs and 100× depth in the tumor, and with at least 1× read depth on each strand, were retained (Tables 3, 20 and 21). While the selector was designed to predominantly capture exons, in practice, it also captures limited sequence content flanking each targeted region. For instance, this phenomenon is the basis for the (thus far) uniformly successful recovery by CAPP-Seq of fusion partners (which are not included within the selector) for kinase genes such as ALK and ROS1 recurrently rearranged in NSCLC. As such, we also considered variant calls detected within 500 bps of defined selector coordinates. These calls were eliminated if present in non-coding repeat regions, since repeats may confound mapping accuracy. Repeat sequence coordinates were obtained using the RepeatMasker track in the UCSC table browser (hg19). Given a low, but measurable cross-contamination rate of ~0.06% in multiplexed cfDNA samples, (FIG. 14) we also excluded any SNVs found as germline SNPs in samples from the same lane. Additionally, we excluded SNVs in the top 99.9$^{th}$ percentile of global selector background (>0.27% sample-wide background rate; see FIG. 2*d* and section B1.1 above). Finally, we excluded any SNVs not present at a depth of at least 500× in at least 1 cfDNA sample. Variant annotation was automatically downloaded from the SeattleSeq Annotation 137 web server. Complete details for all identified SNVs and indels are provided in Tables 3, 20 and 21. Of note, all depth thresholds refer to pre-duplication removal reads.

Mutation Discovery: Fusions. For practical and robust de novo enumeration of genomic fusion events and breakpoints from paired-end next-generation sequencing data, we developed a novel heuristic approach, termed FACTERA (FACile Translocation Enumeration and Recovery Algorithm). FACTERA has minimal external dependencies, works directly on a preexisting.bam alignment file, and produces easily interpretable output. Major steps of the algorithm are summarized below, and are complemented by a graphical schematic to illustrate key elements of the breakpoint identification process (FIG. 8). FACTERA is coded in Perl and freely available upon request.

As input, FACTERA requires a .bam alignment file of paired-end reads produced by BWA, exon coordinates in .bed format (e.g., hg19 RefSeq coordinates), and a 0.2 bit reference genome to enable fast sequence retrieval (e.g., hg19). In addition, the analysis can be optionally restricted to reads that overlap particular genomic regions (.bed file), such as the CAPP-Seq selector used in this work.

FACTERA processes the input in three sequential phases: identification of discordant reads, detection of breakpoints at base pair-resolution, and in silico validation of candidate fusions. Each phase is described in detail below.

Identification of discordant reads. To iteratively reduce the sequence space for gene fusion identification, FACTERA, like other algorithms (e.g. BreakDancer), identifies and classifies discordant read pairs. Such reads indicate a nearby fusion event since they either map to different chromosomes or are separated by an unexpectedly large insert size (e.g. total fragment length), as determined by the BWA mapping algorithm. The bitwise flag accompanying each aligned read encodes a variety of mapping characteristics (e.g., improperly paired, unmapped, wrong orientation, etc.) and is leveraged to rapidly filter the input for discordant pairs. The closest exon of each discordant read is subsequently identified, and used to cluster discordant pairs into distinct gene-gene groups, yielding a list of genomic regions R adjacent to candidate fusion sites. For each member gene of a discordant gene pair, the genomic region $R_i$ is defined by taking the minimum of all 3' exon/read coordinates in the cluster, and the maximum of all 5' exon/read coordinates in the cluster. These regions are used to prioritize the search for breakpoints in the next phase (FIG. 8*a*).

Detection of breakpoints at base pair-resolution. Discordant read pairs may be introduced by NGS library preparation and/or sequencing artifacts (e.g., jumping PCR). However, they are also likely to flank the breakpoints of bona fide fusion events. As such, all discordant gene pairs identified in the preceding phase are ranked in decreasing order of discordant read depth (duplicate fragments are eliminated to correct for possible PCR bias), and genomic regions with a depth of at least 2× (by default) are further evaluated for potential breakpoints. Within each region, FACTERA analyzes all properly paired reads in which one of the two reads is "soft-clipped," or truncated (see FIG. 8*a*). Soft-clipped reads allow for precise breakpoint determination, and are easily identified by parsing the CIGAR string associated with each mapped read, which compactly specifies the alignment operation used on each base (e.g. My=y contiguous bases were mapped, Sx=x bases were skipped). To simplify this step, only soft-clipped reads with the following two patterns are considered, SxMy and MySx, and the number of skipped bases x is required to be at least 16 (≤1 in 4.3B by random chance) to reduce the impact of non-specific sequence alignments.

Figures 8D, 8E:
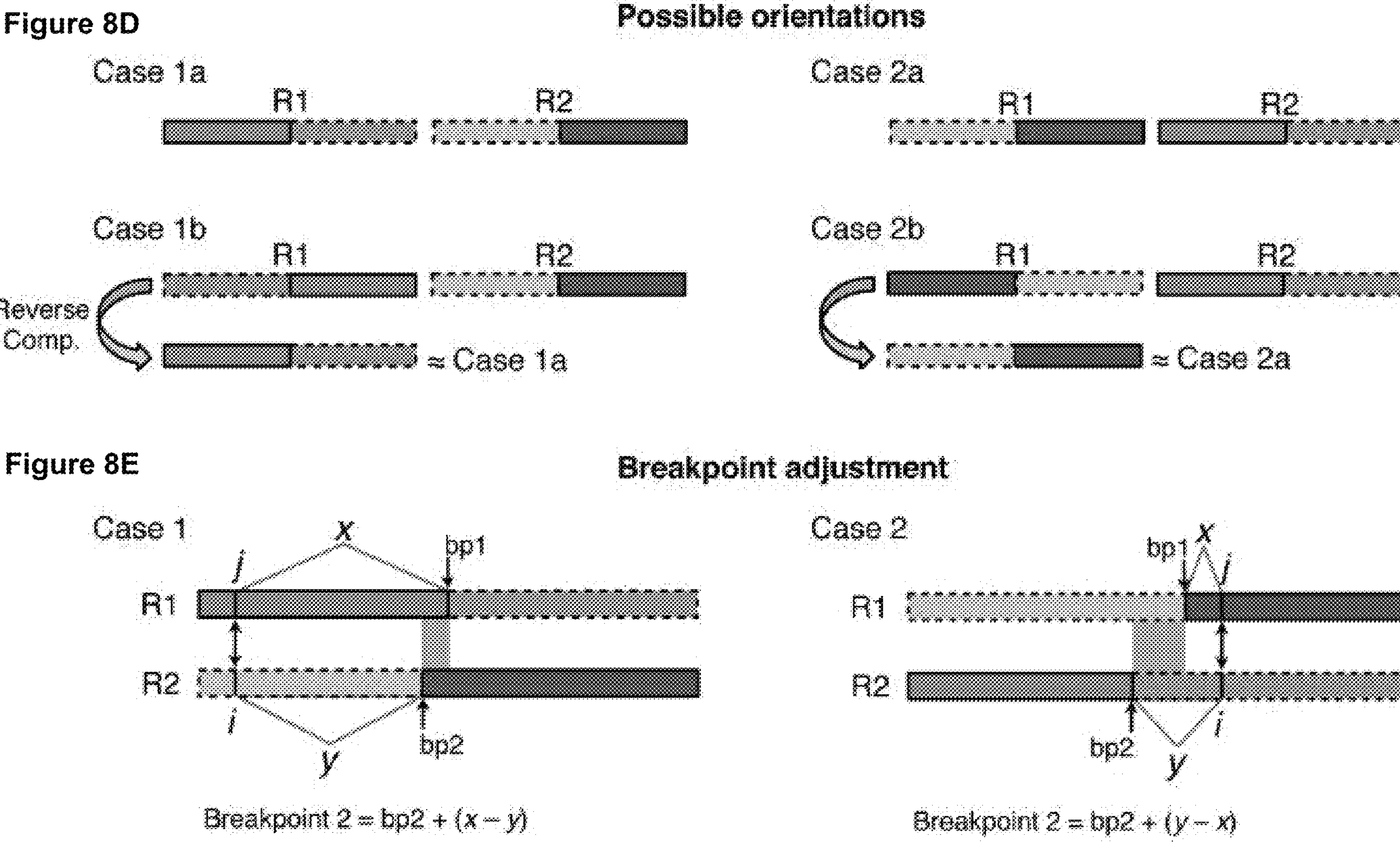
Figure 9A:
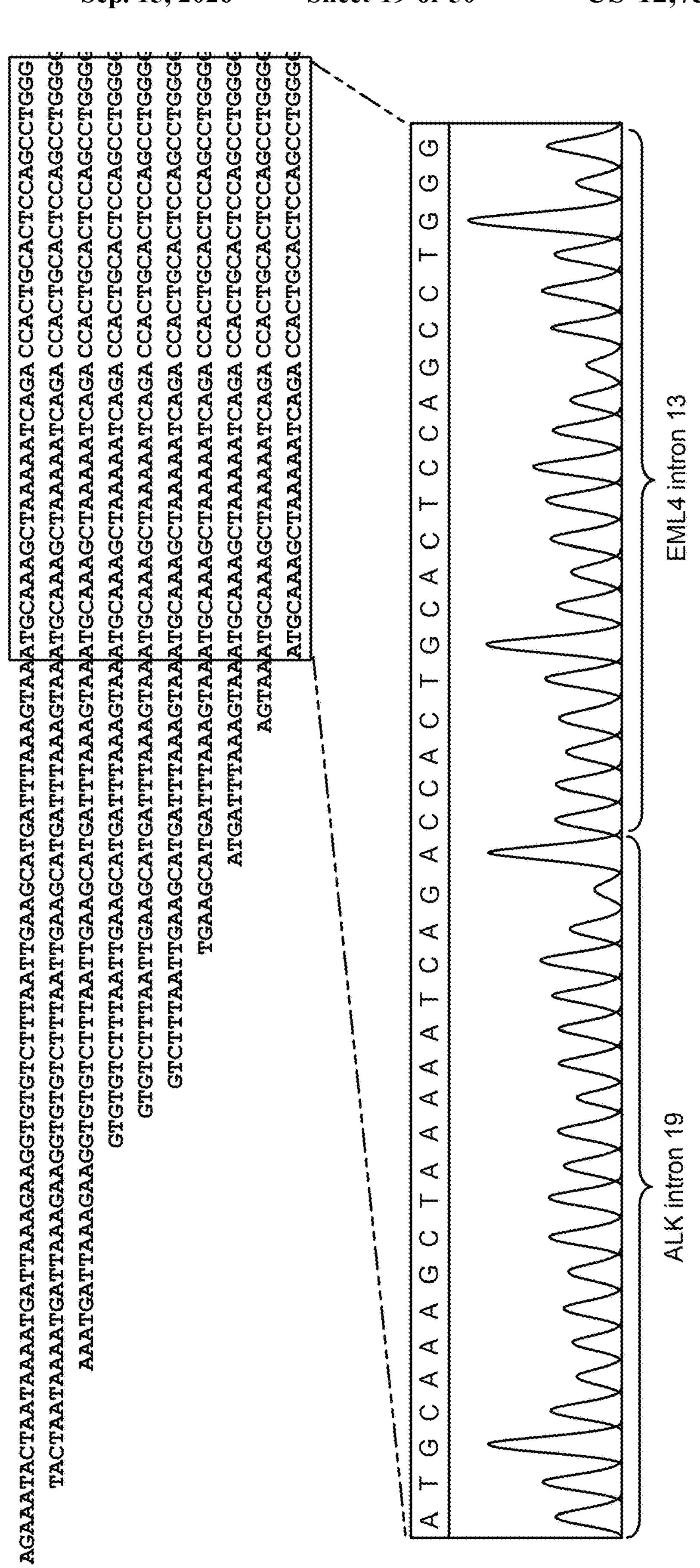
FIG. 9A-9B: Application of FACTERA to NSCLC cell lines NCI-H3122 and HCC78, and Sanger-validation of breakpoints.
Figure 9B:
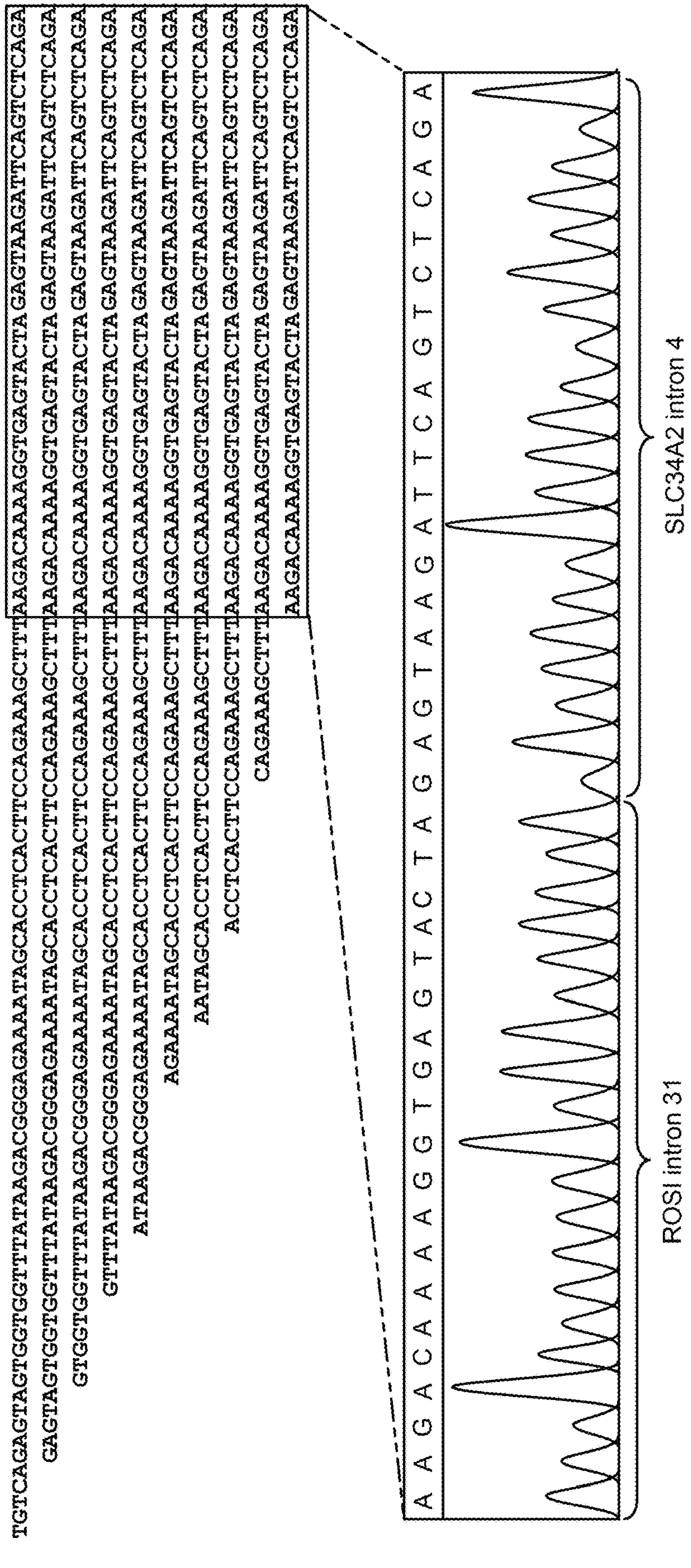
Figure 10A:
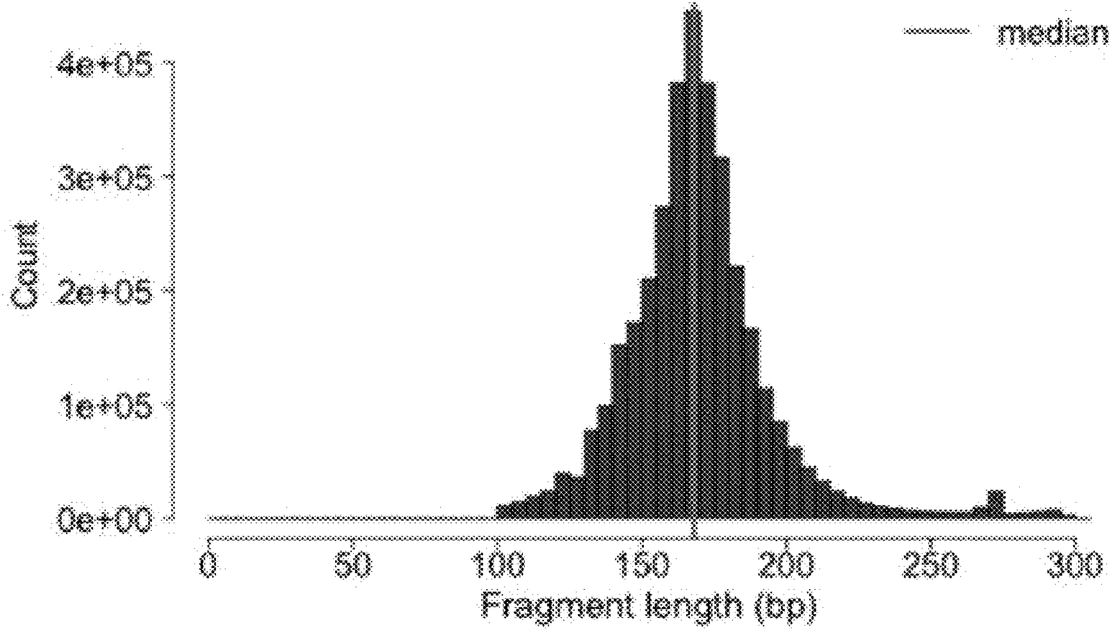
FIG. 10A-10C: Improvements in CAPP-Seq performance with optimized library preparation procedures. Using 32 ng of input cfDNA from plasma, we compared standard versus 'with bead' 5 library preparation methods, as well as two commercially available DNA polymerases (Phusion and KAPA HiFi). We also compared template pre-amplification by Whole Genome Amplification (WGA) using Degenerate Oligonucleotide PCR (DOP). Indices considered for these comparisons included (FIG. 10A) length of the captured cfDNA fragments sequenced, (FIG. 10B) depth and uniformity of sequencing coverage across all genomic regions in the selector, and (FIG. 10C) sequence mapping and capture statistics, including uniqueness. Collectively, these comparisons identified KAPA HiFi polymerase and a "with bead" protocol as having most robust and uniform performance.
Figure 10A:
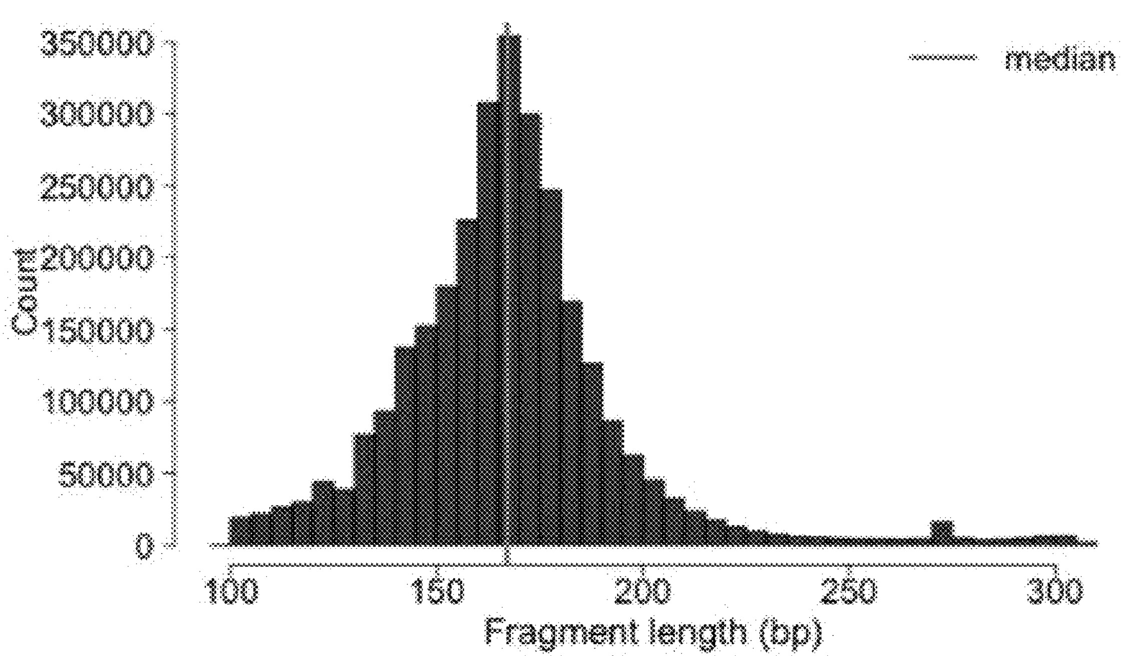
Figure 10A:
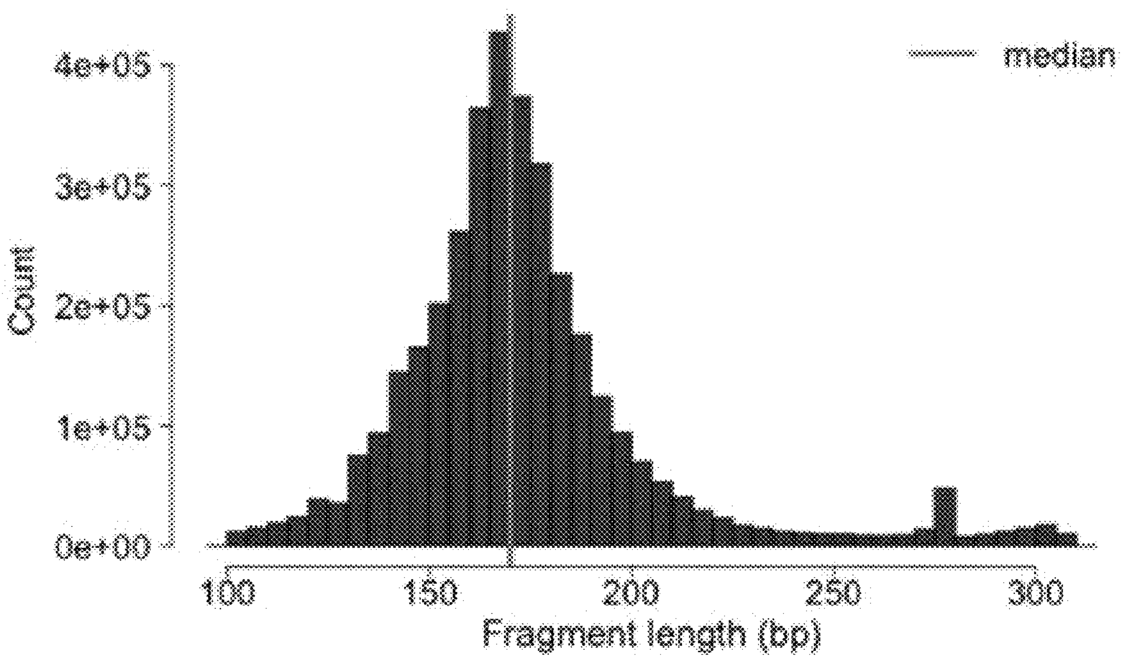
Figure 10A:
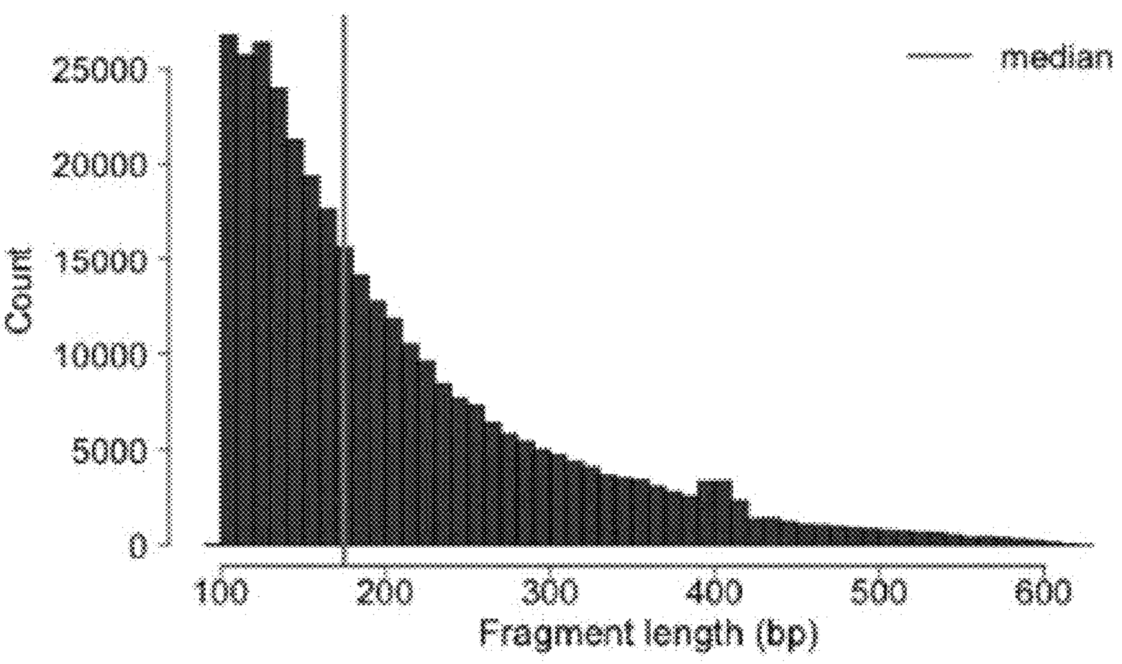
Figure 10B:
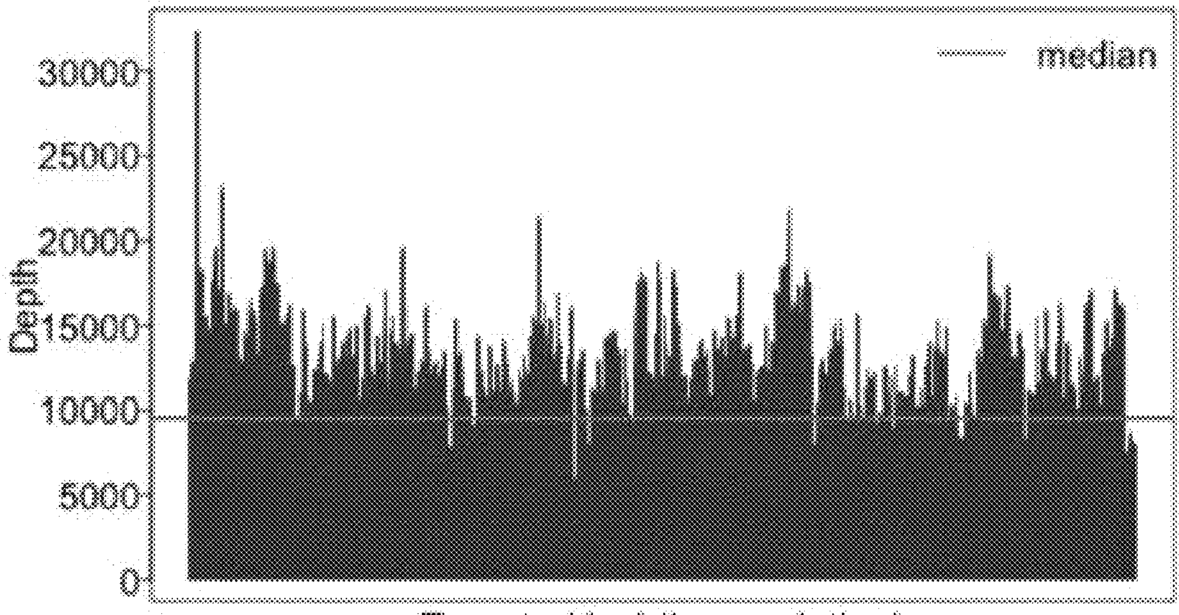
Figure 10B:
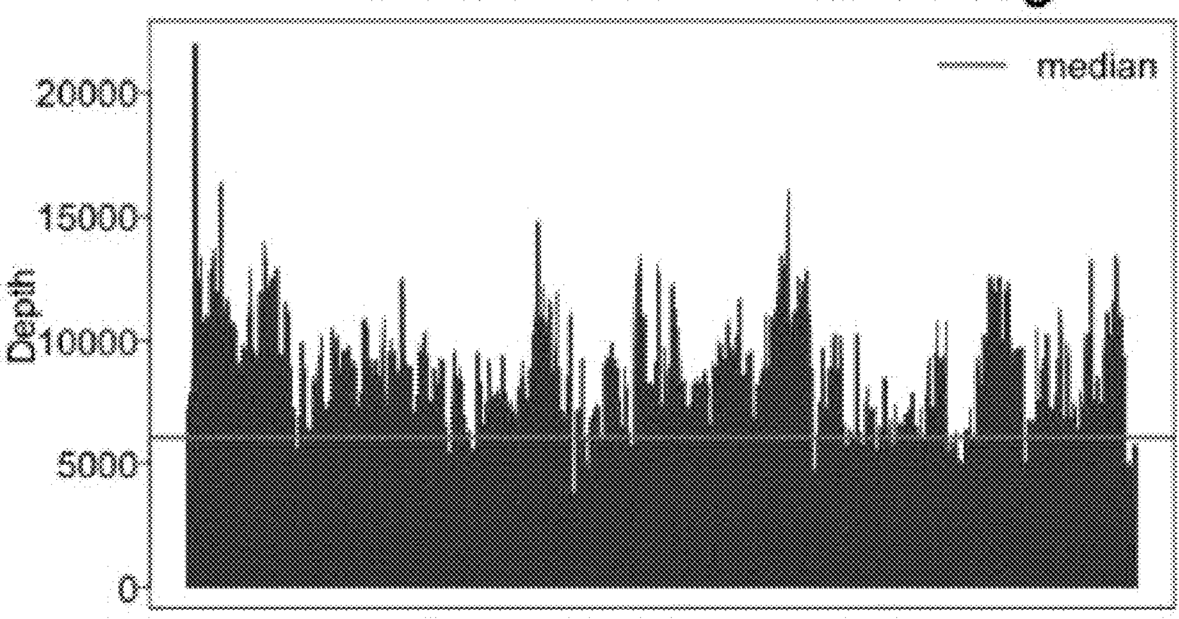
Figure 10B:
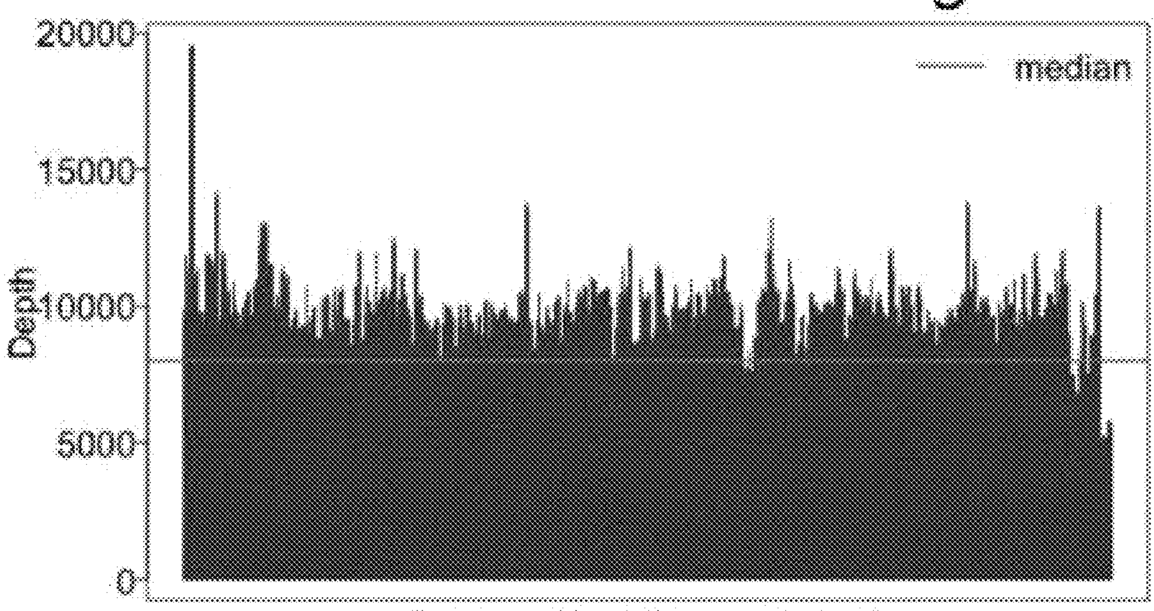
Figure 10B:
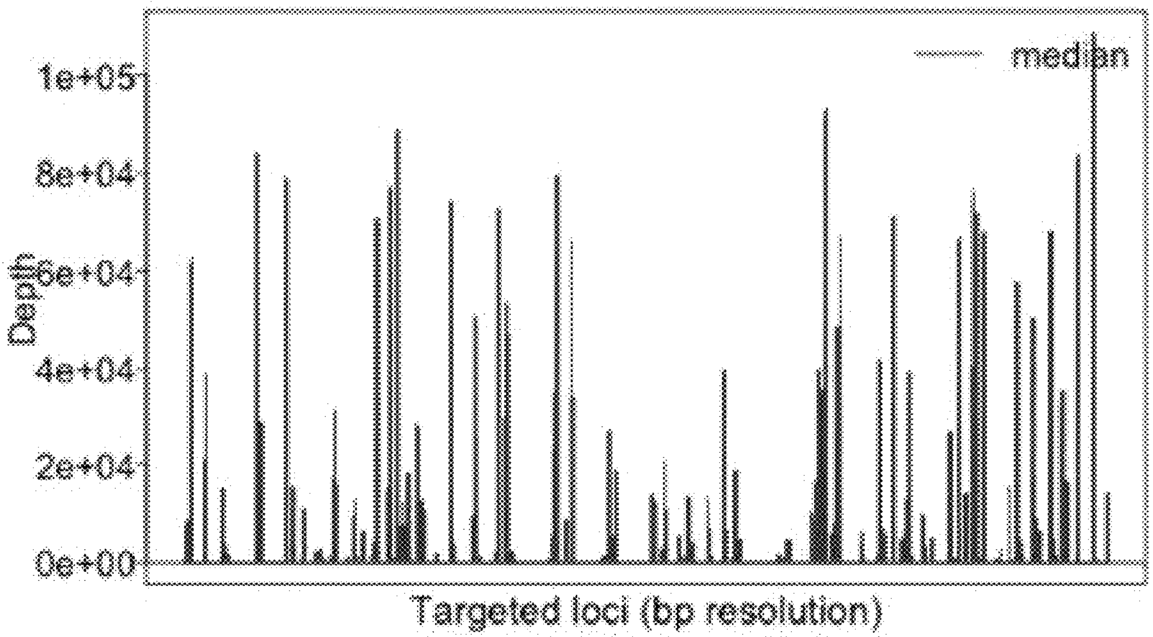
Figure 10C:
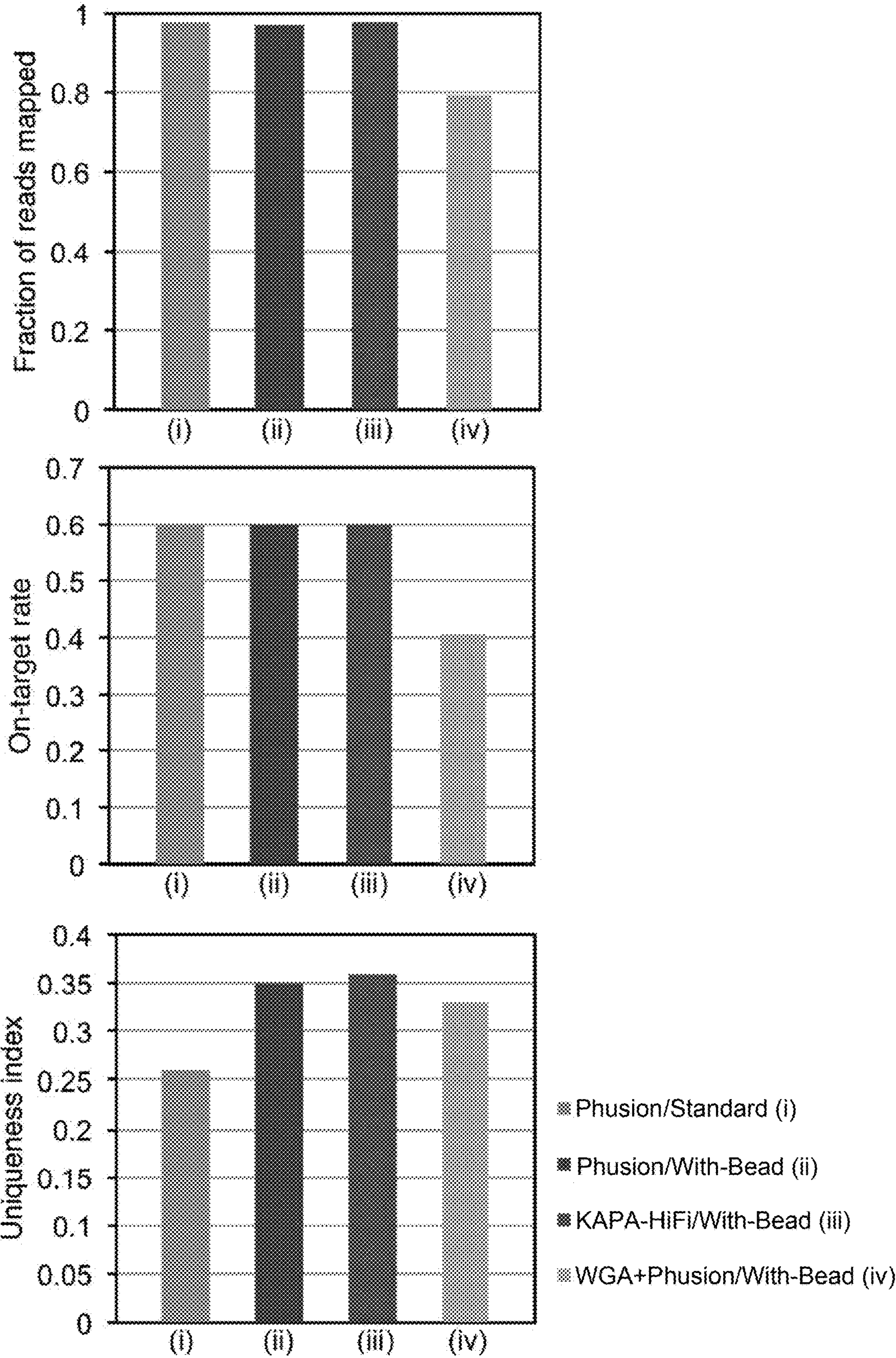
Figure 11A:
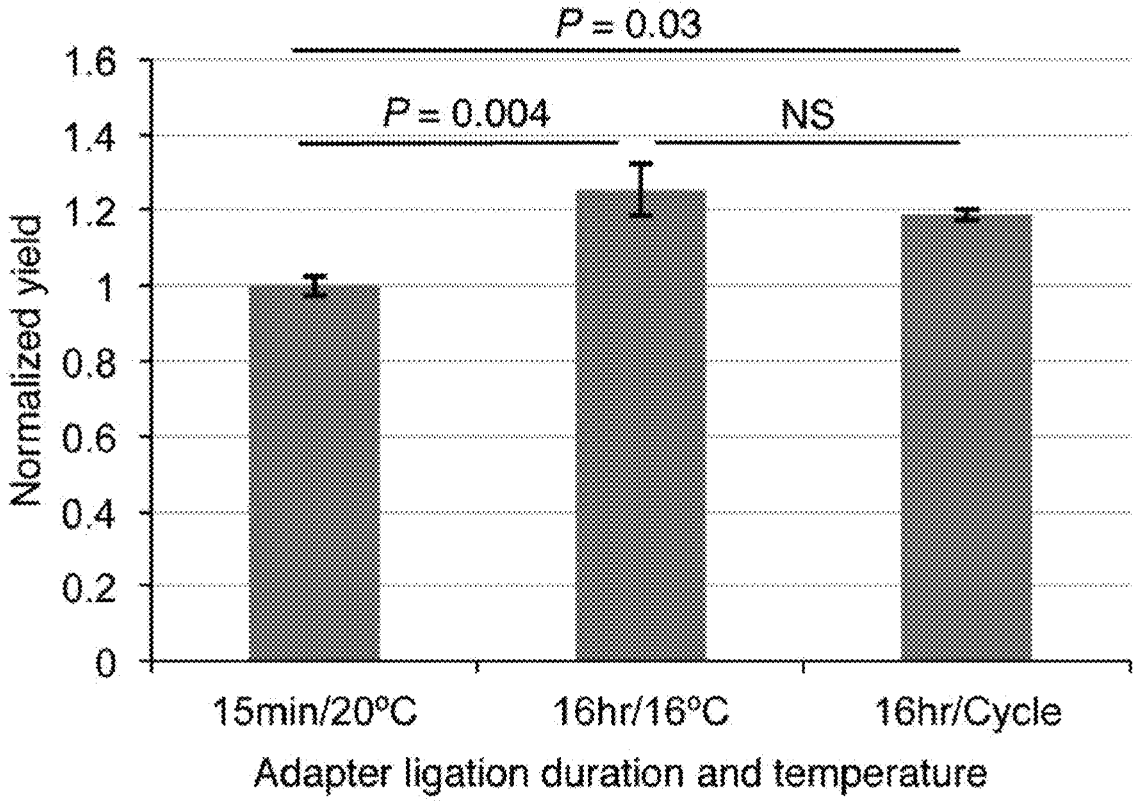
FIG. 11A-11F: Optimizing allele recovery from low input cfDNA during Illumina library preparation. Bars reflect the relative yield of CAPP-Seq libraries constructed from 4 ng cfDNA, calculated by averaging quantitative PCR measurements of n=4 pre-selected reporters within CAPP-Seq with pre-defined amplification efficiencies.
Figure 11B:
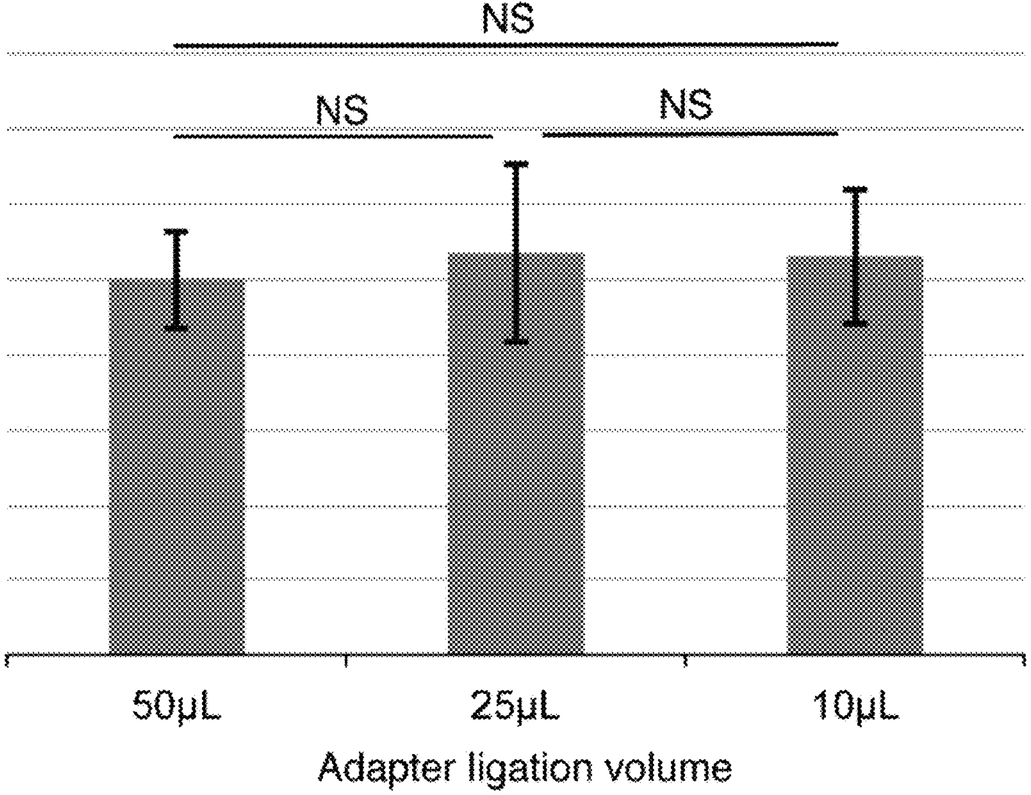
Figure 11C:
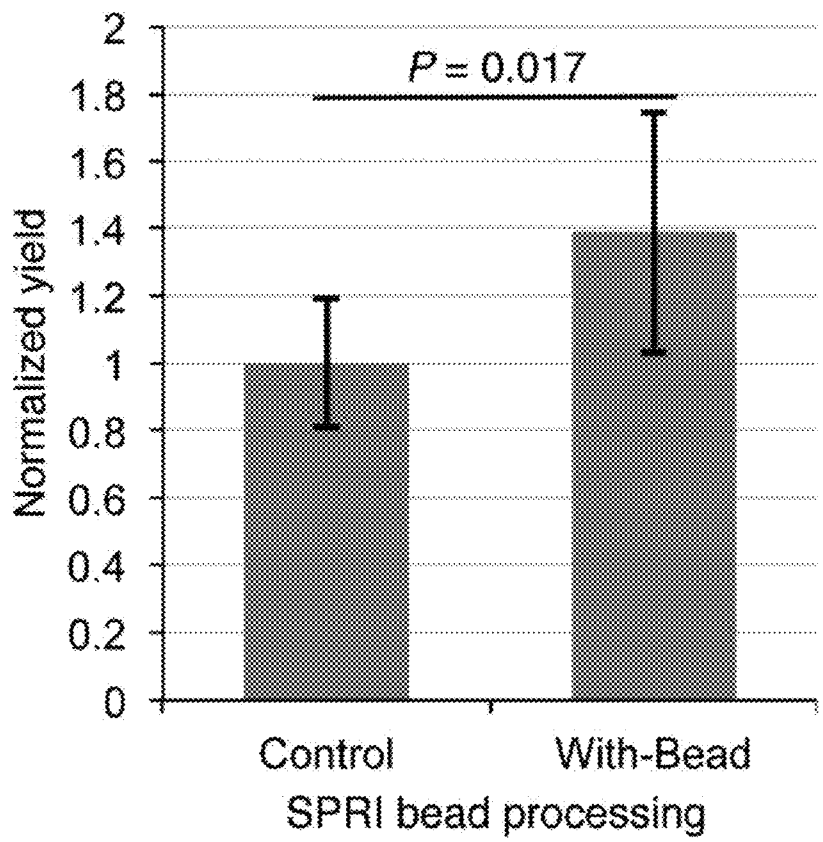
Figure 11D:
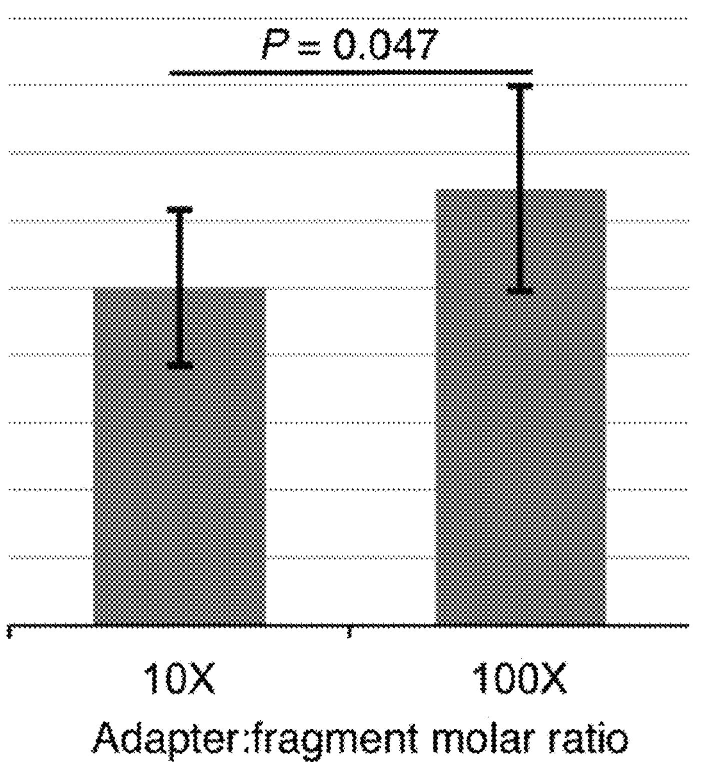
Figure 11E:
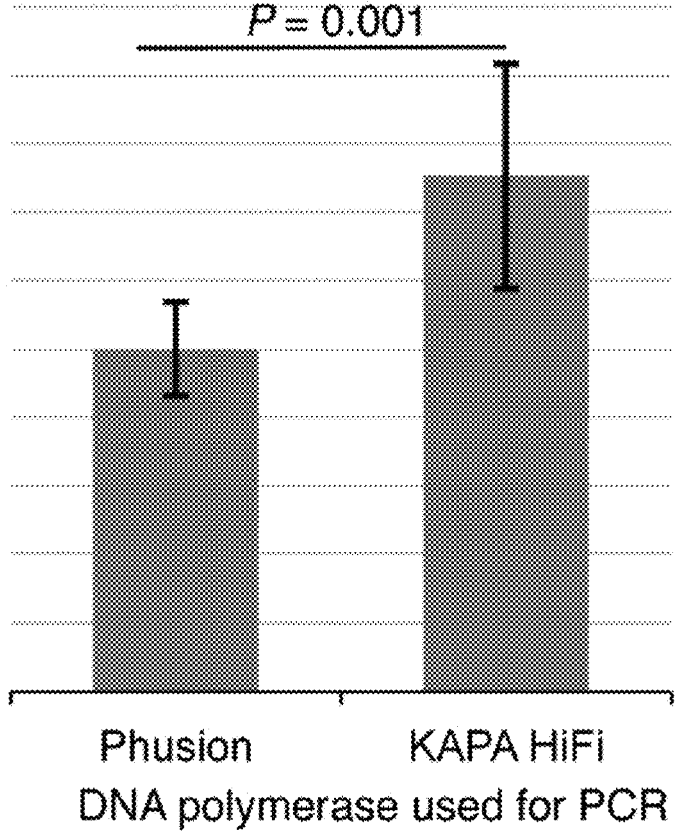
Figure 11F:
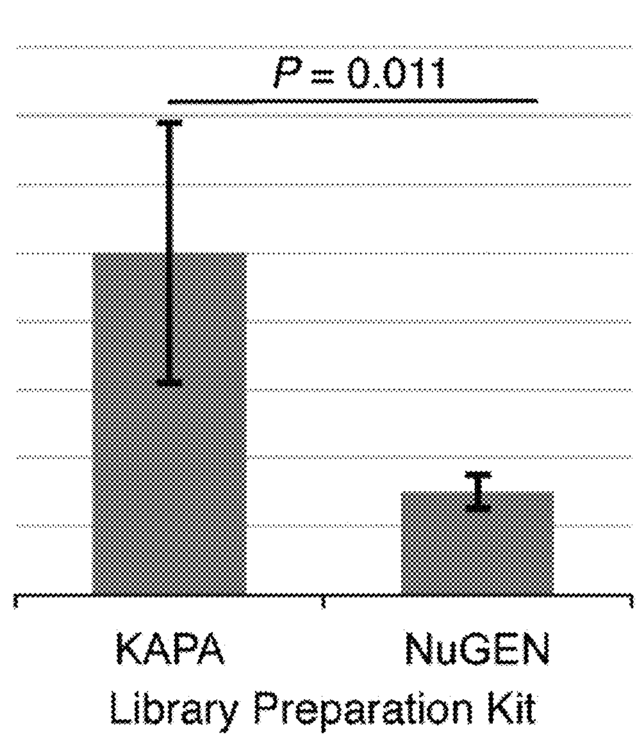
Figure 12A:
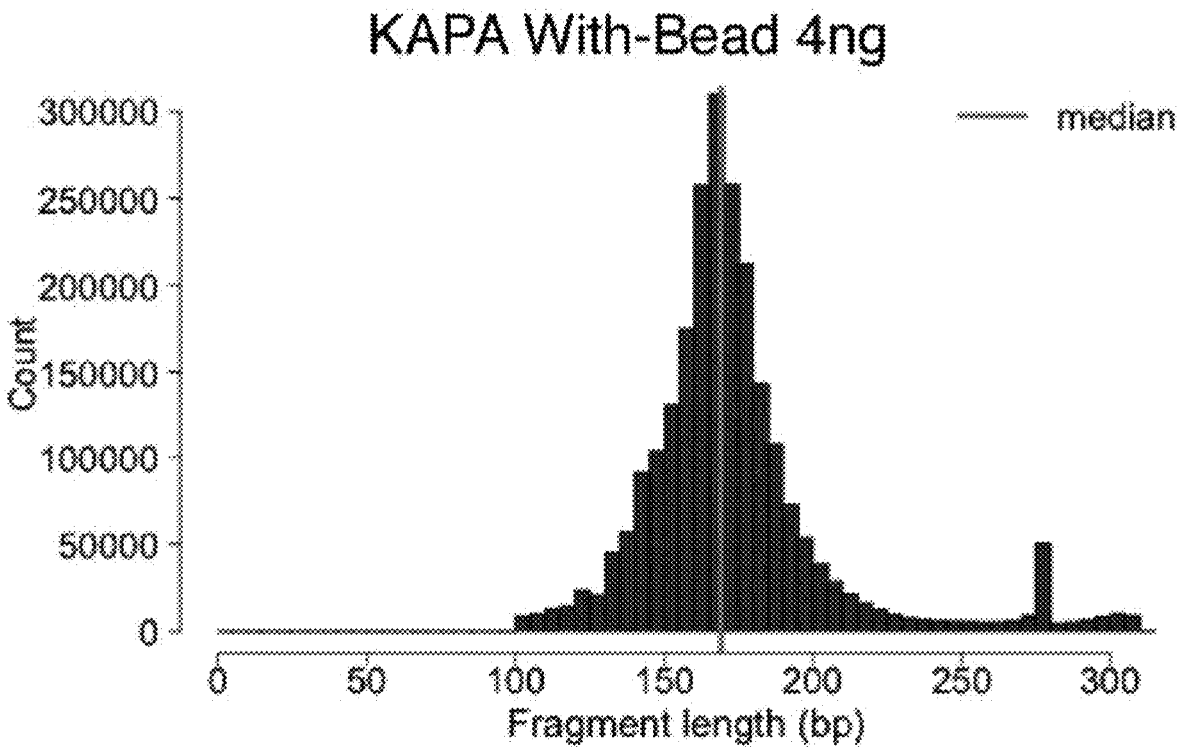
FIG. 12A-12C: CAPP-Seq performance with various amounts of input cfDNA.
Figure 12A:
Figure 12A:
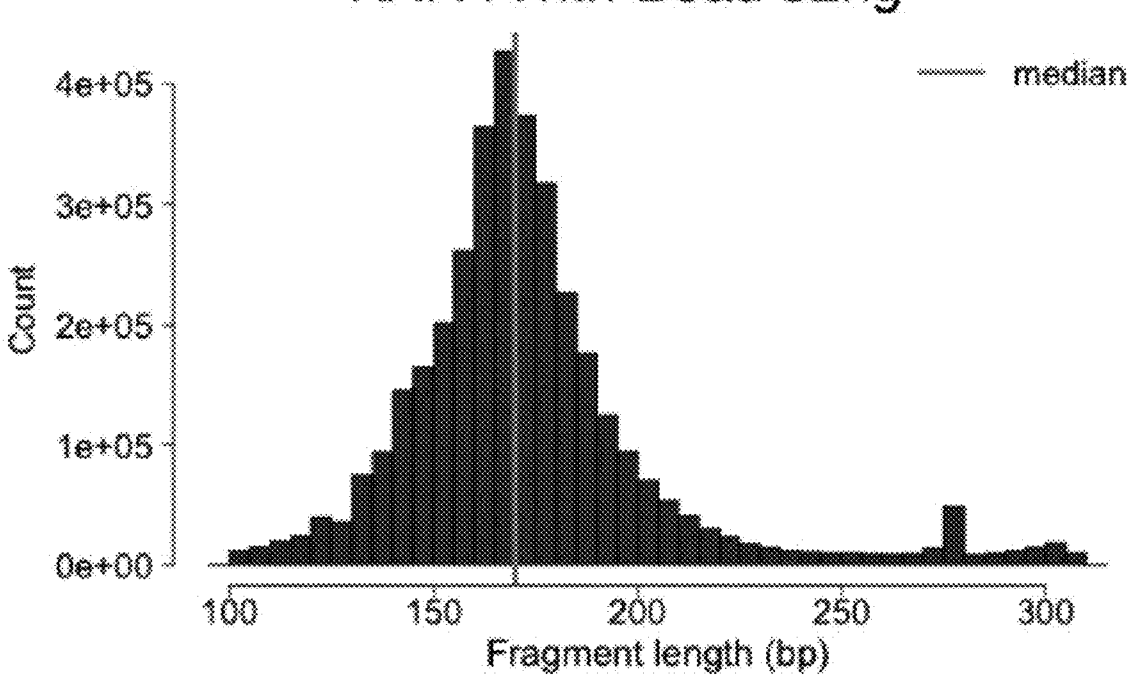
Figure 12B:
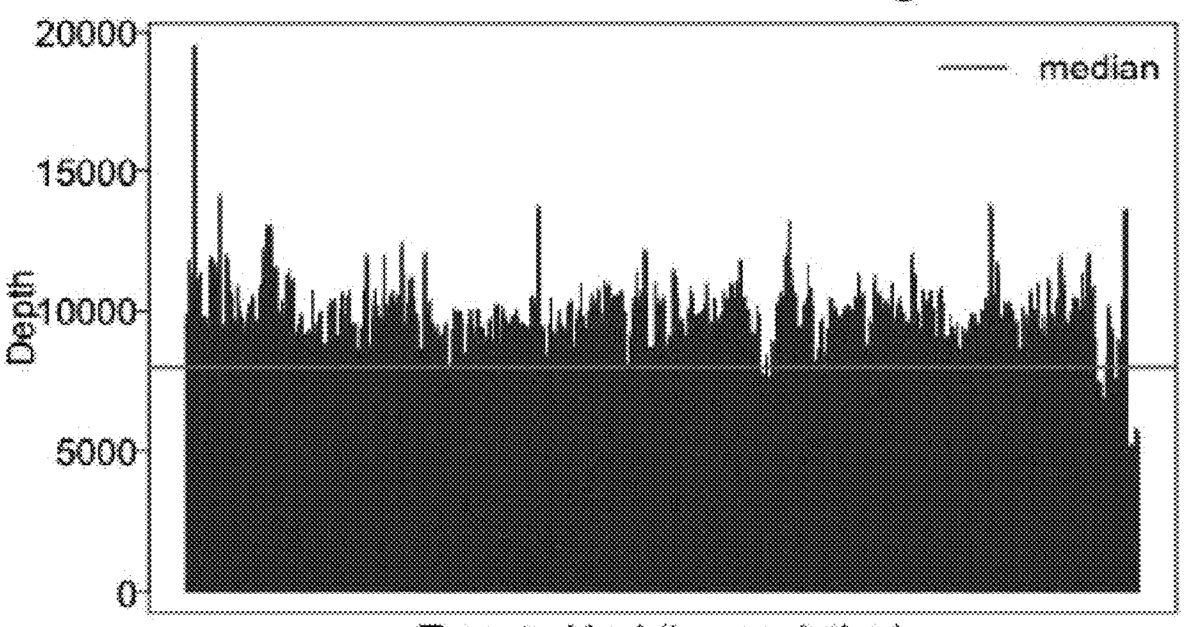
Figure 12B:
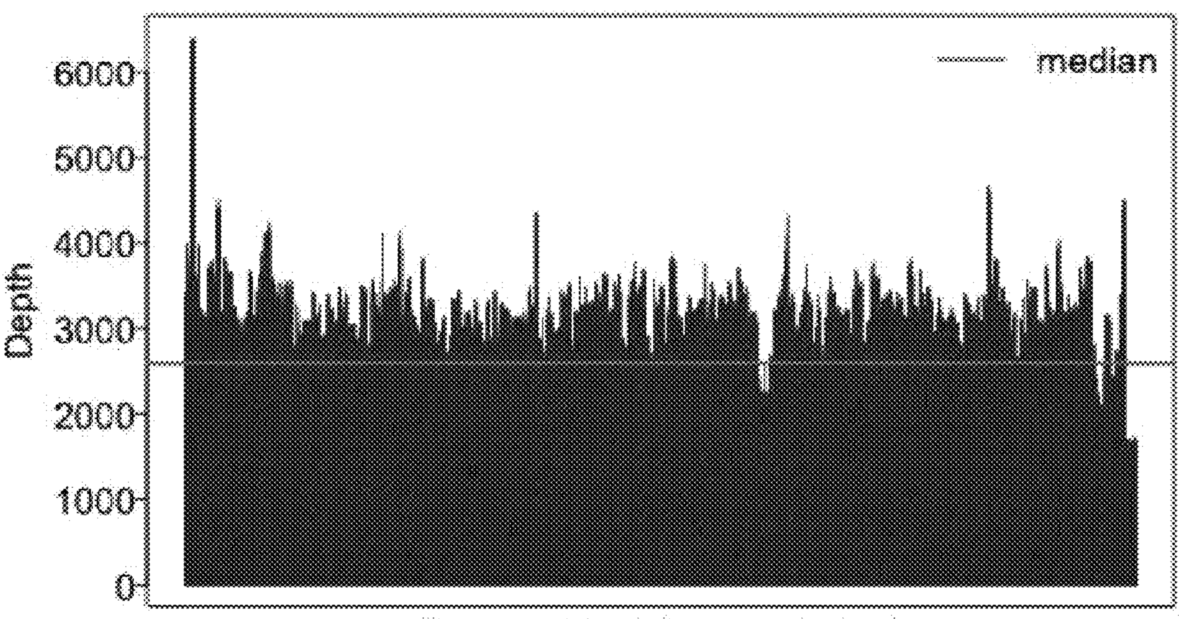
Figure 12C:
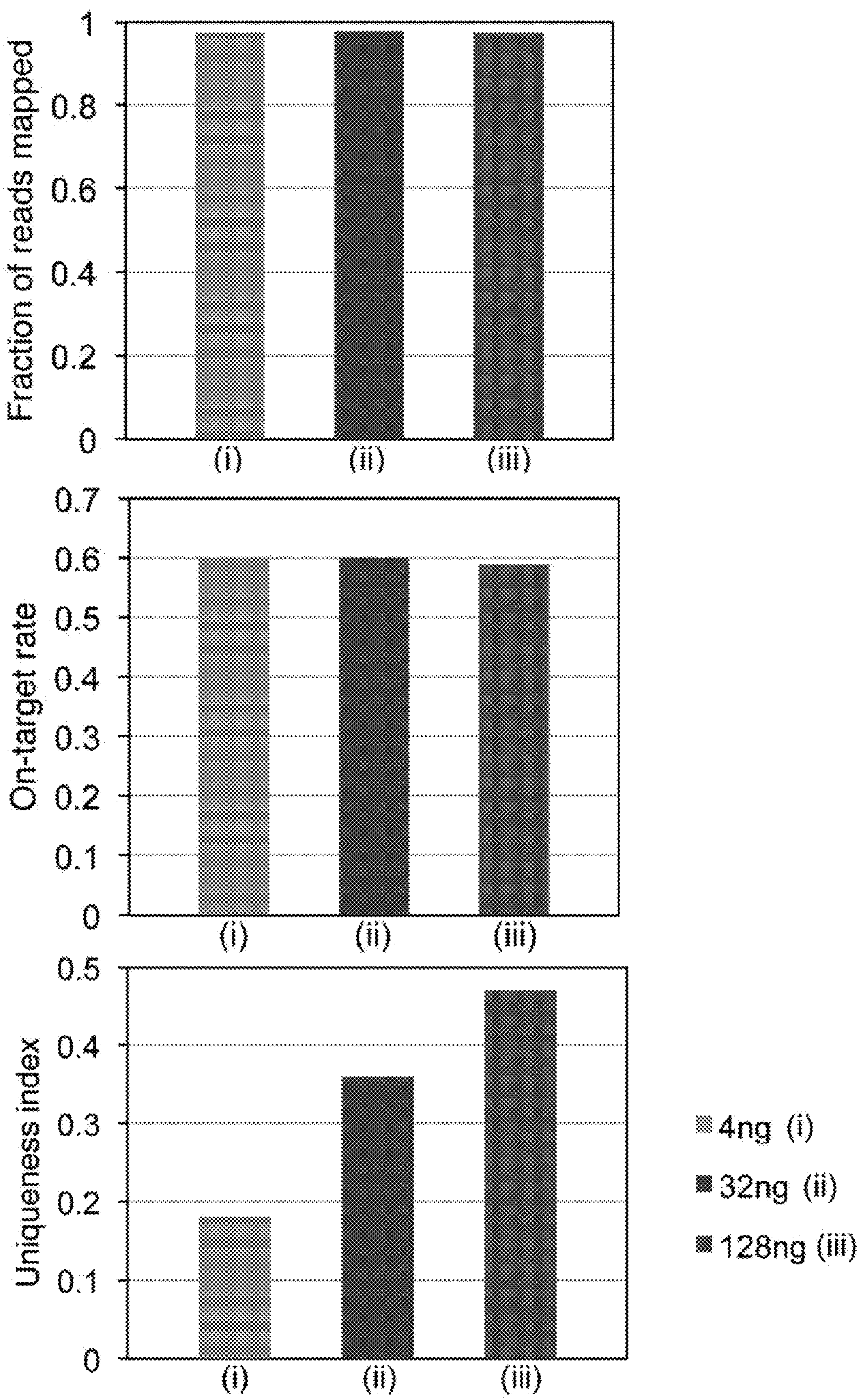

To validate potential genomic breakpoints, defined as the edges of soft-clipped reads, FACTERA executes the following routine, depicted in FIG. 8. For each discordant gene pair (e.g. genes w and v in FIG. 8*a*), all candidate breakpoints are tabulated, and the support (e.g. read frequency) for each is determined. Breakpoints supported by less than 2 reads (by default) are excluded from further analysis. Starting with the two breakpoints with highest support, FACTERA selects a representative soft-clipped read for each breakpoint, such that the length of the clipped sequence is closest to half of the read length (FIG. 8*b*). If the mapped region of one read matches the soft-clipped region of the other, FACTERA records a putative fusion event. To assess inter-read concordance (e.g. see reads 1 and 2 in FIG. 8*c*), FACTERA employs the following algorithm. The mapped region of read 1 is parsed into all possible subsequences of length k (e.g., k-mers) using a sliding window (k=10, by default). Each k-mer, along with its lowest sequence index in read 1, is stored in a hash table data structure, allowing k-mer membership to be assessed in constant time (FIG. 8*c*, left panel). Subsequently, the soft clipped sequence of read 2 is parsed into subsequences of length k, and the hash table is interrogated for matching k-mers (FIG. 8*c*, right panel). If a minimum matching threshold is achieved (=0.5× the minimum length of the two compared subsequences), then the two reads are considered concordant. FACTERA will process at most 1000 (by default) putative breakpoint pairs for each discordant gene pair. Moreover, for each gene pair, FACTERA will only compare reads whose orientations are compatible with valid fusions. Such reads have soft-clipped sequences facing opposite directions (FIG. 8*d*, top panel). When this condition is not satisfied, FACTERA uses the reverse complement of read 1 for k-mer analysis (FIG. 8*d*, bottom panel).

In some instances, genomic subsequences flanking the true breakpoint may be nearly or completely identical, causing the aligned portions of soft-clipped reads to overlap. Unfortunately, this prevents an unambiguous determination of the breakpoint. As such, FACTERA incorporates a simple algorithm to arbitrarily adjust the breakpoint in one read (e.g., read 2) to match the other (e.g., read 1). Depending upon read orientation, there are two ways this can occur, both of which are illustrated in FIG. 8*e*. For each read, FACTERA calculates the distance between the breakpoint and the read coordinate corresponding to the first k-mer match between reads. For example, as anecdotally illustrated in FIG. 8*e, x* is defined as the distance between the breakpoint coordinate of read 1 and the index of the first matching k-mer, j, whereas y denotes the corresponding distance for read 2. The offset is estimated as the difference in distances (x, y) between the two reads (see FIG. 8*e*).

In silico validation of candidate fusions. To confirm each candidate breakpoint in silico, FACTERA performs a local realignment of reads against a template fusion sequence (+500 bp around the putative breakpoint) extracted from the 0.2 bit reference genome. BLAST is currently employed for this purpose, although BLAT or other fast aligners could be substituted. A BLAST database is constructed by collecting all reads that map to each candidate fusion sequence, including discordant reads and soft-clipped reads, as well as all unmapped reads in the original input .bam file. All reads that map to a given fusion candidate with at least 95% identity and a minimum length of 90% of the input read length (by default) are retained, and reads that span or flank the breakpoint are counted. As a final step, output redundancies are minimized by removing fusion sequences within a 20 bp interval of any fusion sequence with greater read support and with the same sequence orientation (to avoid removing reciprocal fusions).

FACTERA produces a simple output text file, which includes for each fusion sequence, the gene pair, the chromosomal sequence coordinates of the breakpoint, the fusion orientation (e.g., forward-forward or forward-reverse), the genomic sequences within 50 bp of the breakpoint, and depth statistics for reads spanning and flanking the breakpoint. Fusions identified in patients analyzed in this work are provided in Tables 3, 20 and 21.

Experimental validation of FACTERA. To experimentally evaluate the performance of FACTERA, we generated NGS data from two NSCLC cell lines, HCC78 (21.5M×100 bp paired-end reads) and NCI-H3122 (19.4M×100 bp paired-end reads), each of which has a known rearrangement (ROS1 and ALK, respectively) with a breakpoint that has, to the best of our knowledge, not been previously published. FACTERA readily revealed evidence for a reciprocal SLC34A2-ROS1 translocation in the former and an EML4-ALK fusion in the latter. Precise breakpoints predicted by FACTERA were experimentally validated by PCR amplification and Sanger sequencing (FIG. 9; see also Validation of Variants Detected by CAPP-Seq). Importantly, FACTERA completed each run in practical time (~90 sec), using only a single thread on a hexa-core 3.4 GHZ Intel Xeon E5690 chip. These initial results illustrate the utility of FACTERA as part of the CAPP-Seq analysis pipeline.

Templated fusion discovery. We implemented a user-directed option to "hunt" for fusions within expected candidate genes. A fusion could be missed by FACTERA if the fusion detection criteria employed by FACTERA are incompletely satisfied—such as if discordant reads, but not soft-clipped reads, are identified—and will most likely occur when fusion allele frequency in the tumor is extremely low. As input, the method is supplied with candidate fusion gene sequences as "baits". All unmapped and soft-clipped reads in the input.bam file are subsequently aligned to these templates (using blastn) to identify reads that have sufficient similarity to both (for each read, 95% identity, e-value <1.0e-5, and at least 30% of the read length must map to the template, by default). Such reads are output as a list to the user for manual analysis.

We tested this simple approach on a low purity tumor sample found to harbor an ALK fusion by FISH, but not FACTERA (e.g., case P9). Using templates for ALK and its common fusion partner, ELM4, we identified 4 reads that mapped to both, in a region with an overall depth of ~1900×. The estimated allele frequency of 0.21% is strikingly similar to the 0.22% tumor purity measured by FACS (FIG. 17), confirming the utility of the templated fusion discovery method. We subsequently FACS-depleted CD45+ immune populations and re-sequenced this patient's tumor. In the enriched tumor sample, FACTERA identified the EML4-ALK fusion, along with two novel ROS1 fusions (FIG. 4*b*, Tables 3, 20 and 21).

Mutation Recovery: SNVs/indels. Using a custom Perl script, previously identified reporter alleles were intersected with a SAMtools mpileup file generated for each plasma cfDNA sample, and the number and frequency of supporting reads was calculated for each reporter allele. Only reporters in properly paired reads at positions with at least 500× overall depth (pre-duplication removal) were considered (Table 4).

Mutation Recovery: Fusions. For enumeration of fusion frequency in sequenced plasma DNA, FACTERA executes the last step of the discovery phase (e.g., in silico validation of candidate fusions, above) using the set of previously identified fusion templates. The fusion allele frequency is calculated as $\alpha/\beta$, where $\alpha$ is the number of breakpoint-spanning reads, and $\beta$ is the mean overall depth within a genomic region ±5 bps around the breakpoint. Regarding the NSCLC selector described in this work, the latter calculation was always performed on the single gene contained in the NSCLC selector library. If both fusion genes are targeted within a selector library, overall depth is estimated by taking the mean depth calculated for both genes.

Notably, in some cases we observed lower fusion allele frequencies than would be expected for heterozygous alleles (e.g., see cell line fusions in Tables 3, 20 and 21). This was seen in cell lines, in an empirical spiking experiment, and in one patient's tumor and plasma samples (e.g., P6), and could potentially result from inefficient "pull-down" of fusions whose partners are not represented in the selector. Regardless, fusions are useful reporters—they possess virtually no background signal and show linear behavior over defined concentrations in a spiking experiment (FIG. 16*d*). Moreover, allelic frequencies in plasma are easily adjusted for such inefficiencies by dividing the measured frequency in plasma by the corresponding frequency in the tumor. In cases where sequenced tumor tissue is impure, tumor content can be estimated using the frequencies of SNVs (or indels) as a reference frame, allowing the fusion fraction to be normalized accordingly (Table 4).

Screening Plasma cfDNA without Knowledge of Tumor DNA. We devised the following statistical algorithm as an initial step toward non-invasive tumor genotyping and cancer screening with CAPP-Seq. The method identifies candidate SNVs using iterative models of (i) background noise in paired germline DNA (in this work, PBLs), (ii) base-pair resolution background frequencies in plasma cfDNA across the selector, and (iii) sequencing error in cfDNA. Examples are provided in FIG. 21. The algorithm works in four main steps, detailed below.

As input, the algorithm takes allele frequencies from a single plasma cfDNA sample and analyzes high quality background alleles, defined in a first step for each genomic position as the non-dominant base with highest fractional abundance. Only alleles with depth of at least 500× and strand bias <90% (conservative, by default) are analyzed. For consistency with variant calling, we allowed the screening approach to interrogate selector regions within 500 bp of defined coordinates, expanding the effective sequence space from ~125 kb to ~600 kb.

Figures 21A, 21B:
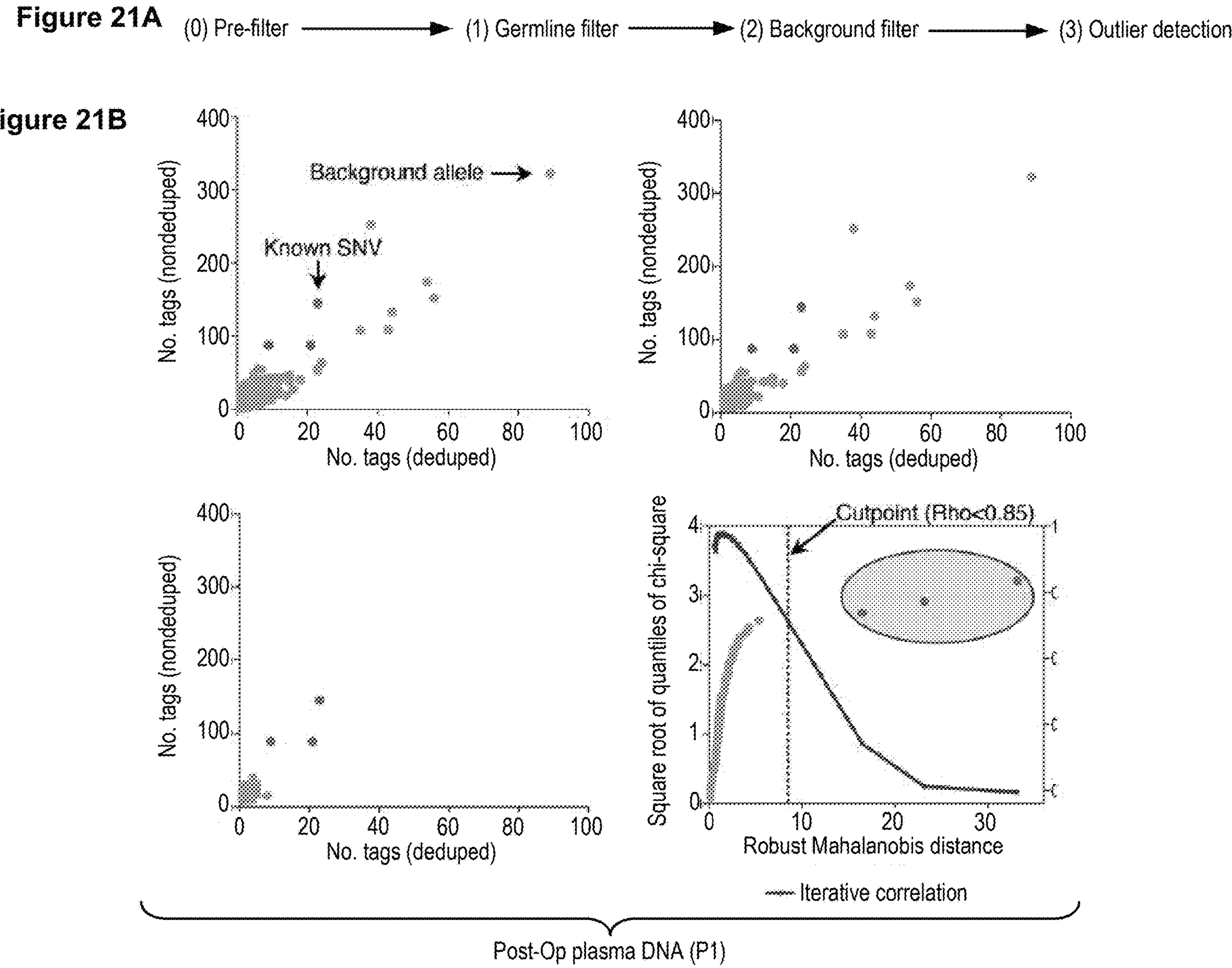
FIG. 21A-21D. Non-invasive cancer screening with CAPP-Seq, related to FIG. 4I.

Second, the binomial distribution is used to test whether a given input cfDNA allele is significantly different from the corresponding paired germline allele (FIG. 21*a-b*). Here the probability of success is taken to be the frequency of the background allele in PBLs, and the number of trials is the allele's corresponding depth in plasma cfDNA. To avoid contributions from alleles in rare circulating tumor cells that might contaminate PBLs, input alleles with a fractional abundance greater than 0.5% in paired PBLs (by default) or a Bonferroni-adjusted binomial probability greater than $2.08\times10^{-8}$ are not further considered (alpha of 0.05/[~600 kb*4 alleles per position]).

Third, a database of cfDNA background allele frequencies is assembled. Here, we used samples analyzed in the present study (e.g., pre-treatment NSCLC samples and 1 sample from a healthy volunteer), except the input sample is left out to avoid bias. Based on the assumption that all background allele fractions follow a normal distribution, a Z-test is employed to test whether a given input allele differs significantly from typical cfDNA background at the same position (FIG. 21*a-b*). All alleles within the selector are evaluated, and those with an average background frequency of 5% or greater (by default) or a Bonferroni-adjusted single-tailed Z-score <5.6 are not further considered (alpha of 0.05, adjusted as above).

Figure 21C:
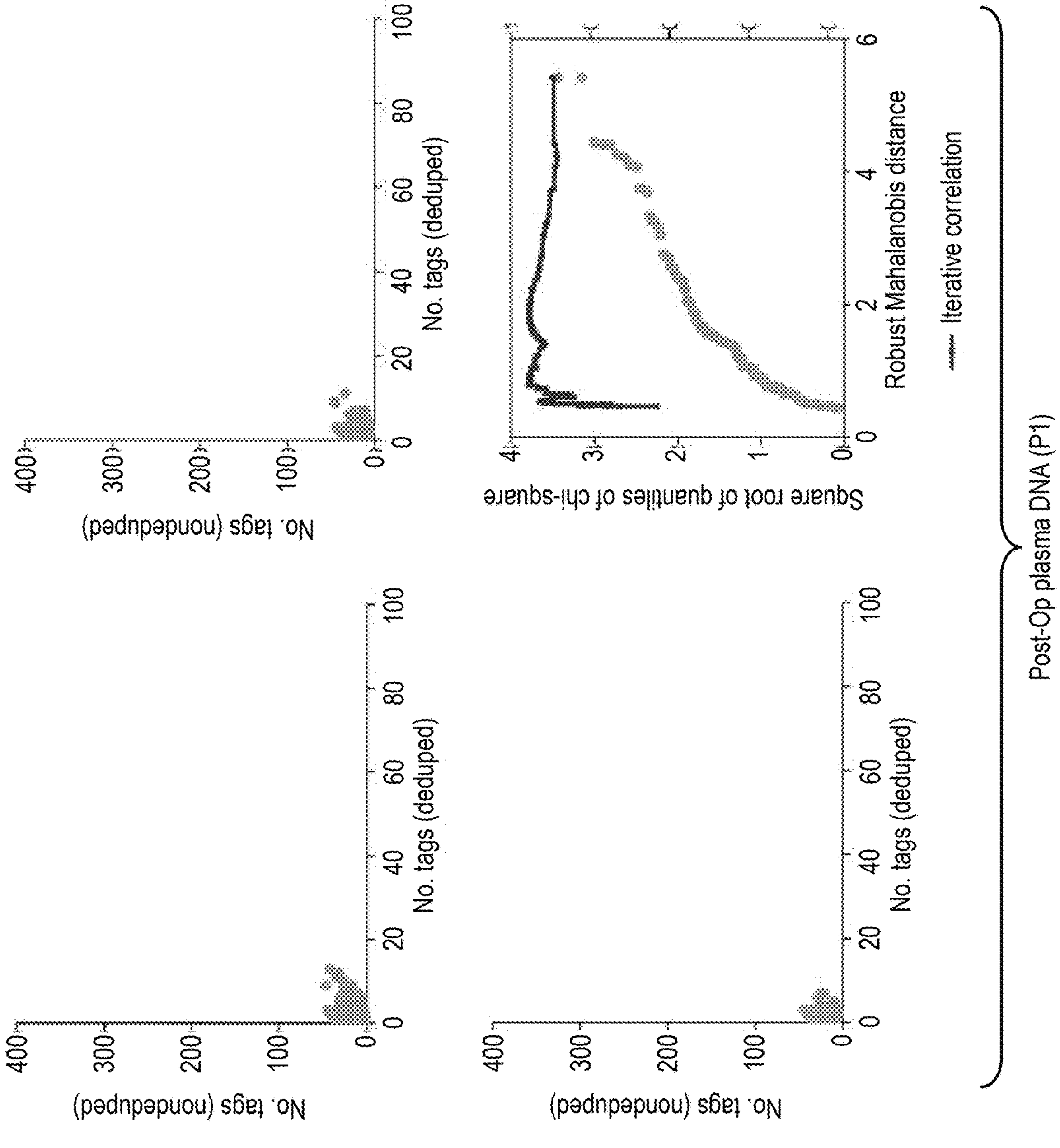
Figure 21D:
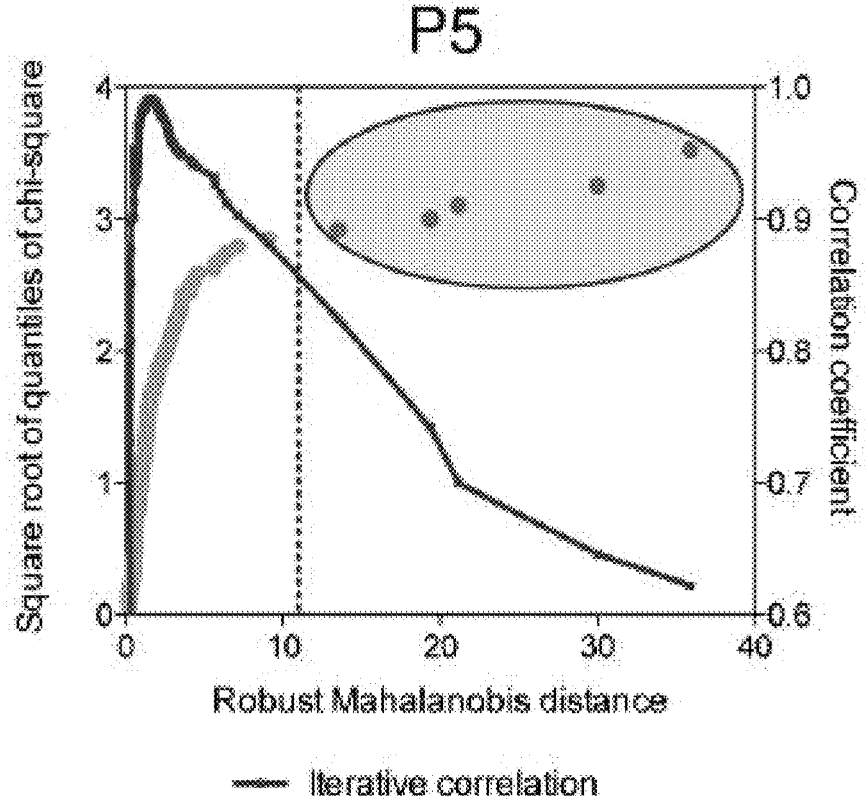
Figure 21D:
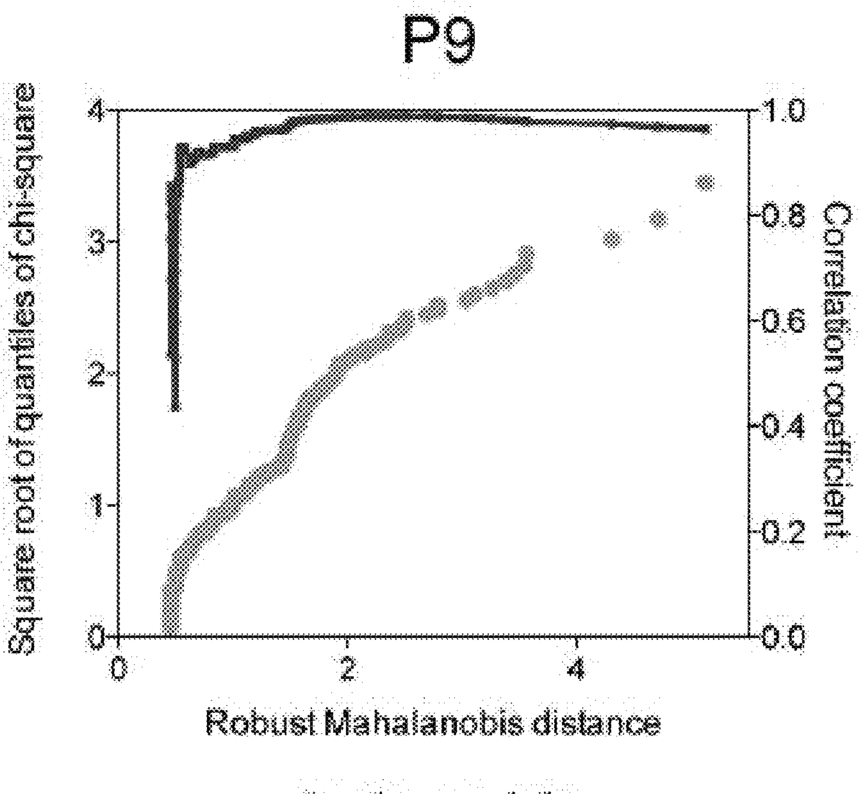

Finally, candidate alleles are tested for remaining possible sequencing errors. This step leverages the observation that non-tumor variants (e.g., "errors") in plasma cfDNA tend to have a higher duplication rate than bona fide variants detectable in the patient's tumor (data not shown). As such, the number of supporting reads is compared for each input allele between nondeduped (all fragments meeting QC criteria) and deduped data (only unique fragments meeting QC criteria). An outlier analysis is then used to distinguish candidate tumor-derived SNVs from remaining background noise (FIG. 21*a-c*). Specifically, to reveal outlier tendency in the data, the square root of the robust distance Rd (Mahalanobis distance) is compared against the square root of the quantiles of a chi-squared distribution Cs. This transformation reveals natural separation between true SNVs and false positives in cancer patients (FIG. 21*a, c*), and notably, reveals an absence of outlier structure in patient samples lacking tumor-derived SNVs (FIG. 21*b, c*). To automatically call SNVs without prior knowledge, the screening approach iterates through data points by decreasing Rb and recalculating the Pearson's correlation coefficient Rho between Rd and Cs for points 1 to i, where $Rd_i$ is the current maximum Rd. The algorithm iteratively reports outliers (e.g., candidate SNVs) until it terminates when Rho≥0.85

Example 2: Designing a Personalized Selector Set

In certain circumstances, monitoring tumor burden in a patient known to have cancer is likely to be impractical using an 'off-the-shelf' strategy applying knowledge from a cohort of patients with the same tumor type, to selectively capture genomic regions that are recurrently mutated in that tumor type using CAPP-Seq. These situations include, but are not limited to, cases where (1) the tumor is of an unknown primary histology (e.g., CUP); (2) the histology is known, but is too rare to have a sufficient number of patients with that tumor type previously profiled to define the average patient's tumor somatic genetic landscape (e.g., soft tissue sarcoma subtyped); (3) the histology is known but the average/median number of recurrent somatic lesions in that tumor type are too low to achieve desired sensitivity levels (e.g., pediatric tumors, etc.); or (4) the histology is known and the average/median number of recurrent somatic lesions is reasonable, but the average burden of tumor volume is so small that additional sensitivity can be achieved using more mutations per tumor (e.g., early stages of malignant melanoma). In such cases, a personalized strategy for monitoring tumor burden is likely to overcome these hurdles for disease monitoring.

Here, tumor(s) from a patient known to have cancer are genotyped by profiling the tumor genome, exome, or targeted region expected to be enriched for somatic aberrations. The genotype of the cancer may be compared to a genotype of the germline of the same patient. The resulting lesions are then catalogued and used to build a custom, personalized selector comprising a set of biotinylated oligonucleotides for selective hybrid affinity capture of corresponding circulating tumor DNA (ctDNA) molecules. Cell-free DNA circulating in blood or body fluids and harboring such ctDNA molecules would be isolated, and used to build shotgun genomic libraries that include ligation of molecular tags ('barcodes') that distinguish such sequences from others, allowing for suppression of spurious errors introduced during the amplification of cfDNA using thermostable DNA polymerases as part of polymerase chain reaction. The personalized selector would then be applied for capture of the fragments of interest, sequenced and analyzed in the same manner as the 'off-the-shelf' CAPP-Seq workflow, allowing the tracking and quantitation of those mutations originally discovered in the primary tumor within the corresponding cfDNA. As an alternative to affinity based hybrid capture of ctDNA/cfDNA, amplicons specific to the corresponding region could be interrogated by PCR, with such fragments selectively indexed using molecular barcodes that similarly allow distinction of sequencing errors introduced during PCR.

Example 3. Use of a Selector Set to Diagnose a Cancer

A plasma sample is obtained from a female subject with an abnormal lump in her breast. Cell-free DNA (cfDNA) is extracted from the plasma sample. An end repair reaction is performed on the cfDNA by mixing the components in a sterile microfuge tube (or other suitable sterile container) as follows:

| Component | Volume (μL) |
|---|---|
| cfDNA | 1-75 |
| Phosphorylation Reaction Buffer (10X) | 10 |
| T4 DNA polymerase | 5 |
| T4 Polynucleotide kinase | 5 |
| dNTPs | 4 |
| DNA Polymerase I, Large (Klenow) | 1 |
| Sterile $H_2O$ | -bring total volume up to 100 μL |

The end repair reaction mixture is incubated in a thermal cycler for 30 minutes at 20° C.

Clean-up of the end repaired cfDNA is performed by adding 160 μL (1.6×) of resuspended AMPure XP beads to the end repair reaction mixture. The AMPure beads are mixed into the solution on a vortex mixer or by pipetting up and down (e.g., 10 times or more). The reaction is incubated for 5 minutes at room temperature. The reaction is placed on a magnetic stand to separate the beads from the supernatant. After the solution is clear (approximately 5 minutes), the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 10 minutes while the reaction is on the magnetic stand. cfDNA is eluted from the beads by adding 40 μL of sterile water and vortexing or pipetting the water up and down. The reaction is placed back on the magnetic stand. Once the solution is clear, 32 μL of the supernatant is transferred to a fresh, sterile container (e.g., microfuge tube).

dA-tailing of the end repaired cfDNA is performed by mixing the following components in the sterile microfuge tube as follows:

| Component | Volume (μL) |
|---|---|
| End repaired cfDNA | 32 |
| NEBuffer 2 (10X) | 5 |
| Deoxyadenosine 5'-Triphosphate | 10 |
| Klenow Fragment (3'→5' exo-) | 3 |

The dA-tailing reaction is incubated in a thermal cycle for 30 minutes at 37° C.

Clean-up of the dA-tailed cfDNA is performed by adding 90 μL (1.8×) of resuspended AMPure XP beads to the dA-tailing reaction mixture. The AMPure beads are mixed into the solution on a vortex mixer or by pipetting up and down (e.g., 10 times or more). The reaction is incubated for 5 minutes at room temperature. The reaction is placed on a magnetic stand to separate the beads from the supernatant. After the solution is clear (approximately 5 minutes), the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 10 minutes while the reaction is on the magnetic stand. cfDNA is eluted from the beads by adding 15 μL of sterile water and vortexing or pipetting the water up and down. The reaction is placed back on the magnetic stand. Once the solution is clear, 10 μL of the supernatant is transferred to a fresh, sterile container (e.g., microfuge tube).

Adaptor ligation of the dA-tailed cfDNA is performed by mixing the following components in the sterile microfuge tube as follows:

| Component | Volume (μL) |
|---|---|
| dA-tailed cfDNA | 10 |
| Quick Ligation Reaction Buffer (2X) | 25 |
| Illumina Adaptor | 10 |
| Quick T4 DNA Ligase | 5 |

The adaptor ligation reaction is incubated at 16° C. for 16 hours. The adaptor ligation reaction is terminated by adding 3 μL of USER™ enzyme mix by pipetting up and down and incubation at 37° C.

Clean-up of the adaptor-ligated cfDNA is performed by adding 90 μL (1.8×) of resuspended AMPure XP beads to the adaptor ligation reaction mixture. The AMPure beads are mixed into the solution on a vortex mixer or by pipetting up and down (e.g., 10 times or more). The reaction is incubated for 5 minutes at room temperature. The reaction is placed on a magnetic stand to separate the beads from the supernatant. After the solution is clear (approximately 5 minutes), the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 10 minutes while the reaction is on the magnetic stand. cfDNA is eluted from the beads by adding 105 μL of sterile water and vortexing or pipetting the water up and down. The reaction is placed back on the magnetic stand. Once the solution is clear, 100 μL of the supernatant is transferred to a fresh, sterile container (e.g., microfuge tube).

Universal PCR amplification is performed on the adaptor-ligated cfDNA using primers targeting the adaptors. The PCR amplification is conducted using 14 amplification cycles. Selector set probes are used to selectively capture a subset of the amplified products of the adaptor ligated cfDNA. Sequencing reactions are performed on the captured amplified products. The captured amplified cfDNA is sequenced on a paired-end 100 bp lane of an Illumina HiSeq 2000.

The sequencing information is analyzed by detecting mutations in one or more genomic regions based on a selector set. The selector set contains information pertaining to mutations occurring in one or more genomic regions, wherein the mutations are present in at least about 70% of a population of subjects suffering from a breast cancer. In order to determine the statistical significance of the mutations detected in the sample, p-values for the different classes of mutations are calculated. A ctDNA detection index is used to evaluate the statistical significance of detecting two or more classes of mutations.

A report of the mutations detected in the sample and the statistical significance of the detection of the mutations is provided to a physician. Based on the detection of at least three mutations in three genomic regions, the physician diagnoses a breast cancer in the subject.

Example 4. Use of a Selector Set to Determine a Status or Outcome of a Cancer Cell-free DNA (cfDNA) is purified from a sample from a subject diagnosed with a prostate cancer. An end repair reaction is performed on the cfDNA by mixing the components in a sterile microfuge tube (or other suitable sterile container) as follows:

| Component | Volume (μL) |
|---|---|
| 1-5 μg cfDNA | 1-85 |
| 10X End Repair Buffer | 10 |
| End Repair Enzyme Mix | 5 |
| Sterile $H_2O$ | -bring total volume up to 100uL |

The end repair reaction mixture is incubated in a thermal cycler for 30 minutes at 20° C.

Clean-up of the end repaired cfDNA is performed by adding 160 μL (1.6×) of resuspended AMPure XP beads to the end repair reaction mixture. The AMPure beads are mixed into the solution on a vortex mixer or by pipetting up and down (e.g., 10 times or more). The reaction is placed on a magnetic stand and incubated at room temperature for 15 minutes or until the solution is clear. After the solution is clear, the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 15 minutes while the reaction is on the magnetic stand. cfDNA is eluted from the beads by resuspending the beads thoroughly in 32.5 μL of elution buffer and incubating at room temperature for 2 minutes. The reaction is placed back on the magnetic stand at room temperature for 15 minutes or until the solution is clear. 30 μL of the supernatant is transferred to a fresh, sterile container (e.g., microfuge tube).

dA-tailing of the end repaired cfDNA is performed by mixing the following components in the sterile microfuge tube as follows:

| Component | Volume (μL) |
|---|---|
| End repaired cfDNA | 30 |
| 10X A-tailing buffer | 5 |
| A-tailing enzyme | 3 |
| Sterile water | 12 |

The dA-tailing reaction is incubated in a thermal cycle for 30 minutes at 30° C.

Clean-up of the dA-tailed cfDNA is performed by adding 90 μL (1.8×) of resuspended AMPure XP beads to the dA-tailing reaction mixture. The AMPure beads are mixed into the solution on a vortex mixer or by pipetting up and down (e.g., 10 times or more). The reaction is placed on a magnetic stand and incubated at room temperature for 15 minutes or until the reaction is clear. After the solution is clear (approximately 5 minutes), the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 15 minutes while the reaction is on the magnetic stand. cfDNA is eluted from the beads by resuspending the beads thoroughly in 32.5 μL of elution buffer and incubating at room temperature for 2 minutes. The reaction is placed back on the magnetic stand for 15 minutes at room temperature or until the solution is clear. 30 μL of the supernatant is transferred to a fresh, sterile container (e.g., microfuge tube).

Adaptor ligation of the dA-tailed cfDNA is performed by mixing the following components in the sterile microfuge tube as follows:

| Component | Volume (μL) |
|---|---|
| dA-tailed cfDNA | 30 |
| 5X Ligation Buffer | 10 |
| Illumina Adaptor | 5 |
| DNA Ligase | 5 |

The adaptor ligation reaction is incubated at 16° C. for 16 hours.

Clean-up of the adaptor-ligated cfDNA is performed by adding 50 μL of resuspended AMPure XP beads to the adaptor ligation reaction mixture. The AMPure beads are mixed into the solution on a vortex mixer or by pipetting up and down (e.g., 10 times or more). The reaction is placed on a magnetic stand and incubated at room temperature for 15 minutes or until the solution is clear. After the solution is clear, the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 15 minutes while the reaction is on the magnetic stand. The beads are resuspended in 52.5 μL of elution buffer. The reaction is placed back on the magnetic stand and incubated at room temperature for 15 minutes or until the solution is clear. 50 μL of the supernatant is transferred to a fresh, sterile container (e.g., microfuge tube).

A second clean-up of the adaptor-ligated cfDNA is performed by adding 50 μL of resuspended AMPure XP beads to the adaptor ligation reaction mixture. The AMPure beads are mixed into the solution on a vortex mixer or by pipetting up and down (e.g., 10 times or more). The reaction is placed on a magnetic stand and incubated at room temperature for 15 minutes or until the solution is clear. After the solution is clear, the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 15 minutes while the reaction is on the magnetic stand. The beads are resuspended in 32.5 μL of elution buffer and incubated at room temperature for 2 minutes. The reaction is placed back on the magnetic stand and incubated at room temperature for 15 minutes or until the solution is clear. 30 μL of the supernatant is transferred to a fresh, sterile container (e.g., microfuge tube).

Universal PCR amplification is performed on the adaptor-ligated cfDNA using primers targeting the adaptors. The PCR amplification is conducted using 16 amplification cycles. Selector set probes are used to selectively capture a subset of the amplified adaptor ligated cfDNA. The amplified cfDNA is sequenced on a paired-end 100 bp lane of an Illumina HiSeq 2000.

The sequencing information is analyzed by detecting mutations in one or more genomic regions based on a selector set. The selector set contains information pertaining to mutations occurring in one or more genomic regions, wherein the mutations are present in at least about 70% of a population of subjects suffering from a breast cancer. A quantity of circulating tumor-DNA (ctDNA) is determined based on the sequencing reads.

A report comprising the quantity of the ctDNA is provided to a physician. Based on the quantity of the ctDNA, the physician provides a prognosis of the prostate cancer in the subject.

Example 5. Use of a Selector Set to Determine a Therapeutic Regimen for the Treatment of a Cancer Cell-free DNA (cfDNA) is purified from a sample from a subject diagnosed with a thyroid cancer. An end repair reaction is performed on the cfDNA by mixing the components in a sterile microfuge tube (or other suitable sterile container) as follows:

| Component | Volume (μL) |
|---|---|
| 1-5 μg cfDNA | 1-85 |
| 10X End Repair Buffer | 10 |
| End Repair Enzyme Mix | 5 |
| Sterile $H_2O$ | -bring total volume up to 100 μL |

The end repair reaction mixture is incubated in a thermal cycler for 30 minutes at 20° C.

Clean-up of the end repaired cfDNA is performed by adding 160 μL (1.6×) of resuspended AMPure XP beads to the end repair reaction mixture. The AMPure beads are mixed into the solution on a vortex mixer or by pipetting up and down (e.g., 10 times or more). The reaction is placed on a magnetic stand and incubated at room temperature for 15 minutes or until the solution is clear. After the solution is clear, the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 15 minutes while the reaction is on the magnetic stand. cfDNA is eluted from the beads by resuspending the beads thoroughly in 32.5 μL of elution buffer and incubating at room temperature for 2 minutes. The reaction is placed back on the magnetic stand at room temperature for 15 minutes or until the solution is clear. 30 μL of the supernatant is transferred to a fresh, sterile container (e.g., microfuge tube).

dA-tailing of the end repaired cfDNA is performed by mixing the following components in the sterile microfuge tube as follows:

| Component | Volume (μL) |
|---|---|
| End repaired cfDNA | 30 |
| 10X A-tailing buffer | 5 |
| A-tailing enzyme | 3 |
| Sterile water | 12 |

The dA-tailing reaction is incubated in a thermal cycle for 30 minutes at 30° C.

Clean-up of the dA-tailed cfDNA is performed by adding 90 μL (1.8×) of resuspended AMPure XP beads to the dA-tailing reaction mixture. The AMPure beads are mixed into the solution on a vortex mixer or by pipetting up and down (e.g., 10 times or more). The reaction is placed on a magnetic stand and incubated at room temperature for 15 minutes or until the reaction is clear. After the solution is clear (approximately 5 minutes), the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 15 minutes while the reaction is on the magnetic stand. cfDNA is eluted from the beads by resuspending the beads thoroughly in 32.5 μL of elution buffer and incubating at room temperature for 2 minutes. The reaction is placed back on the magnetic stand for 15 minutes at room temperature or until the solution is clear. 30 μL of the supernatant is transferred to a fresh, sterile container (e.g., microfuge tube).

Adaptor ligation of the dA-tailed cfDNA is performed by mixing the following components in the sterile microfuge tube as follows:

| Component | Volume (μL) |
|---|---|
| dA-tailed cfDNA | 30 |
| 5X Ligation Buffer | 10 |
| Adaptor | 5 |
| DNA Ligase | 5 |

The adaptor ligation reaction is incubated at 16° C. for 16 hours. The concentration of the adaptor is increased through the duration of the incubation. The adaptor is a Y-shaped adaptor. The 5' strand of the split portion of the Y-shaped contains a molecular barcode and a sample index. The double stranded portion of the Y-shaped adaptor contains a universal sequence. The universal sequence is used for PCR enrichment and sequencing.

Clean-up of the adaptor-ligated cfDNA is performed by adding 50 μL of resuspended AMPure XP beads to the adaptor ligation reaction mixture. The AMPure beads are mixed into the solution on a vortex mixer or by pipetting up and down (e.g., 10 times or more). The reaction is placed on a magnetic stand and incubated at room temperature for 5 minutes or until the solution is clear. After the solution is clear, the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 15 minutes while the reaction is on the magnetic stand. The beads are resuspended in 52.5 μL of elution buffer. The reaction is placed back on the magnetic stand and incubated at room temperature for 5 minutes or until the solution is clear. 50 μL of the supernatant is transferred to a fresh, sterile container (e.g., microfuge tube).

A second clean-up of the adaptor-ligated cfDNA is performed by adding 50 μL of resuspended AMPure XP beads to the adaptor ligation reaction mixture. The AMPure beads are mixed into the solution on a vortex mixer or by pipetting up and down (e.g., 10 times or more). The reaction is placed on a magnetic stand and incubated at room temperature for 5 minutes or until the solution is clear. After the solution is clear, the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 10 minutes while the reaction is on the magnetic stand. The beads are resuspended in 105 μL of elution buffer and incubated at room temperature for 2 minutes. The reaction is placed back on the magnetic stand and incubated at room temperature until the solution is clear. 100 μL of the supernatant is transferred to a fresh, sterile container (e.g., microfuge tube).

Bead based size selection of the adaptor ligated cfDNA is performed by adding 80 μL of AMPure XP beads to the adaptor ligated cfDNA. The reaction is mixed by vortexing the reaction or pipetting the solution up and down at least 10 times. The reaction is incubated at room temperature for 5 minutes. The reaction is placed on a magnetic stand for 5 minutes or until the solution is clear. Once the solution is clear, the supernatant is transferred to a new tube. 20 μL of AMPure XP beads are added to the supernatant (vortex or pipet up and down to mix) and incubated at room temperature for 5 minutes. The reaction is placed on the magnetic stand for 5 minutes or until the solution is clear. Once the solution is clear, the supernatant is removed and discarded. While on the magnetic stand, the beads are washed twice using 200 μL of freshly prepared 80% ethanol. The ethanol washes are incubated at room temperature for 30 seconds and removed and discarded. The beads are air dried at room temperature for 10 minutes. cfDNA is eluted from the beads by resuspending the beads in 25 μL of sterile water or 0.1× TE Buffer. The reaction is placed back on the magnetic stand. Once the solution is clear, 20 μL of the supernatant is transferred to a new microfuge tube.

PCR enrichment of the adaptor ligated cfDNA is by mixing the following components:

| Component | Volume (μL) |
|---|---|
| Adaptor ligated cfDNA | 20 |
| Universal PCR Primer (25 μM) | 2.5 |
| Index Primer (25 μM) | 2.5 |
| Phusion High-Fidelity PCR Master Mix | 25 |

The PCR enrichment is performed using the cycling conditions of 1 cycle at 98° C. for 30 seconds, 17 cycles of 98° C. for 10 seconds, 65° C. for 30 seconds, and 72° C. for 30 seconds, followed by 1 cycle of 72° C. for 5 minutes and a hold at 4° C.

Clean-up of the PCR enriched cfDNA is performed by adding 50 μL (1×) of resuspended AMPure XP beads to the PCR enriched cfDNA reaction mixture. The AMPure beads are mixed into the solution on a vortex mixer or by pipetting up and down (e.g., 10 times or more). The reaction is placed on a magnetic stand and incubated at room temperature for 5 minutes or until the solution is clear. After the solution is clear, the supernatant is removed and discarded. The beads are washed twice by adding 200 μL of 80% freshly prepared ethanol to the reaction while in the magnetic stand. For each wash, the ethanol solution is added at room temperature for 30 seconds. The supernatant is removed and discarded. The beads are air dried for 10 minutes while the reaction is on the magnetic stand. The beads are resuspended in 30 μL of 0.1×TE. The reaction is placed back on the magnetic stand and incubated at room temperature for until the solution is clear. 25 μL of the supernatant is transferred to a fresh, sterile container (e.g., microfuge tube). The enriched cfDNA is diluted 20-fold with the addition of nuclease free water The enriched cfDNA is hybridized to an array comprising selector set probes. The quantity of the circulating tumor DNA (ctDNA) is determined using array-based hybridization. An image of the array is obtained and the quantity of the ctDNA is calculated based on the intensity signals on the array.

A report comprising the quantity of the ctDNA, the mutations found, and a list of anti-cancer therapies is provided to a physician. Based on the quantity of the ctDNA, the types of mutations found, and the list of anti-cancer therapies, the physician provides a therapeutic regimen for treating of the thyroid cancer in the subject.

Lengthy table referenced here

US12735750-20260915-T00001

Please refer to the end of the specification for access instructions.

Lengthy table referenced here

US12735750-20260915-T00002

Please refer to the end of the specification for access instructions.

Lengthy table referenced here

US12735750-20260915-T00003

Please refer to the end of the specification for access instructions.

Lengthy table referenced here

US12735750-20260915-T00004

Please refer to the end of the specification for access instructions.

Lengthy table referenced here

US12735750-20260915-T00005

Please refer to the end of the specification for access instructions.

Lengthy table referenced here

US12735750-20260915-T00006

Please refer to the end of the specification for access instructions.

Lengthy table referenced here

US12735750-20260915-T00007

Please refer to the end of the specification for access instructions.

Lengthy table referenced here

US12735750-20260915-T00008

Please refer to the end of the specification for access instructions.

Lengthy table referenced here

US12735750-20260915-T00009

Please refer to the end of the specification for access instructions.

Lengthy table referenced here

US12735750-20260915-T00010

Please refer to the end of the specification for access instructions.

Lengthy table referenced here

US12735750-20260915-T00011

Please refer to the end of the specification for access instructions.

Lengthy table referenced here

US12735750-20260915-T00012

Please refer to the end of the specification for access instructions.

Lengthy table referenced here

US12735750-20260915-T00013

Please refer to the end of the specification for access instructions.

Lengthy table referenced here

US12735750-20260915-T00014

Please refer to the end of the specification for access instructions.

Lengthy table referenced here

US12735750-20260915-T00015

Please refer to the end of the specification for access instructions.

Lengthy table referenced here

US12735750-20260915-T00016

Please refer to the end of the specification for access instructions.

Lengthy table referenced here

US12735750-20260915-T00017

Please refer to the end of the specification for access instructions.

Lengthy table referenced here

US12735750-20260915-T00018

Please refer to the end of the specification for access instructions.

Lengthy table referenced here

US12735750-20260915-T00019

Please refer to the end of the specification for access instructions.

Lengthy table referenced here

US12735750-20260915-T00020

Please refer to the end of the specification for access instructions.

Lengthy table referenced here

US12735750-20260915-T00021

Please refer to the end of the specification for access instructions.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

LENGTHY TABLES

The patent contains a lengthy table section. A copy of the table is available in electronic form from the USPTO web site (https://seqdata.uspto.gov/docdetail?docId=US12735750B2). An electronic copy of the table will also be available from the USPTO upon request and payment of the fee set forth in 37 CFR 1.19(b)(3).

What is claimed is:

1. A method of detecting somatic mutations in a sample of cfDNA of a subject suffering from a cancer, wherein the somatic mutation is associated with cancer, the method comprising:

(i) obtaining a first cell-free DNA (cfDNA) sample comprising circulating tumor DNA (ctDNA) comprising somatic mutations from the subject, (ii) performing hybrid capture on the first cfDNA sample using a selector set comprising a plurality of oligonucleotides to enrich for cfDNA corresponding to genomic regions known to contain tumor-specific somatic mutations identified in (b) to produce a hybrid captured first cfDNA sample, (iii) sequencing the hybrid captured first cfDNA sample to generate sequencing information; and (iv) analyzing the sequence information of the hybrid captured first cfDNA sample to detect ctDNA in the sample;

wherein:

the method is capable of detecting a percentage of ctDNA that is less than or equal to 2% of total cfDNA, the cancer is lung cancer, and the selector set is produced according to a method comprising:

(a) performing a sequencing reaction on a plurality of tumor samples and a plurality of non-tumor samples from a population of subjects suffering from the cancer;

(b) comparing the sequencing information of the plurality of tumor samples to sequencing information from the plurality of non-tumor samples from the population of subjects to identify fifty or more somatic mutations specific to the sequencing information of the plurality of tumor samples; and (c) producing the selector set corresponding to the 50 or more genomic regions comprising the one or more mutations specific to the sequencing information of the plurality of tumor samples.

2. The method of claim 1, wherein the sequencing information of step (iv) comprises information related to at least 2, 3, 5, 8, 10, 20, 30, 40, 100, 200, or 300 genomic regions.

3. The method of claim 2, wherein the genomic regions of step (c) comprise two or more of exonic regions, intronic regions, and untranslated regions.

4. The method of claim 3, wherein the genomic regions of step (c) comprise less than 1.5 megabases (Mb), 1 Mb, 500 kb, 350 kb, 100 kb, 75 kb, 50 kb or 25 kb of the genome.

5. The method of claim 1, further comprising attaching adaptors to the cfDNA prior to step (ii).

6. The method of claim 5, wherein the adaptors comprise a molecular barcode.

7. The method of claim 5, wherein the adaptors comprise a sample index.

8. The method of claim 5, wherein the adaptors comprise a primer sequence.

9. The method of claim 5, wherein the adaptors comprise a Y-shaped adaptor.

10. The method of claim 1, further comprising conducting an amplification reaction on the cfDNA, wherein the amplification reaction comprises 20 or fewer amplification cycles prior to or immediately after step (ii).

11. The method of claim 10, wherein the amplification reaction comprises 15 or fewer amplification cycles.

12. The method of claim 10, further comprising end-repairing the cfDNA prior to step (ii).

13. The method of claim 10, further comprising A-tailing the cfDNA prior to step (ii).

14. The method of claim 1, wherein the sequencing reaction of step (a) is whole genome sequencing or whole exome sequencing.

15. The method of claim 1, wherein analyzing the sequencing information comprises using a computer readable medium to quantify ctDNA in the cfDNA sample.

16. The method of claim 15, further comprising obtaining a second cfDNA sample from the subject following a treatment for the cancer and performing steps (ii)-(iv) on the second cfDNA sample.

17. The method of claim 16, further comprising comparing the quantity of the ctDNA in the first cfDNA sample to the quantity of the ctDNA in the second cfDNA sample.

18. The method of claim 17, further comprising providing a treatment modification recommendation to the subject based on the comparison of the quantity of the ctDNA in the first and the second cfDNA sample, wherein the treatment modification recommendation is selected from the group consisting of terminating the treatment, increasing a dosage or frequency of the treatment, and decreasing a dosage or frequency of the treatment.

* * * * *

```
                              SEQUENCE LISTING


Sequence total quantity: 51
SEQ ID NO: 1            moltype = DNA  length = 101
FEATURE                 Location/Qualifiers
source                  1..101
                        mol_type = other DNA
                        organism = Homo sapiens
SEQUENCE: 1
agaaatacta ataaaatgat taaagaaggt gtgtctttaa ttgaagcatg atttaaagta  60
aatgcaaagc taaaaatcag accactgcac tccagcctgg g                      101

SEQ ID NO: 2            moltype = DNA  length = 101
FEATURE                 Location/Qualifiers
source                  1..101
                        mol_type = other DNA
                        organism = Homo sapiens
SEQUENCE: 2
tactaataaa atgattaaag aaggtgtgtc tttaattgaa gcatgattta aagtaaatgc  60
aaagctaaaa atcagaccac tgcactccag cctggggaac a                      101

SEQ ID NO: 3            moltype = DNA  length = 101
FEATURE                 Location/Qualifiers
source                  1..101
                        mol_type = other DNA
                        organism = Homo sapiens
SEQUENCE: 3
aaatgattaa agaaggtgtg tctttaattg aagcatgatt taaagtaaat gcaaagctaa  60
aaatcagacc actgcactcc agcctgggga acaagagtga a                      101

SEQ ID NO: 4            moltype = DNA  length = 101
FEATURE                 Location/Qualifiers
source                  1..101
                        mol_type = other DNA
                        organism = Homo sapiens
SEQUENCE: 4
gtgtgtcttt aattgaagca tgatttaaag taaatgcaaa gctaaaaatc agaccactgc  60
actccagcct ggggaacaag agtgaaaccc catctcaaaa a                      101

SEQ ID NO: 5            moltype = DNA  length = 100
FEATURE                 Location/Qualifiers
source                  1..100
                        mol_type = other DNA
                        organism = Homo sapiens
SEQUENCE: 5
gtgtctttaa ttgaagcatg atttaaagta aatgcaaagc taaaaatcag accactgcac  60
tccagcctgg ggaacaagag tgaaacccca tctcaaaaac                        100

SEQ ID NO: 6            moltype = DNA  length = 100
FEATURE                 Location/Qualifiers
source                  1..100
                        mol_type = other DNA
                        organism = Homo sapiens
SEQUENCE: 6
gtctttaatt gaagcatgat ttaaagtaaa tgcaaagcta aaaatcagac cactgcactc  60
cagcctgggg aacaagagtg aaaccccatc tcaaaaacaa                        100

SEQ ID NO: 7            moltype = DNA  length = 92
FEATURE                 Location/Qualifiers
source                  1..92
                        mol_type = other DNA
                        organism = Homo sapiens
SEQUENCE: 7
tgaagcatga tttaaagtaa atgcaaagct aaaaatcaga ccactgcact ccagcctggg  60
gaacaagagt gaaaccccat ctcaaaaaca aa                                92
```

```
SEQ ID NO: 8            moltype = DNA  length = 92
FEATURE                 Location/Qualifiers
source                  1..92
                        mol_type = other DNA
                        organism = Homo sapiens
SEQUENCE: 8
atgatttaaa gtaaatgcaa agctaaaaat cagaccactg cactccagcc tggggaacaa  60
gagtgaaacc ccatctcaaa aacaaacaaa ca                                92

SEQ ID NO: 9            moltype = DNA  length = 92
FEATURE                 Location/Qualifiers
source                  1..92
                        mol_type = other DNA
                        organism = Homo sapiens
SEQUENCE: 9
agtaaatgca aagctaaaaa tcagaccact gcactccagc ctggggaaca agagtgaaac  60
cccatctcaa aaacaaacaa acaaaacaaa ac                                92

SEQ ID NO: 10           moltype = DNA  length = 100
FEATURE                 Location/Qualifiers
source                  1..100
                        mol_type = other DNA
                        organism = Homo sapiens
SEQUENCE: 10
atgcaaagct aaaaatcaga ccactgcact ccagcctggg gaacaagagt gaaaccccat  60
ctcaaaaaca aacaaacaaa acaaaacaaa aaaaactaag                        100

SEQ ID NO: 11           moltype = DNA  length = 40
FEATURE                 Location/Qualifiers
source                  1..40
                        mol_type = other DNA
                        organism = Homo sapiens
SEQUENCE: 11
atgcaaagct aaaaatcaga ccactgcact ccagcctggg                        40

SEQ ID NO: 12           moltype = DNA  length = 101
FEATURE                 Location/Qualifiers
source                  1..101
                        mol_type = other DNA
                        organism = Homo sapiens
SEQUENCE: 12
tgtcagagta gtggtggttt ataagacggg agaaaatagc acctcacttc cagaaagctt  60
taagacaaaa ggtgagtact agagtaagat tcagtctcag a                      101

SEQ ID NO: 13           moltype = DNA  length = 101
FEATURE                 Location/Qualifiers
source                  1..101
                        mol_type = other DNA
                        organism = Homo sapiens
SEQUENCE: 13
gagtagtggt ggtttataag acgggagaaa atagcacctc acttccagaa agctttaaga  60
caaaaggtga gtactagagt aagattcagt ctcagatctg g                      101

SEQ ID NO: 14           moltype = DNA  length = 103
FEATURE                 Location/Qualifiers
source                  1..103
                        mol_type = other DNA
                        organism = Homo sapiens
SEQUENCE: 14
gtggtggttt ataagacggg agaaaatagc acctcacttc cagaaagctt taagacaaaa  60
ggtgagtact agagtaagat tcagtctcag atctgggtga cac                    103

SEQ ID NO: 15           moltype = DNA  length = 101
FEATURE                 Location/Qualifiers
source                  1..101
                        mol_type = other DNA
                        organism = Homo sapiens
SEQUENCE: 15
gtttataaga cgggagaaaa tagcacctca cttccagaaa gctttaagac aaaaggtgag  60
tactagagta agattcagtc tcagatctgg gtgacacaaa g                      101

SEQ ID NO: 16           moltype = DNA  length = 101
FEATURE                 Location/Qualifiers
source                  1..101
                        mol_type = other DNA
                        organism = Homo sapiens
SEQUENCE: 16
ataagacggg agaaaatagc acctcacttc cagaaagctt taagacaaaa ggtgagtact  60
agagtaagat tcagtctcag atctgggtga cacaaaggac c                      101
```

```
SEQ ID NO: 17          moltype = DNA  length = 101
FEATURE                Location/Qualifiers
source                 1..101
                       mol_type = other DNA
                       organism = Homo sapiens
SEQUENCE: 17
agaaaatagc acctcacttc cagaaagctt taagacaaaa ggtgagtact agagtaagat  60
tcagtctcag atctgggtga cacaaaggac catggatttc t                      101

SEQ ID NO: 18          moltype = DNA  length = 101
FEATURE                Location/Qualifiers
source                 1..101
                       mol_type = other DNA
                       organism = Homo sapiens
SEQUENCE: 18
aatagcacct cacttccaga aagctttaag acaaaaggtg agtactagag taagattcag  60
tctcagatct gggtgacaca aaggaccatg gatttctgca a                      101

SEQ ID NO: 19          moltype = DNA  length = 104
FEATURE                Location/Qualifiers
source                 1..104
                       mol_type = other DNA
                       organism = Homo sapiens
SEQUENCE: 19
acctcacttc cagaaagctt taagacaaaa ggtgagtact agagtaagat tcagtctcag  60
atctgggtga cacaaaggac catggatttc tgcaaccctt ggtg                   104

SEQ ID NO: 20          moltype = DNA  length = 101
FEATURE                Location/Qualifiers
source                 1..101
                       mol_type = other DNA
                       organism = Homo sapiens
SEQUENCE: 20
cagaaagctt taagacaaaa ggtgagtact agagtaagat tcagtctcag atctgggtga  60
cacaaaggac catggatttc tgcaaccctt ggtgcctttc t                      101

SEQ ID NO: 21          moltype = DNA  length = 101
FEATURE                Location/Qualifiers
source                 1..101
                       mol_type = other DNA
                       organism = Homo sapiens
SEQUENCE: 21
aagacaaaag gtgagtacta gagtaagatt cagtctcaga tctgggtgac acaaaggacc  60
atggatttct gcaacccttg gtgcctttct tgggaaccca t                      101

SEQ ID NO: 22          moltype = DNA  length = 40
FEATURE                Location/Qualifiers
source                 1..40
                       mol_type = other DNA
                       organism = Homo sapiens
SEQUENCE: 22
aagacaaaag gtgagtacta gagtaagatt cagtctcaga                        40

SEQ ID NO: 23          moltype = DNA  length = 20
FEATURE                Location/Qualifiers
misc_feature           1..20
                       note = synthetic polynucleotide
source                 1..20
                       mol_type = other DNA
                       organism = synthetic construct
SEQUENCE: 23
agacgggaga aaatagcacc                                              20

SEQ ID NO: 24          moltype = DNA  length = 20
FEATURE                Location/Qualifiers
misc_feature           1..20
                       note = synthetic polynucleotide
source                 1..20
                       mol_type = other DNA
                       organism = synthetic construct
SEQUENCE: 24
accaagggtt gcagaaatcc                                              20

SEQ ID NO: 25          moltype = DNA  length = 24
FEATURE                Location/Qualifiers
misc_feature           1..24
                       note = synthetic polynucleotide
source                 1..24
```

```
                        mol_type = other DNA
                        organism = synthetic construct
SEQUENCE: 25
gagatggagt ttcactcttg ttgc                                        24

SEQ ID NO: 26           moltype = DNA  length = 27
FEATURE                 Location/Qualifiers
misc_feature            1..27
                        note = synthetic polynucleotide
source                  1..27
                        mol_type = other DNA
                        organism = synthetic construct
SEQUENCE: 26
gaacctttcc atcatactta gaaatac                                     27

SEQ ID NO: 27           moltype = DNA  length = 17
FEATURE                 Location/Qualifiers
misc_feature            1..17
                        note = synthetic polynucleotide
source                  1..17
                        mol_type = other DNA
                        organism = synthetic construct
SEQUENCE: 27
tccatggaag ccagaac                                                17

SEQ ID NO: 28           moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 28
atgctaagat gtgtctgtca                                             20

SEQ ID NO: 29           moltype = DNA  length = 25
FEATURE                 Location/Qualifiers
misc_feature            1..25
                        note = synthetic polynucleotide
source                  1..25
                        mol_type = other DNA
                        organism = synthetic construct
SEQUENCE: 29
ccttaacaca gatggctctt gatgc                                       25

SEQ ID NO: 30           moltype = DNA  length = 23
FEATURE                 Location/Qualifiers
misc_feature            1..23
                        note = synthetic polynucleotide
source                  1..23
                        mol_type = other DNA
                        organism = synthetic construct
SEQUENCE: 30
tcctctttcc accttggctt tcc                                         23

SEQ ID NO: 31           moltype = DNA  length = 23
FEATURE                 Location/Qualifiers
misc_feature            1..23
                        note = synthetic polynucleotide
source                  1..23
                        mol_type = other DNA
                        organism = synthetic construct
SEQUENCE: 31
ggttcagaac taccaataac aag                                         23

SEQ ID NO: 32           moltype = DNA  length = 24
FEATURE                 Location/Qualifiers
misc_feature            1..24
                        note = synthetic polynucleotide
source                  1..24
                        mol_type = other DNA
                        organism = synthetic construct
SEQUENCE: 32
acctgatgtg tgacctgatt gatg                                        24

SEQ ID NO: 33           moltype = DNA  length = 12
FEATURE                 Location/Qualifiers
source                  1..12
                        mol_type = other DNA
```

```
                        organism = Homo sapiens
SEQUENCE: 33
tctggctata gc                                                      12

SEQ ID NO: 34           moltype = DNA  length = 10
FEATURE                 Location/Qualifiers
source                  1..10
                        mol_type = other DNA
                        organism = Homo sapiens
SEQUENCE: 34
ctggggaaca                                                         10

SEQ ID NO: 35           moltype = DNA  length = 13
FEATURE                 Location/Qualifiers
source                  1..13
                        mol_type = other DNA
                        organism = Homo sapiens
SEQUENCE: 35
gaacaagagt gaa                                                     13

SEQ ID NO: 36           moltype = DNA  length = 28
FEATURE                 Location/Qualifiers
source                  1..28
                        mol_type = other DNA
                        organism = Homo sapiens
SEQUENCE: 36
gaacaagagt gaaaccccat ctcaaaaa                                     28

SEQ ID NO: 37           moltype = DNA  length = 29
FEATURE                 Location/Qualifiers
source                  1..29
                        mol_type = other DNA
                        organism = Homo sapiens
SEQUENCE: 37
gaacaagagt gaaaccccat ctcaaaaac                                    29

SEQ ID NO: 38           moltype = DNA  length = 31
FEATURE                 Location/Qualifiers
source                  1..31
                        mol_type = other DNA
                        organism = Homo sapiens
SEQUENCE: 38
gaacaagagt gaaaccccat ctcaaaaaca a                                 31

SEQ ID NO: 39           moltype = DNA  length = 32
FEATURE                 Location/Qualifiers
source                  1..32
                        mol_type = other DNA
                        organism = Homo sapiens
SEQUENCE: 39
gaacaagagt gaaaccccat ctcaaaaaca aa                                32

SEQ ID NO: 40           moltype = DNA  length = 38
FEATURE                 Location/Qualifiers
source                  1..38
                        mol_type = other DNA
                        organism = Homo sapiens
SEQUENCE: 40
gaacaagagt gaaaccccat ctcaaaaaca aacaaaca                          38

SEQ ID NO: 41           moltype = DNA  length = 47
FEATURE                 Location/Qualifiers
source                  1..47
                        mol_type = other DNA
                        organism = Homo sapiens
SEQUENCE: 41
gaacaagagt gaaaccccat ctcaaaaaca aacaaacaaa acaaaac                47

SEQ ID NO: 42           moltype = DNA  length = 60
FEATURE                 Location/Qualifiers
source                  1..60
                        mol_type = other DNA
                        organism = Homo sapiens
SEQUENCE: 42
gaacaagagt gaaaccccat ctcaaaaaca aacaaacaaa acaaaacaaa aaaaactaag  60

SEQ ID NO: 43           moltype =   length =
SEQUENCE: 43
000
```

-continued

```
SEQ ID NO: 44          moltype = DNA  length = 16
FEATURE                Location/Qualifiers
source                 1..16
                       mol_type = other DNA
                       organism = Homo sapiens
SEQUENCE: 44
cagatctggg tgacac                                                16

SEQ ID NO: 45          moltype = DNA  length = 20
FEATURE                Location/Qualifiers
source                 1..20
                       mol_type = other DNA
                       organism = Homo sapiens
SEQUENCE: 45
cagatctggg tgacacaaag                                            20

SEQ ID NO: 46          moltype = DNA  length = 24
FEATURE                Location/Qualifiers
source                 1..24
                       mol_type = other DNA
                       organism = Homo sapiens
SEQUENCE: 46
cagatctggg tgacacaaag gacc                                       24

SEQ ID NO: 47          moltype = DNA  length = 34
FEATURE                Location/Qualifiers
source                 1..34
                       mol_type = other DNA
                       organism = Homo sapiens
SEQUENCE: 47
cagatctggg tgacacaaag gaccatggat ttct                            34

SEQ ID NO: 48          moltype = DNA  length = 38
FEATURE                Location/Qualifiers
source                 1..38
                       mol_type = other DNA
                       organism = Homo sapiens
SEQUENCE: 48
cagatctggg tgacacaaag gaccatggat ttctgcaa                        38

SEQ ID NO: 49          moltype = DNA  length = 47
FEATURE                Location/Qualifiers
source                 1..47
                       mol_type = other DNA
                       organism = Homo sapiens
SEQUENCE: 49
cagatctggg tgacacaaag gaccatggat ttctgcaacc cttggtg              47

SEQ ID NO: 50          moltype = DNA  length = 54
FEATURE                Location/Qualifiers
source                 1..54
                       mol_type = other DNA
                       organism = Homo sapiens
SEQUENCE: 50
cagatctggg tgacacaaag gaccatggat ttctgcaacc cttggtgcct ttct       54

SEQ ID NO: 51          moltype = DNA  length = 65
FEATURE                Location/Qualifiers
source                 1..65
                       mol_type = other DNA
                       organism = Homo sapiens
SEQUENCE: 51
cagatctggg tgacacaaag gaccatggat ttctgcaacc cttggtgcct ttcttgggaa  60
cccat                                                             65
```